United States Patent
Herrlein et al.

(10) Patent No.: US 12,053,542 B2
(45) Date of Patent: Aug. 6, 2024

(54) MULTICOMPONENT SILICONE COMPOSITION

(71) Applicant: Wella International Operations Switzerland Sàrl, Petit-Lancy (CH)

(72) Inventors: Mathias Kurt Herrlein, Darmstadt (DE); Graham Neil McKelvey, Darmstadt (DE); Matija Crne, Darmstadt (DE); Corinne Mohr, Darmstadt (DE); Simon Paul Godfrey, Darmstadt (DE); Andrej Gross, Darmstadt (DE); Petra Braun, Darmstadt (DE); Michael A. Brook, Ontario (CA); Richard Taylor, Vale of Glamorgan (GB); Yan Wang, Darmstadt (DE); Axel Meyer, Frankfurt am Main (DE)

( * ) Notice: Subject to any disclaimer, the term of this patent is extended or adjusted under 35 U.S.C. 154(b) by 792 days.

(21) Appl. No.: 17/258,425

(22) PCT Filed: Mar. 27, 2019

(86) PCT No.: PCT/EP2019/057813
§ 371 (c)(1),
(2) Date: Jan. 6, 2021

(87) PCT Pub. No.: WO2020/007511
PCT Pub. Date: Jan. 9, 2020

(65) Prior Publication Data
US 2021/0290519 A1   Sep. 23, 2021

Related U.S. Application Data

(60) Provisional application No. 62/694,808, filed on Jul. 6, 2018, provisional application No. 62/694,739, filed
(Continued)

(51) Int. Cl.
A61K 8/892 (2006.01)
A61K 8/04 (2006.01)
(Continued)

(52) U.S. Cl.
CPC .............. *A61K 8/892* (2013.01); *A61K 8/046* (2013.01); *A61K 8/35* (2013.01); *A61K 8/416* (2013.01);
(Continued)

(58) Field of Classification Search
CPC .......... A61Q 5/10; A61K 8/416; A61K 8/466; A61K 8/585; A61K 8/893; A61K 8/895;
(Continued)

(56) References Cited

U.S. PATENT DOCUMENTS 4,559,057 A   12/1985  Bogaty et al.
5,258,481 A   11/1993  Hesselmans et al.
(Continued)

FOREIGN PATENT DOCUMENTS

CN   111432887 A   7/2020
CN   111432888 A   7/2020
(Continued)

OTHER PUBLICATIONS

International Search Report issued in connection with PCT Application No. PCT/EP2019/057811 dated Sep. 4, 2019.
(Continued)

*Primary Examiner* — Blessing M Fubara
(74) *Attorney, Agent, or Firm* — Dennemeyer & Associates LLC; Victoria Friedman

(57) ABSTRACT

The instant disclosure generally relates to a multicomponent composition for coloring mammalian or synthetic substrate material and textiles, the composition comprising a first and second components and a third component. The first and second components comprise first and second silicone poly-
(Continued)

mers respectively. Any one or more of the first, second and third components may also comprise pigment microparticles. The first, second and third compounds meld together on substrate material and textiles and especially on hair to form a highly remanent colored coating. The multicomponent composition formed and set in situ as a solid linked coating has a substantially permanent pigment lastingness and minimally alters the substrate material and textiles.

19 Claims, 10 Drawing Sheets

Related U.S. Application Data on Jul. 6, 2018, provisional application No. 62/694,781, filed on Jul. 6, 2018, provisional application No. 62/694,570, filed on Jul. 6, 2018, provisional application No. 62/739,592, filed on Oct. 1, 2018, provisional application No. 62/740,027, filed on Oct. 2, 2018, provisional application No. 62/769,239, filed on Nov. 19, 2018.

(51) Int. Cl.
  *A61K 8/35*     (2006.01)
  *A61K 8/41*     (2006.01)
  *A61K 8/46*     (2006.01)
  *A61K 8/58*     (2006.01)
  *A61K 8/893*    (2006.01)
  *A61K 8/895*    (2006.01)
  *A61K 8/898*    (2006.01)
  *A61Q 5/10*     (2006.01)

(52) U.S. Cl.
  CPC .............. *A61K 8/466* (2013.01); *A61K 8/585* (2013.01); *A61K 8/893* (2013.01); *A61K 8/895* (2013.01); *A61K 8/898* (2013.01); *A61Q 5/10* (2013.01); *A61K 2800/412* (2013.01); *A61K 2800/4324* (2013.01); *A61K 2800/594* (2013.01); *A61K 2800/884* (2013.01); *A61K 2800/95* (2013.01)

(58) Field of Classification Search
  CPC .............. A61K 8/898; A61K 2800/412; A61K 2800/4324; A61K 2800/594; A61K 2800/884; A61K 2800/95
  See application file for complete search history.

(56) References Cited

U.S. PATENT DOCUMENTS

| | | | |
|---|---|---|---|
| 5,567,428 | A | 10/1996 | Hugehes |
| 5,990,479 | A | 11/1999 | Weiss et al. |
| 6,225,198 | B1 | 5/2001 | Alivisatos et al. |
| 6,451,747 | B1 | 9/2002 | Decoster |
| 6,492,484 | B2 | 12/2002 | Misumi et al. |
| 9,546,301 | B2 | 1/2017 | Derksen et al. |
| 9,949,542 | B2 * | 4/2018 | Crne ............ A61K 8/731 |
| 10,011,677 | B2 | 7/2018 | Yamashita et al. |
| 10,959,919 | B2 | 3/2021 | Dahne et al. |
| 10,973,754 | B2 | 4/2021 | Herrlein et al. |
| 11,324,688 | B2 * | 5/2022 | Herrlein ............ A61K 8/8176 |
| 11,478,415 | B2 * | 10/2022 | Herrlein ............ A61Q 5/10 |
| 2003/0203978 | A1 | 10/2003 | O'Brien |
| 2004/0010863 | A1 | 1/2004 | Gawtrey et al. |
| 2005/0226838 | A1 | 10/2005 | Krause et al. |
| 2006/0041026 | A1 | 2/2006 | Mahr et al. |
| 2007/0134180 | A1 | 6/2007 | Simard et al. |
| 2008/0108740 | A1 | 5/2008 | Evers |
| 2008/0184496 | A1 | 8/2008 | Brun et al. |
| 2009/0233062 | A1 | 9/2009 | Nakamura et al. |
| 2010/0083446 | A1 | 4/2010 | Brun et al. |
| 2010/0088036 | A1 | 4/2010 | Goddard-Clark et al. |
| 2011/0061179 | A1 | 3/2011 | Cremer et al. |
| 2011/0083284 | A1 | 4/2011 | Suddaby et al. |
| 2014/0242281 | A1 | 8/2014 | Swarup et al. |
| 2014/0336093 | A1 | 11/2014 | Koellnberger |
| 2015/0174051 | A1 | 6/2015 | Teboul |
| 2016/0120284 | A1 | 5/2016 | Crne et al. |
| 2016/0120285 | A1 | 5/2016 | Crne et al. |
| 2016/0175212 | A1 | 6/2016 | Zhou et al. |
| 2016/0235655 | A1 | 8/2016 | Herrlein et al. |
| 2016/0271049 | A1 | 9/2016 | Schulze et al. |
| 2017/0001045 | A1 | 1/2017 | Aubert et al. |
| 2017/0158888 | A1 | 6/2017 | Kang et al. |
| 2017/0189312 | A1 | 7/2017 | Van Nguyen et al. |
| 2017/0189314 | A1 | 7/2017 | Elsen-wahrer et al. |
| 2018/0105718 | A1 | 4/2018 | Swarup et al. |
| 2018/0263353 | A1 | 9/2018 | Crne et al. |
| 2018/0263354 | A1 | 9/2018 | Crne et al. |
| 2021/0220251 | A1 | 7/2021 | Speckbacher et al. |
| 2021/0401713 | A1 | 12/2021 | Herrlein et al. |
| 2022/0054392 | A1 | 2/2022 | Herrlein et al. |

FOREIGN PATENT DOCUMENTS

| | | | | |
|---|---|---|---|---|
| DE | 19913625 | A1 | 9/2000 | |
| DE | 102006011271 | A1 | 9/2007 | |
| EP | 132960 | A2 | 2/1985 | |
| EP | 1184426 | A2 | 3/2002 | |
| EP | 1600148 | A1 | 11/2005 | |
| EP | 1600149 | A1 | 11/2005 | |
| EP | 1825883 | A1 | 8/2007 | |
| EP | 3015134 | A1 | 5/2016 | |
| EP | 3015135 | A1 | 5/2016 | |
| EP | 3058934 | A1 | 8/2016 | |
| EP | 3058989 | A1 | 8/2016 | |
| EP | 3397346 | A1 | 11/2018 | |
| FR | 2899795 | A1 | 10/2007 | |
| FR | 2992559 | A1 | 1/2014 | |
| JP | S 50-034400 | A | 4/1975 | |
| JP | S 60-105608 | A | 6/1985 | |
| JP | 2005-350460 | A | 12/2005 | |
| JP | 2007-084510 | A | 4/2007 | |
| JP | 2008-502613 | A | 1/2008 | |
| JP | 2009-520002 | A | 5/2009 | |
| JP | 2010-530842 | A | 9/2010 | |
| JP | 2012-515219 | A | 7/2012 | |
| JP | 2012-530841 | A | 12/2012 | |
| JP | 2015-521646 | A | 7/2015 | |
| JP | 2017-533224 | A | 11/2017 | |
| KR | 101603845 | B1 | 3/2016 | |
| KR | 2019-0028636 | A | 3/2019 | |
| KR | 20190028636 | A | 3/2019 | |
| WO | 2005065632 | A1 | 7/2005 | |
| WO | 2007071706 | A2 | 6/2007 | |
| WO | 2011128255 | A1 | 10/2011 | |
| WO | WO-2011128255 | A1 * | 10/2011 | ............ A61K 8/891 |
| WO | 2009073759 | A1 | 11/2014 | |
| WO | 2015097308 | A1 | 7/2015 | |
| WO | 2016066747 | A1 | 5/2016 | |
| WO | 2017108599 | A1 | 6/2017 | |
| WO | 2017117543 | A1 | 7/2017 | |
| WO | 2017189585 | A1 | 11/2017 | |
| WO | 2017220781 | A1 | 12/2017 | |
| WO | 2018039314 | A1 | 3/2018 | |
| WO | 2018130912 | A1 | 7/2018 | |
| WO | 2018185345 | A1 | 10/2018 | |
| WO | 2018234530 | A1 | 12/2018 | |
| WO | 2019071204 | A1 | 4/2019 | |
| WO | 2019071207 | A1 | 4/2019 | |
| WO | 2019211050 | A1 | 11/2019 | |
| WO | 2020007511 | A1 | 1/2020 | |
| WO | 2020008073 | A2 | 1/2020 | |
| WO | 2020008074 | A1 | 1/2020 | |
| WO | 2020035362 | A1 | 2/2020 | |
| WO | 2020114647 | A | 6/2020 | |

(56) References Cited

FOREIGN PATENT DOCUMENTS

| WO | 2021032837 A1 | 2/2021 |
| WO | 2021032873 A1 | 2/2021 |

OTHER PUBLICATIONS

International Search Report and Written Opinion received for PCT Patent Application No. PCT/EP2019/057814, mailed on Sep. 16, 2019.

International Application Serial No. PCT/EP2019/057814, Invitation to Pay Additional Fees mailed Jul. 26, 2019.

International Search Report and Written Opinion received for PCT Patent Application No. PCT/EP2019/068186, mailed on Feb. 2, 2020.

International Search Report and Written Opinion received for PCT Patent Application No. PCT/EP2019/068187, mailed on Dec. 4, 2019.

International Search Report and Written Opinion received for PCT Patent Application No. PCT/EP2019/076647, mailed on Jan. 9, 2020.

European Search Report received for EP Patent Application No. 17195273.2, Extended European Search Report mailed Jan. 11, 2018.

International Search Report and Written Opinion received for PCT Patent Application No. PCT/US2018/054717, Mailed on Dec. 20, 2018.

International Search Report and Written Opinion received for PCT Patent Application No. PCT/US2018/054724, mailed on Feb. 26, 2019.

International Search Report and Written Opinion received for PCT Patent Application No. PCT/US2019/057812, mailed on Jan. 7, 2019.

International Search Report and Written Opinion received for PCT Patent Application No. PCT/EP2019/057811, mailed on Sep. 4, 2019.

International Search Report and written opinion received in PCT Patent Application No. PCT/EP2021/067927, mailed on Dec. 6, 2021.

International Search Report and written opinion received in PCT Patent Application No. PCT/EP2021/067926, mailed on Dec. 7, 2021.

Cansu et al, "Atmospheric Pressure Plasma Jet Treatment of Human Hair Fibers", Journal of Bio- and Tribo-Corrosion, vol. 1:7, No. 1, Feb. 4, 2015.

Zheng et al, "Adhesion of aqueous polyurethane adhesive to human hair", International Journal of Adhesion and Adhesives, Elsevier, Amsterdam, NL, vol. 48, Sep. 30, 2013, pp. 14-19.

Shima et al, "The effect of nitrogen plasma on the skin and hair follicles : a possible promising future for the treatment of alopecia", Archives of Dermatological Research, Springer Berlin Heidelberg, Berlin/Heidelberg, vol. 312, No. 5, Dec. 6, 2019 , pp. 361-371.

Shao et al.: "Surface Treatment of Wool to Achieve Hydrophilic Fibre and the Effect on Subsequent Dyeing and Protease Treatment", Advanced Materials Research; ISSN 1662-8985; Eco-Dyeing, Finishing and Green Chemistry : Selected, Peer Reviewed Papers From the 2011 International Conference on Eco-Dyeing, Finishing and Green Chemistry (EDFGC 2011), Jun. 8-12, 2011, Hangzhou, China, vol. 441, Jan. 1, 2012 (Jan. 1, 2012), pp. 249-254.

International Search Report and written opinion received in PCT Patent Application No. PCT/EP2021/067928, mailed on Dec. 22, 2021.

International Search Report and written opinion received in PCT Patent Application No. PCT/EP2021/067925, mailed on Nov. 22, 2021.

International Search Report and written opinion received in PCT Patent Application No. PCT/EP2021/057812, mailed on Jan. 7, 2019.

International Search Report and written opinion received in PCT Patent Application No. PCT/EP2021/067924, mailed on Nov. 26, 2021.

Campiglio Chiara Emma et al., "Coss-Linking Strategies for Electrospun Gelatin Scaffolds", Materials, vol. 1, No. 15, Aug. 4, 2019.

International Search Report issued in connection with Application No. PCT/EP2019/057813, dated Jul. 11, 2019.

* cited by examiner

MULTICOMPONENT SILICONE COMPOSITION

CROSS-REFERENCE TO RELATED APPLICATIONS

This is a 35 U.S.C. 371 National Stage Patent Application of International Application No. PCT/EP2019/057813, filed Mar. 27, 2019, which claims priority to the following United States Provisional Patent Applications, each of which are hereby incorporated by reference in their entirety: Application No. 62/694,808, filed Jul. 6, 2018; Application No. 62/694,739, filed Jul. 6, 2018; Application No. 62/694,781, filed Jul. 6, 2018; Application No. 62/694,570, filed Jul. 6, 2018; Application No. 62/739,592, filed Oct. 1, 2018; Application No. 62/740,027, filed Oct. 2, 2018; and Application No. 62/769,239, filed Nov. 19, 2018.

BACKGROUND

Treatments to mammalian or synthetic keratin fibers are known. Mammalian keratin fibers (natural hair) is structured as a cuticle or outer surface layer, a cortex which is an internal layer containing melanin or color bodies and keratin bundles, and sometimes a central core termed the medulla. Typical dye treatments focus on changes of the cortex. Another treatment focuses on addition of pigments to the surfaces of hair strands. Typical treatment for surface coloration attaches pigment particles with glue-like material. Of particular note for all of these treatments is their ability to alter the appearance of the hair, for example by changing the color or reflective properties of hair.

For dye treatments the alteration of appearance can be achieved through treating hair with a formulation containing dye molecules (so call direct dyes) which diffuse into or are absorbed on and sometimes through the cuticles of the hair fibers. Alternatively, so called oxidative dyes may be employed wherein the dye precursors diffuse into the hair and then react to from colored species within the hair including within the cortex of the hair. Often the oxidative dye products are designed to also lighten the hair, decolorizing some of the melanin within the cortex to enable a wider range of colors to be achieved. Over time the color imparted to the hair is removed during washing. This can happen rapidly for so called direct dyes and leads to a short term change in hair appearance, typically lasting for a few washes. The so called oxidative dyes may last considerably longer, and indeed removing the color can be hard to achieve, even after a considerable number of washes. When oxidative dyes are eventually removed by washing out, the melanin has also been decolorized by bleaching so that it will not return to its original color but to a lighter color. Unfortunately, the process of decolorizing hair leads not only to a lightening of the hair but also to a change in the perceived tone of the hair, leading to what is often described as an off tone or brassy result where the hair looks more orange than untreated hair of a similar lightness.

One disadvantage of the known oxidative dye technologies in this area is that the methods involve applying coloring compositions for an extended period of time to enable the color to develop within the hair. These compositions in some cases may also lead to some temporary scalp irritation. Together, the extended waiting time and potential irritation, prevents the hair coloration process for some users from being a pleasant or a so-called wellness experience. Such coloring compositions may also alter the hair structure itself, leading to oxidation of the hair surface, and partial degradation of the keratinous proteins from which the hair structure is constructed. With repeated coloring, these changes in hair structure become more pronounced and can be felt as poor hair condition. The color obtained when coloring with such a composition is also hard to predict, and even highly experienced users can still be surprised with the actual results that are obtained for a given product. Yet another drawback known to such coloring technologies is that, once the color is on and within the hair, the dye based coloring material is difficult to remove and/or cannot be completely removed. Another drawback for the dye based approach is that the application of hair coloration materials can yield uneven results as adherence to the surface and/or penetration of hair coloration materials into the hair can vary with hair type for example for a consumer differing color results may be visible between hair roots and hair tips. This can lead to an unnatural looking result. Some desired differences may still be visible due to the non-uniformity in coloration of the underlying hair, for example subtle difference in strand to strand levels of pheomelanin and eumelanin in a consumer may yield slightly different color results, even when the same color pigments or dyes are applied to a consumer. While some strand to strand variation is needed to provide natural looking hair, too much or too little can again lead to an unnatural looking color result. Due to the number of factors that determine the final hair color result for example, the length of application time, the underlying hair color, the hair changes from root to tip, it's hard for even experienced users to accurately predict the final color result and look. There is therefore a need for compositions and methods that not only make the multicomponent experience a beauty/wellness experience, but also address, among other things, the foregoing drawbacks of known technologies.

As mentioned at the outset, alternative multicomponent techniques have also been investigated. One such approach has involved coating hair strands with color pigment particles. This approach has proved difficult at best as it is fraught with particle agglomeration and clumping, stickiness, matted hair strands and ready removal by washing. The attachment techniques often leave clumps of particles on the hair strands and the glue-like material used for attachment is often sticky and can glue strands together. Moreover, the pigment particles typically do not distribute appropriately, leave an artificial appearance and are not user friendly. The color effect is also typically very short lived and is removed within a couple of hair washes.

It is therefore an object to develop a multicomponent technique that does not result in harm to hair protein, is user friendly, provides appropriate color and luster, and leaves the hair manageable, free flowing and capable of moving naturally.

SUMMARY

These and other objects are accomplished by aspects of the composition and method of use of the present invention. According to aspects of the invention, the multicomponent composition, method and coated substrate material embodiments such as hair of any sort, nails and other substrate material as well as textiles and paper provide a surface coloration of substrate material, textiles and paper (hereinafter substrate material). Especially for hair of all kinds, the coloration that may be substantially uniform to significantly varied, may give hair strands an appearance of lower or higher chroma, shiny or reflective nature. These aspects provide color fastness during a series of washes with shampoo or soap yet with appropriate formulations can be readily removed to leave the natural shade of the hair. These aspects significantly lessen and/or avoid treatment of hair that may cause breakage of keratin protein intermolecular bonds.

An aspect of the invention concerning the multicomponent composition provides embodiments comprising first and second components, each comprising a functional silicone polymer. The first component comprises a linear and/or branched first silicone polymer with functional groups. The second component comprises a second linear or branched silicone polymer with functional groups. Generally, the first and second silicone polymers may comprise the same linear and/or branched silicone structure or different linear and/or branched silicone structures. The silicone polymers can be conceptualized as being random and/or block portions of linear and/or branched silicone polymer moieties with no functional groups (non-reactive silicone or organosilicone units) with interspersed reactive siloxane monomeric units carrying the functional groups. The functional groups may be attached through connecting units to the backbones of the silicone polymers, to the branch chains of the silicone polymers or to both.

The functional groups of these silicone polymers typically are complementarily reactive and are arranged with the silicone polymers so as to provide complementary reactive pairs. The complementary pairs may be designated as first and second functional groups. In some instances, the first and second functional groups may be the same, such as mercapto and mercapto, so that a reactive pair may be, but not necessarily be, the same functional group (hereinafter a self-reactive functional group). The silicone polymers presenting the complementary reactive pairs of functional groups are first and second silicone polymers. The complementary reactive pairs and the self-reactive functional group can be reactively combined in situ to covalently bond together. Because the complementary reactive pairs and self-reactive functional groups are parts of large molecules having dipolar groups, hydrogen bonding groups and large lipophilic groups, the in situ interaction may also involve electrostatic, ionic, hydrogen bond, coordinate or entanglement interaction. Embodiments of the first and second silicone polymers with different first and second functional groups typically are kept separate until application to substrate material.

Embodiments of the multicomponent composition also provide a third component comprising a base compound. The base compound comprises a small molecule, a dimer, trimer, oligomer or polymer of organic or silicone construction which carries one or more pendant and/or terminal third functional groups which are amine groups, mercapto groups, sulfonate groups, carboxylate groups or carbamate groups. Especially preferred are base compounds with amine groups. The third functional groups of the base compound interact with the first and second functional groups through covalent, ionic, entanglement, dipolar, electronic and/or electrostatic linking or any combination thereof to meld together the first silicone polymer, the second silicone polymer and the base compound. The third component is typically and usually adapted to be combined with the substrate material as a pretreatment prior to sequential, simultaneous or mixed application of the first and second components.

Embodiments of the multicomponent composition also provide a fourth component comprising an agent, such as a catalyst, an accelerator, a curing agent, an enhancer and/or an inorganic complexer, for efficiently and preferably gently facilitating the melding together of the first, second and third components.

One or both or all of the first, second and third components may also comprise pigment particles (also synonymously described herein as pigment microparticles) and both typically comprise a medium. The pigment particles may comprise irregular shapes of at least one pigment color and have at least one dimension of less than one micron.

It has been discovered that the interactive character of the first and second components applied to the substrate material delivers good remanence and desirable qualities to the substrate material such as hair coated with the composition. It has further been discovered that pretreatment with the third component designed to interact with the first and second components unexpectedly delivers significantly increased remanence. Although the unexpected significant remanence as well as other desirable qualities are achieved irrespective of the specific nature of the silicone polymers, these properties are especially surprising when covalent and hydrogen bonding properties among the silicone polymers and the third component are incorporated. The in situ linkable combination of the pretreatment base compound with the two silicone polymers achieves unexpected, remarkable remanence.

Embodiments of the first and second silicone polymers include reactive silicone monomeric units that may be paired together to enable in situ linking of the first and second silicone polymers. The first reactive silicone monomeric units of the first silicone polymer comprise siloxane units with pendant or terminal organic connecting units or a combination thereof with one or more of the first functional groups selected from isocyanato, carboxyl, linear, branched or cyclic alkylepoxy, olefinoyloxy, malonic anhydride, formyl, mercapto, vinyl and/or alkynyl. The first reactive silicone monomeric units also include the functional groups alkoxy, hydroxy, oxime, acetoxy or vinyl or a combination thereof bonded directly to silicon so that an organic connecting group between the functional group and silicon is absent.

The second reactive silicone monomeric units of the second silicone polymer comprise siloxane units with pendant or terminal organic groups or a combination thereof with one or more of the second functional groups selected from hydroxyl, amino, azido, mercapto, furanyl and/or pentadienyl. The second reactive silicone monomeric units also include the functional groups alkoxy, hydroxy, oxime, acetoxy or hydrogen or a combination thereof bonded directly to silicon so that an organic connecting group between the functional group and silicon is absent. As discussed above, some instances of the first and second functional groups may be the same, such as mercapto and mercapto.

The non-reactive portions of the first and second silicone polymers are based upon MDTQ units, $(R)_n Si(O)_{(4-n)/2}$ wherein n is zero or an integer of 1-3. The organic moiety R of the MDTQ units may be a C1-C6 alkyl or phenyl.

Embodiments of the pigment microparticles used on the multicomponent composition described herein may comprise organic pigment microparticles, which imparts color to the hair, having a given D50[vol], and pigment microparticles, for providing light scattering properties to the colored hair, having a D50[vol] which is larger than the D50[vol] value of the organic pigment microparticles. Embodiments may also include microparticle metal flakes for light reflection to add shine to the desired color or to make the hair appear to be lighter than the starting hair color.

Embodiments of the method for applying the multicomponent composition to substrate material focus on the reactive features of the first, second and third functional groups.

Embodiments of the method utilize first the first and second components. The first and second components of the multicomponent composition may be mixed together before application to the substrate material, may be applied separately and simultaneously to the substrate material, or may be applied sequentially to the substrate material. Upon the combination of the first and second components, the first and second silicone polymers interact through their functional groups by covalent, ionic, entanglement, dipolar, electronic and/or electrostatic linking to form a wash resistant coating with pigment microparticles on the substrate material. Prior to sequential, simultaneous or mixed application of the first and second components to the substrate material, the third component is applied as a pretreatment of the substrate material. The fourth component may be combined with the first and second components during their application to accelerate, catalyze, cure, aid and/or otherwise promote the in situ linking among the constituents of the first, second and third components as well as with the substrate material. For embodiments incorporating the first, second and third components, it is believed that the combination of first, second and third functional groups enables the covalent, ionic, entanglement, dipolar, electronic and/or electrostatic linking or any combination thereof among the first and second silicone polymers, the base compound and the substrate material. These embodiments enable linkage of all substances together to make them resistant to removal by ordinary means. Indeed, this combination with the pretreatment melding the components together as a highly remanent coating on substrate material. The embedded pigment microparticles are distributed in and throughout the coating.

In addition to the first and second silicone polymers, base compound, agent and pigment microparticles of the first, second, third and fourth components, the multicomponent composition may optionally contain additional ingredients helpful and beneficial to the substrate material and/or its coloration. These additional ingredients include but are not limited to one or more of dispersants, surface treatment agents for the pigment microparticles, plasticizers, conditioners, suspending agents, thickening agents, adjuvants, moisturizers, surfactants, fatty substances, waxes, fatty amides and soluble organic dyes of colors different from those of the pigment microparticles.

An aspect of the invention concerning the wash-fastness or remanence of the coating on the substrate material, and especially on hair strands, comprises the ability of the coating to resist dissolution by ordinary cleaning of the substrate material such as hair. Ordinary cleaning may involve washing with soap and water, washing with an aqueous dilution of shampoo and washing with water.

An aspect of the invention concerning removal of the coating on the substrate material, such as on hair strands, comprises application of a medium of a trigger formulation designed to remove the coating. The trigger formulation embodiments of the invention comprise media with strongly solvating surfactant, media with fluoride compounds, with fluoride salts, and/or media with base or acid and/or ionic media, and combinations of such media. Embodiments of the base include organic and inorganic compounds that provide a stronger basic medium than does a dilute aqueous mixture of soap or a shampoo containing an anionic surfactant. Embodiments of the acid include organic and inorganic compounds that provide a strong acidic medium. Additionally, mildly abrasive particles may also be added to the composition to help with the removal of the coating, for example silicas.

An additional aspect of the invention concerns the application of the multicomponent composition to substrate material such as brows, lashes, nails and skin as well as to hair on the scalp. Additionally, the multicomponent composition may be applied to textiles made of plant material, animal hair or fur or synthetic material including but not limited to paper, woven cloth, interconnected textile fibers, cellulosic fibers and similar materials. The multicomponent composition may be applied to these kinds of substrate materials and to textiles with appropriate adjustments of the composition parameters within the parameters described for hair on the scalp. Typically, the eyebrow hair may be treated with the multicomponent composition using parameters similar to or the same as those of the multicomponent composition for hair on the scalp. The hair of eyelashes typically can be similarly treated with the multicomponent composition for eyebrows and the viscosity adjusted to provide a somewhat more viscous composition for application to the eye lashes. For nails and skin, the parameters of the multicomponent composition may have a higher solids content and higher number of first, second and third functional groups for in in situ linking than the parameters for the hair and viscosity may be adjusted to provide embodiments that will not readily drip or otherwise flow off the nail or skin surface to which the multicomponent composition is applied. The multicomponent composition for nails and skin will preferably have higher in situ linking to provide a durable coating or covering on the keratin nail and skin substrate.

DEFINITIONS

Figure 1:
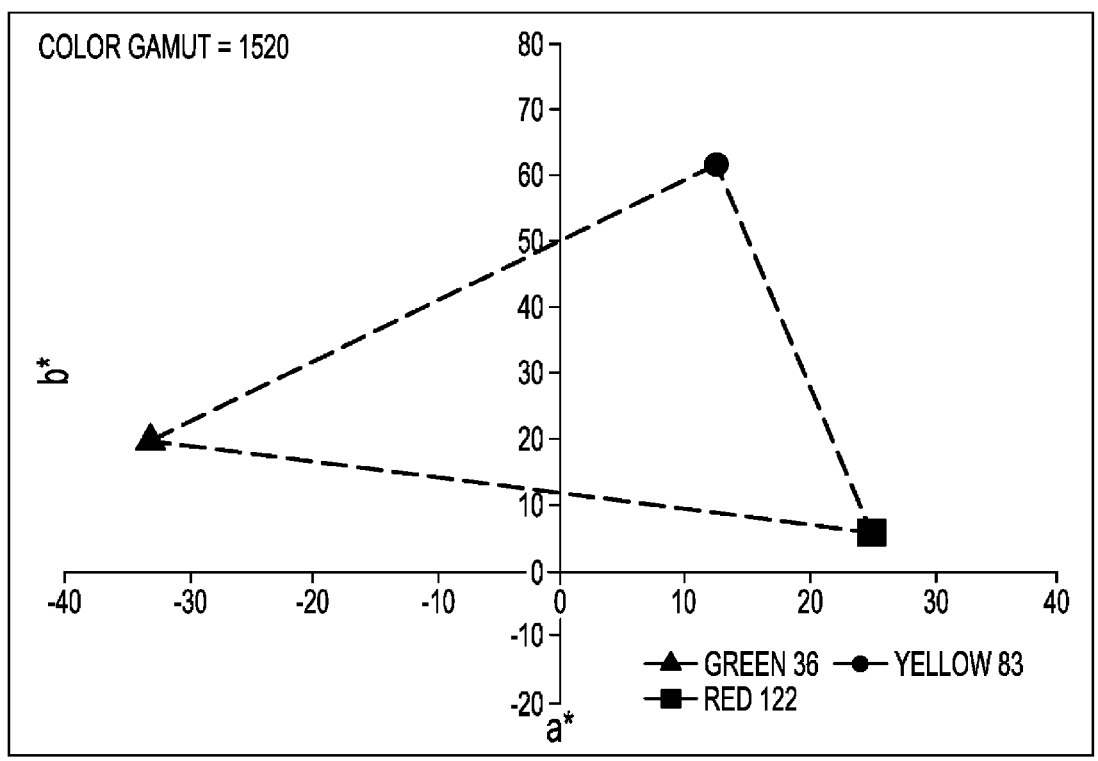
FIG. 1 shows a Gamut plot of green, yellow and red pigments.

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as daltons (Da), kiloDaltons (KDa) and megaDaltons, which is million daltons or (MDa). The acronym Mw stands for weight average molecular weight, $M_n$ is the number average molecular weight of a given polymer.

Polydispersity is a unit-less number and indicates the breadth of the distribution of the polymer molecular weights and is defined as the $M_w/M_n$.

The term "about" is understood to mean±10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

In addition, where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

Hair and hair strands mean natural or synthetic keratin fibers. Hair, hair strands and keratin fibers are used interchangeably in this document. Natural keratin fibers include those from mammals and/or on mammals including human, primate, ruminant, camelid, equine, rodent and neovison including but not limited to cow, sheep, deer, goat, buffalo, *lama*, alpaca, camel, guanaco, vicuna, horse, antelope, moose, elk, rat, mouse, beaver, rabbit, mink, monkey, ape and similar species. Natural keratin fibers may include hair, fur or nails. Synthetic fibers include polyamides, polyacrylic and polyester fibers, especially polyamide fibers which are used for artificial hair implantation.

As used herein, the terms "covalent, coordinate, electrostatic, ionic, dipolar and entanglement or entwining interactions" mean a chemical relationship between two atoms or two groups of atoms. The interaction includes a covalent bond between the atoms such as the covalent bond between the two carbons of ethane. The interaction includes a coordinate bond between two or more atoms such as the coordinate bond between oxygen and sulfur of the sulfate anion ($SO_4^{2-}$) or a complex of zinc and EDTA. The interaction includes an electrostatic or ionic interaction between two charged atoms or particles such as the interaction between sodium and chloride of salt or between ammonium and acetate of ammonium acetate. Dipolar interaction includes hydrogen bonding such as the interaction between water and the hydroxyl of methyl alcohol. The interaction includes entanglement or entwining which is lipophilic interaction or mechanical/physical twisting together such as is present in the molecules of polyethylene.

As used herein, the term "transfer resistance" generally refers to the quality exhibited by compositions that are not readily removed by contact with another material, such as, for example, an item of clothing or the skin. Transfer resistance can be evaluated by any method known in the art for evaluating such transfer. For example, transfer resistance of a composition can be evaluated by the amount of product transferred from a wearer to any other substrate after the expiration of a certain amount of time following application of the composition to the hair. The amount of composition transferred to the substrate can then be evaluated and compared. For example, a composition can be transfer resistant if a majority of the product is left on the wearer's hair. Preferably little or no composition is transferred to the substrate from the hair.

As used herein, the term "minimally alters the keratin material or fibers, upon application" generally means that after removal of the composition coating on the keratin fibers such as hair, the keratin fibers are returned to a substantially unaltered state. The state of the keratin fibers such as hair can be assessed for example using ATR FT-IR for oxidative damage as described later or through tensile testing methods known to those skilled in the art for assessing fiber strength for example using equipment such as those designed and sold by Dia-Stron™.

As used herein, the term "setting" means converting the multicomponent composition to a solid coating through the application of means designed to remove or otherwise separate the medium from the other constituents of the multicomponent composition so as to leave a solid coating of the organic polymer, in situ linking material and base compound and other optional ingredients of the composition.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms.

This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing may or may not be present. It includes both possibilities.

"Alkyl" refers to a straight or branched or cyclic hydrocarbon chain group consisting solely of carbon and hydrogen atoms, unless otherwise specifically described as having additional heteroatoms or heterogroups. The alkyl group contains no unsaturation, having from one to twenty four carbon atoms (e.g., $C_1$-$C_{24}$ alkyl). Whenever it appears herein, a numerical range such as for example but not limited to "1 to 24" refers to each integer in the given range; e.g., "1 to 24 carbon atoms" means that the alkyl group may consist of 1 carbon atom, 2 carbon atoms, 3 carbon atoms, etc., up to and including 24 carbon atoms, although the present definition also covers the occurrence of the term "alkyl" where no numerical range is designated. In some embodiments, it is a $C_1$-$C_4$ alkyl group. In other instances it is a $C_1$-$C_6$ alkyl group and in still other instances it is a $C_1$-$C_{24}$ alkyl group Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

"Alkylenyl" refers to a straight or branched divalent hydrocarbon chain consisting solely of carbon and hydrogen atoms, unless otherwise specifically described as having additional heteroatoms or heterogroups. The alkylenyl group contains no unsaturation has a valence bond at either end of the chain and has a numerical range of carbon atoms of 1 to 24, which numerical range includes each integen in the range. An example of a divalent hydrocarbon chain designated as an alkylenyl group is —$CH_2$—$CH_2$—$CH_2$—$CH_2$— which is butylenyl.

"Cycloalkyl" is a subcategory of "alkyl" and refers to a monocyclic or polycyclic group that contains only carbon and hydrogen, and may be saturated, or partially unsaturated. Cycloalkyl groups include groups having from 3 to 24 ring atoms (i.e., $C_3$-$C_{24}$ cycloalkyl). Whenever it appears herein, a numerical range such as but not limited to "3 to 24" refers to each integer in the given range; e.g., "3 to 24 carbon atoms" means that the cycloalkyl group may consist of 3 carbon atoms, etc., up to and including 24 carbon atoms. In some embodiments, it is a $C_3$-$C_8$ cycloalkyl group. In some embodiments, it is a C3-C5 cycloalkyl group. Illustrative examples of cycloalkyl groups include but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

"Alkoxy" refers to the group —O-alkyl, including from 1 to 24 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl is an alkyl group which encompasses both straight and branched chain alkyls of from 1 to 4 carbon atoms.

"Amino" or "amine" refers to an —$N(R^a)_2$ group, where each $R^a$ is independently hydrogen or linear, branched or cyclic alkyl of 1 to 6 carbons. When an-$N(R^a)_2$ group has two $R^a$ groups other than hydrogen, they can be combined with the nitrogen atom to form a 4-, 5-, 6-, or 7-membered ring.

"Aryl" refers to a conjugated pi group with six or ten ring atoms which has at least one ring having a conjugated pi electron system which is carbocyclic (e.g., phenyl, fluorenyl, and naphthyl). Bivalent groups formed from substituted benzene derivatives and having the free valences at ring atoms are named as substituted phenylene groups. Bivalent groups derived from univalent polycyclic hydrocarbon groups whose names end in "-yl" by removal of one hydrogen atom from the carbon atom with the free valence are named by adding "-idene" to the name of the corresponding univalent group, e.g., a naphthyl group with two points of attachment is termed naphthylidene. The term includes monocyclic or monocyclic-ring polycyclic (i.e., rings which share adjacent pairs of ring atoms) groups.

"Heteroalkyl" "heteroalkenyl" and "heteroalkynyl" include optionally substituted alkyl, alkenyl and alkynyl groups and which have one or more skeletal chain atoms selected from an atom other than carbon, e.g., oxygen, nitrogen, sulfur, phosphorus or combinations thereof. A numerical range may be given, e.g. $C_1$-$C_{24}$ heteroalkyl which refers to the chain length in total, which in this example may be as long as 24 atoms long. For example, a —$CH_2OCH_2CH_3$ group is referred to as a "$C_4$" heteroalkyl, which includes the heteroatom center in the atom chain length description. Connection to the rest of the molecule may be through either a heteroatom or a carbon in the heteroalkyl chain.

"Heteroaryl" or heteroaromatic refers to a 5, 6 or 10-membered aromatic group (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be monocyclic or non-monocyclic. The heteroatom(s) in the heteroaryl group is optionally oxidized. One or more nitrogen atoms, if present, are optionally quaternized. The heteroaryl is attached to the rest of the molecule through any atom of the ring(s). Examples of heteroaryls include, but are not limited to adeninyl, azabenzimidazolyl, azaindolyl, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d] pyridazinyl, 5,6,7,8,9,10-hexahydrocycloocta[d]pyridinyl, isothiazolyl, imidazolyl, imidazopyridinyl, isoxazolopyridinyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-TH-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thianaphthalenyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl), xanthinyl, guaninyl, quinoxalinyl, and quinazolinyl groups.

"Heterocyclic" refers to any monocyclic or polycyclic moiety comprising at least one heteroatom selected from nitrogen, oxygen and sulfur. As used herein, heterocyclyl moieties can be aromatic or nonaromatic. The moieties heteroaryl and heterocyclyl alkyl are members of the heterocyclic group.

The terms "In situ linking" and "in situ linkable" and "Cross linkable" mean the potential at a future time to form covalent bonds, coordinate linkages, ionic linkages, electrostatic linkages, polar couplings, hydrogen bonds and polymer entanglement to provide interactions and/or connections between molecules. The terms "in situ linked" and "cross linked" mean that in the present state, covalent bonds, coordinate linkages, ionic linkages, electrostatic linkages, polar couplings, hydrogen bonds and entanglement arrangements have already occurred.

"in situ" is a latin phase meaning in its original place. In the context of this invention, it means an activity such a cross linking that takes place on the hair.

Zeta potential relating to pigment microparticles means the electrokinetic potential of extremely small particles suspended in colloidal dispersions. It is caused by the net electrical charge at the particle interface with the suspending fluid. It is an indicator of the stability of a colloidal dispersion. The magnitude indicates the degree of electrostatic repulsion between adjacent similar charged particles in a dispersion. At zero or minimal + or − potential, rapid coagulation can occur. At a + or − zeta potential above about 40, good colloidal stability is maintained. Zeta potential can be measured using approaches known to those skilled in the art. For example a Zetasizer Nano Z from Malvern Panalytical may be used to assess the zeta potential of the components.

The term "textile" as used herein has its ordinary and customary meaning and includes cloth, fabric or other material made out of natural plant fibers, synthetic fibers, metal fibers, carbon fibers, animal fibers such as may be derived from feathers, sinew, ligament, muscle and/or bone. The fibers are combined by weaving, felting, gluing, tacking, spinning, extruding, blowmelting or other-wise formed into at least a somewhat coherent mass typically considered to be cloth, fabric, sponge rubber, foam, woven or nonwoven material. Rugs, bedsheets, clothing, coats, hats, underwear, socks, seat covers, seat cushions, pillows, and similar materials are textiles. Included also is paper made of plant or synthetic material such as typing paper, writing paper, foil, parchment papers, wax paper, aluminum foil and similar flat, thin materials.

DETAILED DESCRIPTION

Embodiments of the instant invention generally relate to a silicone polymeric coating with colored pigment microparticles coating on the surfaces of substrate material, and especially on mammalian or synthetic keratin fibers. The coating is formed by treatment of the substrate material, especially keratin fibers such as hair with the embodiments of the above described multicomponent composition. The coating is wash resistant yet through use of a triggering formulation can be removed without damage to the substrate material such as hair. The embodiments of the multicomponent composition minimize or avoid damage to keratin proteins within the substrate material, particularly after repeated dying events. The embodiments of the multicomponent composition limit irritation of the scalp which may result from application of known hair dye compositions. The present invention is directed to embodiments of multicomponent compositions for coloration of substrate material in such a way that the color can be applied and will remain until it is desired to remove the color. This makes the treatment process more pleasurable for the user and or stylist. It is also desired that the results are predictable, enabling the users to achieve their target hair color result.

The composition, method and coating aspects of the invention are directed to embodiments of a multicomponent composition that are adapted to provide colored coating embodiments on the surfaces of substrate material and textiles, especially hair strands. The colored coating embodiments have remanence that enables them to remain in somewhat to substantial to essential original composition especially upon the hair embodiment of substrate material through at least a series of washings with diluted aqueous media containing soap and/or shampoo. The multicomponent composition embodiments minimally alter substrate material upon their application.

The embodiments of the multicomponent composition according to the invention comprise first, second and third components which meld together in situ on substrate material, especially on keratin material and most especially hair, to form a colored coating that surprisingly is durable and resistant to repeated washings with ordinary shampoos, soap, detergent and water. The first, second and third components comprise constituents with first, second and third functional groups respectively that in situ form covalent, coordinate, entanglement, electrostatic, ionic and/or dipolar linkages. It is believed that the melding together to form in situ linkages produces an arrangement of coating, microparticles and substrate material surfaces that are interconnected and develop the unexpected, surprising long standing remanence.

Embodiments of the invention also include methods for preparation of the multicomponent composition, kits for storage and delivery of the multicomponent composition, methods for application of the multicomponent composition to substrate material, especially keratin material such as hair, the colored coating on substrate material as well as methods for removal of the colored coating on substrate material, especially keratin material such as hair so that the substrate material is minimally altered. As used herein, the term "minimally alters the substrate material" generally means that after removal of the coloring composition the substrate material is returned to a substantially unaltered state.

The Multicomponent Composition

First and Second Silicone Polymers

The multicomponent composition comprises first, second and third components with optional fourth component for production of a remanent colored coating on substrate material and especially on keratin material and fibers such as hair. The components interact in situ to provide covalent bonding among the first, second, third components and the substrate material. The third and fourth components are discussed in separate sections below.

The first and second components which form a part of the embodiments of the multicomponent composition include as active constituents linear and/or branched silicone polymers with pendant and/or terminal functional groups that are complementary reactive pairs when different or are self-reactive pairs when the same. The silicone polymers comprise non-reactive organosiloxane monomeric units and reactive siloxane monomeric units to which are bonded the functional groups. The silicone polymers divide into first and second silicone polymers when the reactive siloxane units bear different functional groups as complementary reactive pairs. Embodiments of the silicone polymers that bear a self-reactive functional group can be viewed as a single silicone polymer with a sole functional group that can covalently bind with itself to accomplish the melding together of the compositional substituents. Examples of such self-reactive functional groups include but are not limited to mercapto and mercapto, Si—OH and Si—OH as well as Si—OMe and Si—OMe.

Embodiments of a silicone polymer with a self-reactive functional group can have variations of the structure of the silicone polymer so that fraction of the polymer may be of high $M_n$ or while another fraction may be of low $M_n$. Alternatively, one fraction may be linear while the other fraction may be branched. Other variations are also possible based on these same considerations. Variations of these kinds segment the silicone polymer with a self-reactive functional group into first and second silicone polymers even through only one functional group is present. Nevertheless, although multicomponent composition may be composed of two silicone polymers of differing structure and/or complementary reactive pairs or may be composed of a single silicone polymer with a self-reactive functional group, the silicone polymer components can be addressed as a single entity with functional group and structural variations.

The silicone polymer may be arranged as portions of linear and/or branched silicone polymer moieties with no functional groups (non-reactive silicone or organosiloxane units) interspersed with reactive organosiloxane monomeric units bearing the complementary reactive pairs or the self-reactive pairs. The reactive organosiloxane monomeric units are linked to the functional groups through connecting units which typically are organic bivalent connecting units.

The linear and/or branched silicone polymer comprises polymerized units of a non-reactive organosiloxane monomer and at least two pendant and/or terminal reactive organosiloxane monomer units having functional groups. The functional groups may be complementary reactive pairs which will parse the silicone polymer into first and second silicone polymers or may be a self-reactive functional group. While the complementary reactive pairs and the two of the self-reactive functional group covalently bond together in situ, the melding of the first, second and third components to form a remanent coating also includes ionic, electrostatic, entanglement and/or coordination interactions between the molecules of these components.

The reactive organosiloxane monomeric units are distributed throughout the backbones and branch chains of the silicone polymers. The reactive organosiloxane units carry the functional groups which comprise isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, pentadienyl, azido, Si—OH, Si—OR, Si—O—N=CHR, Si—O—N=CR$_2$, Si—OAc, Si—CH=CH$_2$ or Si—H where is R is C1-C6 alkyl. The functional groups may be selected as first and second functional groups of the silicone polymers according to their action as complementary reactive pairs. A complementary reactive pair means that the pair can react together under ordinary environmental conditions or can react together with the help of a fourth component such as catalyst or substance that will lower the reaction activation energy needed for the reactive pair bonding. If the complementary pair can react together under ordinary environmental conditions without the help of a fourth component such as a catalyst, the pair cannot appear on the same silicone polymer. Complementary reactive groups that can react together under ordinary environmental conditions without help of a fourth component are well-known. Some functional groups are capable of functioning as self-reactive groups such as mercapto, the Si—O functional groups or isocyanato. Such self-reactive groups do not ordinarily react together under ordinary environmental conditions. A fourth component such as a catalyst usually will enable the bonding of such self-reactive groups.

As mentioned above, the arrangement and distribution of functional groups may follow the complementary reactive pair concept or may follow the self-reactive functional group concept. While at a conceptual level, the first and second silicone polymers are simply silicone polymers bearing the complementary reactive pair or bearing the self-reactive functional group, at a functional level, differences in silicone structure separate a silicone polymer with a self-reactive functional group into first and second silicone polymers. With the understanding that first and second silicone polymers may actually be a single silicone polymer under certain circumstances and may be two separate and distinct silicone polymers under other circumstances, the structural details of the silicone polymer with complementary reactive pairs or with self-reactive pairs are described in greater detail in the following passages about the first and second silicone polymers.

The First and Second Silicone Polymers

With appropriate selection of the functional groups from the complementary reactive pair category these functional groups can be designated as X groups. With appropriate selection of the corresponding functional groups from the complementary reactive pair category these functional groups can be designated as Y groups. The groups X and Y can also be a self-reactive functional group. The X and Y groups may be bonded through connector units CU to the silicon of the reactive siloxane monomeric unit. The combination of connector units CU and X as well as CU and Y are designated as CU-X and CU-Y. These reactive siloxane monomer units respectively have Formulas I and II:

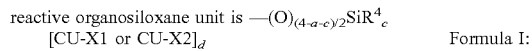

reactive organosiloxane unit is $—(O)_{(4-a-c)/2}SiR^4_c$
[CU-X1 or CU-X2]$_d$            Formula I:

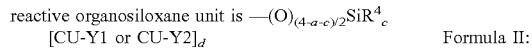

reactive organosiloxane unit is $—(O)_{(4-a-c)/2}SiR^4_c$
[CU-Y1 or CU-Y2]$_d$            Formula II:

d is 1 to 3, c is 0 to 2 and d+c is between 1 and 3; R is C1-C6 alkyl or phenyl, Because of the differentiation of the functional groups as complementary reactive pair or a self-reactive functional group, the CU-X units are divided into CU-X1 and CU-X2 and the CU-Y units are divided into CU-Y1 and CU-Y2. The X1 of CU-X1 and Y1 of CU-Y1 are the complementary reactive pair functional groups. The X2 of CU-X2 and Y2 of CU-X2 are the self-reactive functional group.

The functional group of CU-X1, X1, is isocyanato, thioisocyanato, carboxyl, linear, branched or cyclic epoxyalkyl, olefinoyloxy, malonic anhydrido, formyl, mercapto, vinyl, alkynyl. The functional group Y1 of CU-Y1 is hydroxyl, amino, mercapto, furanyl, pentadienyl or azido. X1 and Y1 may both be mercapto or both may also be isocyanato in which instance they may also be a self-reactive functional group.

The CU-X2 and CU-Y2 units of Formulas I and II provide a self-reactive reactive functional group that will covalently link together through silanol/alkoxysilane condensation. The functional group for this embodiment is bonded to the silicone and may be —Si—OH, —Si—OR$^5$ with R$^{15}$ being a C1-C6 alkyl group, Si-oxime, Si-acetoxy or Si-vinyl/Si-hydrogen. With CU-X2 and CU-Y2 as the choices for Formulas I and II, these functional groups are bonded to the siloxane moiety $[—(O)_{(4-a-c)/2}SiR^4_c]$ by the CU organic group or are bonded directly to the siloxane moiety without the CU unit.

Exemplary embodiments of these self-reactive functional groups coupled to CU units either through oxygen or directly have any of the following structures: wherein d is an integer of 1 to 3 and c is 3-d.

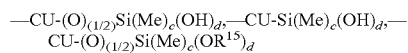

—CU-(O)$_{(1/2)}$Si(Me)$_c$(OH)$_d$,—CU-Si(Me)$_c$(OH)$_d$,—
CU-(O)$_{(1/2)}$Si(Me)$_c$(OR$^{15}$)$_d$

[which includes —CU-O$_{(1/2)}$Si (OR$^{15}$)$_3$],—CU-Si (Me)$_c$(OR$^{15}$)$_d$,—CU-Si(OR$^{15}$)$_3$,

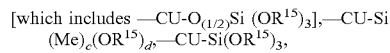

—CU-(O)$_{(1/2)}$Si(Me)$_c$(O—N=CR$^{15}$)$_d$,—CU-Si(Me)$_c$(O—N=CR$^{15}$)$_d$,

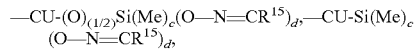

—CU-(O)$_{(1/2)}$Si (Me)$_c$(OCOMe)$_d$,—CU-Si (Me)$_c$(OCOMe)$_d$, or the couple —CU-SiMe$_2$H/—CU-SiMe$_2$-vinyl.

Exemplary embodiments of these self-reactive functional groups coupled directly to the siloxane moiety $[—(O)_{(4-a-c)/2}SiR^4_c]$ without the CU unit have any of the following structures:

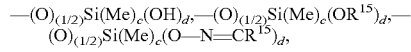

—(O)$_{(1/2)}$Si(Me)$_c$(OH)$_d$,—(O)$_{(1/2)}$Si(Me)$_c$(OR$^{15}$)$_d$,—
(O)$_{(1/2)}$Si(Me)$_c$(O—N=CR$^{15}$)$_d$,

—(O)$_{(1/2)}$Si (Me)$_c$(OCOMe)$_d$

While the SiH/Si-vinyl couple is not technically a self-reactive group, it is placed in the CU-X2/CU-Y2 category so as to distinguish it from the vinyl—mercapto complementary reactive pair. The SiH/Si-vinyl pair provides a hydrosilation in situ bonding arrangement.

The siloxane moieties of Formulas I and II $[—(O)_{(4-a-c)/2}SiR^4_c]$ are the silicons of the reactive siloxane units which form part of the backbone and/or the branch chains of the silicone polymer. The silicons of Formulas I and II may be bonded to 1, 2 or 3 CU-X units or CU-Y units as indicated by the designator d (an integer of 1-3). If less than three CU-X/CU-Y units are present on the silicon, the remaining silicon valences may be bonded to an oxygen or to an R$^4$ group when R$^4$ is C1-C6 alkyl or phenyl. When bonded to one oxygen, the reactive siloxane units, Formula I and Formula II, will be terminal reactive siloxane units of a backbone or branch of the silicone polymer, e.g., M units according to the nomenclature MDTQ. When bonded to two oxygens, the reactive siloxane units, Formulas I and Formula II, will be parts of linear portions of the backbone and/or branch of the silicone polymer, D units. When bonded to three oxygens, the reactive siloxane units will be branching groups of the backbone and/or branch of the silicone polymer, T units.

The CU units of Formulas I and II provide the pendant organic chains to which the functional groups are bonded. The CU units are linear and/or branched saturated aliphatic chains or linear and/or branched saturated heteroaliphatic chains of one to forty-eight carbons, preferably one to twenty-four carbons, more preferably one to twelve carbons, or aromatic and/or heteroaromatic groups of one, two or three separate or fused rings, each ring being a 5 or 6 single ring or a bicyclic 10 member ring as described in the Definitions Section. The CU units may also be combinations of the saturated aliphatic and/or heteroaliphatic chains and the aromatic and/or heteroaromatic groups. The aliphatic chains may be linear and/or branched polymethylenyl chains. The CU heteroaliphatic chains may be linear and/or branched polymethylenyl chains in which parts of the polymethylenyl chains are linked together by heteroatom linking groups such as ether, sulfur, amino, carboxyl, amido, urethano, ureido, carbonyl, carbonato and/or imino. The heteroatom linking groups preferably are compatible with the particular X or Y functional group chosen for an embodiment of the silicone polymer. Exemplary aromatic and heteroaromatic rings include phenyl, naphthyl, thiophenyl, pyridinyl, pyrazinyl, quinolinyl, quinazolinyl, imidazolyl, benzimidazolyl, thiazolyl, benzothiazolyl, indolyl, indenyl, indanyl and similar aromatic and heteroaromatic groups.

Preferred Embodiments of CU-X1 and CU-Y1

Some preferred embodiments of the CU-X1 unit and the CU-Y1 unit may have the following Formula III. The selections of the atoms and integer designators for CU-X1 and CU-Y1 according to Formula III are independent. The unattached valence of O$_q$ (oxygen) of Formula III binds oxygen to the silicon of Formula I/II when q is 1. When q is zero, one of the carbons of groups R$^1$ or A or R$^2$ or the heteroatom Z binds to silicon. Selection of R$^1$, Z, A or R$^2$ depends on which of the designators y, p, f, b and t is one and which is zero. The group $[A_bR^3_{3-e}]_t(R^2)_e]$ is structured to show that as many as three functional groups X/Y may be bound to single reactive siloxane monomeric unit, i.e., bound to silicon through the connecting unit CU. The connecting unit description (O—R$^1$—Z—R$^1$-A-R$^2$) is a preferred embodiment of the general foregoing description of CU: linear and/or branched saturated aliphatic chains or heteroaliphatic chains.

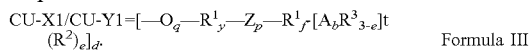

Formula III

The symbols and designations of the preferred embodiments of Formula III are defined as follows.
  i) The designators e and d are integers 1, 2 or 3, with d being the same as given for Formula I.
  ii) The designators q, y, p, f, t and b are zero or the integer 1.
  iii) The symbol $R^1$ for each instance independently is hydrogen or $-(CHR^6)_m$ wherein m is zero or an integer of 1 to 10.
  iv) The symbol $R^2$ is Q-X for CU-X1 and Q-Y for CU-Y1.
  v) The symbol $R^3$ is hydrogen or C1-C6 linear or branched alkyl.
  vi) The symbol $R^5$ is hydrogen, C1-C6 alkyl or branched alkyl.
  vii) The symbol $R^6$ is hydrogen or C1-C6 linear or branched alkyl.
  viii) The symbol Z is O, $CHOR^5$, COO, OCONH, OCOO, $-S-$, $NR^5$; or Z is a bond or hydrogen when the designator p is zero.
  ix) For the symbol A: when b is 1, A is carbon to which is bonded $R^3$ and $R^2$; when b is zero, A is a bond to $R^2$ if $[A_b R^3_{3-e}]$ is present.
  x) When t is 1, the group $[A_b R^3_{3-e}]$ is present.
  xi) When t is zero, the group $[A_b R^3_{3-e}]$ is absent and $R^2$ is bonded to one of O, either instance of $R^1$ or Z when the designator q, y, p of O, $R^1$ and Z closest to $R^2$ is 1 and the others are 1 or zero.
  xii) The symbol Q is a bond, a C1-C10 linear or branched alkylenyl or a C1-C10 linear or branched oxyalkyl.
  xii) The symbol X is isocyanato, thioisocyanato, carboxyl, linear, branched or cyclic epoxyalkyl, olefinoyloxy, malonic anhydrido, formyl, mercapto, vinyl or alkynyl;
  xiii) Y is hydroxyl, amino, mercapto, furanyl, pentadienyl or azido or
  xiii) Q and X together are Si—CH=$CH_2$ and Q and Y together are Si—H.

Number and Distribution of Reactive Siloxane Units in Silicone Polymers

The silicone polymers (e.g. first and second silicone polymers) are linear and/or branched silicone polymers with at least two reactive siloxane monomeric units per molecule and a majority of non-reactive siloxane units $(R)_n Si(O)_{(4-n)/2}$ wherein R is a C1-C6 alkyl or phenyl and n is zero or an integer of 1 to 3. In terms of the well-understood siloxane nomenclature MDTQ, the nonreactive siloxane units of the silicone polymers can be M units with three organic groups ($R^3 SiO_{1/2}$), D units with two organic groups ($R^2 SiO_{2/2}$), T units with one organic group ($RSiO_{3/2}$) and Q units with no organic groups ($SiO_{4/2}$). The M units are terminal units. The D units are linear chain units. The T units provide pre-formed branching of the silicone polymer backbone and the T and Q units enable pre-formed cross link and star arrangements of either the silicone polymer backbones. Preferably, very few T and Q units, if any, are present in the silicone polymers to provide preformed cross link connections between the silicone polymer molecules. Several T units may be present to provide branching of the silicone polymers. More preferably, the silicone polymers primarily have linear backbones with optional short silicone chain branching and little or no cross link or star arrangements between polymer molecules of the silicone polymer.

The preferred arrangement of the functional groups in each of the first and second silicone polymers provides that each member of the functional group list individually and separately is present at a minimum number of two per majority of silicone polymer molecules and may be distributed throughout the polymer backbone and/or along the branch chains. In addition, multiple functional groups may be present at a single position on the backbone and especially on branch chains. An example of such a multiplicity would be a branch chain ending with a t-butyl group, the three termini of which have hydroxyl groups. The number of a particular functional group present in a molecule can be assessed by calculating the number average polymer molecular weight divided by the functional group equivalent weight where the equivalent weight refers to the mass of polymer which has one equivalent reactive group. If this calculation gives a value of 2, this shows that the average polymer has two functional groups. The minimum means only that a minimum of two of a single member of the functional group class may be present or there may be present multiples of two of any one or more of the other members of a functional group class. This arrangement provides minimums, without reference to the presence of other functional groups, of two hydroxyl groups, two amine groups, two mercapto groups, two carboxylic or sulfonic acid groups, two vinyl groups and two olefinoyloxy groups. A minimum number of three is preferred individually and separately for each kind of functional group. A minimum number of four is more preferred individually and separately for each kind of functional group. A minimum number of five is most preferred for carboxyl and hydroxyl groups and a minimum number of at least two or three carboxyl groups is preferred in the presence of other functional groups provided that the multiple presence is mutually compatible. Not all silicone polymer molecules will have the same number of functional groups; however, a majority to substantially greater than a majority of the silicone polymer molecules such as from 95 mole percent to 98 mole percent will statistically have the same number of functional groups. Some silicone polymer molecules may have more than the specified number of functional groups; however, statistically this number will be less than a majority and preferably statistically will be significantly less than a majority such as less that a 10 mole percent, more preferably less than a 5 mole percent and most preferably less than a 2 mole percent.

For all versions of the silicone polymer, the portion of the reactive silicone units relative to the total of reactive and non-reactive silicone units present in the silicone polymer may range in mole percent from as little as about 0.05-2 mole percent to as much as 34 mole percent. Said in another fashion, the molar ratio of non-reactive to reactive silicone units may range of about 2000:1 to about 3:1; preferably about 1250:1 to about 3:1, more preferably about 800:1 to about 3:1, most preferably about 500:1 to 3:1, especially most preferably about 250:1 to about 3:1 with especially preferred molar ratios being about 4:1 to about 3:1 or about 20 mole percent to about 30 mole percent of the reactive silicone units.

Examples of CU Units

Some examples of the aliphatic groups as a polymethylenyl chain, the heteroaliphatic group as a heteropolymethylenyl chain and the aromatic/heteroaromatic group of the CU connector unit may comprise but are not limited to any of the following divalent formulas of charts I, II, III and IV. In these charts, the group My represents methylenyl ($-CH_2-$), the group Me represents methyl ($-CH_3$), the group Bz represents phenylenyl (a benzene ring with two free valences), the group Py represents pyridylenyl (a pyridine ring with two free valences), the group Th represents thiophenylenyl with two free valences and the group Bi represents benzimidazolylenyl with two free valences. The left and right valences of these examples of the CU units may be bonded respectively to the silicone and to the X or Y of Formula I or II above. The group $R^{20}$ is a branch polymethylenyl group ending with a methyl group and may have from one to twelve carbons (with one carbon, $R^{20}$ is methyl). The heteroatoms are selected so that they would not interfere with the complementary reactive pairs or the self-reactive groups or with the left valence bond between these CU units and the silicon of the reactive siloxane monomeric unit, Formula I and Formula II.

Chart I-Saturated Aliphatic CU Units

| | |
|---|---|
| -My- | -My-My(Me)-My- |
| -My-My- | -My-My-My($R^{20}$)-My-My-My- |
| -My-My-My- | -My-My-My($R^{20}$))-My- |
| -My-My-My-My- | -My-My-My($R^{20}$)-My-My- |
| -My-My-My-My-My- | -My-My(My-My-My-My-Me)My-My-My-My- |
| -My-My-My-My-My-My- | -My-My-My-My-My(Me)My- |

Chart II-Saturated Heteroaliphatic CU Units

| | |
|---|---|
| -My-O-My-O-My- | -My-My-My-O-My-My-My-O-My-My-My- |
| -My-My-O-My-My-O-My-My-O-My-My | -My-My-My-CHOH-My-My($R^{20}$)-My-O-My-My-My- |
| -My-My-My-$NR^3$-My-My-O-My-My- | -My-My-My$CHOR^3$-My-My(My-My-Me)-O-My-My-My- |
| -My-My-My-CHOH-My-My-O-My-My- | -My-CHOH-My-My-My-$NR^3$-My-My-My- |
| -My-My-My-My-CHOH-My-My-My-$NR^3$-My-My-My- | -My-My-My-O-My-O-My- |
| -My-My-My-O-My-My-My-$NR^3$-My-My-My- | -My-My-My-$NR^3$-My-My-My-$NR^3$-My-My-My- |
| -My-My-My-CHOH-My-My-My-O-My-My-My- | -My(Me)-My-O-My(Me)-My-O-My(Me)-My-O-My(Me)-My-O-My(Me)-My- |
| -My-My-My-CHOH-My-My-My- | -My-My-My(My-My-My-My-Me)-O-My-My-My- |
| -My-My-My-CHOH-My($R^8$)-My-My- | -My-My-My-O-My-My($R^8$)-My-O-My-My-My- |
| -My-My-My-$NR^3$-My($R^8$)-My-My- | -My-My-My-CHOH-My($R^8$)-My-O-My-My-My- |
| -My-My-O-My(Me)-My-O-My-My-O-My(Me)-My-O-My-My-O-My(Me)-My-O-My-My- | -My-My(OH)-My-My-O-My-My-My- |
| -My-My-My-O-My-My(MyOH)-My-My-O-My-My(Me)-My-My | -My-My(OH)-My-My-$NR^3$-My-My- |

Chart III-Additional Saturated Heteroaliphatic CU Units

| | |
|---|---|
| -My-NH-My-O-My- | -My-My-My-$CO^2$-My-My-My-O-My-My-My- |
| -My-My-My-S-My-My-My- | -My-My-My-CHOH-My-My($R^{20}$)-My-O-My-My-My- |
| -My-My-My-$NR^3$-My-My-CONH-My-My- | -My-My-My$CHOR^3$-My-My(My-My-Me)-O-My-My-My- |
| -My-My-My-CHOH-My-My-CONH-My-My- | -My-CHOH-My-My-My-$NR^3$-My-My-My- |
| -My-My-My-My-CHOH-My-My-$NR^3$-My-My-My- | -My-My-My-CONH-My-O-My- |
| -My-My-My-My-NHCOO-My-My-My-$NR^3$-My-My-My- | -My-My-My-$NR^3$-My-My-My-My-$CONR^3$-My-My-My- |
| -My-My-My-CHOH-My-My-My-O-My-My-My- | -My-My-My-My-NHCOO-My-My-My-My-My- |
| -My-My-My-NHCOO-My-My-My-My- | -My-My-My(My-My-My-My-Me)-OCONH-My-My-My- |
| -My-My-My-CHOH-My($R^{20}$)-My-My- | -My-My-My-O-My-My($R^{20}$)-My-O-My-My-My- |
| -My-My-My-$NR^3$-My($R^{20}$)-My-My- | -My-My-My-CHOH-My($R^{20}$)-My-My-OCONH-My-My-My- |

Chart IV-Aromatic and Heteroaromatic CU units

| | |
|---|---|
| —Bz—Bz—O—Bz—Bz—O-My-My-O-My-My | -My-My-Bz-My-My- |
| —Bz—O-My-My- | -My-Bz-My- |
| —Bz— | -My-Py-My- |
| —Py— | -My-My-Py-My-My- |
| —Bz—Py—O—Bz—O-My-My- | -My-O—Bz—O-My- |
| —O—Bz-My- | —O—Py-My- |
| —O—Bz— | —O—Py— |
| —Th— | —Bi— |
| -My-Th-My- | -My-Bi-My- |

Preferred CU's include monomethylenyl, trimethylenyl, hexamethylenyl, methylenyl-[branch dimethylenylmethyl)]-methylenyl and tetramethylenyl-[branch methylenylmethyl]-methylenyl. More preferred CU's include monomethylenyl, trimethylenyl, tetramethylenyl, hexamethylenyl and dimethylenyl-[branch methylenylmethyl]-dimethylenyl, divalent benzylenyl, divalent pyridylenyl, methylenyl-benzylenyl, methylenyl-pyridylenyl, thiophenylenyl, quinolinylenyl, benzimidazolylenyl and dimethylenyl-benzylenyl-dimethylenyl.

Combining the CU units with embodiments of X as isocyanate provides the preferred embodiments of the isocyanate CU-X1 groups for Formula I.

i) —$(CH_2)_3OCONH$—$(CH_2)_6NCO$, ii) —$(CH_2)_3OCH_2C(CH_2OCONH$—$(CH_2)_6NCO)_2(CH_2CH_3)$ [two isocyanate groups on branched alkylenyl group], iii) —$(CH_2)_3O(CH_2)C(CH_2OCONH$—$(CH_2)_6NCO)_3$ [three isocyanate groups on branched alkylenyl group], iv) —$(CH_2)_3OCH_2CH(CH_3)_p[O(CH_2)_2OCH_2$—$OCONH$—$(CH_2)_6NCO]_q$ wherein p is zero or 1 and p+q is 2.

v) —$(CH_2)_3OCONH$—$(CH_2)_6$—$CH_2$—$(CH_2)_6$—NCO.

Preferred embodiments of the epoxy CU-X1 groups for Formula I include:

i) —$(CH_2)_3OCH_2$-epoxy, ii) —$(CH_2)_3OCH_2C(CH_2$-epoxy$)_2CH_2CH_3$ [two epoxy groups on branched alkylenyl group], iii) —$(CH_2)_3O(CH_2)C(CH_2$-epoxy$)_3$ [three epoxy groups on branched alkylenyl group], iv) —$(CH_2)_3OCH_2CH(CH_3)_p[O(CH_2)_2O$—$CH_2$-epoxy$]_q$ [wherein p is zero or 1 and p+q is 2].

Preferred embodiments of olefinoyloxy CU-X1 groups for Formula I include i) —$(CH_2)_3OC(O)C(CH_3)$=$CH_2$, —$(CH_2)_3OC(O)C(H)$=$CH_2$, ii) —$(CH_2)_3OCH_2CH(OH)CH_2OC(O)C(CH_3)$=$CH_2$, iii) —$(CH_2)_3OCH_2CH(OH)CH_2OC(O)C(H)$=$CH_2$, iv) —$(CH_2)_3[O(CH_2)_2]q[O(CH_2)CH(CH_3)]_rOC(O)C(CH_3)$=$CH_2$, where r+q is greater than 1 and less than 10 v) —$(CH_2)_3[O(CH_2)_2]q[O(CH_2)CH(CH_3)]_rOC(O)C(H)$=$CH_2$, where r+q is greater than 1 and less than 11.

Preferred embodiments of formyl CU-X1 groups for Formula I include:
i) —(CH$_2$)$_3$CHO,
ii) —(CH$_2$)$_3$OCH$_2$C(CH$_2$ CHO)$_2$(CH$_2$CH$_3$) [two formyl groups on branched alkylenyl group],
iii) —(CH$_2$)$_3$O(CH$_2$)$_2$C(CH$_2$CHO)$_3$ [three formyl groups on branched alkylenyl group],
iv) —(CH$_2$)$_3$[O(CH$_2$)$_2$CH(CH$_3$)]$_p$[O(CH$_2$)$_2$]$_q$ OCH$_2$—CHO wherein p+q is greater than 1 and less than 11.

Preferred embodiments of amino CU-Y1 groups for Formula II include:
i) —(CH$_2$)$_3$NH$_2$,
ii) —CH$_2$CH(CH$_3$)CH$_2$NH$_2$,
iii) —(CH$_2$)$_3$NH(CH$_2$)$_2$NH$_2$,
iv) —CH$_2$CH(CH$_3$)CH$_2$NH(CH$_2$)$_2$NH$_2$,
v) —(CH$_2$)NH$_2$,
vi) —(CH$_2$)NH(CH$_2$)$_2$NH$_2$ Preferred embodiments of mercapto CU-Y1 groups for Formula II include:
i) —(CH$_2$)$_3$SH,
ii) —CH$_2$CH(CH$_3$)CH$_2$SH.

Preferred embodiments of the hydroxyl CU-Y1 groups for Formula II include:
i) —(CH$_2$)$_3$OH,
ii) —(CH$_2$)$_3$O(CH$_2$)$_2$OH,
iii) —(CH$_2$)$_3$O(CH$_2$)C(CH$_2$OH)$_2$(CH$_2$CH$_3$),
iv) —(CH$_2$)$_3$[OCH$_2$CH(CH$_3$)]$_p$[O(CH$_2$)$_2$]$_q$ OH, wherein p+q is greater than 1 and less than 11.

In addition to X or Y being a single occurrence on a reactive siloxane unit, the foregoing Formulas and description show that X and Y may be multiple occurrences on a single reactive siloxane unit. For example, a precursor compound with multiple X or Y groups such as multiple isocyanate groups and multiple hydroxyl groups may be used to form CU with multiple functional groups. In this example, a dihydroxy reactive siloxane unit may be prepared by combining trimethylolpropane and dimethyl dichlorosilane to form a precursor reactive siloxane unit. This unit can be combined with a silicone polymer having hydroxyl groups so as to add the chlorosilane moiety to the silanol —(O)$_{(1/2)}$SiMe$_2$OH moiety of the silicone polymer. The result produces a silicone polymer with a pendant hydroxyl functional group:

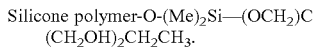
Silicone polymer-O-(Me)$_2$Si—(OCH$_2$)C(CH$_2$OH)$_2$CH$_2$CH$_3$.

Once this unit is combined with the polysiloxane compound, the resulting compound may further be combined with hexamethylene diisocyanate to add one of its isocyanate groups to each of the two remaining hydroxyl groups. The resulting isocyanate reactive siloxane unit bound to the silicone polymer has the formula

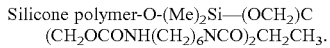
Silicone polymer-O-(Me)$_2$Si—(OCH$_2$)C(CH$_2$OCONH(CH$_2$)$_6$NCO)$_2$CH$_2$CH$_3$.

These two units CU-X1 and CU-Y1 may be combined with an appropriate polysiloxane to provide first and second silicone polymer examples.

Generally, when the third component is present, the weight average polymer molecular weight Mw of the first and second silicone polymers may be in a range from about 1000 Da to about 1 MDa, preferably about 1100 Da to about 500 KDa, more preferably about 1.2 KDa to about 500 KDa, especially more preferably about 1.5 KDa to about 300 KDa, most preferably about 1.5 KDa to about 150 KDa. Preferably one of the silicone polymers may have a minimum Mw of about 150 Da and the other may have a minimum Mw of about 1.5 KDa. These Mw ranges apply to the first and second silicone polymer having all first and second functional groups when the third component with the base compound is included in the multicomponent composition.

When the third component is absent and the first and second components alone form the multicomponent composition, the weight average molecular weights of the first and second silicone polymers having CU-X1 and CU-Y1 units are in a range from about 1000 Da to about 1MDa, preferably about 1100 Da to about 500 KDa, more preferably about 1.2 KDa to about 500 KDa, especially more preferably about 1.5 KDa to about 300 KDa, most preferably about 1.5 KDa to about 150 KDa.

When the third component is absent and the first and second silicone polymers have CU-X2 and CU-Y2 units alone or the complementary reactive pair Si—H and Si—CH=CH$_2$, the weight average molecular weights of the first and second silicone polymers are in a range from about 1100 Da to about 150 KDa, preferably a range of 1.5 KDa to 150 KDa, and a polydispersity wherein the molecular weight fraction below 1KDa of the first and second silicone polymers is less than 5 wt %, preferably less than 1 wt %, more preferably less than 0.1 wt % or virtually indetectable relative to the average molecular weights of the first and second silicone polymers.

In one embodiment, the properties of the coating produced by the combination of the first and second silicone polymers and optionally the amine polymer as the base compound coupled with the reactive pairing of the first and second functional groups produces a coating with a Shore 00 Hardness of greater than 10, more preferably greater than 15 even more preferably greater than 20, most preferably greater than 25, as measured using the test method described in the examples section.

As an option, a quantity of non-reactive organosilicone polymer such as up to about 0.1 wt %, or up to about 1 wt %, or up to about 35 wt % or higher such as up to about 60 wt % or 75 wt % relative to the total weight of the first and second silicone polymer can be included with the first and second silicone polymers. The presence of a non-reactive silicone polymer along with the first and second silicone polymers enables dilution of the first and second silicone polymers. The dilution may have an effect upon the in situ melding of the composition. The non-reactive polyorganosilicone of this embodiment has a M$_n$ of at least about 2.5 KDa or preferably at least about 5 KDa. It is recognized that a low M$_n$ silicone may also be present as a medium or as a component of a medium. Decamethylcyclopentasiloxane or d5 is an example of a silicone as a medium. Low M$_n$ silicones of this kind are volatile so that they do not remain with the composition following its application and in situ interaction on the substrate material.

The in situ melding is also affected by the number in situ linkages between and among the components providing the first and second silicone polymers and the base compound delivers primary control of the degree of network and star interconnections among these components. Too many interconnections may tend to increase a degree of inflexibility to the resulting coating. Too few interconnections may tend to decrease the remanence of the resulting coating. In addition to this primary control, dilution of the first and second silicone polymers with a non-reactive silicone polymer can help with coating flexibility and other physical parameters such as elasticity, inter-strand interaction for hair strands and tactile sensation. Modification of primary control may also be established by M$_n$, position of functional groups along the chains of the first and second silicone polymers and ancillary components such as surfactants, diluents, dispersants and other excipients discussed below.

Coordination of First, Second and Third Functional Groups

The first and second functional groups of the first and second components form complementary reactive pairs of functional groups according to the following pairings. The third component containing the base compound also participates in the pairing as one of the functional groups. (The third component is described below).

These pairings include:
i) isocyanate or thioisocyanate and hydroxyl, amine or mercapto or any combination of hydroxyl, amine and mercapto;
ii) carboxyl and hydroxyl, amine or mercapto or any combination of hydroxyl, amine and mercapto;
iii) alkylepoxy and hydroxyl, amine or mercapto or any combination of hydroxyl, amine and mercapto;
iv) olefinoyloxy and hydroxyl, amine or mercapto or any combination of hydroxyl, amine and mercapto (an example of olefinoyloxy is acrylyloxy or crotonyloxy);
v) olefinoyloxy and furanyl or pentadienyl or a combination of furanyl and pentdientyl;
vi) malonic anhydrido and hydroxyl, amine or mercapto or any combination of hydroxyl, amine and mercapto;
vii) formyl and amine or mercapto or any combination of amine and mercapto;
viii) vinyl and amine or mercapto or a combination of amine and mercapto;
ix) vinyl and furanyl or pentadienyl or a combination of furanyl and pentdienyl;
x) azido and alkynyl;
xi)) when the functional groups are a self-reactive functional group, mercapto and mercapto to form disulfide;
xii) when the functional groups are a self-reactive functional group, any combination of one silanol groups (SiOH) and/or silylalkoxy groups (SiOR) and/or siyloxime groups (Si—O—N=CHR) and/or silylacetoxy groups (Si—OAc) to form Si—O—Si bonds; and,
xiii) when the first functional group is Si-vinyl and the second functional group is Si—H.

The reactive siloxane units of the first and second silicone polymers are coordinated so that the multicomponent composition comprises first and second components having first and second functional group pairings according to the foregoing list.

Preferred reactive pairs of the first and second silicone polymers having reactive organosiloxane monomeric units of Formulas I and II include:
i) isocyanate and hydroxyl, amine or mercapto or any combination of hydroxyl, amine and mercapto;
ii) epoxy and hydroxyl, amine, or mercapto or any combination any two or more of hydroxyl, amine and mercapto;
iii) olefinoyloxy and hydroxyl, amine or mercapto or any combination of any two or more of hydroxyl and amine and mercapto, and a preferred embodiment of the olefinoyloxy group is (meth)acrylyloxy or crotonyloxy;
iii) carboxyl and hydroxyl, amine or mercapto or any combination of any two or more of hydroxyl, amine and mercapto;
iv) any combination of silanol, silanol, silylalkoxy and silylalkoxy.

Especially preferred reactive pairs of the first and second silicone polymers having reactive organosiloxane monomeric units of Formulas I and II include:
i) isocyanate and hydroxyl, amine or mercapto or any combination of hydroxyl, amine and mercapto;
ii) epoxy and hydroxyl, amine or mercapto or any combination of hydroxyl, amine and mercapto;
iii) carboxyl and hydroxyl or amine or a combination of hydroxyl and amine Most preferred reactive pairs of the first and second silicone polymers respectively having reactive organosiloxane monomeric units of Formulas I and II include:
i) isocyanate and hydroxyl, amine or mercapto or any combination of hydroxyl, amine and mercapto;
ii) epoxy and hydroxyl, amine or mercapto or any combination of hydroxyl, amine and mercapto;
iii) any combination of silanol, silanol, silylalkoxy and silylalkoxy.

In a further embodiment, variations of Formulas I and II can be adapted to form disulfide or urea groups through use of mercapto groups or isocyanate groups as a self-reactive group.

Ratios

Generally, the first and second silicone polymers comprise at least a majority of non-reactive organosiloxane monomeric units. Both silicone polymers may be linear, branched and optionally and to a minor extent networked through interchain linkages through T and Q units. When either or both first and second silicone polymers are branched, and/or have very long linear chains, the reactive first and second siloxane monomeric units of Formulas I and II are preferably positioned along or within the silicone polymer chain so that in situ linkages can be obtained. In other words, the reactive siloxane monomeric units preferably are not sterically hindered. The ratio of non-reactive organosiloxane monomeric units to reactive organosiloxane monomeric units for each silicone polymer bears on the extent to which in situ linking between the silicone polymers and with the base compound can be produced. The amount of reactive siloxane units with the silicone polymers can be calculated as discussed in preceding paragraph 0063.

Embodiments of the multicomponent composition manage the number of functional groups per silicone molecule so as to provide statistically a uniform number of functional groups per molecule throughout the volume of molecules present. Nevertheless, it is possible that not all of the molecules of the silicone polymers will contain precisely the same number of functional groups. The number of functional groups in a silicone polymer may spread at least by ±1 or 2 groups from the average. The spread can be due in part to the variation of molecular weights of the silicone polymers and in part due to the polymerization and coupling methods associated with any chemical reaction. It is preferred that a substantial majority of the silicone polymers, and preferably at least almost all of the silicone polymers such as about 95 to 98 percent of the silicone polymers preferably have at least two reactive pairs, more preferably have at least three reactive pairs, most preferably have at least four reactive pairs and especially most preferably have at least five reactive pairs per molecule. It is especially preferred that at least about 98% of the silicone polymers have statistically uniform numbers of reactive siloxane units per molecule.

An overall range for the molar ratio of non-reactive organosiloxane monomeric units to reactive organosiloxane monomeric units of the first and second silicone polymers runs from as little as about 2000:1 to as much as about 3:1 considering the range of weight average molecular weight for the silicone polymers. Preferably, this range extends from about 1250:1 to about 3:1, more preferably about 800:1 to about 3:1 and most preferably about 500:1 to 3:1 and especially most preferably a range of about 250:1 to 3:1. A typical range in many circumstances is especially most preferably from 5:1 to 1:5.

G Factor Analysis

When the silicone polymers with complementary reactive pairs or with self-reactive functional groups are applied to the hair, they will undergo an in situ covalent linking reaction leading to the formation of new covalent bonds. According to the multicomponent process of the invention, application to the substrate material and especially the hair of the multicomponent composition results in the formation of a solid, flexible silicone coating having a network and/or star three dimensional configuration. Colored pigment particles are embedded in the coating. The new in situ formed bonds can change the rheological characteristics of the silicone polymers.

Whilst not wishing to be bound to any particular theory, it believed to be advantageous if the silicone polymer components change from having a substantial G" component, the so called loss modulus, and a negligible G' component, the so called storage modulus, prior to application to the hair, to the reverse situation where there is negligible G" component and a substantial G' component. This can also be considered by consider the phase angle φ, where $$\varphi = \arctan\left(\frac{G''}{G'}\right)$$

When the complex shear modulus changing from more the 45 degrees to less than 45 degrees. Both the phase angle of the resulting film or coating, and the complex shear modulus can be optimized for performance. Alternatively, it may be possible to quantify the resulting coating properties in terms of Young's Modulus and elongation at breaking.

The following parameters further help to define the properties of the materials that are particularly useful. Whilst not wishing to be bound by any particular theory, the degree of connectedness, i.e. formation of new in situ connections and the separation between these new connections can impact the performance of the resulting composition on substrate material such as hair. With too many connections and too little separation between the connections the resulting interconnected material can be too stiff, leading to poor performance on hair, both tactile perception and permanence through extended hair washing. This negative performance can also be expressed as having a phase angle φ less than 30 degrees, more particularly less than 15 degrees, even more less than 2 degrees. Conversely if there are insufficient connections and the separation between them is too great, the material is too fluid like leading to sticky feel, a potential for transfer of the color to other surfaces, and lower permanence and resistance to washing. This negative performance can also be expressed as having a phase angle φ greater than 60 degrees, more particularly greater than 75 degrees, even more particularly, greater than 88 degrees.

The average length between new in situ connections can be described as the average in situ link length for a given polymer and is the average distance between successive reactive organosiloxane monomeric units, Formulas I and II (which are OZ of the following mathematical formula) of a molecule, expressed in terms of $Si(R)_2O_{2/2}$ or D units:

$$\text{Cross link length} = \frac{100}{\sum_{n=1}^{n=n} MPC(OZ)_n}$$

for a series of n potential OZ groups (Formulas I and II) within a given polymer and the term MPC is defined as Mole Percent, which is equal to the number of modifications of the given species per 100 Si groups within the silicone material.

The cross linking role for a given species is given by:

$$\text{Cross link role} = \frac{\sum_{n=1}^{n=n} N_n MPC_n DP}{200}$$

For a series of n potential reactive siloxane units (OZ, Formulas I and II) within a given polymer where N is the number of OZ groups for the given functional group that can form cross links with other functional groups, MPC is the mole percent of the given group within the polymer and DP is the number average degree of polymerization of the polymer. When present, silicone polymers which do not have any OZ functionality have a cross link role=0, they will not form any new silicone connections. When the cross link role=1, the first and second silicone polymers only perform the role of chain extension when used by themselves, although those skilled in the art would understand that such chain extension would not necessarily have to occur through terminal ends of the silicone chain. When the cross link role >1 the first and second silicone polymers can perform network building, the higher this number the greater the impact of the network building. The properties of the resulting film or coating will depend on a complex relationship of the in situ link length and the in situ link role and dilution roles of all of the constituents of the composition including but not limited to the first and second silicone polymers and non cross linkable silicone polymers used.

Where more than one functional and non functional silicone polymer is used the following factors need to be considered. For each silicone polymer added, the reduced fraction of the given silicone polymer needs to be calculated.

$$\text{Reduced Fraction} = \frac{\frac{\text{Mass Fraction silicone component}}{DP}}{\int_{n=1}^{n=n} \frac{\text{Mass Fraction silicone component}_n}{DP_n}}$$

Where the mass fraction of the silicone component is the percent of the non-volatile silicone phase. A volatile silicone is one with a boiling point less than 225 C. If present, silicones which do not have an OZ (Formulas I and II) functionality are also included within the calculation to determine the reduced fraction of the total silicone phase. The DP is the number average degree of polymerization, i.e. the number of Si atoms within the polymer. This effectively factors the number of each type of silicone polymer added by the number of individual polymer entities versus just using the weight of the amount of silicone species added. Thus, the effect of a low DP material, e.g. with a DP=10 can produce a larger effect versus the same addition of a higher DP material, e.g. with a DP of 10,000. When added at equal weights, there are 100 times more of the low DP polymer entities versus the high DP polymer chains.

For the mixed system the following terms can be calculated.

Average cross link length =
$$\int_{n=1}^{n=n} \text{Cross linked length}_n \times \text{Reduced Fraction}_n$$

For n silicone polymer materials within the formulation.

$$\text{Average cross link role} = \int_{n=1}^{n=n} \text{Cross linked role}_n \times \text{Reduced Fraction}_n$$

For n silicone polymer materials within the formulation.

Using these terms for the silicone phase, non-limiting material combinations which are preferred include those where the average cross link length is greater than 5, more preferably greater than 10, even more preferably greater than 15, and where the average cross link role is greater than 1.3, more preferably greater than 1.5, even more preferably greater than 1.6. Preferably the average cross link length is less than 400, more preferably less than 350, even more preferably less than 250, and where the average cross link role is less than 6, more preferably less than 4.5, even more preferably less than 4.

The Third Component

The third component is a base compound with third functional groups. The base compound may be a small molecule, a dimer, trimer, tetramer, pentamer, hexamer, oligomer, small or large polymer having pendant and/or terminal third functional groups which may be amine, mercapto, carboxylate, sulfonate or carbamate groups, preferably amine groups. In combination with the first and second functional groups, it is believed that the third functional groups meld together with the first and second functional groups to form a coating having a network and/or star arrangement that is interconnected throughout the first and second silicone polymers and the base compound as well as interconnected with the substrate material. Embodiments of the third component combine with embodiments of the first and second components of the multicomponent composition to meld together (e.g., covalently bond as well as entangle large chains together, blend, combine and unite together as one) these components into a colored coating on substrate material that displays significant remanence. Embodiments of the substantive feature of the third component are the base compound. Embodiments of the base compound incorporate amine groups, carboxylate groups, sulfonate groups, carbamoyl groups and/or mercapto groups and most preferably amine groups into and onto an organic or silicone core or chain.

The base compound preferably has a weight average molecular weight of about 150 Da to about 1MDa. When the base compound is a polymer, its $M_n$ is preferably about 400 Da to about 500 KDa, more preferably about 400 Da to about 250KDa, most preferably about 2 KDa to about 100 KDa.

Preferred embodiments of the base compound as an organic core with amine groups may be one or more polymer(s). The amine polymer(s) may comprise one or more amino functional group(s) per polymer chain, wherein the amino functional group(s) are selected from the group consisting of primary, secondary, tertiary amino functional groups and mixtures thereof.

Embodiments of the base compound may be selected from the group consisting of polyethyleneimine, polyallylamine hydrochloride, polydiallyldimethylammonium chloride, polyvinylamine, aminopolysaccharides, aminopolysilicones, copolymers thereof and mixtures thereof. The amine polymer(s) may preferably be selected from the group consisting of polyethyleneimine, polydiallyldimethylammonium chloride, copolymers thereof and mixtures thereof.

Additional embodiments of the base compound include tri and tetra mercapto branched alkyl compounds wherein the mercapto groups are the termini and the branches are C3-C10 methylenyl groups on a C3-C10 polymethylenyl backbone.

These embodiments of the base compound may be linear or branched and/or may be random or block copolymers.

As amino polymer(s) such as the embodiments of the base compound described above, exemplary selections include:

a) Linear polyethyleneimine of the formula:

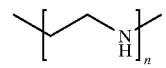

in which n is an integer representing the degree of polymerization, wherein n ranges from 50 to 20,000, alternatively from 100 to 3,500;

b) Branched polyethyleneimine consisting of primary, secondary and tertiary amine groups of the formula:

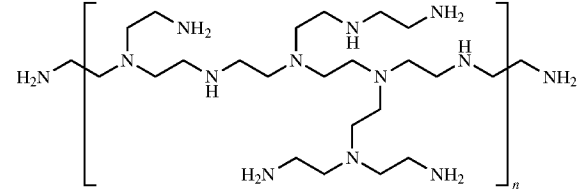

in which n is an integer representing the degree of polymerization, wherein n ranges from 5 to 4,000, alternatively from 50 to 500;

c) Polyallylamine hydrochloride of the formula:

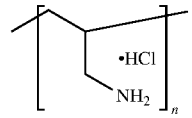

in which n is an integer representing the degree of polymerization, wherein n ranges from 50 to 20,000, alternatively from 150 to 2000;

d) Polydiallyldimethylammonium chloride of the formula:

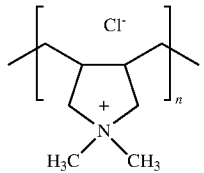

in which n is an integer representing the degree of polymerization, wherein n ranges from 10 to 20,000, alternatively from 150 to 4,000;

copolymers thereof and mixtures thereof.

These embodiments of the base compound, e.g., the amine polymer(s) may have a charge density when fully protonated of at least 0.3, preferably at least 0.6, more preferably at least 0.8, even more preferably at least 1.0 positive charges per monomer unit.

Embodiments of the base compound may also be amino silicone compounds. Embodiments of the amino silicone polymer base compound may comprise any silicone polymer chain that incorporates amine functional groups into the silicone polymer. The amino silicone compounds may also be aminosiloxane compounds or oligomers and aminosilane small molecule (monomeric) compounds such as $Me_3Si$—O—$SiMe_2$-O—$SiMe_2NH_2$ and $(CH_3O)_3Si(CH_2)_3NH_2$, $(CH_3CH_2O)_3Si(CH_2)_3NH_2$, $(CH_3O)_3Si(CH_2)_3NH(CH_2)_2NH_2$, $(CH_3CH_2O)_3Si(CH_2)_3NH(CH_2)_2NH_2$ A preferred amino silicone base compound is one having amine functional groups (hereinafter an aminosilicone polymer). The molar ratio of siloxane monomeric units with at least one pendant organic amine group (hereinafter SiA moieties) to siloxane monomeric units having silicon bonded to a substituent selected from the group consisting of alkyl (C1 to C6) or phenyl (hereinafter SiC moieties) is in the range of from about 1:1000 to 1:10 (ratio of SiA units to SiC units), preferably 1:1000 to 1:25, more preferably 1:600 to 1:35, most preferably 1:400 to 1:35 or 1:300 to 1:40. An SiA moiety may contain more than one amine group in which case it counts as just one SiA moiety. An SiC moiety may contain any number of other pendant groups as long as a primary, secondary, tertiary or quaternary amine group is not present. The aminosilicone polymer may have a weight average molecular weight ranged from about 5 KDa to about 150 KDa, preferably about 6 KDa to about 130 KDa, more preferably about 8 KDa to about 120 KDa.

The amine functional groups of the aminosilicone polymer may be primary, secondary, tertiary amine groups or quaternary ammonium groups or any combination thereof. The secondary, tertiary or quaternary amine groups may be substituted by alkyl groups of 1 to 6 carbons, such as methyl, ethyl, propyl, butyl, pentyl or hexyl or any combination thereof. The amine functional groups may be organic pendant groups wherein the amine group terminates the end of the organic group. The pendant organic amine group is bonded to the silicone backbone by a carbon to silicon bond between the organic group and a siloxane monomeric unit as —O—$Si(R')_2$—O—wherein each R' is independently selected from a pendant organic amine group and an alkyl group of 1 to 6 carbons and at least one R' group is a pendant organic amine group. The organic amine group may be a linear alkyl group of 1 to 16 carbons or a branched or cyclic alkyl group of 3 to 16 carbons. The alkyl group may contain one or more heteroatoms and/or hetero-groups in the chain including such groups as —NH—, —O—, —S—, —CONH— or —NHCO—, —$SO_2$NH— or —NH$SO_2$—. Typical pendant amine groups include such arrangements as:

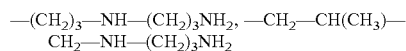
—$(CH_2)_3$—NH—$(CH_2)_3NH_2$, —$CH_2$—$CH(CH_3)$—$CH_2$—NH—$(CH_2)_3NH_2$

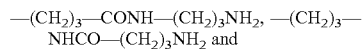
—$(CH_2)_3$—CONH—$(CH_2)_3NH_2$, —$(CH_2)_3$—NHCO—$(CH_2)_3NH_2$ and single amine groups such as —$(CH_2)_n$—$NH_2$ wherein n is 1 to 6, preferably 1 or 4 or branched chain versions thereof such as —$CH_2$—$CH(CH_3)$—$CH_2$—$NH_2$.

The amine group or groups may be pendant to the silicone chain at uniform or random locations along and within the silicone chain. The amine functional group may also terminate the ends of the silicone chain but an aminosilcone polymer having terminal amine groups preferably will also have pendant amine groups along the silicone chain.

The silicone chain of the aminosilicone polymer may be linear, branched or crosslinked. In addition to the SiA and SiC moieties, aminosilicone may also include any one or more of MDTQ groups of the formulas A, B, C and D wherein R is a methyl group:

A) —$O(R)_2Si$—O— (known as a D siloxane unit)
B) —$O(R)SI(-O-)_2$ or —O—$Si(-O-)_2$—O— (known as T siloxane unit and Q sesquisilicate unit respectively)
C) $(R)_3SI$—O— (known as M siloxane unit).

For this embodiment of the aminosilicone polymer component of the base compound the A), B), C) and D) groups constitute together the SiC moieties defined above. The A) group provides a linear silicone chain link, the B) group provides a branched or crosslinked silicone chain link, the C and D groups provide a silicone chain termination. The distribution of the SiA moiety and the A), B), C), and D) groups of the SiC moiety follows ordered or random arrangement and the SiA to SiC ratios and weight average molecular weight ranges given above The Fourth Component The fourth component is an agent that catalyzes the in situ covalent reaction of the complementary reactive pairs and self-reactive functional groups. The agent may also be a chemical enhancer for overcoming activation energy of the in situ reaction, an enzyme, a coordination complex or complexing agent for promoting the functional group interaction. Lewis acids, enzymes for ester and amide formation, carbodiimides, Friedel Crafts catalysts, Lewis bases, mixed anhydrides, leaving group donors, and similar chemical entities are examples of such agents. The fourth component is optional and typically is added when the complementary reactive pair or the self-reactive functional group typically does not covalently react under normal environmental conditions. For the silanol/alkoxysilane condensations, a typical activation agent is water.

Substitution of an Organic Polymer for One of the Silicone Polymers

The multicomponent composition is generally characterized as a linear and/or branched silicone polymer having units of a non-reactive organosiloxane monomer and at least two pendant and/or terminal reactive organosiloxane monomer units having functional groups. The reactive siloxane monomeric units are distributed throughout the backbones and branch chains of the silicone polymer and carry functional groups comprising isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, cyclopentadienyl, azido, Si—OH, Si—OR, Si—O—N=CHR. Si—OAc, Si—CH=$CH_2$ or Si—H. The functional groups may be complementary reactive pairs which will parse the silicone polymer into first and second silicone polymers or may be a self-reactive functional group. Hence, the silicone polymer can be segregated into first and second silicone polymers each carrying one part of the complementary reactive pair of the reactive organosilicone units or each carrying a self-reactive organosilicone unit. One of these two segregated silicone polymer may alternatively be an organic polymer. Any organic polymer can be modified to carry half of the complementary reactive pair of functional groups or carry half of the self-reactive functional group combination. The organic polymer also may contain other functional groups as long as these other groups do not reactively interfere with the in situ covalent bonding of the complementary reactive pair or the self-reactive functional group.

Embodiments of the organic polymer can be adapted to have pendant or terminal or pendant and terminal functional groups selected from either part of the complementary reactive pairs of functional groups. One part presents the functional groups of isocyanato, thioisocyanato, carboxyl, linear, branched or cyclic epoxyalkyl, olefinoyloxy, malonic anhydrido, formyl, mercapto, vinyl, alkynyl or Si—CH═CH$_2$. The other part presents the functional groups of hydroxyl, amino, mercapto, furanyl, cyclopentadienyl, azido or Si—H. One part will be bonded to the organic polymer. The other part will be bonded to the silicone polymer as described above. Together the organic polymer and silicone polymer constitute polymers presenting the complementary reactive pairs of functional groups. Alternatively, the organic polymer and the silicone polymer may both be bonded to a self-reactive functional group including Si—OH, Si—OR, Si—O—N═CHR. Si—OAc, mercapto or isocyanate.

Organic compounds serving this role are organic polymers including but not limited to oligomers and polymers of appropriate monomeric units such as but not limited to one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers or of amino acid monomeric units, amino acid units providing peptides, gelatin or biopolymers; carbohydrate monomeric units providing alginates, cellulosic derivatives, cellulose esters, polysaccharides; hydroxylated polyester, acrylate functionalized polyester, polyester polyurethane acrylic copolymer, polyurethane-polyglycol copolymer, polycarbonate diols, styrene-allyl alcohol copolymer, ketone resins; as well as other repeating residues based on carbon or carbon in combination with other atoms such as oxygen and/or nitrogen, and any combination thereof. Additional precursor organic polymers include but are not limited to non-polar olefinic polymers, polar, non-protonic olefinic polymers, vinyl polymers, polyethers, polycondensates, block polymers and any compound with repeating carbon unit residues. Preferably the precursor organic polymers are polyolefins including polyvinyl compounds, polyesters, polyethers, polyurethanes or polyamides or any combination thereof. More preferably, the organic polymers are polyolefins including polyvinyl compounds, polyesters or polyurethanes or any combination thereof. Especially more preferably, the organic polymers are polyolefins, polyvinyl compounds or polyesters.

Organic polymers containing acid groups may be developed from any monomeric unit containing acid groups such as carboxylic acid, sulfonic acid, sufinic acid, phosphoric acid. The acidic units may be combined with non acidic units which are hydrophilic or hydrophobic to provide appropriate precursor organic polymers. Such polymers are described in the following passages.

Organic polymers may include copolymers of (meth) acrylic acid and of at least one linear, branched or cyclic (cycloaliphatic or aromatic) (meth)acrylic acid ester monomer and/or of at least one linear, branched or cyclic (cycloaliphatic or aromatic) mono- or disubstituted (meth)acrylic acid amide monomer.

Included are copolymers such as acrylic acid/ethyl acrylate/N-tert-butylacrylamide terpolymers such as the product sold under the name Ultrahold 8 and that sold under the name Ultrahold Strong by the company BASF; (meth) acrylic acid/tert-butyl (meth)acrylate and/or isobutyl (meth) acrylate/C1-C4 alkyl (meth)acrylate copolymers such as the acrylic acid/tert-butyl acrylate/ethyl acrylate terpolymer sold by the company BASF under the name Luvimer 100P; (meth)acrylic acid/ethyl acrylate/methyl methacrylate terpolymers and tetrapolymers such as the ethyl acrylate/methyl methacrylate/acrylic acid/methacrylic acid copolymer such as the product sold under the name Amerhold DR-25 by the company Amerchol; methyl methacrylate/ butyl or ethyl acrylate/hydroxyethyl or 2-hydroxypropyl acrylate or methacrylate/(meth)acrylic acid tetrapolymers such as the methyl methacrylate/butyl acrylate/hydroxyethyl methacrylate/methacrylic acid tetrapolymers sold by the company Rohm & Haas under the name Acudyne 255.

Additional examples of organic polymers include copolymers of acrylic acid and of C1-C4 alkyl methacrylate and terpolymers of vinylpyrrolidone, of acrylic acid and of C1-C20 alkyl, for example lauryl, methacrylate, such as that sold by the company ISP under the name Acrylidone M and the copolymer of methacrylic acid and of ethyl acrylate sold under the name Luvimer MAEX by the company BASF.

Yet other examples of organic polymers include amphoteric copolymers such as N-octylacrylamide/methyl methacrylate/hydroxypropyl methacrylate/acrylic acid/tert-butylaminoethyl methacrylate copolymers, in particular that sold under the name Amphomer by the company National Starch, or the copolymer Lovocryl L47 sold by the same company.

Additional examples of organic polymer include copolymers of (meth)acrylic acid and of (meth)acrylic acid esters or amides furthermore containing linear, branched or cyclic (cycloaliphatic or aromatic, which may or may not be substituted) vinyl esters, such as vinyl acetate; vinyl propionate; vinyl esters of branched acid such as vinyl versatate; vinyl esters of substituted or unsubstituted benzoic acid; these copolymers may furthermore also contain groups resulting from the copolymerization with styrene, alpha-methylstyrene or a substituted styrene. Other examples include copolymers of (meth)acrylic acid and of at least one olefinic monomer chosen from vinyl esters such as those mentioned above and containing no (meth)acrylic acid acrylamide or ester monomer. These copolymers may also contain olefinic groups resulting from the copolymerization with styrene, .alpha.-methylstyrene, a substituted styrene and optionally monoethylenic monomers such as ethylene.

Still other examples include copolymers of vinyl monoacid such as crotonic acid and vinylbenzoic acid and/or of allylic monoacid such as allyloxyacetic acid.

Organic polymers include copolymers of crotonic acid containing vinyl acetate or propionate units in their chain and optionally of other monomers such as allylic or methallylic esters, vinyl ethers or vinyl esters of a saturated, linear or branched carboxylic acid containing a long hydrocarbon chain, such as those containing at least 5 carbon atoms, it being possible for these polymers optionally to be grafted and crosslinked, or alternatively a vinyl, allylic or methallylic ester of an alpha- or beta-cyclic carboxylic acid. These copolymers may also contain olefinic groups resulting from the copolymerization with styrene, alpha-methylstyrene, a substituted styrene and optionally monoethylenic monomers such as ethylene.

Organic polymers include vinyl polymers such as vinyl acetate/crotonic acid/polyethylene glycol copolymers such as that sold by the company Hoechst under the name "Aristoflex A"; vinyl acetate/crotonic acid copolymers such as that sold by the company BASF Additional examples of precursor organic polymers include the polyolefins, polyvinyls, polyesters, polyurethanes, polyethers, polycondensates and natural polymers of the following passages.

Additional organic polymers include but are not limited to homopolymers and copolymers of olefins; cycloolefins; butadiene; isoprene; styrene; vinyl ethers, esters, or amides; (meth)acrylic acid esters or amides containing a linear, branched, or cyclic C1-C24 alkyl group, a C6-C24 aryl group or a C2-C24 hydroxyalkyl group. These polymers may be obtained from monomers such as isooctyl(meth) acrylate, isononyl(meth)acrylate, 2-ethylhexyl(meth)acrylate, lauryl(meth)acrylate, isopentyl(meth)acrylate, n-butyl (meth)acrylate, isobutyl(meth)acrylate, ethyl(meth)acrylate, methyl(meth)acrylate, tert-butyl(meth)acrylate, tridecyl (meth)acrylate, stearyl(meth)acrylate, hydroxyethyl(meth) acrylate, 2-hydroxypropyl(meth)acrylate, benzyl acrylate, phenyl acrylate, and mixtures thereof. Amides monomers include but are not limited to (meth)acrylamides, such as N-alkyl(meth)acrylamides, for example of a C2-C12 alkyl, such as N-ethylacrylamide, N-t-butylacrylamide, and N-octylacrylamide; N-di(C1-C4)alkyl (meth)acrylamides and perfluoroalkyl(meth)acrylates.

Organic polymers may also include embodiments based upon attachment of a vinyl group to a diverse number of compounds. Polymerization delivers the polyvinyl compound (e.g., a version of polyolefins) with a large variation of substituent identity. Examples of vinyl monomers for such polymerization include but are not limited to vinyl alkanoate such as vinyl acetate, N-vinylpyrrolidone, vinylcaprolactam, vinyl N—(C1-C6)alkylpyrroles, vinyloxazoles, vinylthiazoles, vinylpyrimidines, vinyl pyridine, vinyl thiophene, and vinylimidazoles, olefins such as ethylene, propylene, butenes, isoprene, and butadienes.

Organic polymers also include but are not limited to, for example, of the alkyl acrylate/cycloalkyl acrylate copolymer, the acrylates/C12-22 alkyl methacrylate copolymer and vinylpyrrolidone copolymers, such as copolymers of a C2-C30 alkene, such as a C3-C22 alkene, and combinations thereof. VP copolymers include but are not limited to VP/vinyl laurate copolymer, the VP/vinyl stearate copolymer, the butylated polyvinylpyrrolidone (PVP) copolymer, the VP/hexadecene copolymer, the VP/eicosene copolymer, the VP/triacontene copolymer or the VP/acrylic acid/lauryl methacrylate copolymer, octylacrylamide/acrylates/butylaminoethyl methacrylate copolymer, acrylates/octylacrylamide copolymer, polymers bearing fluoro groups belonging to one of the classes described in the above text, and the copolymers of alkyl(meth)acrylate and perfluoroalkyl(meth) acrylate. Additional precursor organic polymers include those resulting from the polymerization or copolymerization of an ethylenic monomer, comprising at least one ethylenic bond, which can be, for example, conjugated (or dienes). Precursor organic polymer resulting from the polymerization or copolymerization of an ethylenic monomer, vinyl, acrylic, or methacrylic copolymers are also included without limitation.

Organic polymers as block copolymers are also included, examples of which include but are not limited to a block copolymer comprising at least one block comprising styrene units or styrene derivatives (for example methylstyrene, chlorostyrene, or chloromethylstyrene). The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, or a methacrylate (MA) block, or a combination of these blocks. The copolymer comprising at least one block of styrene units or styrene derivatives may be a diblock or triblock copolymer, for example of the polystyrene/polyisoprene or polystyrene/polybutadiene type, those of the polystyrene/ copoly(ethylene-propylene) type or alternatively of the polystyrene/copoly(ethylene/butylene) type as well as styrene-methacrylate copolymers.

Further embodiments of organic polymers include but are not limited to those chosen from copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group) and of at least one other monomer chosen from vinyl esters (other than the vinyl ester already present), α-olefins (containing from 8 to 28 carbon atoms), alkyl vinyl ethers (in which the alkyl group contains from 2 to 18 carbon atoms), or allylic or methallylic esters (containing a linear or branched saturated hydrocarbon-based radical of 1 to 19 carbon atoms, bonded to the carbonyl of the ester group).

Further non-limiting examples of the organic polymers include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/ vinyl stearate, vinyl propionate/vinyl stearate, vinyl dimethylpropionate/vinyl laurate, vinyl acetate/octadecyl vinyl ether, vinyl acetate/allyl stearate, vinyl acetate/1-octadecene and allyl propionate/allyl stearate.

Additional organic polymer precursors include polyalkenes and copolymers of C2-C20 alkenes, for example polybutene, polymers of natural origin, which are optionally modified, chosen from shellac resin, sandarac gum, dammar resins, elemi gums, copal resins, and polysaccharides comprising alkyl (ether or ester) side chains, for example alkylcelluloses containing a linear or branched, saturated, or unsaturated C1-C8 alkyl radical, such as ethylcellulose and propylcellulose.

Organic polymers of natural origin may be chosen, for example, from cellulose-based polymers such as nitrocellulose, cellulose acetate, cellulose acetobutyrate, or cellulose acetopropionate. Non-limiting examples include the ethylcellulose the cellulose acetobutyrate, and the cellulose acetopropionates.

Organic polymers also include but are not limited to polycondensates which include but are not limited to polyurethanes, polyurethane-acrylics, polyurethane-polyvinylpyrrolidones, polyester-polyurethanes, polyether-polyurethanes, polyureas, polyurea-polyurethanes, and mixtures thereof. The precursor polyurethanes may be, for example, a copolymer of aliphatic, cycloaliphatic, or aromatic polyurethane, or of polyurea-polyurethane.

The polyurethanes may also be obtained from branched or unbranched polyesters or from alkyds comprising mobile hydrogens that are modified via a polyaddition with a diisocyanate and an organic difunctional (for example dihydro, diamino or hydroxy-amino) coreagent.

Non-limiting examples of organic polymer may also include polyesters, polyester amides, fatty-chain polyesters, polyamides, and epoxyester resins. The precursor polyesters may be obtained in a known manner via the polycondensation of aliphatic or aromatic diacids with aliphatic or aromatic diols or with polyols. Succinic acid, glutaric acid, adipic acid, pimelic acid, suberic acid, or sebacic acid may be used as aliphatic diacids. Terephthalic acid or isophthalic acid, or even a derivative such as phthalic anhydride, may be used as aromatic diacids. Ethylene glycol, propylene glycol, diethylene glycol, neopentyl glycol, cyclohexanedimethanol, and 4,4-N-(1-methylpropylidene)bisphenol may be used as aliphatic diols.

The polyesteramides may be obtained in a manner similar to that for the polyesters, via the polycondensation of diacids with amino alcohols. The polyamides may be obtained in a manner similar to that for the polyesters, via the polycondensation of diacids with diamines. Exemplary precursor polyesters that may be mentioned include aliphatic polyesters containing C4-50 alkyl side chains or polyesters resulting from the condensation of fatty acid dimers, or alternatively polyesters comprising a silicone segment in the form of a terminal block, graft, or group.

Transforming the Precursor Organic Polymer to the Organic Polymer

The organic polymers may be transformed to the organic polymer with a functional group by incorporation of one or more polymerization compatible monomeric units bearing carboxylic acid groups, sulfonic acid groups, sulfinic acid groups, hydroxyl groups, mercapto groups, olefinoyloxy groups, vinyl and/or amine groups. Typically, a copolymerization with appropriate monomeric units some of which will bear the first functional group accomplishes the incorporation and development of the organic polymer of the first component. Typically, the organic polymer of the first component will have an acid number ranging from small to large and optionally a hydroxyl number and/or amine number and/or mercapto number ranging from small to large. Incorporation of monomeric first functional groups into precursor organic polymers which are olefinic polymers is straightforward as the olefinic first functional group monomeric unit will copolymerize with the other olefinic units of such polymers. For condensation polymers, incorporation can be accomplished through use of a starting monomeric unit containing a first functional group which optionally may be protected. For naturally derived polymers, conversion and/or derivatization of a pendant group such as a hydroxyl group or acid group to a first functional group can be accomplished through known organic chemistry transformations. These conversions are described in the scientific literature such as in J. March, "Advanced Organic Chemistry", $4^{th}$ Ed. John Wiley & Sons, New York, 1992.

Embodiments of the organic polymer of an alternative to one of the silicone polymers comprise one or more of the above described organic polymers coupled with two or more functional groups, especially polyolefins, polyvinyls, polyesters, polyethers, polyamides, polyurethanes and combinations thereof. Especially preferred are polyolefins, polyvinyls, polyesters, polyurethanes and polyethers. More especially preferred are polyolefins, polyvinyls and polyesters.

Embodiments of the organic polymer may be selected from oligomers and polymers produced from monomers or monomeric units of one or more olefin monomers, ester units of diacids/diol monomers or of hydroxy acid monomers, ether monomeric units, thioether monomeric units, polyol monomeric units, alkylene oxide monomeric units, alkylene imine monomeric units, urethane monomeric units, urea monomeric units, amide units of diacid/diamine monomers or of amino acid monomeric units, amino acid units providing peptides, gelatin or biopolymers; carbohydrate monomeric units providing alginates, cellulosic derivatives or polysaccharides; as well as other repeating residues based on carbon or carbon in combination with other atoms such as oxygen and/or nitrogen, and any combination thereof. The organic polymer may comprise a polyolefin, a polyester, a hydroxylated polyester, an acrylate functionalized polyester, a polycarbonate, a polyallyl alcohol, a ketone resin, a polyether, a polyimine, a polyurethane, a polyurea, a polyglycol, a polyamide, a polypeptide, poly (2-oxazoline) and its derivatives, a carbohydrate compound, a cellulose, a cellulose derivative such as a cellulose ester or a hydroxylated cellulose or a carboxyl cellulose or a hydroxyl cellulose ester or carboxylic acid, an alginate, a gum, a polysaccharide, an amino acid polymer, a gelatin, an oligopeptide, a polypeptide or a protein, a carbohydrate-amino acid such as a glycosylated peptide or a carbohydrate-purine/pyrimidine base such as a polynucleoside, a biopolymer, a (meth) acrylic copolymer, a crotonic copolymer, a polyurethane-polyglycol copolymer, a polycarbonate diol, a styrene-allyl alcohol copolymer, a polyol, a natural gum, polyvinyl acetate, polyvinylpyrrolidone, polynipam, a polymer based on one or more olefin monomers, a polymer based on ester units of diacids/diol monomers, a polymer based on ester units of hydroxy acid monomers, a polymer based on ether monomeric units, a polymer based on thioether monomeric units, a polymer based on polyol monomeric units, a polymer based on alkylene oxide monomeric units, a polymer based on of alkylene imine monomeric units, a polymer based on urethane monomeric units, a polymer based on urea monomeric units, a polymer based on amide units of diacid/diamine monomers, a polymer based on amide units of amino acid monomeric units or other polymer having repeating residues based on carbon or carbon in combination with other atoms such as oxygen and/or nitrogen, and any combination thereof. Preferred organic polymers include polyolefins, polyvinyls, polyesters, polyethers, polyamides, polyurethanes and combinations thereof. Additional preferred organic polymers include polymers and copolymers based on polyurethane, polyacrylate, silicone resins, polyurea/polyurethane silicones, and copolymers based on silicone resin and on dimethiconol which either have first functional groups or are adapted to have first functional groups. Especially preferred organic polymers include polyolefins, polyvinyls, polyesters, polyurethanes and polyethers and combinations thereof. More especially preferred organic polymers include polyolefins, polyvinyls and polyesters and combinations thereof.

The organic polymer may be linear and/or branched and may incorporate along the polymer backbone, as well as along the branches, pendant moieties such as esters, ethers, oxycarbonyls, amides, aliphatic groups, aromatic groups, linear, branched or cyclic alkyl groups or similar groups that are other than polar and protic. Examples of pendant moieties include but are not limited to such moieties as an alkyl carboxyl ester resulting from polymerization of an alkyl (meth)acrylate, or phenyl resulting from polymerization of styrene. The organic polymer may incorporate any of either part of the complementary reactive pairs of functional groups with the silicone polymer incorporating the other part or the organic polymer may incorporate the self-reactive functional group. Formulas I and II above may be employed to add the functional group to the organic polymer and a chloro precursor of the siloxane moiety $[-(O)_{(4-d-c)/2}SiR^4_c]$ as $[ClSiR^4_c-CU]$ can act as a linker or connecting group. An allyl Grignard compound may be reacted with the chloro silicon compound to add an allyl group to the silicon atom. The resulting allyl silicon compound can be polymerized into an olefinic organic polymer. The allyl group may be epoxidized and opened to provide a hydroxyl group. The hydroxyl may be oxidized to carboxyl and the resulting epoxy and/or hydroxyl and/or carboxyl compounds can be polymerized with appropriate organic polymers to form polyesters, polyamides, polyols and similar organic polymers.

Glass Transition Temperature

Almost all of the first and second silicone polymer embodiments for the first and second components are viscous liquids and/or gels at ambient temperature and pressure but have a glass transition temperature (Tg) at very low temperatures such as about −30° C. to about −150° C. or −200° C. The base compound as well as substitute organic polymers typically will have a somewhat higher glass transition temperature. Because the Tg's of the silicone polymer components are so low, the starting material Tg's will not play a role in the hardness, stiffness, flexibility and softness of the linked multicomponent composition as a coating on the substrate material.

In general, the glass transition temperature or $T_g$ determines the solid-solid transition of a material such as a polymer from a hard glassy material to a soft rubbery material. If the $T_g$ of the material is too high, and the material is a solid, it will be stiff and inflexible at normal temperatures. For coatings with the silicone polymers and base compound this would be an undesirable result. The coating should be soft, flexible and unnoticeable to touch and sight yet should not flake, break-up or otherwise release from the keratin fiber, and especially from human hair, when stroked by a hand or brushed with a brush. Because the Tg of the silicone polymers is so low, coatings prepared from them will usually exhibit the desirable qualities described above. However, if the in situ linked connections of the first and second silicone polymers and the base compound produces a silicone network coating or with the organic polymer produces an organic-silicone network that does not exhibit the foregoing desirable qualities, a plasticizer can be added to lower the Tg of this linked silicone network.

B. Plasticizer

If the glass transition temperature of the linked polymer network coating is too high for the desired use yet the other properties of the polymer coating are appropriate, such as but not limited to color and wash fastness, one or more plasticizers can be combined with the multicomponent composition embodiments so as to lower the $T_g$ of the components or the linked network coating and provide the appropriate feel and visual properties to the coating. The plasticizer can be incorporated directly in the coloring composition or can be applied to the in situ hair before or after the coloring composition. The plasticizer can be chosen from the plasticizers usually used in the field of application.

The plasticizer or plasticizers can have a molecular mass of less than or equal to 5,000 g/mol, such as less than or equal to 2,000 g/mol, for example less than or equal to 1,000 g/mol, such as less than or equal to 900 g/mol. In at least one embodiment, the plasticizer, for example, has a molecular mass of greater than or equal to 40 g/mol.

Thus, the multicomponent composition can also comprise at least one plasticizer. For example, non-limiting mention can be made, alone or as a mixture, of common plasticizers such as: glycols and derivatives thereof, silicones, silicone polyethers, polyesterpolyols; adipic acid esters (such as diisodecyladipate), trimellitic acid esters, sebacic acid esters, azalaeic acid esters; nonlimiting examples of glycol derivatives are diethylene glycol ethyl ether, diethylene glycol methyl ether, diethylene glycol butyl ether or diethylene glycol hexyl ether, ethylene glycol ethyl ether, ethylene glycol butyl ether, or ethylene glycol hexyl ether; polyethylene glycols, polypropylene glycols, polyethylene glycol-polypropylene glycol copolymers, and mixtures thereof, such as high molecular weight polypropylene glycols, for example having a molecular mass ranging from 500 to 15,000, for instance glycol esters; propylene glycol derivatives such as propylene glycol phenyl ether, propylene glycol diacetate, dipropylene glycol ethyl ether, tripropylene glycol methyl ether, diethylene glycol methyl ether, and dipropylene glycol butyl ether. Such compounds are sold by Dow Chemical under the names DOWANOL PPH and DOWANOL DPnB; acid esters, for example esters of carboxylic acids, such as triacids, citrates, phthalates, adipates, carbonates, tartrates, phosphates, and sebacates; esters derived from the reaction of a monocarboxylic acid of formula $R_{11}COOH$ with a diol of formula $HOR_{12}OH$ in which $R_{11}$ and $R_{12}$, which can be identical or different, are chosen from a linear, branched or cyclic, saturated, or unsaturated hydrocarbon-based chain containing, for example, from 3 to 15 carbon atoms for example the monoesters resulting from the reaction of isobutyric acid and octanediol such as 2,2,4-trimethyl-1,3-pentanediol, such as the product sold under the reference TEXANOL ESTER ALCOHOL by the company Eastman Chemical; oxyethylenated derivatives, such as oxyethylenated oils, such as plant oils, such as castor oil; mixtures thereof.

Among the esters of tricarboxylic acids mention can be made of the esters of triacids wherein the triacid corresponds to formula

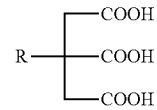

wherein R is a group —H, —OH or —OCOR' wherein R' is an alkyl group containing from 1 to 6 carbon atoms. For example, R can be a group —OCOCH$_3$. The esterifying alcohol for such tricarboxylic acids may be those described above for the monocarboxylic acid esters.

The plasticizer can be present in the composition of the present disclosure in an amount from about 0.01% to 20%.

Exemplary Embodiments

Exemplary embodiments of a multicomponent composition may be depicted as first and second components with reactive organosiloxane monomeric units and a third component with an amine base compound. While the examples can be refrained to depict any of the complementary reactive pairs or self-reactive functional groups described above, a first illustration of the first and second silicone polymer in situ reaction incorporates a first silicone polymer with first reactive organosiloxane monomeric units bearing isocyanate as the functional group X and a second silicone polymer with a second reactive organosiloxane monomeric units bearing hydroxyl as the second functional group Y. A second illustration is composed of a first silicone polymer with first reactive organosiloxane monomeric units bearing epoxy as the functional group X and a second silicone polymer with a second reactive organosiloxane monomeric units bearing amine as the second functional group Y. A third illustration is composed of a first silicone polymer with first reactive organosiloxane monomeric units bearing acrylyloxy as the functional group X and a second silicone polymer with a second reactive organosiloxane monomeric units bearing amine as the second functional group Y. In all illustrations, the base compound may be an organic amine polymer, polyethyleneimine or may alternatively be a mercaptosilane such as KBE 803 from Shin Etsu.

For the isocyanate version of this composition, the first and second silicone polymers and base compound may be selected as follows:
  i) a silicone polymer bearing pendant hydroxyalkyl groups, Silmer OHT C50 and
  ii) a silicone polymer bearing pendant isocyanate groups, Silmer NCO Di 50 and
  iii) polyethylene imine Epomin P-1050.

For the epoxy silicone version of this composition, an example is
  i) silicone polymer bearing pendant epoxy groups, Silmer EP C50 from Siltech,
  ii) a quasi-reactive amino silicone, for example Silmer NH C50 from Siltech, optionally in the presence of a Lewis acid catalyst such as K-Pure CXC-1613 from King Industries; and,
  iii) polyethylene imine Epomin P-1050 The acryloyl version of this embodiment is exemplified by
  i) a silicone acrylate, for example Silmer OH ACR Di10 from Siltech,
  ii) quasi-reactive amino silicone described above, e.g., Formula X, for example, Silmer NH Di8 from Siltech Formula X

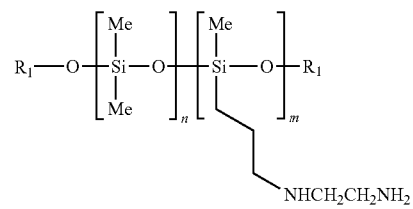

Formula X and
  iii) polyethylene imine Epomin P-1050.

Such systems can be optimized by selecting the degree of functionality of the isocyanate and hydroxy groups, the epoxy and amine groups or the acrylyloxy and amine groups of the two silicones, the concentration of the amines of the polyethylene imine and the relative ratio among these three starting materials.

Idealized reaction depictions of these three versions of these exemplary embodiments are presented by reaction schemes 20, 30 and 40. The combination of the base compound is omitted. It will react with the isocyanate, the epoxy and the acrylate as depicted for the reactions of these groups with the functional group partner of the complementary reactive pair. For the isocyanate, Scheme 20 the amine base compound will produce urea linking groups in addition to the urethane groups show.

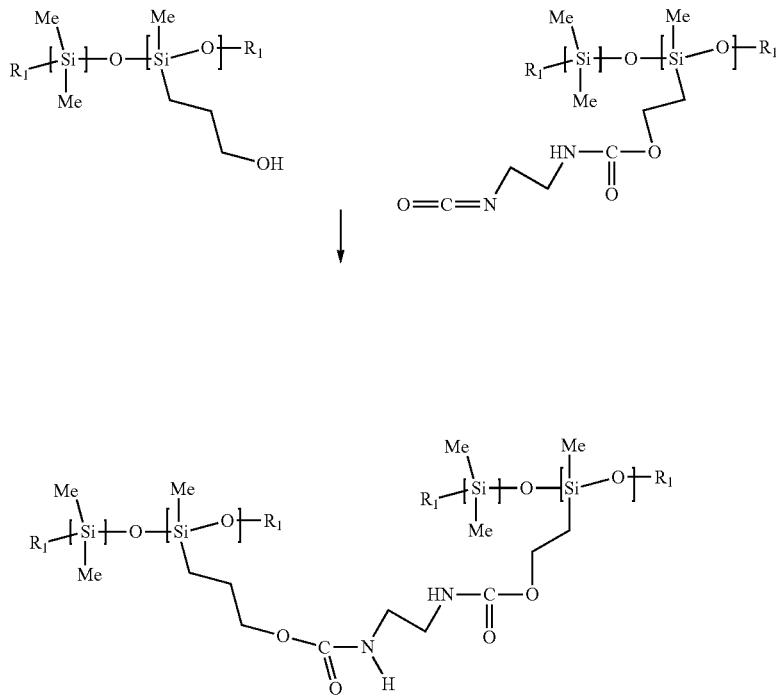

Scheme 20

For Scheme 30, the amine base compound can be considered to be the same aminosilicone used as the second silicone polymer.
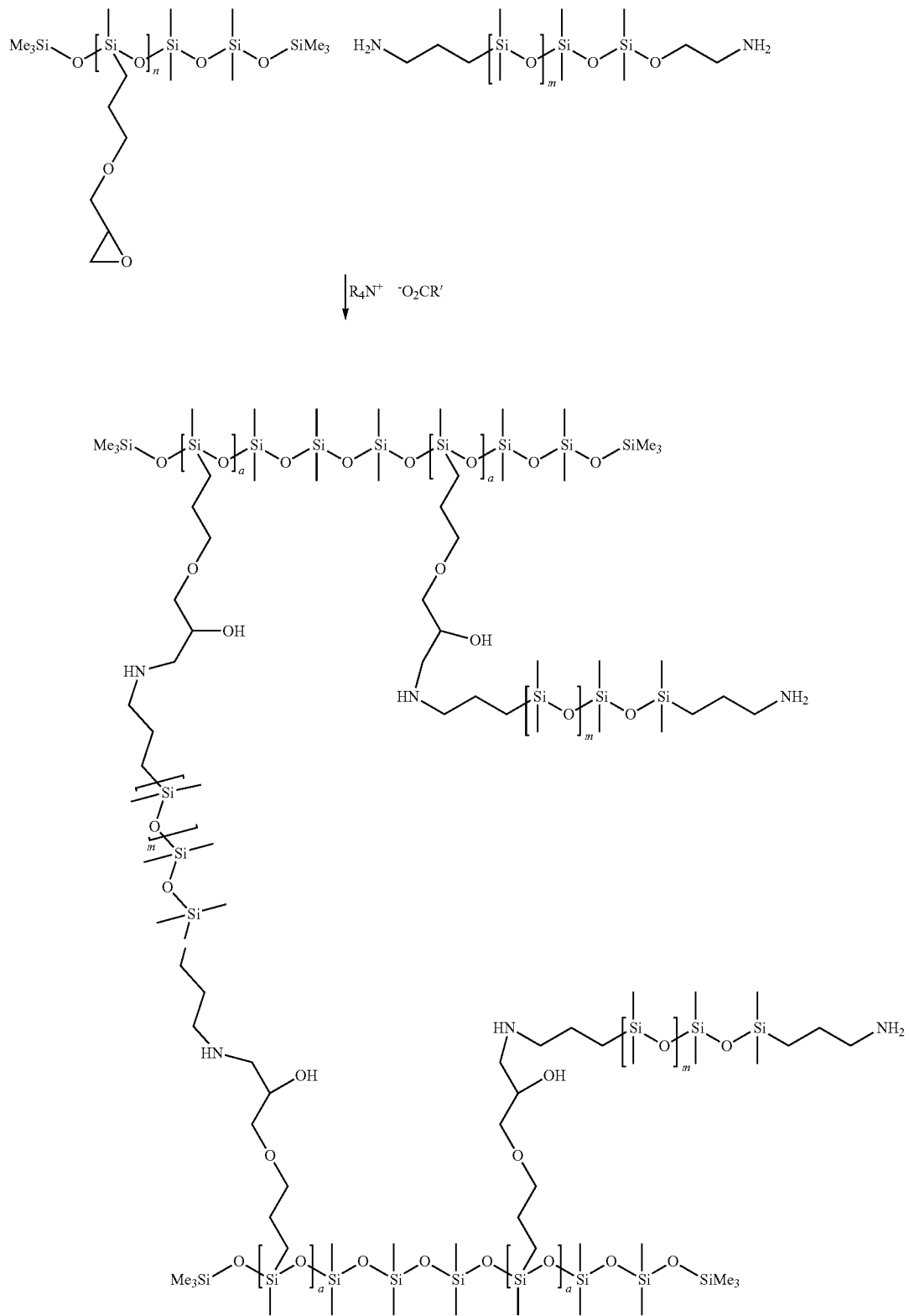

For Scheme 40 an amino base compound such as polyethyleneimine will produce the same Michael addition product shown for addition of the amino silicone to the acryloyl group.
Scheme 40
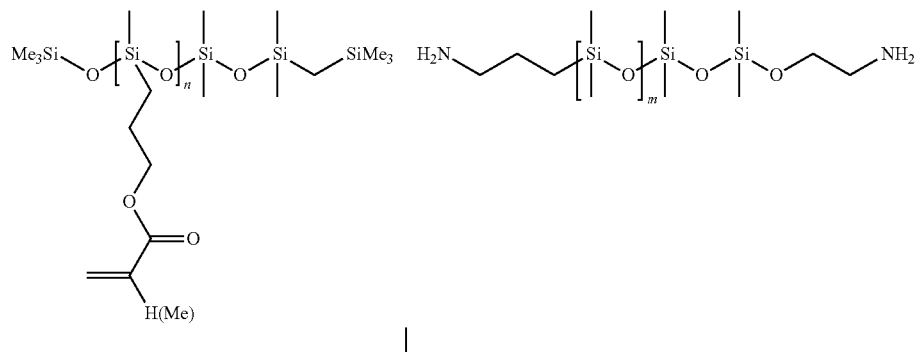
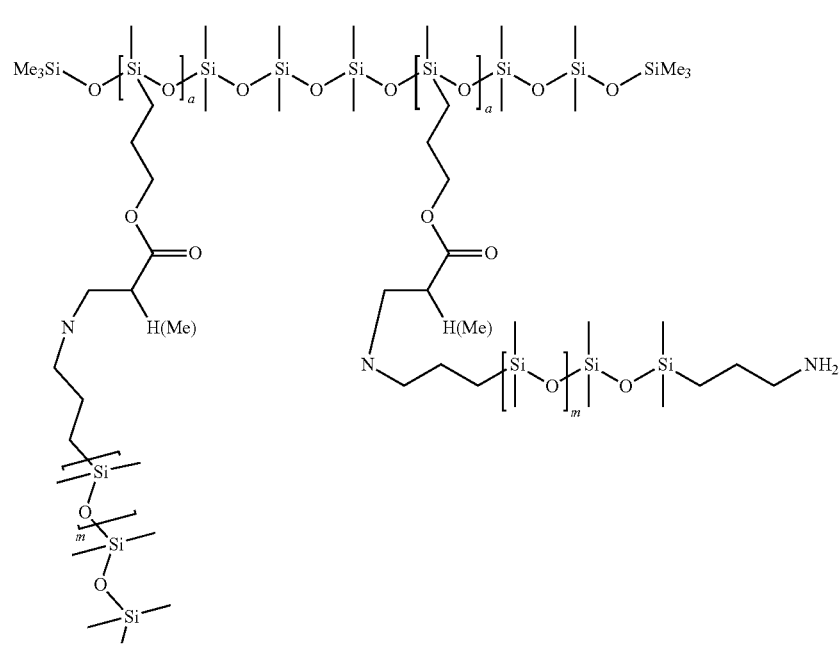
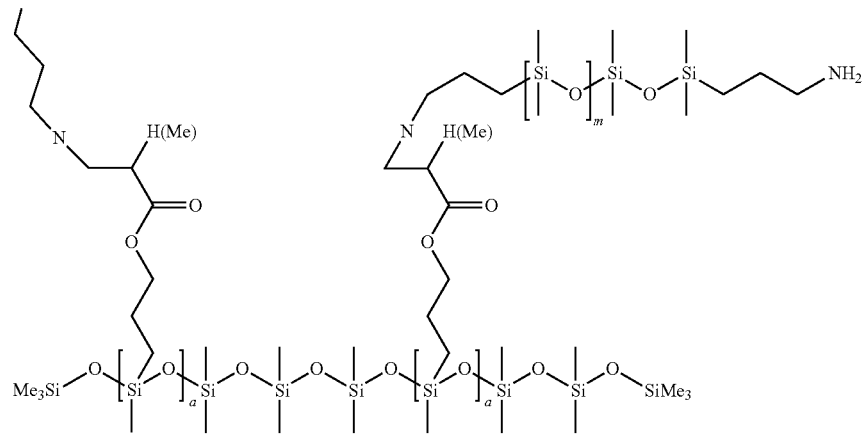

Another Preferred Embodiment

A preferred embodiment of the multicomponent composition comprises a first component containing a first silicone polymer with isocyanate reactive organosiloxane units of foregoing paragraph 0075(i); and a second component containing a second silicone polymer with hydroxyl reactive siloxane units of foregoing paragraph 0081(i) or containing a second silicone polymer with amine reactive siloxane units of foregoing paragraph 0079(i). The third component is poly ethyleneimine.

Viscosity, Composition Concentrations

The viscosity of the composition functions to hold the composition with pigment microparticles in place on the substrate material while the in situ linked coating is formed. The viscosity substantially avoids free translational flow of the composition. Free translation flow would cause the composition to rapidly run and drip off the surfaces of the hair strands. Nevertheless, the viscosity is not so high that it will not undergo self-leveling to substantially uniformly coat the substrate material. Appropriate viscosity of the composition is the result of the interaction of the first and second silicone polymers and the base compound, their concentrations, the pigment microparticles, and as appropriate, an optional viscosity control agent, an optional suspending agent and an optional thickening agent. Generally, the viscosity of the composition may range from about 0.1 to about 200 Pa s$^{-1}$, preferably 1 to 100 Pa s$^{-1}$, more preferably 10 to 75 Pa s$^{-1}$. Viscosity measurements are carried out on a controlled stress rheometer eg. Using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 sec$^{-1}$ shear rate is obtained from the shear stress vs. shear rate curve, and the corresponding viscosity is calculated by dividing the obtained shear stress by 10.

The concentration of each of the first and second silicone polymers in the multicomponent composition with first, second and third components may range from about 0.25% to about 20%, preferably about 0.5% to about 15%, more preferably about 0.75% to about 10% relative to the total weight of the multicomponent composition. A preferred concentration of the combination of the first and second silicone polymers in the multicomponent composition with first, second and third component ranges from about 0.5% to about 35%, more preferably about 1.0% to about 25% and most preferably about 1.5% to about 15% by weight relative to the total weight of the multicomponent composition.

C. Medium

The medium of the multicomponent composition embodiments of the invention may be water alone, water in mixture with a volatile polar protic or aprotic organic solvent, or a non-aqueous non-polar solvent or a mixture of non-aqueous solvents with polar protic or aprotic non-polar organic solvent, a volatile low Mw silicone solvent or a mixture of such a volatile silicone solvent with a non-polar non-protic organic solvent or a polar, protic organic solvent or mixtures thereof. In general, the medium is any solvent suitable for dispersing the silicone polymers and the base compound of the embodiments of the multicomponent composition described herein. In addition to water present in the medium, a volatile solvent may be present including a volatile polar protic or aprotic organic solvent, or a silicone solvent or mixtures thereof. Volatile organic solvents of which non-limiting mention may be made include: volatile pyrolidones 1-methylpyrrolidin-2-one, volatile C1-C4 alkanols such as methanol, ethanol or isopropanol; esters of liquid C2C6 acids and of volatile $C_1$-$C_8$ alcohols such as methyl acetate, n-butyl acetate, ethyl acetate, propyl acetate, isopentyl acetate, or ethyl 3-ethoxypropionate; ketones that are liquid at room temperature and volatile, such as methyl ethyl ketone, methyl isobutyl ketone, diisobutyl ketone, isophorone, cyclohexanone, or acetone; volatile polyols such as ethylene glycol and propylene glycol. Additional solvents include cyclic silicone solvents such as decamethylcyclopentasiloxane, octamethylcyclotetrasiloxane, dowsil polymethyl siloxanes.

According to at least one embodiment of the present disclosure, the organic solvent is chosen from ethanol, isopropanol, acetone, and isododecane.

The medium may be present in the composition according to the present disclosure in an amount ranging from about 0.1% to about 95% by weight, such as from about 1% to about 70% by weight, for example ranging from 5% to 90% by weight relative to the total weight of the composition.

D. Pigments

The color composition embodiments of the present invention make it possible to obtain colored and remnant coatings, without substantially altering the keratin fibers. As used herein, the term "pigment" generally refers to any particle colorant having or containing pigment material that gives hair fibers color including black and white, such as titanium dioxide that give only white to hair fibers. The pigments, to distinguish from dyes presented in molecular from, are also referred to as pigment microparticles or pigment particles. The terms pigment microparticles and pigment particles are synonymous and are used herein interchangeably. The pigments can be organic, inorganic, or a combination of both. The pigments may be in pure form or coated, for example with a polymer or a dispersant.

Selections, multiple kinds and varying forms of the pigment microparticles as described in the following passages can be incorporated in any of the first, second and third components of the multicomponent composition, or can be incorporated in any two of these components or in all three. Preferably, pigment microparticles can be incorporated in either or both of the first and second components. More preferably, pigment particles can be incorporated in the first component.

The at least one pigment that can be used can be chosen from the organic and/or mineral pigments known in the art, such as those described in Kirk-Othmer's Encyclopedia of Chemical Technology and in Ullmann's Encyclopedia of Industrial Chemistry. The pigments comprised in the microparticles comprising at least one pigment will not substantially diffuse or dissolve into keratin fibers. Instead, the pigment comprised in the microparticles comprising at least one pigment will substantially remain separate from but attached to the keratin fibers.

The at least one pigment can be in the form of powder or of pigmentary paste. It can be coated or uncoated. The at least one pigment can be chosen, for example, from mineral pigments, organic pigments, elemental metal and their oxides, and other metal modifications, lakes, pigments with special effects such as nacres or glitter flakes, and mixtures thereof.

Pigment Shape

The pigment microparticles can have any suitable shape, including substantially spherical. But the pigment microparticles can also be oval, elliptical, tubular, irregular, etc., or even combinations of various shapes. In addition, the pigment microparticles can have two dimensions, length and width/diameter, of similar magnitude. In addition, the pigment microparticles can be micro platelets, i.e. having a thickness that is substantially smaller than the planar dimension. For example, five, ten or even 20 times smaller in thickness than in the planer dimension. In one embodiment with any of the reactive components of the instant invention, the pigments may be surface treated, surface coated or encapsulated.

In a particular aspect, the pigment microparticles can have a shape approximating that of a sphere, in which case the microparticles are referred to as being microspheres. Pigment microparticles which can be described as microspheres are understood as particles having an aspect ratio, defined as a function of the largest diameter, or largest dimension, dmax and the smallest diameter, or smallest dimension, dmin, which can be orthogonal to each other: AR=dmax/dmin which is from about 1:1 to 10:1, preferably from 1:1 to 5:1, more preferably from 1:1 to 4:1, such as from 1:1 to 3:1. More particularly, the expression "spherical-type" means that the pigment microparticles have a shape approximating that of a sphere. In other words, the pigment microparticles can be nearly orbicular in shape and can have a cross-sectional geometry that is essentially circular. Although not excluded, this does not necessarily mean that the pigment microparticles have the shape of a perfect sphere or ball. More likely, the shape of the pigment microparticles can exhibit a certain deviation from a sphere as long as the skilled person considers the shape as being similar to a sphere or as an approximation of a sphere.

In addition, the pigment microparticles can have a rather two-dimensional shape, with the smallest dimension substantially smaller than the two other dimensions, in which case the microparticles are referred to as being 2-dimensional microparticles. For example, the thickness of the microparticles can be significantly less than their length and width. The length and width can be of similar magnitude. Examples includes pigment microparticles having a shape of platelets, i.e. with a thickness that is substantially smaller than the planar dimension. For example, the aspect ratio AR=dmax/dmin, as defined above, of microparticles having a substantially two-dimensional shape, can be from about 10:1 to about 1000:1, preferably from about 10:1 to about 800:1, preferably from about 20:1 to about 800:1, preferably from about 10:1 to about 600:1, preferably from about 20:1 to about 600:1. Typically, the 2D-microparticles have a largest and a smallest dimension in their planer dimension, which both are significantly larger than the smallest dimension of the 2D-microparticles extending perpendicular to the planer dimension.

According to an embodiment, the pigments can include pigment microparticles of different shape. For example, microparticles of different size can be used to provide different reflecting and absorbing properties. Microparticles having different shape can also be formed of different pigment material. Furthermore, microparticles having different shape can also formed of different pigment material to provide different color.

Pigment Size

The pigments can be present in the composition in undissolved form. Depending on the shape, the pigments can have a D50[vol] particle diameter of from 0.001 micron to 1 micron.

For example, pigments that can be described as being microspheres can have a D50[vol] particle diameter of from 0.01 micron to 1 micron, preferably of from 0.015 micron to 0.75 micron, more preferably of from 0.02 micron to 0.50 micron. The microspheres can also have a D50[vol] particle diameter of from 0.6 micron to 0.9 micron, preferably of from 0.08 micron to 0.9 micron, and more preferably between of from 0.08 micron to 0.9 micron, such as from 0.08 micron to 0.8 micron, or such as of from 0.8 micron to 0.6 micron. According to an embodiment, the microspheres can also have a D50[vol] particle diameter of from 0.1 micron to 1 micron, preferably of from 0.12 micron to 1 micron, and more preferably between of from 0.16 micron to 1 micron, such as of from 0.2 micron to 1 micron, or such as of from 0.08 micron to 0.4 micron. The terms "micron" and "microns" describe the size in micrometers [μm].

In further embodiments, which can be combined with other embodiments described herein, the pigments, which can be described as microspheres, can have a D90[vol] particle diameter of from 0.1 micron to 1 micron, preferably of from 0.2 micron to 1 micron, and more preferably between of from 0.3 micron to 1 micron, such as of from 0.3 micron to 0.9 micron, or such as of from 0.4 micron to 0.8 micron, or such as of from 0.5 micron to 0.9 micron.

In some embodiments described herein, the pigments, which can be described as microspheres, can have a D10[vol] particle diameter of from 0.02 micron to 0.3 micron, preferably of from 0.06 micron to 0.3 micron, more preferably of from 0.08 micron to 0.3 micron, such as of from 0.08 micron to 0.2 micron, or such as of from 0.1 micron to 0.2 micron, or such as 0.12 micron to 0.3 micron.

In embodiments described herein, the DIO[vol] particle diameter can be of from 0.02 micron to 0.3 micron and the D90[vol] can be of from 0.3 micron to 1 micron. In further embodiments, the D10[vol] particle diameter can be of from 0.06 micron to 0.2 micron and the D90[vol] can be of from 0.4 micron to 1 micron.

The particle diameter is represented by D10, D50 and/or by D90, which is the median diameter by volume. D10, D50 and D90 is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.01 micron to 2000 micron. D50 is expressed as x50 in ISO 13320:2009(en).

The term "D10," as used herein refers, to the 10th percentile number- or volume-based median particle diameter, which is the diameter below which 10% by number or volume of the particle population is found. The term "D50," as used herein refers, to the 50th percentile number- or volume-based median particle diameter, which is the diameter below which 50% by number or volume of the particle population is found. The term "D90," as used herein refers, to the 90th percentile number- or volume-based median particle diameter, which is the diameter below which 90% by number or volume of the particle population is found. The number or volume measurement is indicated by [num] for number or [vol] for volume. If not indicated otherwise, the particle size is given as D10[vol], D50[vol], and D90[vol], respectively.

Laser diffraction measures particle size distributions by measuring the angular variation in intensity of light scattered as a laser beam passes through a dispersed particulate sample analyzer and the particle size is reported as a volume equivalent sphere diameter. A discussion of calculating D50 is provided in Barber et al, Pharmaceutical Development and Technology, 3(2), 153-161 (1998), which is incorporated herein by reference. Pigment microparticles having a D50[vol] particle diameter of less than 20 nm may enter the cuticles and are therefore difficult to remove. For scattering purposes, Pigment(s) having a D10[vol] particle diameter of at least 60 nm, or at least 80 nm can be used. Pigment(s) having a D50[vol] particle diameter of more than 1 micron typically do not sufficiently adhere onto hair fibers.

According to an embodiment, the particle size distribution, either relative to the number or volume of the particles, of the pigment microparticles can be at least bi-modal. A bi-modal particle size distribution has two distinct peaks which are spaced relative from, while tri-modal particle size distribution has three distinct peaks. The term "peak" means a local maximum of the distribution curve. The "distance" between two peaks, expressed relative to the particle size, can be at least 0.05 micron, preferably at least 0.1 micron, such as at least 0.2 micron. Providing an at least bi-modal particle size distribution allows to tailor the optical appearance of the colored hair. For example, the scattering properties varies with the particle size so that particles of different size scatter the light into different directions.

The at least bi-modal particle size distribution can be relative to pigment microparticles formed by the same pigment material. In addition to that or alternatively, the at least bi-model particle size distribution can be provided by pigment microparticles of different pigment material.

The size of pigment microparticles which can be described to have a 2-dimensional shape, and which are referred to as 2-dimensional microparticles can be determined by SEM. The size of 2-dimensional microparticles can also be determined by laser diffraction measurements. The particle size determined by laser diffraction is a mean size of the different dimensions of the 2-dimensional particles. The apparent D50[vol] particle diameter of 2-dimensional microparticles, as measured by SEM, can be from 0.5 micron to 50 microns, more preferably from 0.8 micron to 20 microns, more preferably from 1 micron to 15 microns, more preferably from 1.5 micron to 10 microns.

According to an embodiment, pigment particles are referred to as being microspheres can be used light-scattering and/or light absorbing purposes. Those particles, due to their pigment material, impart the hair with a specific color.

According to an embodiment, pigment particles are referred to as being 2-dimensional microparticles can be mainly used for light-reflecting and/or light absorbing purposes. Those particles, due to their pigment material, mainly reflect the light without significantly alter the color of the light.

The pigment microparticles can be light absorbing, but which for wavelengths of visible light provide negligible to low or no scattering. While not wishing to bound by any specific theory, it is believed that such pigments can provide more chromatic colors. Such pigment microparticles can have a D50[vol] value between about 0.001 micron and about 0.15 micron, between about 0.005 micron and about 0.1 micron or between about 0.010 micron and about 0.075 micron.

The pigment microparticles can be predominantly light scattering for wavelengths of visible light and provide low light absorption. While not wishing to bound by any specific theory, it is believed that such pigments can provide the visual effect of lightening the hair. Such pigment microparticles, which can be microspheres, can have a D50[vol] value between about 0.05 micron to about 1 micron, between 0.08 micron to about 0.9 micron, between about 0.05 micron and about 0.75 micron, between about 0.1 micron and about 0.5 micron or about 0.15 micron and about 0.4 micron. Such materials can have a refractive index above 1.5, above 1.7 or above 2.0.

Pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal.

Such pigment microparticles can be platelets, e.g., having a thickness that is substantially smaller than the planar dimension. For example about five, about 10 or even about 400 times smaller in thickness than in the planer. Such platelets can have a planar dimension less than about 30 nm, but with a thickness less than about 10 micron wide. This includes a ratio of 10000 to 30, or 333. Platelets larger in size, such as 50 microns are even available in this thickness of 10 microns, and so the ratios can even go up to 2000.

The pigment microparticles can be a composite formed by two different types of pigment microparticles. Examples include a composite of a 2-dimensional microparticle and at least one micro spherical particle (microsphere), a composite of different micro spherical particles, and a composite of different 2-dimensional particles. Composite particles formed by 2-dimensional microparticles to which micro spherical particles adhere provide an attractive alternative to a pure mixture of 2-dimensional microparticles and micro spherical particles. For example, a metallic 2-dimensional microparticle can carry one or more micro spherical particle such as one or more organic micro spherical particle. The micro spherical particles attached or bonded to the 2-dimensional microparticle can be formed of the same pigment material or can be formed of different pigment material. Composite microparticles formed of 2-dimensional microparticles and micro spherical particles can provide multiple functionality in one particle such as (metallic) reflectance and dielectric scattering, reflectance and absorption.

Pigment microparticles may be materials which are composite comprising a core of pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Upon this pigment light absorbing microparticles is immobilized. Such pigment microparticles can be platelets, e.g., having a thickness that is substantially smaller than the planar dimension. For example, five, ten or even 20 times smaller in thickness than in the planer. Such platelets can have a planer dimension less than 15 microns, but with a thickness less than 1 microns, more preferably with a planer dimension less than 12 microns but with a thickness less than 750 nm, even more preferably with a plan dimension less than 10 microns and a thickness less than 0.5 micron. The light absorbing microparticles can have D50[vol] value between 0.001 micron and 0.15 micron, more preferably between 0.002 micron and 0.1 micron and even more preferable between 0.005 micron and 0.075 micron.

The light absorbing microparticles may also include dyes, pigments, or materials with color centers in the crystal structure, or photonic structures resulting in destructive or constructive interference, diffraction or other structures and materials mentioned in the book "The Physics and Chemistry of Color: the Fifteen Causes of Color", 2$^{nd}$ Edition by K. I. Nassau (ISBN 978-O-471-39106-7).

The pigment microparticles can be both light scattering and absorbing for wavelengths of visible light. While not wishing to bound by any specific theory, it is believed that such pigments can provide both some visual effect of lightening the hair. Such pigment microparticles can have a D50[num] value between about 50 nm and about 750 nm, between about 100 nm and about 500 nm or between about 150 nm and about 400 nm. Such materials have a refractive index above about 1.5, above about 1.7 or above about 2.0.

According to an embodiment, different pigment microparticles are combined to provide reflective, transmitting and refractive properties of the hair colored with the color composition described herein. A microparticle combination can be a material composite using at least two different pigment materials to form the pigment microparticles. In addition to, or alternating to, the microparticle combination, a mixture of separate pigment microparticles of different type can be used to bring about the desired reflective, transmitting and refractive properties.

The composite pigments, combination of pigments, and mixtures of pigment microparticles eliminate, or at least significantly reduce, hair penetration and scattering by light and thus eliminate the perception of pigment of natural hair color change.

Pigment Concentration

The color composition for coloring hair fibers according to the present disclosure comprises microparticles comprising at least one pigment. The color composition comprises from about 0.01% to about 40%, about 0.05% to about 35%, about 0.1 to about 25%, or about 0.15% and about 20% pigment(s), by weight of the color composition.

Pigment Material

The material of the pigment microparticles can be inorganic or organic. Inorganic-organic mixed pigments are also possible.

According to an embodiment, inorganic pigment(s) are used. The advantage of inorganic pigment(s) is their excellent resistance to light, weather, and temperature. The inorganic pigment(s) can be of natural origin, and are, for example, derived from material selected from the group consisting of chalk, ochre, umber, green earth, burnt sienna, and graphite. The pigment(s) can preferably be white pigments, such as, for example, titanium dioxide or zinc oxide. The pigment(s) can also be colored pigments, such as, for example, ultramarine or iron oxide red, luster pigments, metal effect pigments, pearlescent pigments, and fluorescent or phosphorescent pigments. The pigment(s) can be selected from the group consisting of metal oxides, hydroxides and oxide hydrates, mixed phase pigments, sulfur-containing silicates, metal sulfides, complex metal cyanides, metal sulfates, chromates and molybdates, alloys, and the metals themselves. The pigment(s) can be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), zinc sulfide, barium sulfate, zinc oxide, siliconised titanium dioxide, siliconised zinc sulfide, siliconised zinc oxide, and mixtures thereof. The pigment(s) can be selected from the group consisting of iron oxide, titanium dioxide, mica, borosilicate, and combinations thereof. The pigment(s) can comprise an iron oxide ($Fe_2O_3$) pigment. The pigment(s) can comprise a combination of mica and titanium dioxide.

The pigment(s) can be pearlescent and colored pigment(s), and can preferably be based on mica which are coated with a metal oxide or a metal oxychloride, such as titanium dioxide or bismuth oxychloride, and optionally further color-imparting substances, such as iron oxides, Prussian blue, ultramarine, and carmine. The color exhibited by a pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for color travel pigments that display color shifting effects depending on the viewing angle and are based on either natural mica, $SiO_2$ or calcium aluminum borosilicate flakes, coated with varying layers of $TiO_2$. Pigment(s) from the line KTZ® from Kobo Products, Inc., 3474 So. Clinton Ave., So. Plainfield, USA, are also useful herein, in particular the Surface Treated KTZ® Pearlescent Pigments from Kobo. Particularly useful are KTZ® FINE WHITE (mica and $TiO_2$) having a D50 particle diameter of 5 to 25 micron and also KTZ® CELESTIAL LUSTER (mica and $TiO_2$, 10 to 60 micron) as well as KTZ® CLASSIC WHITE (mica and $TiO_2$, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection color and is composed of platelets of synthetic fluorphlogopite and coated with titanium dioxide and iron oxides. Also useful is Duocrome® RV 524C from BASF, which provides a two color look via a lustrous red powder with a violet reflection powder due to its composition of mica, titanium dioxide and carmine. The colored pigment(s) can be lightly bright colored pigment(s), and can particularly be white color variations.

The pigment(s) can be organic pigments. The at least one pigment can be an organic pigment. As used herein, the term "organic pigment" means any pigment that satisfies the definition in Ullmann's encyclopedia in the chapter on organic pigments. For instance, the at least one organic pigment can be chosen from nitroso, nitro, azo, xanthene, quinoline, anthraquinone, phthalocyanin, copper phthalocyanin, copper hexadecachlorophthalocyanine, 2-[(2-Methoxy-4-nitrophenyl)azo]-N-(2-methoxyphenyl)-3-oxobutyramide, metal-complex, isoindolinone, isoindoline, quinacridone, perinone, perylene, diketopyrrolopyrrole, thioindigo, dioxazine, triphenylmethane, dimethylquinacridone and quinophthalone compounds, Azo-dyes, Nonionic azo dyes, Anionic Azo dyes, Cationic azo dyes, Complex forming azo dye, aza annulene dyes, aza analogue of diarylmethane dyes, aza annulene dyes, Nitro-dyes and their pigments, Carbonyl dyes and their pigments (for example, Anthrachinon dyes, indigo), Sulfur dyes, Florescence dyes, Anthracene or Insoluble alkali or earth metal acid dyes.

Or the pigment can be at least one of uncolored and UV absorbing.

The organic pigment(s) can be selected from the group consisting of natural pigments sepia, gamboge, bone charcoal, Cassel brown, indigo, chlorophyll and other plant pigments. The synthetic organic pigments can be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof. A particularly preferred pigment is 7-Bis(1,3-dichloropropan-2-yl)benzo[lmn][3,8]phenanthrolin-1,3,6,8(2H,7H)-tetraon.

According to an embodiment, the pigment(s) can be selected from the pigment group consisting of, including any combination thereof (with CI meaning color index and CAS meaning Chemical Abstract Service Number)
Pigment Black 10 [C.I. 77265, (CAS: 7782-42-5)], Pigment Black 11 [C.I. 77499, (CAS: 12227-89-3)], Pigment Black 12 [C.I. 77543, (CAS: 68187-02-0)], Pigment Black 13 [C.I. 77322, (CAS: 1307-96-6)], Pigment Black 14 [C.I. 77728, (CAS: 83512-98-5)], Pigment Black 15 [C.I. 77403, (CAS: 1317-38-0)], Pigment Black 17 [C.I. 77975, (CAS: 1314-98-3)], Pigment Black 18 [C.I. 77011, (CAS: 12001-98-8)], Pigment Black 23 [C.I. 77865, (CAS: 68187-54-2)], Pigment Black 24 [C.I. 77898, (CAS: 68187-00-8)], Pigment Black 25 [C.I. 77332, (CAS: 68186-89-0)], Pigment Black 26 [C.I. 77494, (CAS: 68186-94-7)], Pigment Black 27 [C.I. 77502, (CAS: 68186-97-0)], Pigment Black 28 [C.I. 77428, (CAS: 68186-91-4)], Pigment Black 29 [C.I. 77498, (CAS: 68187-50-8)], Pigment Black 30 [C.I. 77504, (CAS: 71631-15-7)], Pigment Black 31 [C.I. 71132, (CAS: 67075-37-0)], Pigment Black 32 [C.I. 71133, (CAS: 83524-75-8)], Pigment Black 33 [C.I. 77537, (CAS: 188735-18-4)], Pigment Black 34 [C.I. 77770, (CAS: 1317-33-5)], Pigment Black 6 [C.I. 77266, (CAS: 1333-86-4)], Pigment Black 7 [C.I. 77266, (CAS: 1333-86-4)], Pigment Black 8 [C.I. 77268, (CAS: 1339-82-8)], Pigment Black 9 [C.I. 77267, (CAS: 8021-99-6)], Pigment Blue 10 [C.I. 44040, (CAS: 1325-93-5)], Pigment Blue 15 [C.I. 74160, (CAS: 147-14-8)], Pigment Blue 16 [C.I. 74100, (CAS: 574-93-6)], Pigment Blue 18 [C.I. 42770, (CAS: 1324-77-2)], Pigment Blue 21 [C.I. 69835, (CAS: 1324-26-1)], Pigment Blue 22 [C.I. 69810, (CAS: 1324-27-2)], Pigment Blue 25 [C.I. 21180, (CAS: 10127-03-4)], Pigment Blue 26 [C.I. 21185, (CAS: 5437-88-7)], Pigment Blue 28 [C.I. 77346, (CAS: 1345-16-0)], Pigment Blue 29 [C.I. 77007, (CAS: 57455-37-5)], Pigment Blue 30 [C.I. 77420, (CAS: 1339-83-9)], Pigment Blue 32 [C.I. 77365, (CAS: 69458-70-4)], Pigment Blue 33 [C.I. 77112, (CAS: 8046-59-1)], Pigment Blue 34 [C.I. 77450, (CAS: 1317-40-4)], Pigment Blue 35 [C.I. 77368, (CAS: 83712-59-8)], Pigment Blue 36 [C.I. 77343, (CAS: 68187-11-1)], Pigment Blue 56 [C.I. 42800, (CAS: 6417-46-5)], Pigment Blue 57 [C.I. 42795, (CAS: 5905-38-4)], Pigment Blue 60 [C.I. 69800, (CAS: 81-77-6)], Pigment Blue 61 [C.I. 42765, (CAS: 1324-76-1)], Pigment Blue 62 [C.I. 42595, (CAS: 82338-76-9)], Pigment Blue 63 [C.I. 73015, (CAS: 16521-38-3)], Pigment Blue 64 [C.I. 69825, (CAS: 130-20-1)], Pigment Blue 65 [C.I. 59800, (CAS: 116-71-2)], Pigment Blue 66 [C.I. 73000, (CAS: 482-89-3)], Pigment Blue 71 [C.I. 77998, (CAS: 68186-95-8)], Pigment Blue 72 [C.I. 77347, (CAS: 68186-87-8)], Pigment Blue 73 [C.I. 77364, (CAS: 68187-40-6)], Pigment Blue 74 [C.I. 77366, (CAS: 68412-74-8)], Pigment Blue 75 [C.I. 74160, (CAS: 3317-67-7)], Pigment Blue 76 [C.I. 742520, (CAS: 176365-61-0)], Pigment Blue 78 [C.I. 42090, (CAS: 68921-42-6)], Pigment Blue 79 [C.I. 741300, (CAS: 14154-42-8)], Pigment Blue 9 [C.I. 42025B, (CAS: 596-42-9)], Pigment Brown 1 [C.I. 12480, (CAS: 6410-40-8)], Pigment Brown 10 [C.I. 77227, (CAS: 12013-69-3)], Pigment Brown 11 [C.I. 77495, (CAS: 64294-89-9)], Pigment Brown 2 [C.I. 12071, (CAS: 10279-43-3)], Pigment Brown 22 [C.I. 10407, (CAS: 29398-96-7)], Pigment Brown 23 [C.I. 20060, (CAS: 35869-64-8)], Pigment Brown 24 [C.I. 77310, (CAS: 68186-90-3)], Pigment Brown 26 [C.I. 71129, (CAS: 81-33-4)], Pigment Brown 27 [C.I. 73410, (CAS: 3989-75-1)], Pigment Brown 28 [C.I. 69015, (CAS: 131-92-0)], Pigment Brown 33 [C.I. 77503, (CAS: 68186-88-9)], Pigment Brown 34 [C.I. 77497, (CAS: 68187-10-0)], Pigment Brown 35 [C.I. 77501, (CAS: 68187-09-7)], Pigment Brown 37 [C.I. 77890, (CAS: 70248-09-8)], Pigment Brown 38 [C.I. 561660, (CAS: 126338-72-5)], Pigment Brown 39 [C.I. 77312, (CAS: 71750-83-9)], Pigment Brown 6 [C.I. 77491, 77492 and 77499, (CAS: 52357-70-7)], Pigment Brown 9 [C.I. 77430, (CAS: 8014-85-5)], Pigment Green 10 [C.I. 12775, (CAS: 61725-51-7)], Pigment Green 12 [C.I. 10020, (CAS: 84682-41-7)], Pigment Green 15 [C.I. 77600, (CAS: 12224-92-9)], Pigment Green 17 [C.I. 77288, (CAS: 1308-38-9)], Pigment Green 18 [C.I. 77289, (CAS: 12001-99-9)], Pigment Green 19 [C.I. 77335, (CAS: 8011-87-8)], Pigment Green 20 [C.I. 77408, (CAS: 8007-61-2)], Pigment Green 21 [C.I. 77410, (CAS: 12002-03-8)], Pigment Green 22 [C.I. 77412, (CAS: 1345-20-6)], Pigment Green 23 [C.I. 77009, (CAS: 1344-98-5)], Pigment Green 24 [C.I. 77013, (CAS: 1345-00-2)], Pigment Green 26 [C.I. 77344, (CAS: 68187-49-5)], Pigment Green 27 [C.I. 77520, (CAS: 15418-51-6)], Pigment Green 36 [C.I. 74265, (CAS: 14302-13-7)], Pigment Green 37 [C.I. 74255, (CAS: 1330-37-6)], Pigment Green 38 [C.I. 74265, (CAS: 14302-13-7)], Pigment Green 42 [C.I. 74260, (CAS: 1328-53-6)], Pigment Green 47 [C.I. 59825, (CAS: 128-58-5)], Pigment Green 50 [C.I. 77377, (CAS: 68186-85-6)], Pigment Green 51 [C.I. 77300, (CAS: 68553-01-5)], Pigment Green 54 [C.I. 59830, (CAS: 25704-81-8)], Pigment Green 58 [C.I. 742655, (CAS: 1143572-73-9)], Pigment Green 8 [C.I. 10006, (CAS: 16143-80-9)], Pigment Green 9 [C.I. 49415, (CAS: 1326-13-2)], Pigment Orange 1 [C.I. 11725, (CAS: 6371-96-6)], Pigment Orange 13 [C.I. 21110, (CAS: 3520-72-7)], Pigment Orange 14 [C.I. 21165, (CAS: 6837-37-2)], Pigment Orange 15 [C.I. 21130, (CAS: 6358-88-9)], Pigment Orange 16 [C.I. 21160, (CAS: 6505-28-8)], Pigment Orange 17 [C.I. 15510, (CAS: 15782-04-4)], Pigment Orange 17 [C.I. 15510, (CAS: 15876-51-4)], Pigment Orange 18 [C.I. 15970, (CAS: 1325-14-0)], Pigment Orange 19 [C.I. 15990, (CAS: 5858-88-8)], Pigment Orange 20 [C.I. 77202, (CAS: 12656-57-4)], Pigment Orange 21 [C.I. 77601, (CAS: 1344-38-3)], Pigment Orange 22 [C.I. 12470, (CAS: 6358-48-1)], Pigment Orange 23 [C.I. 77201, (CAS: 1345-09-1)], Pigment Orange 24 [C.I. 12305, (CAS: 6410-27-1)], Pigment Orange 3 [C.I. 12105, (CAS: 6410-15-7)], Pigment Orange 31 [C.I. 20050, (CAS: 5280-74-0)], Pigment Orange 34 [C.I. 21115, (CAS: 15793-73-4)], Pigment Orange 39 [C.I. 45370, (CAS: 15876-57-0)], Pigment Orange 4 [C.I. 12459, (CAS: 21889-27-0)], Pigment Orange 40 [C.I. 59700, (CAS: 128-70-1)], Pigment Orange 43 [C.I. 71105, (CAS: 4424-06-0)], Pigment Orange 44 [C.I. 21162, (CAS: 17453-73-5)], Pigment Orange 45 [C.I. 77601, (CAS: 59519-55-0)], Pigment Orange 46 [C.I. 15602, (CAS: 63467-26-5)], Pigment Orange 5 [C.I. 12075, (CAS: 3468-63-1)], Pigment Orange 6 [C.I. 12730, (CAS: 6407-77-8)], Pigment Orange 61 [C.I. 11265, (CAS: 40716-47-0)], Pigment Orange 64 [C.I. 12760, (CAS: 72102-84-2)], Pigment Orange 65 [C.I. 48053, (CAS: 20437-10-9)], Pigment Orange 66 [C.I. 48210, (CAS: 68808-69-5)], Pigment Orange 67 [C.I. 12915, (CAS: 74336-59-7)], Pigment Orange 68 [C.I. 486150, (CAS: 42844-93-9)], Pigment Orange 69 [C.I. 56292, (CAS: 85959-60-0)], Pigment Orange 7 [C.I. 15530, (CAS: 5850-81-7)], Pigment Orange 71 [C.I. 561200, (CAS: 84632-50-8)], Pigment Orange 72 [C.I. 211095, (CAS: 384329-80-0)], Pigment Orange 73 [C.I. 561170, (CAS: 84632-59-7)], Pigment Orange 75 [C.I. 772830, (CAS: 12014-93-6)], Pigment Orange 77 [C.I. 59105, (CAS: 1324-11-4)], Pigment Red 10 [C.I. 12440, (CAS: 6410-35-1)], Pigment Red 100 [C.I. 13058, (CAS: 6371-55-7)], Pigment Red 101 [C.I. 77491, (CAS: 1309-37-1)], Pigment Red 101 [C.I. 77015, (CAS: 529484-30-8)], Pigment Red 103 [C.I. 77601, (CAS: 59519-56-1)], Pigment Red 104 [C.I. 77605, (CAS: 12656-85-8)], Pigment Red 105 [C.I. 77578, (CAS: 1314-41-6)], Pigment Red 106 [C.I. 77766, (CAS: 1344-48-5)], Pigment Red 107 [C.I. 77060, (CAS: 1345-04-6)], Pigment Red 108 [C.I. 77202, (CAS: 58339-34-7)], Pigment Red 109 [C.I. 77482, (CAS: 1345-24-0)], Pigment Red 11 [C.I. 12430, (CAS: 6535-48-4)], Pigment Red 112 [C.I. 12370, (CAS: 6535-46-2)], Pigment Red 113 [C.I. 77201, (CAS: 1345-09-1)], Pigment Red 114 [C.I. 12351, (CAS: 6358-47-0)], Pigment Red 115 [C.I. 15851, (CAS: 6358-40-3)], Pigment Red 117 [C.I. 15603, (CAS: 10142-77-5)], Pigment Red 119 [C.I. 12469, (CAS: 72066-77-4)], Pigment Red 12 [C.I. 12385, (CAS: 6410-32-8)], Pigment Red 121 [C.I. 77302, (CAS: 12125-42-7)], Pigment Red 122 [C.I. 73915, (CAS: 980-26-7)], Pigment Red 13 [C.I. 12395, (CAS: 6535-47-3)], Pigment Red 133 [C.I. 15920, (CAS: 5280-67-1)], Pigment Red 14 [C.I. 12380, (CAS: 6471-50-7)], Pigment Red 141 [C.I. 20044, (CAS: 3864-06-0)], Pigment Red 144 [C.I. 20735, (CAS: 5280-78-4)], Pigment Red 146 [C.I. 12485, (CAS: 5280-68-2)], Pigment Red 147 [C.I. 12433, (CAS: 68227-78-1)], Pigment Red 148 [C.I. 12369, (CAS: 94276-08-1)], Pigment Red 149 [C.I. 71137, (CAS: 4948-15-6)], Pigment Red 15 [C.I. 12465, (CAS: 6410-39-5)], Pigment Red 150 [C.I. 12290, (CAS: 56396-10-2)], Pigment Red 151 [C.I. 15892, (CAS: 61013-97-6)], Pigment Red 157 [C.I. 12355, (CAS: 6471-49-4)], Pigment Red 16 [C.I. 12500, (CAS: 6407-71-2)], Pigment Red 162 [C.I. 12431, (CAS: 6358-59-4)], Pigment Red 163 [C.I. 12455, (CAS: 6410-37-3)], Pigment Red 164 [C.I. 212855, (CAS: 72659-69-9)], Pigment Red 166 [C.I. 20730, (CAS: 3905-19-9)], Pigment Red 168 [C.I. 59300, (CAS: 4378-61-4)], Pigment Red 169 [C.I. 45160, (CAS: 12237-63-7)], Pigment Red 17 [C.I. 12390, (CAS: 6655-84-1)], Pigment Red 170 [C.I. 12475, (CAS: 2786-76-7)], Pigment Red 170 [C.I. 12474, (CAS: 36968-27-1)], Pigment Red 171 [C.I. 12512, (CAS: 6985-95-1)], Pigment Red 172 [C.I. 45430, (CAS: 12227-78-0)], Pigment Red 173 [C.I. 45170, (CAS: 12227-77-9)], Pigment Red 174 [C.I. 45410, (CAS: 15876-58-1)], Pigment Red 175 [C.I. 12513, (CAS: 6985-92-8)], Pigment Red 177 [C.I. 65300, (CAS: 4051-63-2)], Pigment Red 179 [C.I. 71130, (CAS: 5521-31-3)], Pigment Red 18 [C.I. 12350, (CAS: 3564-22-5)], Pigment Red 181 [C.I. 73360, (CAS: 2379-74-0)], Pigment Red 184 [C.I. 12487, (CAS: 99402-80-9)], Pigment Red 185 [C.I. 12516, (CAS: 51920-12-8)], Pigment Red 187 [C.I. 12486, (CAS: 59487-23-9)], Pigment Red 188 [C.I. 12467, (CAS: 61847-48-1)], Pigment Red 189 [C.I. 71135, (CAS: 2379-77-3)], Pigment Red 19 [C.I. 12400, (CAS: 6410-33-9)], Pigment Red 190 [C.I. 71140, (CAS: 6424-77-7)], Pigment Red 192 [C.I. 739155, (CAS: 61968-81-8)], Pigment Red 193 [C.I. 16185, (CAS: 12227-62-2)], Pigment Red 195 [C.I. 70320, (CAS: 4203-77-4)], Pigment Red 196 [C.I. 67000, (CAS: 2379-79-5)], Pigment Red 198 [C.I. 73390, (CAS: 6371-31-9)], Pigment Red 2 [C.I. 12310, (CAS: 6041-94-7)], Pigment Red 200 [C.I. 15867, (CAS: 58067-05-3)], Pigment Red 200 [C.I. 15867, (CAS: 32041-58-0)], Pigment Red 202 [C.I. 73907, (CAS: 3089-17-6)], Pigment Red 208 [C.I. 12514, (CAS: 31778-10-6)], Pigment Red 21 [C.I. 12300, (CAS: 6410-26-0)], Pigment Red 210 [C.I. 12477, (CAS: 61932-63-6)], Pigment Red 211 [C.I. 15910, (CAS: 85702-54-1)], Pigment Red 212 [C.I. 12360, (CAS: 6448-96-0)], Pigment Red 214 [C.I. 200660, (CAS: 40618-31-3)], Pigment Red 216 [C.I. 59710, (CAS: 1324-33-0)], Pigment Red 22 [C.I. 12315, (CAS: 6448-95-9)], Pigment Red 220 [C.I. 20055, (CAS: 68259-05-2)], Pigment Red 221 [C.I. 20065, (CAS: 71566-54-6)], Pigment Red 222 [C.I. 123665, (CAS: 20981-12-8)], Pigment Red 224 [C.I. 71127, (CAS: 128-69-8)], Pigment Red 226 [C.I. 597200, (CAS: 72828-01-4)], Pigment Red 229 [C.I. 77006, (CAS: 85536-78-3)], Pigment Red 230 [C.I. 77003, (CAS: 68187-27-9)], Pigment Red 231 [C.I. 77005, (CAS: 68186-99-2)], Pigment Red 232 [C.I. 77996, (CAS: 68412-79-3)], Pigment Red 233 [C.I. 77301, (CAS: 68187-12-2)], Pigment Red 235 [C.I. 77290, (CAS: 68201-65-0)], Pigment Red 236 [C.I. 77863, (CAS: 68187-53-1)], Pigment Red 242 [C.I. 20067, (CAS: 52238-92-3)], Pigment Red 243 [C.I. 15910, (CAS: 50326-33-5)], Pigment Red 243 [C.I. 15910, (CAS: 431991-58-1)], Pigment Red 247 [C.I. 15915, (CAS: 43035-18-3)], Pigment Red 248 [C.I. 200552, (CAS: 80648-58-4)], Pigment Red 251 [C.I. 12925, (CAS: 74336-60-0)], Pigment Red 253 [C.I. 12375, (CAS: 85776-13-2)], Pigment Red 254 [C.I. 56110, (CAS: 84632-65-5)], Pigment Red 255 [C.I. 561050, (CAS: 54660-00-3)], Pigment Red 256 [C.I. 124635, (CAS: 79102-65-1)], Pigment Red 257 [C.I. 562700, (CAS: 70833-37-3)], Pigment Red 258 [C.I. 12318, (CAS: 57301-22-1)], Pigment Red 259 [C.I. 77007, (CAS: 113956-14-2)], Pigment Red 260 [C.I. 56295, (CAS: 71552-60-8)], Pigment Red 261 [C.I. 12468, (CAS: 16195-23-6)], Pigment Red 264 [C.I. 561300, (CAS: 88949-33-1)], Pigment Red 265 [C.I. 772830, (CAS: 12014-93-6)], Pigment Red 267 [C.I. 12396, (CAS: 68016-06-8)], Pigment Red 268 [C.I. 12316, (CAS: 16403-84-2)], Pigment Red 269 [C.I. 12466, (CAS: 67990-05-0)], Pigment Red 271 [C.I. 487100, (CAS: 85958-80-1)], Pigment Red 273 [C.I. 16035, (CAS: 68583-95-9)], Pigment Red 274 [C.I. 16255, (CAS: 12227-64-4)], Pigment Red 3 [C.I. 12120, (CAS: 2425-85-6)], Pigment Red 30 [C.I. 12330, (CAS: 6471-48-3)], Pigment Red 32 [C.I. 12320, (CAS: 6410-29-3)], Pigment Red 37 [C.I. 21205, (CAS: 6883-91-6)], Pigment Red 38 [C.I. 21120, (CAS: 6358-87-8)], Pigment Red 39 [C.I. 21080, (CAS: 6492-54-2)], Pigment Red 4 [C.I. 12085, (CAS: 2814-77-9)], Pigment Red 40 [C.I. 12170, (CAS: 2653-64-7)], Pigment Red 41 [C.I. 21200, (CAS: 6505-29-9)], Pigment Red 42 [C.I. 21210, (CAS: 6358-90-3)], Pigment Red 48 [C.I. 15865, (CAS: 3564-21-4)], Pigment Red 48 [C.I. 15865, (CAS: 1325-12-8)], Pigment Red 48 [C.I. 15865, (CAS: 7585-41-3)], Pigment Red 48 [C.I. 15865, (CAS: 7023-61-2)], Pigment Red 48 [C.I. 15865, (CAS: 15782-05-5)], Pigment Red 48 [C.I. 15865, (CAS: 5280-66-0)], Pigment Red 48 [C.I. 15865, (CAS: 71832-83-2)], Pigment Red 48 [C.I. 15865, (CAS: 68966-97-2)], Pigment Red 49 [C.I. 15630, (CAS: 1248-18-6)], Pigment Red 49 [C.I. 15630, (CAS: 1325-06-0)], Pigment Red 49 [C.I. 15630, (CAS: 1103-38-4)], Pigment Red 49 [C.I. 15630, (CAS: 1103-39-5)], Pigment Red 49 [C.I. 15630, (CAS: 6371-67-1)], Pigment Red 5 [C.I. 12490, (CAS: 6410-41-9)], Pigment Red 50 [C.I. 15500, (CAS: 5850-76-0)], Pigment Red 50 [C.I. 15500, (CAS: 6372-81-2)], Pigment Red 51 [C.I. 15580, (CAS: 5850-87-3)], Pigment Red 52 [C.I. 15860, (CAS: 5858-82-2)], Pigment Red 52 [C.I. 15860, (CAS: 1325-11-7)], Pigment Red 52 [C.I. 15860, (CAS: 17852-99-2)], Pigment Red 52 [C.I. 15860, (CAS: 17814-20-9)], Pigment Red 52 [C.I. 15860, (CAS: 12238-31-2)], Pigment Red 53 [C.I. 15585, (CAS: 2092-56-0)], Pigment Red 53 [C.I. 15585, (CAS: 1325-04-8)], Pigment Red 53 [C.I. 15585, (CAS: 67990-35-6)], Pigment Red 53 [C.I. 15585, (CAS: 73263-40-8)], Pigment Red 54 [C.I. 14830, (CAS: 6373-10-0)], Pigment Red 55 [C.I. 15820, (CAS: 141052-43-9)], Pigment Red 57 [C.I. 15850, (CAS: 5858-81-1)], Pigment Red 57 [C.I. 15850, (CAS: 17852-98-1)], Pigment Red 57 [C.I. 15850, (CAS: 55491-44-6)], Pigment Red 58 [C.I. 15825, (CAS: 1325-09-3)], Pigment Red 58 [C.I. 15825, (CAS: 7538-59-2)], Pigment Red 58 [C.I. 15825, (CAS: 15782-03-3)], Pigment Red 58 [C.I. 15825, (CAS:

76613-71-3)], Pigment Red 58 [C.I. 15825, (CAS: 64552-28-9)], Pigment Red 6 [C.I. 12090, (CAS: 6410-13-5)], Pigment Red 60 [C.I. 16105, (CAS: 15782-06-6)], Pigment Red 60 [C.I. 16105, (CAS: 1325-16-2)], Pigment Red 61 [C.I. 24830, (CAS: 1325-29-7)], Pigment Red 62 [C.I. 23295, (CAS: 109823-18-9)], Pigment Red 63 [C.I. 15880, (CAS: 21416-46-6)], Pigment Red 63 [C.I. 15880, (CAS: 6417-83-0)], Pigment Red 63 [C.I. 15880, (CAS: 15792-20-8)], Pigment Red 63 [C.I. 15880, (CAS: 35355-77-2)], Pigment Red 64 [C.I. 15800, (CAS: 16508-79-5)], Pigment Red 64 [C.I. 15800, (CAS: 6371-76-2)], Pigment Red 65 [C.I. 18020, (CAS: 1325-21-9)], Pigment Red 66 [C.I. 18000, (CAS: 1325-19-5)], Pigment Red 67 [C.I. 18025, (CAS: 1325-22-0)], Pigment Red 68 [C.I. 15525, (CAS: 5850-80-6)], Pigment Red 69 [C.I. 15595, (CAS: 5850-90-8)], Pigment Red 7 [C.I. 12420, (CAS: 6471-51-8)], Pigment Red 70 [C.I. 15590, (CAS: 5850-89-5)], Pigment Red 77 [C.I. 15826, (CAS: 6358-39-0)], Pigment Red 8 [C.I. 12335, (CAS: 6410-30-6)], Pigment Red 83 [C.I. 58000, (CAS: 104074-25-1)], Pigment Red 84 [C.I. 58210, (CAS: 1328-07-0)], Pigment Red 85 [C.I. 63350, (CAS: 6370-96-3)], Pigment Red 86 [C.I. 73375, (CAS: 6371-26-2)], Pigment Red 89 [C.I. 60745, (CAS: 6409-74-1)], Pigment Red 9 [C.I. 12460, (CAS: 6410-38-4)], Pigment Red 90 [C.I. 45380, (CAS: 15876-39-8)], Pigment Red 93 [C.I. 12152, (CAS: 6548-36-3)], Pigment Red 95 [C.I. 15897, (CAS: 72639-39-5)], Pigment Red 99 [C.I. 15570, (CAS: 5850-85-1)], Pigment Violet 10 [C.I. 42535, (CAS: 1325-82-2)], Pigment Violet 12 [C.I. 58050, (CAS: 1328-03-6)], Pigment Violet 13 [C.I. 125085, (CAS: 83399-83-1)], Pigment Violet 14 [C.I. 77360, (CAS: 10101-56-1)], Pigment Violet 15 [C.I. 77007, (CAS: 12769-96-9)], Pigment Violet 16 [C.I. 77742, (CAS: 10101-66-3)], Pigment Violet 19 [C.I. 46500, (CAS: 1047-16-1)], Pigment Violet 20 [C.I. 58225, (CAS: 6486-92-6)], Pigment Violet 23 [C.I. 51319, (CAS: 215247-95-3)], Pigment Violet 25 [C.I. 12321, (CAS: 6358-46-9)], Pigment Violet 27 [C.I. 42535, (CAS: 12237-62-6)], Pigment Violet 29 [C.I. 71129, (CAS: 81-33-4)], Pigment Violet 3 [C.I. 42535, (CAS: 68647-35-8)], Pigment Violet 3 [C.I. 42535, (CAS: 68308-41-8)], Pigment Violet 3 [C.I. 42535, (CAS: 67989-22-4)], Pigment Violet 31 [C.I. 60010, (CAS: 1324-55-6)], Pigment Violet 33 [C.I. 60005, (CAS: 1324-17-0)], Pigment Violet 36 [C.I. 73385, (CAS: 5462-29-3)], Pigment Violet 37 [C.I. 51345, (CAS: 17741-63-8)], Pigment Violet 38 [C.I. 73395, (CAS: 2379-75-1)], Pigment Violet 47 [C.I. 77363, (CAS: 68610-13-9)], Pigment Violet 48 [C.I. 77352, (CAS: 68608-93-5)], Pigment Violet 49 [C.I. 77362, (CAS: 16827-96-6)], Pigment Violet 5 [C.I. 58055, (CAS: 1328-04-7)], Pigment Violet 6 [C.I. 58060, (CAS: 6483-85-8)], Pigment Violet 6 [C.I. 58060, (CAS: 1328-05-8)], Pigment Violet 7 [C.I. 58065, (CAS: 1328-06-9)], Pigment Violet 8 [C.I. 18005, (CAS: 1325-20-8)], Pigment Yellow 1 [C.I. 11680, (CAS: 2512-29-0)], Pigment Yellow 10 [C.I. 12710, (CAS: 6407-75-6)], Pigment Yellow 100 [C.I. 19140, (CAS: 12225-21-7)], Pigment Yellow 104 [C.I. 15985, (CAS: 15790-07-5)], Pigment Yellow 105 [C.I. 11743, (CAS: 12236-75-8)], Pigment Yellow 109 [C.I. 56284, (CAS: 5045-40-9)], Pigment Yellow 11 [C.I. 10325, (CAS: 2955-16-0)], Pigment Yellow 110 [C.I. 56280, (CAS: 5590-18-1)], Pigment Yellow 111 [C.I. 11745, (CAS: 15993-42-7)], Pigment Yellow 112 [C.I. 70600, (CAS: 475-71-8)], Pigment Yellow 114 [C.I. 21092, (CAS: 68610-87-7)], Pigment Yellow 115 [C.I. 47005, (CAS: 68814-04-0)], Pigment Yellow 116 [C.I. 11790, (CAS: 61968-84-1)], Pigment Yellow 117 [C.I. 48043, (CAS: 21405-81-2)], Pigment Yellow 118 [C.I. 77894, (CAS: 61512-65-0)], Pigment Yellow 119 [C.I. 77496, (CAS: 68187-51-9)], Pigment Yellow 12 [C.I. 21090, (CAS: 6358-85-6)], Pigment Yellow 123 [C.I. 65049, (CAS: 4028-94-8)], Pigment Yellow 124 [C.I. 21107, (CAS: 67828-22-2)], Pigment Yellow 126 [C.I. 21101, (CAS: 90268-23-8)], Pigment Yellow 127 [C.I. 21102, (CAS: 68610-86-6)], Pigment Yellow 128 [C.I. 20037, (CAS: 79953-85-8)], Pigment Yellow 129 [C.I. 48042, (CAS: 15680-42-9)], Pigment Yellow 13 [C.I. 21100, (CAS: 5102-83-0)], Pigment Yellow 130 [C.I. 117699, (CAS: 23739-66-4)], Pigment Yellow 133 [C.I. 139395, (CAS: 85702-53-0)], Pigment Yellow 134 [C.I. 21111, (CAS: 31775-20-9)], Pigment Yellow 138 [C.I. 56300, (CAS: 30125-47-4)], Pigment Yellow 139 [C.I. 56298, (CAS: 36888-99-0)], Pigment Yellow 14 [C.I. 21095, (CAS: 5468-75-7)], Pigment Yellow 147 [C.I. 60645, (CAS: 4118-16-5)], Pigment Yellow 148 [C.I. 50600, (CAS: 20572-37-6)], Pigment Yellow 15 [C.I. 21220, (CAS: 6528-35-4)], Pigment Yellow 150 [C.I. 12764, (CAS: 872613-79-1)], Pigment Yellow 153 [C.I. 48545, (CAS: 29204-84-0)], Pigment Yellow 155 [C.I. 200310, (CAS: 68516-73-4)], Pigment Yellow 157 [C.I. 77900, (CAS: 68610-24-2)], Pigment Yellow 158 [C.I. 77862, (CAS: 68186-93-6)], Pigment Yellow 159 [C.I. 77997, (CAS: 68187-15-5)], Pigment Yellow 16 [C.I. 20040, (CAS: 5979-28-2)], Pigment Yellow 160 [C.I. 77991, (CAS: 68187-01-9)], Pigment Yellow 161 [C.I. 77895, (CAS: 68611-43-8)], Pigment Yellow 162 [C.I. 77896, (CAS: 68611-42-7)], Pigment Yellow 163 [C.I. 77897, (CAS: 68186-92-5)], Pigment Yellow 164 [C.I. 77899, (CAS: 68412-38-4)], Pigment Yellow 167 [C.I. 11737, (CAS: 38489-24-6)], Pigment Yellow 168 [C.I. 13960, (CAS: 71832-85-4)], Pigment Yellow 169 [C.I. 13955, (CAS: 73385-03-2)], Pigment Yellow 17 [C.I. 21105, (CAS: 4531-49-1)], Pigment Yellow 173 [C.I. 561600, (CAS: 51016-63-8)], Pigment Yellow 174 [C.I. 21098, (CAS: 78952-72-4)], Pigment Yellow 176 [C.I. 21103, (CAS: 90268-24-9)], Pigment Yellow 177 [C.I. 48120, (CAS: 60109-88-8)], Pigment Yellow 179 [C.I. 48125, (CAS: 63287-28-5)], Pigment Yellow 180 [C.I. 21290, (CAS: 77804-81-0)], Pigment Yellow 181 [C.I. 11777, (CAS: 74441-05-7)], Pigment Yellow 182 [C.I. 128300, (CAS: 67906-31-4)], Pigment Yellow 183 [C.I. 18792, (CAS: 65212-77-3)], Pigment Yellow 184 [C.I. 771740, (CAS: 14059-33-7)], Pigment Yellow 185 [C.I. 56290, (CAS: 76199-85-4)], Pigment Yellow 188 [C.I. 21094, (CAS: 23792-68-9)], Pigment Yellow 190 [C.I. 189785, (CAS: 94612-75-6)], Pigment Yellow 191 [C.I. 18795, (CAS: 129423-54-7)], Pigment Yellow 191 [C.I. 18795, (CAS: 154946-66-4)], Pigment Yellow 192 [C.I. 507300, (CAS: 56279-27-7)], Pigment Yellow 193 [C.I. 65412, (CAS: 70321-14-1)], Pigment Yellow 194 [C.I. 11785, (CAS: 82199-12-0)], Pigment Yellow 199 [C.I. 653200, (CAS: 136897-58-0)], Pigment Yellow 2 [C.I. 11730, (CAS: 6486-26-6)], Pigment Yellow 202 [C.I. 65410, (CAS: 3627-47-2)], Pigment Yellow 203 [C.I. 117390, (CAS: 150959-17-4)], Pigment Yellow 213 [C.I. 117875, (CAS: 220198-21-0)], Pigment Yellow 218 [C.I. 561805, (CAS: 910868-14-3)], Pigment Yellow 220 [C.I. 561806, (CAS: 17352-39-5)], Pigment Yellow 227 [C.I. 777895, (CAS: 1374645-21-2)], Pigment Yellow 3 [C.I. 11710, (CAS: 6486-23-3)], Pigment Yellow [C.I. 77592, (CAS: 1345-30-8)], Pigment Yellow 31 [C.I. 77103, (CAS: 10294-40-3)], Pigment Yellow 33 [C.I. 77223, (CAS: 8012-75-7)], Pigment Yellow 34 [C.I. 77603, (CAS: 1344-37-2)], Pigment Yellow 35 [C.I. 77205, (CAS: 90604-89-0)], Pigment Yellow 36 [C.I. 77956, (CAS: 49663-84-5)], Pigment Yellow 37 [C.I. 77199, (CAS: 90604-90-3)], Pigment Yellow 38 [C.I. 77878, (CAS: 1315-01-1)], Pigment Yellow 39 [C.I. 77086, (CAS: 1303-33-9)], Pigment Yellow 4 [C.I. 11665, (CAS:

1657-16-5)], Pigment Yellow 41 [C.I. 77588, (CAS: 8012-00-8)], Pigment Yellow 42 [C.I. 77492, (CAS: 51274-00-1)], Pigment Yellow 43 [C.I. 77492, (CAS: 64294-91-3)], Pigment Yellow 44 [C.I. 77188, (CAS: 1345-08-0)], Pigment Yellow 45 [C.I. 77505, (CAS: 1328-64-9)], Pigment Yellow 46 [C.I. 77577, (CAS: 1317-36-8)], Pigment Yellow 48 [C.I. 77610, (CAS: 592-05-2)], Pigment Yellow 5 [C.I. 11660, (CAS: 4106-67-6)], Pigment Yellow 53 [C.I. 77788, (CAS: 8007-18-9)], Pigment Yellow 55 [C.I. 21096, (CAS: 6358-37-8)], Pigment Yellow 6 [C.I. 11670, (CAS: 4106-76-7)], Pigment Yellow 60 [C.I. 12705, (CAS: 6407-74-5)], Pigment Yellow 61 [C.I. 13880, (CAS: 5280-69-3)], Pigment Yellow 62 [C.I. 13940, (CAS: 12286-66-7)], Pigment Yellow 62 [C.I. 13940, (CAS: 5280-70-6)], Pigment Yellow 65 [C.I. 11740, (CAS: 6528-34-3)], Pigment Yellow 7 [C.I. 12780, (CAS: 6407-81-4)], Pigment Yellow 73 [C.I. 11738, (CAS: 13515-40-7)], Pigment Yellow 74 [C.I. 11741, (CAS: 6358-31-2)], Pigment Yellow 75 [C.I. 11770, (CAS: 52320-66-8)], Pigment Yellow 77 [C.I. 20045, (CAS: 5905-17-9)], Pigment Yellow 81 [C.I. 21127, (CAS: 22094-93-5)], Pigment Yellow 83 [C.I. 21108, (CAS: 5567-15-7)], Pigment Yellow 83 [C.I. 21107, (CAS: 15110-84-6)], Pigment Yellow 9 [C.I. 11720, (CAS: 6486-24-4)], Pigment Yellow 93 [C.I. 20710, (CAS: 5580-57-4)], Pigment Yellow 94 [C.I. 20038, (CAS: 5580-58-5)], Pigment Yellow 95 [C.I. 20034, (CAS: 5280-80-8)], Pigment Yellow 98 [C.I. 11727, (CAS: 32432-45-4)], Prussian blue [C.I. 77510, (CAS: 12240-15-2)], Pigment Blue 1 [(CAS: 1325-87-7)], Pigment Blue 1 [(CAS: 69980-72-9)], Pigment Blue 1 [(CAS: 68409-66-5)], Pigment Blue 10 [(CAS: 84057-86-3)], Pigment Blue 12 [(CAS: 1325-77-5)], Pigment Blue 14 [(CAS: 1325-88-8)], Pigment Blue 2 [(CAS: 1325-94-6)], Pigment Blue 3 [(CAS: 1325-79-7)], Pigment Blue 9 [(CAS: 1325-74-2)], Pigment Green 1 [(CAS: 1325-75-3)], Pigment Green 3 [(CAS: 68845-37-4)], Pigment Green 4 [(CAS: 61725-50-6)], Pigment Red 80 [(CAS: 12224-98-5)], Pigment Red 81 [(CAS: 80083-40-5)], Pigment Red 81 [(CAS: 75627-12-2)], Pigment Red 81 [(CAS: 68310-07-6)], Pigment Red 81 [(CAS: 85959-61-1)], Pigment Red 81 [(CAS: 63022-06-0)], Pigment Red 81 [(CAS: 63022-07-1)], Pigment Violet 1 [(CAS: 1326-03-0)], Pigment Violet 2 [(CAS: 1326-04-1)], Pigment Violet 2 [(CAS: 103443-41-0)], Pigment Violet 4 [(CAS: 1325-80-0)], Pigment Black 1 [(CAS: 73104-73-1)], Pigment Black 1 [(CAS: 9064-44-2)], Pigment Black 11 [(CAS: 120899-48-1)], Pigment Black 11 [(CAS: 128666-38-6)], Pigment Black 11 [(CAS: 128666-37-5)], Pigment Black 11 [(CAS: 128666-36-4)], Pigment Black 11 [(CAS: 147858-25-1)], Pigment Black 16 [(CAS: 7440-66-6)], Pigment Black 19 [(CAS: 874954-47-9)], Pigment Black 2 [(CAS: 12236-57-6)], Pigment Black 20 [(CAS: 12216-93-2)], Pigment Black 21 [(CAS: 12216-94-3)], Pigment Black 22 [(CAS: 55353-02-1)], Pigment Black 3 [(CAS: 945563-42-8)], Pigment Black 35 [(CAS: 945563-51-9)], Pigment Black 5 [(CAS: 945563-45-1)], Pigment Blue 1 [(CAS: 68647-33-6)], Pigment Blue 10 [(CAS: 308086-15-9)], Pigment Blue 11 [(CAS: 71798-70-4)], Pigment Blue 13 [(CAS: 945558-73-6)], Pigment Blue 15-Pigment Green 7 mixt. [(CAS: 1026025-11-5)], Pigment Blue 15-Pigment Red 122-Pigment Yellow 74 mixt. [(CAS: 1357447-02-9)], Pigment Blue 151 [(CAS: 685529-31-1)], Pigment Blue 16 [(CAS: 424827-05-4)], Pigment Blue 17 [(CAS: 153640-87-0)], Pigment Blue 17 [(CAS: 71799-04-7)], Pigment Blue 19 [(CAS: 58569-23-6)], Pigment Blue 2 [(CAS: 1126074-38-1)], Pigment Blue 20 [(CAS: 945558-74-7)], Pigment Blue 209 [(CAS: 215590-82-2)], Pigment Blue 23 [(CAS: 57486-30-3)], Pigment Blue 24 [(CAS: 1042940-03-3)], Pigment Blue 28 [(CAS: 151732-17-1)], Pigment Blue 29 [(CAS: 151732-19-3)], Pigment Blue 31 [(CAS: 945558-75-8)], Pigment Blue 4 [(CAS: 945558-70-3)], Pigment Blue 5 [(CAS: 945558-72-5)], Pigment Blue 52 [(CAS: 945558-90-7)], Pigment Blue 53 [(CAS: 945558-91-8)], Pigment Blue 53 [(CAS: 190454-42-3)], Pigment Blue 56 [(CAS: 64427-27-6)], Pigment Blue 58 [(CAS: 12236-58-7)], Pigment Blue 59 [(CAS: 12236-59-8)], Pigment Blue 6 [(CAS: 371759-37-4)], Pigment Blue 61 [(CAS: 1126075-97-5)], Pigment Blue 63 [(CAS: 815586-00-6)], Pigment Blue 67 [(CAS: 945558-93-0)], Pigment Blue 68 [(CAS: 129406-28-6)], Pigment Blue 69 [(CAS: 945558-94-1)], Pigment Blue 7 [(CAS: 71838-91-0)], Pigment Blue 7 [(CAS: 120177-75-5)], Pigment Blue 70 [(CAS: 72827-99-7)], Pigment Blue 77 [(CAS: 945558-95-2)], Pigment Blue 8 [(CAS: 12224-90-7)], Pigment Blue 80 [(CAS: 391663-82-4)], Pigment Blue 81 [(CAS: 945558-98-5)], Pigment Blue 83 [(CAS: 1126076-49-0)], Pigment Blue 84 [(CAS: 2095508-48-6)], Pigment Brown 126 [(CAS: 128664-60-8)], Pigment Brown 29 [(CAS: 109414-04-2)], Pigment Brown 3 [(CAS: 1325-24-2)], Pigment Brown 30 [(CAS: 135668-57-4)], Pigment Brown 31 [(CAS: 126338-71-4)], Pigment Brown 32 [(CAS: 72828-00-3)], Pigment Brown 36 [(CAS: 945563-08-6)], Pigment Brown 4 [(CAS: 109944-91-4)], Pigment Brown 40 [(CAS: 945563-13-3)], Pigment Brown 41 [(CAS: 211502-16-8)], Pigment Brown 42 [(CAS: 211502-17-9)], Pigment Brown 43 [(CAS: 75864-23-2)], Pigment Brown 44 [(CAS: 945563-18-8)], Pigment Brown 45 [(CAS: 945563-37-1)], Pigment Brown 46 [(CAS: 945563-38-2)], Pigment Brown 47 [(CAS: 945563-39-3)], Pigment Brown 48 [(CAS: 2170864-80-7)], Pigment Brown 5 [(CAS: 16521-34-9)], Pigment Brown 6 [(CAS: 1275574-14-5)], Pigment Green 1 [(CAS: 68814-00-6)], Pigment Green 1 [(CAS: 68123-12-6)], Pigment Green 13 [(CAS: 148092-61-9)], Pigment Green 14 [(CAS: 114013-40-0)], Pigment Green 16 [(CAS: 65505-26-2)], Pigment Green 2 [(CAS: 12213-69-3)], Pigment Green 2 [(CAS: 76963-33-2)], Pigment Green 25 [(CAS: 945560-75-8)], Pigment Green 45 [(CAS: 945561-39-7)], Pigment Green 46 [(CAS: 945561-40-0)], Pigment Green 48 [(CAS: 945561-55-7)], Pigment Green 49 [(CAS: 945561-56-8)], Pigment Green 52 [(CAS: 945562-08-3)], Pigment Green 55 [(CAS: 945563-02-0)], Pigment Green 56 [(CAS: 945563-05-3)], Pigment Green 59 [(CAS: 2170445-83-5)], Pigment Green 6 [(CAS: 945559-56-8)], Pigment Green 62 [(CAS: 2108056-55-7)], Pigment Green 63 [(CAS: 2108056-56-8)], Pigment Green 7 [(CAS: 68022-83-3)], Pigment Green 77 [(CAS: 12715-62-7)], Pigment Green 7-Pigment Yellow 93 mixt. [(CAS: 1046461-83-9)], Pigment Orange 12 [(CAS: 945426-49-3)], Pigment Orange 20 [(CAS: 957128-28-8)], Pigment Orange 25 [(CAS: 12224-97-4)], Pigment Orange 32 [(CAS: 945426-51-7)], Pigment Orange 36 [(CAS: 12236-62-3)], Pigment Orange 38 [(CAS: 12236-64-5)], Pigment Orange 42 [(CAS: 12768-99-9)], Pigment Orange 43-Pigment Orange 64 mixt. [(CAS: 1046461-84-0)], Pigment Orange 47 [(CAS: 71819-73-3)], Pigment Orange 48 [(CAS: 71819-74-4)], Pigment Orange 49 [(CAS: 71819-75-5)], Pigment Orange 50 [(CAS: 76780-89-7)], Pigment Orange 51 [(CAS: 61512-61-6)], Pigment Orange 52 [(CAS: 61512-62-7)], Pigment Orange 53 [(CAS: 945426-52-8)], Pigment Orange 54 [(CAS: 945426-53-9)], Pigment Orange 55 [(CAS: 304891-88-1)], Pigment Orange 56 [(CAS: 74433-73-1)], Pigment Orange 57 [(CAS: 945426-54-0)], Pigment Orange 58 [(CAS: 945426-55-1)], Pigment Orange 59 [(CAS: 304891-93-8)], Pigment Orange 60 [(CAS: 68399-99-5)], Pigment Orange 62 [(CAS: 52846-56-7)], Pigment Orange 63 [(CAS: 76233-79-9)], Pigment Orange 70 [(CAS: 914936-31-5)], Pigment Orange 74

[(CAS: 516493-26-8)], Pigment Orange 76 [(CAS: 945426-61-9)], Pigment Orange 79 [(CAS: 945426-62-0)], Pigment Orange 8 [(CAS: 945426-48-2)], Pigment Orange 80 [(CAS: 945426-63-1)], Pigment Orange 81 [(CAS: 656223-72-2)], Pigment Orange 82 [(CAS: 2170864-77-2)], Pigment Orange 86 [(CAS: 1883421-38-2)], Pigment Orange 9 [(CAS: 71799-05-8)], Pigment Red 1 [(CAS: 39781-24-3)], Pigment Red 102 [(CAS: 1332-25-8)], Pigment Red 108 [(CAS: 918496-78-3)], Pigment Red 110 [(CAS: 854102-21-9)], Pigment Red 111 [(CAS: 12224-99-6)], Pigment Red 118 [(CAS: 945428-13-7)], Pigment Red 120 [(CAS: 57485-96-8)], Pigment Red 123 [(CAS: 24108-89-2)], Pigment Red 134 [(CAS: 12286-59-8)], Pigment Red 135 [(CAS: 945428-14-8)], Pigment Red 136 [(CAS: 945428-21-7)], Pigment Red 137 [(CAS: 71799-07-0)], Pigment Red 139 [(CAS: 12262-44-1)], Pigment Red 140 [(CAS: 383890-12-8)], Pigment Red 142 [(CAS: 109944-97-0)], Pigment Red 143 [(CAS: 12286-63-4)], Pigment Red 152 [(CAS: 405113-25-9)], Pigment Red 154 [(CAS: 109944-98-1)], Pigment Red 155 [(CAS: 109944-99-2)], Pigment Red 156 [(CAS: 109945-00-8)], Pigment Red 158 [(CAS: 945552-90-9)], Pigment Red 159 [(CAS: 109945-01-9)], Pigment Red 160 [(CAS: 854524-60-0)], Pigment Red 161 [(CAS: 945552-91-0)], Pigment Red 165 [(CAS: 12225-03-5)], Pigment Red 167 [(CAS: 12236-66-7)], Pigment Red 176 [(CAS: 12225-06-8)], Pigment Red 178 [(CAS: 3049-71-6)], Pigment Red 17-Pigment Red 150-Pigment White 18 mixt. [(CAS: 2247196-29-6)], Pigment Red 180 [(CAS: 12769-00-5)], Pigment Red 182 [(CAS: 61036-51-9)], Pigment Red 183 [(CAS: 51920-11-7)], Pigment Red 191 [(CAS: 85068-75-3)], Pigment Red 199 [(CAS: 61901-78-8)], Pigment Red 20 [(CAS: 945426-74-4)], Pigment Red 200 [(CAS: 67801-10-9)], Pigment Red 201 [(CAS: 68258-66-2)], Pigment Red 202-Pigment Violet 19 mixt. [(CAS: 1122063-75-5)], Pigment Red 203 [(CAS: 945553-87-7)], Pigment Red 204 [(CAS: 438231-79-9)], Pigment Red 205 [(CAS: 741692-71-7)], Pigment Red 206 [(CAS: 71819-76-6)], Pigment Red 207 [(CAS: 71819-77-7)], Pigment Red 215 [(CAS: 304892-29-3)], Pigment Red 217 [(CAS: 155421-17-3)], Pigment Red 218 [(CAS: 383891-32-5)], Pigment Red 219 [(CAS: 909006-21-9)], Pigment Red 223 [(CAS: 26789-26-4)], Pigment Red 225 [(CAS: 125270-32-8)], Pigment Red 227 [(CAS: 71872-64-5)], Pigment Red 228 [(CAS: 304898-64-4)], Pigment Red 234 [(CAS: 945554-26-7)], Pigment Red 237 [(CAS: 220424-27-1)], Pigment Red 238 [(CAS: 140114-63-2)], Pigment Red 239 [(CAS: 220424-28-2)], Pigment Red 240 [(CAS: 141489-67-0)], Pigment Red 241 [(CAS: 945554-27-8)], Pigment Red 244 [(CAS: 882858-66-4)], Pigment Red 245 [(CAS: 68016-05-7)], Pigment Red 246 [(CAS: 431991-59-2)], Pigment Red 249 [(CAS: 97955-62-9)], Pigment Red 25 [(CAS: 945426-75-5)], Pigment Red 250 [(CAS: 146358-78-3)], Pigment Red 252 [(CAS: 945554-31-4)], Pigment Red 26 [(CAS: 109944-92-5)], Pigment Red 262 [(CAS: 211502-19-1)], Pigment Red 263 [(CAS: 278792-06-6)], Pigment Red 270 [(CAS: 251086-13-2)], Pigment Red 272 [(CAS: 350249-32-0)], Pigment Red 276 [(CAS: 945554-32-5)], Pigment Red 277 [(CAS: 945554-33-6)], Pigment Red 278 [(CAS: 945554-34-7)], Pigment Red 279 [(CAS: 832743-59-6)], Pigment Red 280 [(CAS: 945554-58-5)], Pigment Red 281 [(CAS: 945554-64-3)], Pigment Red 282 [(CAS: 938065-79-3)], Pigment Red 283 [(CAS: 945554-67-6)], Pigment Red 284 [(CAS: 1089180-60-8)], Pigment Red 285 [(CAS: 1248412-35-2)], Pigment Red 29 [(CAS: 109944-93-6)], Pigment Red 34 [(CAS: 71872-60-1)], Pigment Red 35 [(CAS: 104491-86-3)], Pigment Red 46 [(CAS: 945427-33-8)], Pigment Red 47 [(CAS: 945427-55-4)], Pigment Red 48 [(CAS: 16013-44-8)], Pigment Red 48 [(CAS: 17797-35-2)], Pigment Red 48-Pigment Red 122 mixt. [(CAS: 1046461-81-7)], Pigment Red 48 [(CAS: 218138-44-4)], Pigment Red 48 [(CAS: 218138-41-1)], Pigment Red 48 [(CAS: 68023-17-6)], Pigment Red 51 [(CAS: 25705-30-0)], Pigment Red 51 [(CAS: 446242-29-1)], Pigment Red 52 [(CAS: 27757-95-5)], Pigment Red 52 [(CAS: 67828-72-2)], Pigment Red 52 [(CAS: 218138-27-3)], Pigment Red 53 [(CAS: 15958-19-7)], Pigment Red 56 [(CAS: 25310-96-7)], Pigment Red 57 [(CAS: 88593-07-1)], Pigment Red 58 [(CAS: 25310-97-8)], Pigment Red 59 [(CAS: 945427-99-6)], Pigment Red 60 [(CAS: 446245-60-9)], Pigment Red 63 [(CAS: 5858-84-4)], Pigment Red 63 [(CAS: 16510-21-7)], Pigment Red 63 [(CAS: 1325-13-9)], Pigment Red 64 [(CAS: 5858-77-5)], Pigment Red 68 [(CAS: 25311-19-7)], Pigment Red 71 [(CAS: 384329-78-6)], Pigment Red 72 [(CAS: 945428-03-5)], Pigment Red 73 [(CAS: 109944-94-7)], Pigment Red 74 [(CAS: 109944-95-8)], Pigment Red 75 [(CAS: 109944-96-9)], Pigment Red 78 [(CAS: 71799-06-9)], Pigment Red 81-Pigment White 21 mixt. [(CAS: 192390-71-9)], Pigment Red 82 [(CAS: 110927-51-0)], Pigment Red 88 [(CAS: 14295-43-3)], Pigment Red 90 [(CAS: 51868-24-7)], Pigment Red 92 [(CAS: 909006-04-8)], Pigment Red 94 [(CAS: 12213-62-6)], Pigment Red 96 [(CAS: 945428-04-6)], Pigment Red 97 [(CAS: 239795-92-7)], Pigment Red 98 [(CAS: 945428-07-9)], Pigment Violet 1 [(CAS: 63022-09-3)], Pigment Violet 1 [(CAS: 62973-79-9)], Pigment Violet 11 [(CAS: 875014-31-6)], Pigment Violet 11 [(CAS: 765310-46-1)], Pigment Violet 122 [(CAS: 104491-87-4)], Pigment Violet 123 [(CAS: 80619-33-6)], Pigment Violet 17 [(CAS: 945554-69-8)], Pigment Violet 18 [(CAS: 945554-81-4)], Pigment Violet 21 [(CAS: 945555-53-3)], Pigment Violet 26 [(CAS: 945556-80-9)], Pigment Violet 28 [(CAS: 12236-70-3)], Pigment Violet 30 [(CAS: 12225-07-9)], Pigment Violet 32 [(CAS: 12225-08-0)], Pigment Violet 34 [(CAS: 12612-32-7)], Pigment Violet 35 [(CAS: 55177-94-1)], Pigment Violet 39 [(CAS: 64070-98-0)], Pigment Violet 39 [(CAS: 68477-21-4)], Pigment Violet 4 [(CAS: 68310-88-3)], Pigment Violet 40 [(CAS: 61968-83-0)], Pigment Violet 41 [(CAS: 945557-07-3)], Pigment Violet 42 [(CAS: 71819-79-9)], Pigment Violet 43 [(CAS: 79665-29-5)], Pigment Violet 44 [(CAS: 87209-55-0)], Pigment Violet 45 [(CAS: 945557-40-4)], Pigment Violet 46 [(CAS: 945557-42-6)], Pigment Violet 5 [(CAS: 22297-70-7)], Pigment Violet 50 [(CAS: 76233-81-3)], Pigment Violet 51 [(CAS: 945557-43-7)], Pigment Violet 52 [(CAS: 945557-99-3)], Pigment Violet 53 [(CAS: 945558-15-6)], Pigment Violet 54 [(CAS: 1126076-80-9)], Pigment Violet 55 [(CAS: 1126076-86-5)], Pigment Violet 56 [(CAS: 1126076-93-4)], Pigment Violet 7 [(CAS: 16035-60-2)], Pigment Violet 9 [(CAS: 945554-68-7)], Pigment Yellow 1 [(CAS: 12240-03-8)], Pigment Yellow 102 [(CAS: 12236-74-7)], Pigment Yellow 103 [(CAS: 12225-22-8)], Pigment Yellow 106 [(CAS: 12225-23-9)], Pigment Yellow 107 [(CAS: 12270-64-3)], Pigment Yellow 113 [(CAS: 14359-20-7)], Pigment Yellow 120 [(CAS: 29920-31-8)], Pigment Yellow 121 [(CAS: 14569-54-1)], Pigment Yellow 122 [(CAS: 852620-87-2)], Pigment Yellow 125 [(CAS: 304891-45-0)], Pigment Yellow 131 [(CAS: 945423-41-6)], Pigment Yellow 132 [(CAS: 945424-04-4)], Pigment Yellow 135 [(CAS: 945424-77-1)], Pigment Yellow 136 [(CAS: 181285-33-6)], Pigment Yellow 140 [(CAS: 945425-58-1)], Pigment Yellow 141 [(CAS: 945425-59-2)], Pigment Yellow 142 [(CAS: 177020-91-6)], Pigment Yellow 143 [(CAS: 945425-60-5)], Pigment Yellow 144 [(CAS: 945425-61-6)], Pigment Yellow 145 [(CAS: 115742-72-8)], Pigment Yellow 146 [(CAS: 945425-66-1)], Pigment Yellow 149 [(CAS: 945425-67-2)], Pigment Yellow 150 [(CAS: 939382-97-5)], Pigment Yellow 151 [(CAS: 31837-42-0)], Pigment Yellow 154 [(CAS: 68134-22-5)], Pigment Yellow 156 [(CAS: 63661-26-7)], Pigment Yellow 165 [(CAS: 865763-85-5)], Pigment Yellow 166 [(CAS: 76233-82-4)], Pigment Yellow 170 [(CAS: 31775-16-3)], Pigment Yellow 171 [(CAS: 53815-04-6)], Pigment Yellow 172 [(CAS: 76233-80-2)], Pigment Yellow 175 [(CAS: 35636-63-6)], Pigment Yellow 178 [(CAS: 945425-73-0)], Pigment Yellow 17 [(CAS: 221358-38-9)], Pigment Yellow 18 [(CAS: 1326-11-0)], Pigment Yellow 18 [(CAS: 68310-89-4)], Pigment Yellow 186 [(CAS: 945425-92-3)], Pigment Yellow 187 [(CAS: 131439-24-2)], Pigment Yellow 189 [(CAS: 69011-05-8)], Pigment Yellow 191 [(CAS: 1051932-58-1)], Pigment Yellow 195 [(CAS: 135668-58-5)], Pigment Yellow 196 [(CAS: 945425-96-7)], Pigment Yellow 197 [(CAS: 945425-97-8)], Pigment Yellow 198 [(CAS: 516493-10-0)], Pigment Yellow 20 [(CAS: 61512-63-8)], Pigment Yellow 200 [(CAS: 945425-98-9)], Pigment Yellow 201 [(CAS: 945425-99-0)], Pigment Yellow 204 [(CAS: 945426-05-1)], Pigment Yellow 205 [(CAS: 945426-18-6)], Pigment Yellow 206 [(CAS: 945426-19-7)], Pigment Yellow 207 [(CAS: 945426-23-3)], Pigment Yellow 208 [(CAS: 945426-25-5)], Pigment Yellow 209 [(CAS: 945426-27-7)], Pigment Yellow 21 [(CAS: 945421-49-8)], Pigment Yellow 210 [(CAS: 945426-35-7)], Pigment Yellow 211 [(CAS: 945426-36-8)], Pigment Yellow 212 [(CAS: 945426-37-9)], Pigment Yellow 214 [(CAS: 577980-23-5)], Pigment Yellow 215 [(CAS: 913621-26-8)], Pigment Yellow 216 [(CAS: 817181-98-9)], Pigment Yellow 217 [(CAS: 945426-39-1)], Pigment Yellow 219 [(CAS: 874963-72-1)], Pigment Yellow 221 [(CAS: 945426-41-5)], Pigment Yellow 223 [(CAS: 2095507-47-2)], Pigment Yellow 224 [(CAS: 1207669-05-3)], Pigment Yellow 23 [(CAS: 4981-43-5)], Pigment Yellow 231 [(CAS: 2148300-50-7)], Pigment Yellow 25 [(CAS: 945421-63-6)], Pigment Yellow 26 [(CAS: 945421-64-7)], Pigment Yellow 27 [(CAS: 945421-65-8)], Pigment Yellow 28 [(CAS: 945421-66-9)], Pigment Yellow 29 [(CAS: 945421-67-0)], Pigment Yellow 34 [(CAS: 147858-25-1)], Pigment Yellow 36 [(CAS: 37300-23-5)], Pigment Yellow 37 [(CAS: 68859-25-6)], Pigment Yellow 40 [(CAS: 13782-01-9)], Pigment Yellow 47 [(CAS: 12060-00-3)], Pigment Yellow 50 [(CAS: 945421-71-6)], Pigment Yellow 51 [(CAS: 945421-76-1)], Pigment Yellow 56 [(CAS: 12225-09-1)], Pigment Yellow 58 [(CAS: 12225-11-5)], Pigment Yellow 61 [(CAS: 12286-65-6)], Pigment Yellow 72 [(CAS: 945421-81-8)], Pigment Yellow 79 [(CAS: 331414-25-6)], Pigment Yellow 8 [(CAS: 71872-65-6)], Pigment Yellow 80 [(CAS: 945421-85-2)], Pigment Yellow 82 [(CAS: 12225-14-8)], Pigment Yellow 84 [(CAS: 945421-87-4)], Pigment Yellow 85 [(CAS: 12286-67-8)], Pigment Yellow 86 [(CAS: 12286-68-9)], Pigment Yellow 86 [(CAS: 5280-65-9)], Pigment Yellow 88 [(CAS: 945422-67-3)], Pigment Yellow 89 [(CAS: 945422-85-5)], Pigment Yellow 90 [(CAS: 713104-87-1)], Pigment Yellow 91 [(CAS: 945423-18-7)], Pigment Yellow 96 [(CAS: 12213-63-7)], Pigment Yellow 97 [(CAS: 12225-18-2)], Pigment Yellow 99 [(CAS: 12225-20-6)]

The pigment(s) used in the color composition can include at least two different pigments selected from the above pigment group, or can include at least three different pigments selected from the above pigment group. According to an embodiment, the pigment(s) used in the color composition can include at least one yellow pigment selected from the yellow pigment group consisting of: a Pigment Yellow 83 (CI 21108), CAS #5567-15-7, Pigment Yellow 155 (C.I. 200310), (CAS: 68516-73-4), Pigment Yellow 180 (C.I. 21290), (CAS: 77804-81-0).

In addition to the at least one yellow pigment, or alternatively, the pigments(s) used in the color composition can include at least one red pigment selected from the red pigment group consisting of: Pigment Red 5 (CI 12490), (CAS #6410-41-9), Pigment Red 112 (CI 12370), (CAS #6535-46-2), Pigment Red 122 (CI 73915), (CAS #980-26-7).

In addition to the at least one yellow pigment and/or the at least one red pigment, or alternatively, the pigments(s) used in the color composition can include at least one green pigment selected from the green pigment group consisting of: Pigment Green 36, (C.I. 74265), (CAS: 14302-13-7).

In addition to the at least one yellow pigment and/or the at least one red pigment and or the at least one green pigment, or alternatively, the pigments(s) used in the color composition can include at least one blue pigment selected from the blue pigment group consisting of: Pigment Blue 16, (CAS: 424827-05-4), Pigment Blue 60 (C.I. 69800), (CAS: 81-77-6), Pigment Blue 66, (C.I. 73000), (CAS: 482-89-3)

In addition to the at least one yellow pigment and/or the at least one red pigment and/or the at least one green pigment, and/or the at least one blue pigment or alternatively, the pigments(s) used in the color composition can include at least one black pigment selected from the black pigment group consisting of: Pigment Black 6 (C.I. 77266), (CAS 1333-86-4), Pigment Black 7 (C.I. 77266), (CAS 1333-86-4).

The pigment(s) can optionally have a surface zeta potential of $\geq \pm 15$ mV, preferably $\geq \pm 20$ mV, more preferably $\geq \pm 25$ mV. The surface zeta potential can be measured with a zetasizer, for example, a Zetasizer 3000 HS. Surface zeta potential measurements are conducted, for example, according to ISO 13099.

For example, the white or colored organic pigments can be chosen from carmine, carbon black, aniline black, melanin, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21090, 21100, 21108, 47000, 47005 and 77492.

The green pigments codified in the Color Index under the references CI 61565, 61570, 74265, and 74260, the orange pigments codified in the Color Index under the references CI 11725, 12075, 15510, 45370, and 71105, the red pigments codified in the Color Index under the references CI 12085, 12120, 12370, 12420, 12490, 14700, 15525, 15580, 15585, 15620, 15630, 15800, 15850, 15865, 15880, 17200, 26100, 45380, 45410, 45430, 58000, 73360, 73915, 75470, and 77491 and the pigments obtained by oxidative polymerization of indole or phenolic derivatives as described in French Patent Publication No. FR 2 679 771, which is incorporated herein by reference.

Non-limiting examples that can also be mentioned include pigmentary pastes of organic pigments, such as the products sold by the company Hoechst under the names: JAUNE COSMENYL IOG: Pigment Yellow 3 (CI 11710); JAUNE COSMENYL G: Pigment Yellow 1 (CI 11680); ORANGE COSMENYL GR: Pigment Orange 43 (CI 71105); ROUGE COSMENYL R: Pigment Red 4 (CI 12085); CARMINE COSMENYL FB: Pigment Red 5 (CI 12490); VIOLET COSMENYL RL: Pigment Violet 23 (CI 51319); BLEU COSMENYL A2R: Pigment Blue 15.1 (CI 74160); VERT COSMENYL GG: Pigment Green 7 (CI 74260); and NOIR COSMENYL R: Pigment Black 7 (CI 77266).

The at least one pigment in accordance with the present disclosure can also be in the form of at least one composite pigment as described in European Patent Publication No. EP 1 184 426 A2. These composite pigments can be, for example, compounds of particles comprising a mineral core, at least one binder for ensuring the binding of the organic pigments to the core, and at least one organic pigment at least partially covering the core.

The at least one pigment in accordance with the present disclosure can be in the form of small undissolved microparticles, which do not diffuse into the hair color, but deposit on the outer wall of the keratin fiber. Suitable color pigments can be of organic and/or inorganic origin. But the pigments can also be inorganic color pigments, given the excellent light, weather and/or temperature resistance thereof.

Inorganic pigments, whether natural or synthetic in origin, include those produced from chalk, red ocher, umbra, green earth, burnt sienna or graphite, for example. Furthermore, it is possible to use black pigments, such as iron oxide black, color pigments such as ultramarine or iron oxide red, and fluorescent or phosphorescent pigments as inorganic color pigments.

Colored metal oxides, metal hydroxides and metal oxide hydrates, mixed phase pigments, sulfurous silicates, silicates, metal sulfides, complex metal cyanides, metal sulfates, metal chromates and/or metal molybdates are particularly suitable. In particular, preferred color pigments are black iron oxide (Cl 77499), yellow iron oxide (Cl 77492), red and brown iron oxide (Cl 77491), manganese violet (Cl 77742), ultramarine (sodium aluminum sulfosilicates, Cl 77007, Pigment Blue 29), chromium oxide hydrate (CI 77289), iron blue (ferric ferrocyanide, CI 77510) and/or carmine (cochineal).

The at least one pigment can also be colored pearlescent pigments. These are usually mica-based and can be coated with one or more metal oxides from the group consisting of titanium dioxide (CI 77891), black iron oxide (CI 77499), yellow iron oxide (CI 77492), red and brown iron oxide (Cl 77491, CI 77499), manganese violet (Cl 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Mica forms part of the phyllosilicates, including muscovite, phlogopite, paragonite, biotite, lepidolite, and margarite. To produce the pearlescent pigments in combination with metal oxides, the mica, primarily muscovite or phlogopite, is coated with a metal oxide.

As an alternative to natural mica, it is also optionally possible to use synthetic mica coated with one or more metal oxides as the pearlescent pigment. Such suitable pearlescent pigments based on natural micas are described in, e.g., WO 2005/065632. The at least one pigment can also be pearlescent pigments based on natural or synthetic mica and are coated with one or more of the aforementioned metal oxides. The color of the respective pigments can be varied by varying the layer thickness of the metal oxide or metal oxides.

The at least one pigment can also be at least one inorganic color pigment selected from the group consisting of colored metal oxides, metal hydroxides, metal oxide hydrates, silicates, metal sulfides, complex metal cyanides, metal sulfates, bronze pigments and/or colored pigments based on mica, which are coated with at least one metal oxide and/or a metal oxychloride.

The at least one pigment can also be at least one mica-based colored pigment, which is coated with one or more metal oxides from the group consisting of titanium dioxide (CI 77891), black iron oxide (CI 77499), yellow iron oxide (CI 77492), red and/or brown iron oxide (Cl 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

The at least one pigment can also be color pigments commercially available, for example, under the trade names Rona®, Colorona®, Dichrona® and Timiron® from Merck, Ariabel® and Unipure® from Sensient, Prestige® from Eckart Cosmetic Colors, and Sunshine@ from Sunstar.

The at least one pigment can also be color pigments bearing the trade name Colorona® are, for example: Colorona Copper, Merck, MICA, Cl 77491 (IRON OXIDES); Colorona Passion Orange, Merck, Mica, Cl 77491 (Iron Oxides), Alumina; Colorona Patina Silver, Merck, MICA, Cl 77499 (IRON OXIDES), Cl 77891 (TITANIUM DIOXIDE); Colorona RY, Merck, Cl 77891 (TITANIUM DIOXIDE), MICA, Cl 75470 (CARMINE); Colorona Oriental Beige, Merck, MICA, Cl 77891 (TITANIUM DIOXIDE), Cl 77491 (IRON OXIDES); Colorona Dark Blue, Merck, MICA, TITANIUM DIOXIDE, FERRIC FERROCYANIDE; Colorona Chameleon, Merck, Cl 77491 (IRON OXIDES), MICA; Colorona Aborigine Amber, Merck, MICA, Cl 77499 (IRON OXIDES), Cl 77891 (TITANIUM DIOXIDE); Colorona Blackstar Blue, Merck, Cl 77499 (IRON OXIDES), MICA; Colorona Patagonian Purple, Merck, MICA, Cl 77491 (IRON OXIDES), Cl 77891 (TITANIUM DIOXIDE), Cl 77510 (FERRIC FERROCYANIDE); Colorona Red Brown, Merck, MICA, Cl 77491 (IRON OXIDES), Cl 77891 (TITANIUM DIOXIDE); Colorona Russet, Merck, Cl 77491 (TITANIUM DIOXIDE), MICA, Cl 77891 (IRON OXIDES); Colorona Imperial Red, Merck, MICA, TITANIUM DIOXIDE (Cl 77891), D&C RED NO. 30 (Cl 73360); Colorona Majestic Green, Merck, Cl 77891 (TITANIUM DIOXIDE), MICA, Cl 77288 (CHROMIUM OXIDE GREENS); Colorona Light Blue, Merck, MICA, TITANIUM DIOXIDE (Cl 77891), FERRIC FERROCYANIDE (Cl 77510); Colorona Red Gold, Merck, MICA, Cl 77891 (TITANIUM DIOXIDE), Cl 77491 (IRON); Colorona Gold Plus MP 25, Merck, MICA, TITANIUM DIOXIDE (Cl 77891), IRON OXIDES (Cl 77491); Colorona Carmine Red, Merck, MICA, TITANIUM DIOXIDE, CARMINE Colorona Blackstar Green, Merck, MICA, Cl 77499 (IRON OXIDES); Colorona Bordeaux, Merck, MICA, Cl 77491 (IRON OXIDES); Colorona Bronze, Merck, MICA, Cl 77491 (IRON OXIDES); Colorona Bronze Fine, Merck, MICA, Cl 77491 (IRON OXIDES); Colorona Fine Gold MP 20, Merck, MICA, Cl 77891 (TITANIUM DIOXIDE), Cl 77491 (IRON OXIDES); Colorona Sienna Fine, Merck, Cl 77491 (IRON OXIDES), MICA Colorona Sienna, Merck, MICA, Cl 77491 (IRON OXIDES); Colorona Precious Gold, Merck, Mica, Cl 77891 (Titanium dioxide), Silica, Cl 77491 (Iron oxides), Tin oxide; Colorona Sun Gold Sparkle MP 29, Merck, MICA, TITANIUM DIOXIDE, IRON OXIDES, MICA, Cl 77891, Cl 77491 (EU); Colorona Mica Black, Merck, Cl 77499 (Iron oxides), Mica, Cl 77891 (Titanium dioxide) Colorona Bright Gold, Merck, Mica, Cl 77891 (Titanium dioxide), Cl 77491 (Iron oxides); Colorona Blackstar Gold, Merck, MICA, Cl 77499 (IRON OXIDES); color pigments bearing the trade name Unipure® are, for example: Unipure Red LC 381 EM, Sensient Cl 77491 (Iron Oxides), Silica; Unipure Black LC 989 EM, Sensient, Cl 77499 (Iron Oxides), Silica; Unipure Yellow LC 182 EM, Sensient, Cl 77492 (Iron Oxides), Silica.

Depending on the degree of the change in color that is desired on the keratin fiber, the at least one pigment can also be can be used in varying amounts. The more color pigment that is used, the higher is the extent of the change in color in general. Starting at a certain usage amount, however, the adherence of the pigments to the keratin fiber approaches a limiting value, beyond which it is no longer possible to increase the extent of the change in color by further increasing the pigment amount used. While not wishing to be bound by any specific theory, it is believed that when a certain thickness is achieved, an insignificant amount of the incident lights passes through the pigment layer to make a difference to the observed color due to the hair itself. The rest of the light is either scattered back towards the surface, or absorbed.

The at least one pigment can be partially (Scheme 1, (b), where the dark oval represents a pigment, even though the pigment can be white or colorless) or completely enveloped in a matrix (e.g., a polymer matrix or an inorganic matrix; (Scheme 1, (a)). Or the pigment can be adhered to the surface of a matrix that can be colored or colorless (Scheme 1 (c)).

Scheme 1

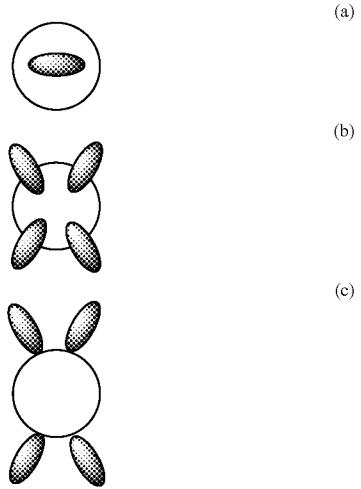

(a)

(b)

(c)

The matrix can be, e.g., $CaCO_3$, $MnCO_3$. Or the matrix can be a melamine formaldehyde matrix.

In another example, the at least one pigment can be encapsulated in silica, as described in Published U.S. Appl. No. 2007/0134180. Other examples of encapsulated pigments include encapsulated Carmine, Iron Oxides, Titanium dioxide, and Chrome Oxide/Hydroxide, the colorants D&C Red 21 Aluminum Lake, D&C Red 7 Calcium Lake, D&C Green 6 Liposoluble, and Aluminium Blue #1 (Indigo Carmine Lake). The encapsulated pigment can be titanium dioxide (used to lighten other pigments and to lend opacity to formulations) in any one of its mineral forms anatase, brookite or rutile, or mixtures thereof. Or the pigment can be at least one iron oxide in any of the 3 basic colors—red, black and yellow iron oxides, or mixtures thereof. From these 3 oxides and the addition of titanium dioxide, any shade of brown (skin tones) can be achieved.

The organic pigment can also be a lake. As used herein, the term "lake" means at least one dye adsorbed onto insoluble particles, the assembly thus obtained remaining insoluble during use. The inorganic substrates onto which the dyes are adsorbed can be, for example, alumina, silica, calcium sodium borosilicate, calcium aluminum borosilicate, calcium carbonate, manganese carbonate, aluminum, nitro-dyes, triarylmethin dyes, Azo-dyes, Anthrazen, Acid dyes, polymethine dyes, triarylmethin dyes, aza annulene dyes and polymethine dyes.

Among the dyes, non-limiting mention can be made of cochineal carmine.

Non-limiting mention can also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), and D&C Blue 1 (CI 42 090). A non-limiting example of a lake that can be mentioned is the product known under the following name: D&C Red 7 (CI 15 850:1).

The at least one pigment can also be a pigment with special effects. As used herein, the term "pigments with special effects" means pigments that generally create a non-uniform colored appearance (characterized by a certain shade, a certain vivacity, and a certain lightness) that changes as a function of the conditions of observation (light, temperature, observation angles, etc.). They thus contrast with white or colored pigments that afford a standard uniform opaque, semi-transparent, or transparent shade.

Several types of pigments with special effects exist, including those with a low refractive index, such as fluorescent, photochromic, or thermochromic pigments, and those with a high refractive index, such as nacres or glitter flakes. Examples of pigments with special effects of which non-limiting mention can be made include nacreous pigments such as mica coated with titanium or with bismuth oxychloride, colored nacreous pigments such as titanium mica with iron oxides, titanium mica for example with ferric blue or with chromium oxide, titanium mica with an organic pigment of the abovementioned type, and also nacreous pigments based on bismuth oxychloride. Nacreous pigments of which non-limiting mention can be made include the CELLINI nacres sold by Engelhard (mica-$TiO_2$-lake), PRESTIGE sold by Eckart (mica-$TiO_2$), PRESTIGE BRONZE sold by Eckart (mica-$Fe_2O_3$), and COLORONA sold by Merck (mica-$TiO_2$—$Fe_2O_3$).

In addition to nacres on a mica support, multilayer pigments based on synthetic substrates such as alumina, silica, sodium calcium borosilicate, calcium aluminum borosilicate, and aluminum, can be envisaged.

Non-limiting mention can also be made of pigments with an interference effect that are not fixed onto a substrate, for instance liquid crystals (HELICONES HC from Wacker) and holographic interference flakes (GEOMETRIC PIGMENTS or SPECTRA F/X from Spectratek). Pigments with special effects also comprise fluorescent pigments, whether these are substances that are fluorescent in daylight or that produce an ultraviolet fluorescence, phosphorescent pigments, photochromic pigments, thermochromic pigments, and quantum dots, sold, for example, by the company Quantum Dots Corporation.

Quantum dots are luminescent semiconductive nanoparticles capable of emitting, under light excitation, irradiation with a wavelength ranging from 400 nm to 700 nm. These nanoparticles are known from the literature. They can be manufactured, for example, according to the processes described, for example, in U.S. Pat. Nos. 6,225,198 or 5,990,479 which are incorporated herein by reference, in the publications cited therein, and also in the following publications: Dabboussi B. O. et al. "(CdSe)ZnS core-shell quantum dots: synthesis and characterization of a size series of highly luminescent nanocrystallites" Journal of Physical Chemistry B, vol. 101, 1997 pp. 9463-9475 and Peng, Xiaogang et al. "Epitaxial growth of highly luminescent CdSe/CdS core/shell nanocrystals with photostability and electronic accessibility", Journal of the American Chemical Society, vol. 119, No. 30, pp. 7019-7029.

The variety of pigments that can be used in the present disclosure makes it possible to obtain a wide range of colors, and also optical effects such as metallic effects or interference effects.

The pigments that can be used in the present disclosure can transmit light of various wavelengths, including visible light (e.g., light having a wavelength of above 350 nm). The pigment(s) can also transmit light of certain wavelengths, but also reflect light of certain wavelengths. And the pigment(s) can also be 100% reflective. For examples, reflective pigments provide a high specular reflection of visible light. Reflective pigments include those that are partially or completely coated with a non-matt and non-scattering surface layer of a metal or metal oxide. The substrate can be chosen from glasses, ceramics, graphite, metal oxides, aluminas, silicas, silicates, especially aluminosilicates and borosilicates and synthetic mica (e.g., fluorophlogopite), to name a few. The metal or metal oxide can be, without limitation, titanium oxides, iron oxides, tin oxide, chromium oxide, barium sulfate, $MgF_2$, $CeF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$ and $MoS_2$, and mixtures thereof. Reflective pigments can have a spectral reflectance in the visible spectrum of at least 70%.

Other reflective pigments include those having non-goniochromatic layered structure of two or more polymeric and/or metallic layers of different refractive indices. For example, reflective particles comprising layers of 2,6-polyethylene naphthalate (PEN) and of polymethyl (meth)acrylate are sold by 3M under the name Mirror Glitter™. Other effect pigments are available under the trade name Metasomes Standard/Glitter in various colors (yellow, red, green, blue) from Flora Tech.

Color Gamut for Pigment Blends

CIE L*a*b* (CIELAB) is a color space specified by the International Commission on Illumination. It describes all the colors visible to the human eye and serves as a device-independent model to be used as a reference.

The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

Since the L*a*b* model is a three-dimensional model, it can be represented properly only in a three-dimensional space. Two-dimensional depictions include chromaticity diagrams: sections of the color solid with a fixed lightness.

Because the red-green and yellow-blue opponent channels are computed as differences of lightness transformations of (putative) cone responses, CIELAB is a chromatic value color space.

In the present invention, the color gamut is determined by adding each pigment to be tested in the hair coloring composition, and then individually tested at a level such that when applied to hair, the resulting CIELAB lightness or L* value of the colored hair is 60±2. The level of pigment needed will depend on the pigment being tested. Two hair tresses (Kerling, Natural White special quality) have the multicomponent composition applied as described herein. A Minolta spectrophotometer CM-2600d is used to measure the color of the dried hair tresses, five points on both the front and back sides, and the values averaged. The D65 L*a*b values are calculated. When at least three pigments have each been measured such that their resulting color reside within the target L* values of 60±2 the color gamut can be calculated. First the lengths of each side of the resulting triangle of each combination of three pigments in the a*b plane are computed using the following expressions. To calculate the distance between pigments 1 and pigment 2 the following equation is used:

$$\text{Side Length } SL_{12} = ((a_{pigment\ 1} - a_{pigment\ 2})^2 + (b_{pigment\ 1} - b_{pigment\ 2})_2)^{0.5}$$

This is computed for each pair of pigments. Then for a series of three pigments.

The resulting color gamut is calculated using the expression:

$$\text{Color Gamut} = (S(S-SL_{12})(S-SL_{13})(S-SL_{23}))^{0.5}$$

wherein $SL_{12}$, $SL_{13}$, and $SL_{23}$ are the three lengths of the sides of the triangle within the a*b plane, and $S=(SL_{12}+SL_{13}+SL_{23})/2$. Where more than three pigments are used, this calculation can be performed for each combination of the three pigment from the more than three pigments used, and the largest Color Gamut is selected.

The hair coloring composition embodiments of the present invention can also have a color gamut of greater than 250, greater than 500, greater than 750, greater than 800, greater than 900, greater than 1100 or even greater than 1250.

Experiments Performed for Color Gamut

Using the above expression, for each combination of three pigments possible from Color Gamut Tables 1, as illustrated below, the color gamut at a nominal L value of 60 was calculated

TABLE 1

Color Gamut

| Pigment | Name | Supplier | wt % level | L | a | b |
|---|---|---|---|---|---|---|
| Blue 15 | PV Fast Blue BG-NIP | Clariant | 0.155 | 59.3 | −18.7 | −2.1 |
| Blue 16 | Phthalocyanine | Carbosynth | 0.280 | 59.4 | −17.3 | 1.5 |
| Blue 66 | Indigo 229296 | Aldrich | 0.105 | 60.0 | −3.1 | 6.8 |
| Blue 60 | Paliogen Blau L 6482 | BASF | 0.260 | 60.7 | −3.9 | 5.9 |
| Black 7 | Midnight Black | Geotech | 0.045 | 59.8 | 0.0 | 12.3 |
| Green 36 | Heliogen Green K 9362 | BASF | 0.509 | 60.1 | −32.8 | 20.2 |
| Red 112 | Permanent Red FGR 250 | Clariant | 0.150 | 60.1 | 29.8 | 18.8 |
| Red 122 | Hostaperm Pink E02-EDW VP4034 | Clariant | 0.140 | 59.5 | 24.9 | 6.1 |
| Violet 19 | Ink Jet Magenta E5B 02 M250 | Clariant | 0.200 | 60.6 | 28.1 | 10.1 |
| Red 5 | Permanent Carmine FB01 | Clariant | 0.140 | 59.7 | 30.1 | 14.4 |
| Yellow 155 | Ink Jet Yellow 4GC | Clariant | 16.92 | 61.8 | 9.6 | 74.4 |
| Yellow 83 | Novoperm Yellow HR 70 | Clariant | 1.059 | 60.0 | 12.5 | 61.8 |
| Yellow 180 | Toner Yellow HG | Clariant | 9.16 | 61.4 | 11.2 | 72.8 |

These were formulated within an example formulation described later using an appropriate level of first, second and third compositions.

A few examples are exemplified of combinations of pigments and their resulting color gamut. One skilled in the art would be able to perform this for all of the possible permutations of pigments that are assessed according to the description above.

FIGS. 1 to 4 show plots of color gamut triangles created for a series of three pigment selections.

FIG. 1 shows that a combination of Pigment Green 36, Pigment Yellow 83 and Pigment Red 122 a large triangle is plotted in the a*b* color plane with an area of 1520.

Figure 2:
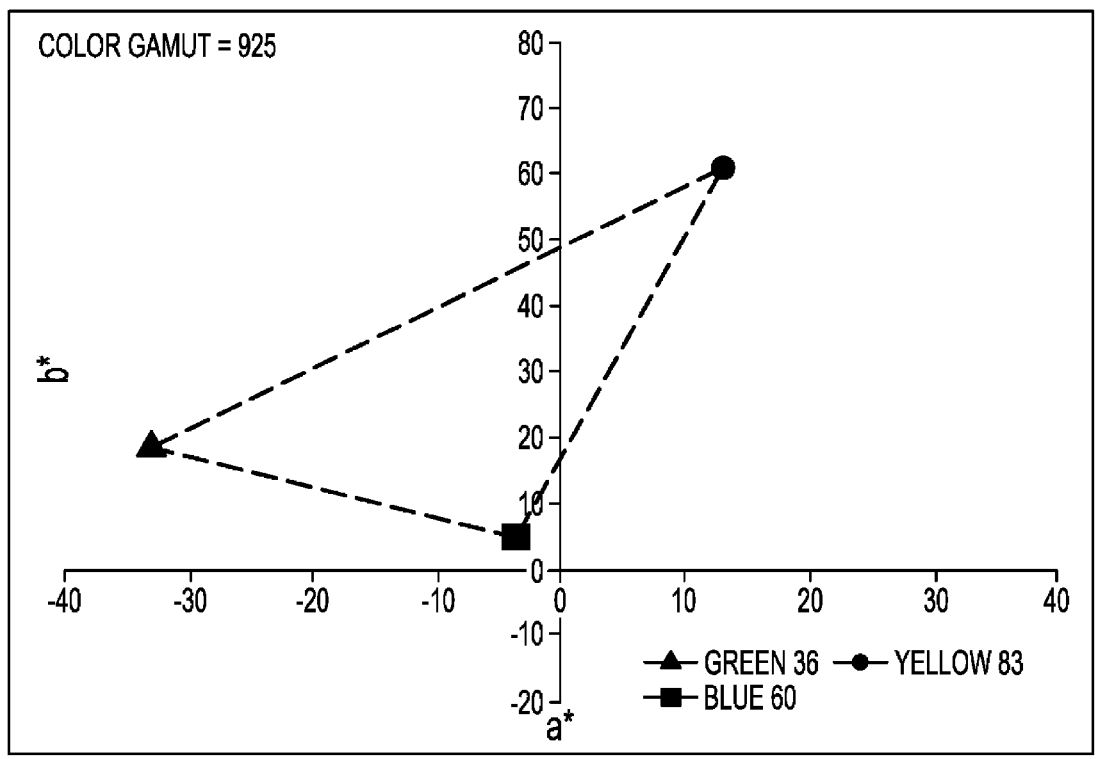
FIG. 2 shows a Gamut plot of green, yellow and blue pigments.

FIG. 2 shows that the combination of Pigment Green 36, Pigment Yellow 83 and Pigment Blue 60 gives a smaller triangle win an area of 925.

Figure 3:
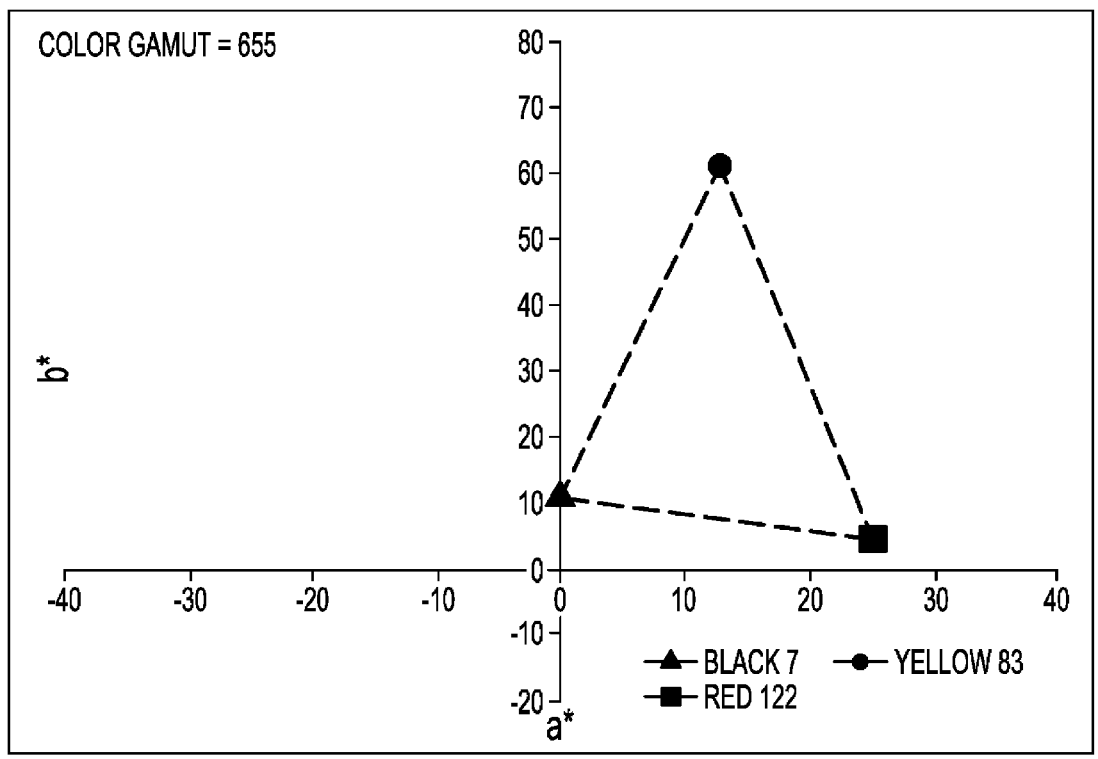
FIG. 3 shows a Gamut plot of black, yellow and red pigments.

FIG. 3 shows the combination of Pigment Black 7, Pigment Yellow 83 and Pigment Red 122 gives a smaller triangle win an area of 655.

Figure 4:
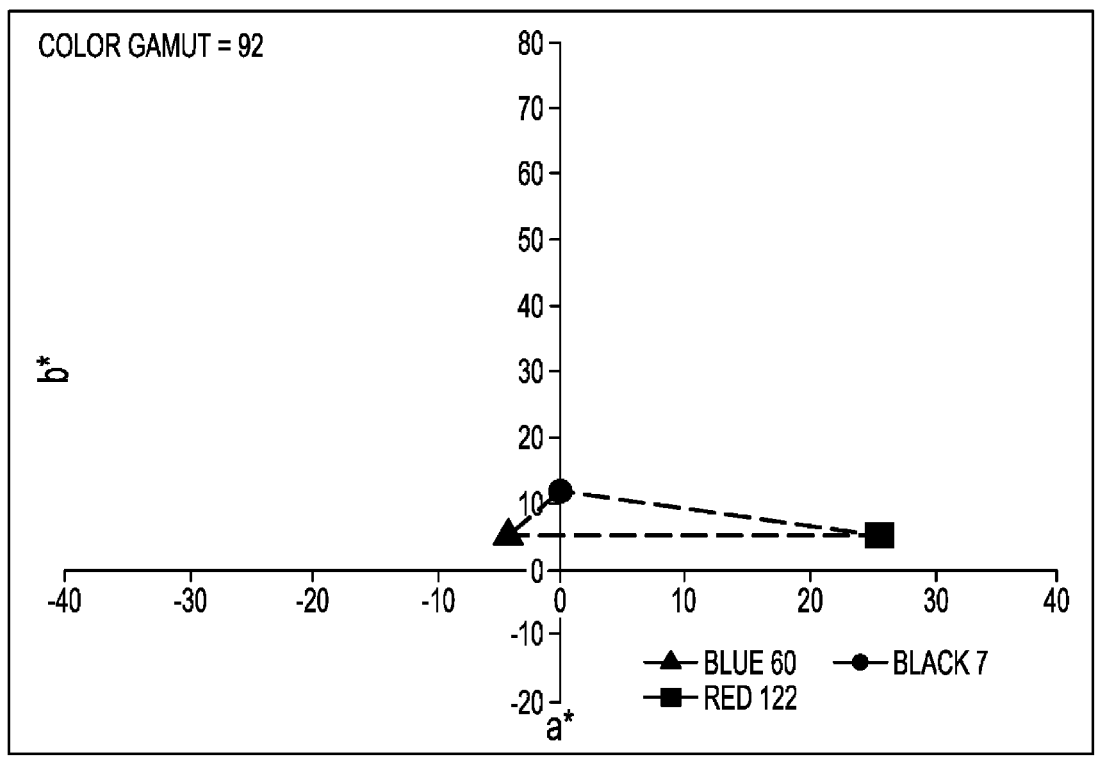
FIG. 4 shows a Gamut plot of black, blue and red pigments.

FIG. 4 shows the combination of Pigment Black 7, Pigment Blue 60 and Pigment Red 122 gives a smaller triangle win an area of 92.

A second series of examples are made for how to assess more than three pigments and their resulting color gamut. When plotted a series of triangles can be plotted as shown and for each the areas is assessed. For such a system the color gamut is defined as the largest of the triangles formed.

Figure 5:
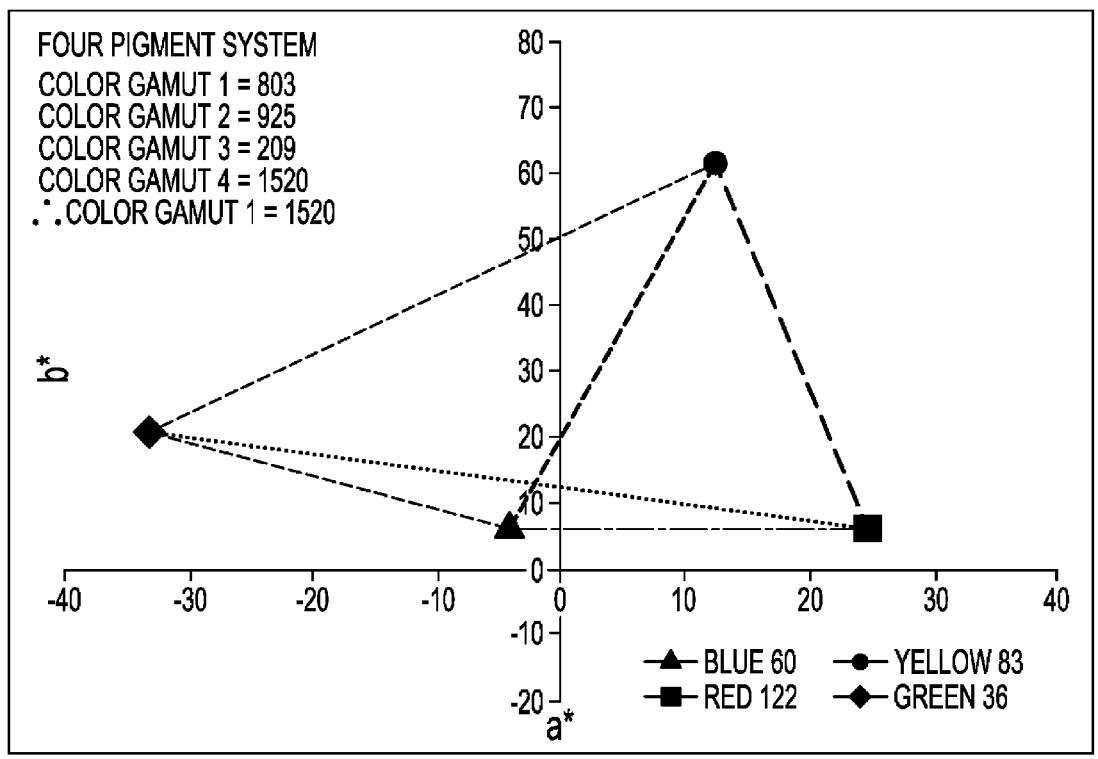
FIG. 5 shows a Gamut plot of green, yellow, blue and red pigments.

FIG. 5 shows a combination of Pigment Green 36, Pigment Yellow 83, Pigment Blue 60 and Pigment Red 122 a series of triangles are plotted with areas of 803, 925, 209 and 1520. The color gamut of this pigment system is 1520.

Figure 6:
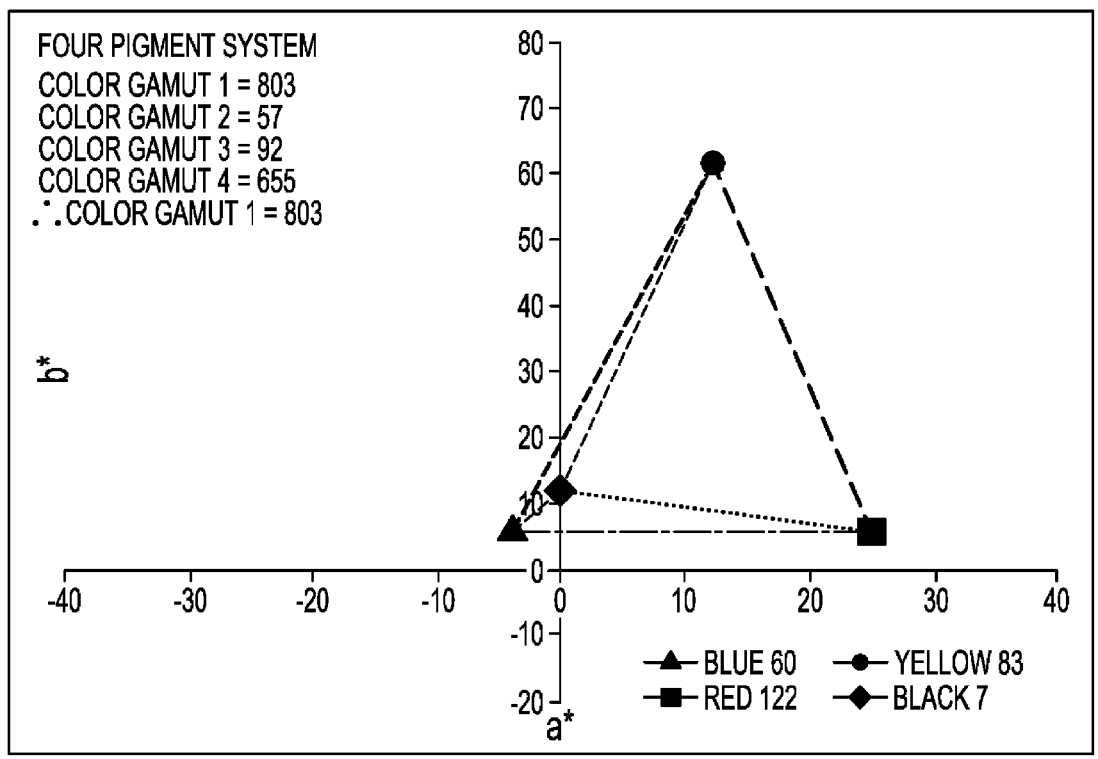
FIG. 6 shows a Gamut plot of black, yellow, blue and red pigments.

FIG. 6 shows a combination of Pigment Black 7, Pigment Yellow 83, Pigment Blue 60 and Pigment Red 122 a series of triangles are plotted with areas of 803, 57, 92 and 655. The color gamut of the pigment system is 803

D. The pH

The multicomponent composition embodiments in accordance with the present disclosure can have a pH ranging from about 3 to about 12, preferably about 4 to about 10 and in many embodiments 6.8 or higher. For example, the pH can be 8 or higher, 9 or higher or at most 12. In some examples, the multicomponent composition embodiments in accordance with the present invention can have a pH of from about 7 to about 10, about 5 to about 11 or about 6 to about 8.

The pH may range from about 3 to about 8 for polar functional silicone polymers that can form cationic groups, e.g., amines and ranging from about 5 to about 11 for polar functional silicone polymer that can form anionic groups, e.g., carboxylic and sulfonic acids. For silicone polymer with cation forming groups (amines), preferably the pH is about 4 to about 7 and in many embodiments 6.8 or lower. In some examples, the multicomponent composition embodiments with silicone polymers having cation forming groups in accordance with the present invention can have a pH of from about 3.0 to about 8.0, preferably about 3.5 to about 6.8, more preferably about 4.5 to about 6.8, most preferably about 5.5 to about 6.5.

The multicomponent composition in accordance with the present disclosure can comprise a pH modifier and/or buffering agent. The amount is sufficiently effective to adjust the pH of the composition/formulation. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, such as sodium hydroxide, sodium silicate, sodium meta silicate and ammonium carbonate, and acids such as inorganic and inorganic acids, e.g., phosphoric acid, acetic acid, ascorbic acid, citric acid or tartaric acid, hydrochloric acid, and mixtures thereof.

E. Dispersants

It will be apparent to one skilled in the art that careful and selective choice of dispersant can help to maximize performance in terms of maximizing the amount of color produced from an immobilized film, maximizing the remanence or washfastness, and enabling removal of the color.

For example, in the case where the binder polymer is anionic in nature, dispersants which are anionic or nonionic are preferably chosen, rather than cationic, as this avoids undesired precipitation in the formula prior to it forming a colored film on the keratin—i.e. utilizing the principle of avoiding opposing charges.

Likewise, the principle of choosing chemically similar dispersant and binder (for example, a silicone binder paired with a silicone dispersant, can be followed to ensure maximum compatibility.

As well as compatibility as noted above, the other critical criterion in selecting dispersant(s) is their ability to enable pigment to be dispersed down to the primary particle size, preferably with the minimum amount of input mechanical energy. It will be recognized by someone skilled in the art that the concentration of dispersing agent is also a critical factor. In general it is usually required that there is a minimum amount for dispersing activity and that below this, the system is either not fully dispersed or, worse, that the dispersant acts as a flocculant.

These two considerations together are used to define preferred materials and their respective concentrations.

It may also be the case, depending on the type of binder polymer used, that the binder itself is also a dispersant (see below for discussion of classes of dispersant). In such cases it is possible that no further dispersing additive may be needed.

Overview Of Dispersant Kinds, Properties and Chemistry

Dispersants are amphiphilic or amphiphathic meaning that they are chemical compounds possessing both hydrophilic (water-loving, polar) and lipophilic (fat-loving) properties. Dispersants are surface-active polymers that allow the homogeneous distribution and stabilization of solids, e.g. pigments in a liquid medium (like a binder), by lowering the interfacial tension between the two components. As a result, agglomerates are broken up into primary particles and protected by a protecting dispersant envelope of a re-agglomeration.

The dispersants can be subdivided on the basis of the stabilization mechanism in
1. Dispersants for electrostatic stabilization
   a. Anionic dispersing additives
      i. Polyacrylates
      ii. Polyphosphates
   b. Neutral dispersing additives
   c. Cationic dispersing additives
2. Dispersants for steric stabilization Electrostatic Stabilization The pigment surface is occupied by an additive carrying an ionic charge. All pigment particles are charged the same. The mutual repulsion by the charge is greater than the attractions of the pigment particles. The electrostatic stabilization has its relevance mostly in water-based paint systems.

Polyanionic dispersing additives: polycarboxylates (mostly salts of polyacrylic acids), polyphosphates divided into linear polyphosphates and cyclic metaphosphates, polyacrylates salts of polyacrylic acid, as cations, sodium and ammonium are preferred, these polyacrylates are water-soluble, technical products have molecular weights in the range of 2000 to 20,000 g/mol, optimum is about 8000 g/mol Sodium and ammonium salts of the homo- or copolymers of acrylic acid, methacrylic acid or maleic acid Steric Stabilization The attractive forces between the pigment particles are effective only over relatively small distances of the particles from each other. The approach of two particles to each other can be prevented by molecules that are firmly anchored to the pigment surface and carry groups that extend from the surface and may reduce the potential for the pigments to contact one another. By sufficiently long chain lengths, agglomeration can be prevented.

Water-soluble polymers

Block or graft copolymers, so-called AB block copolymers

Example: AB block polymer of 2-vinylpyridine and methacrylic acid ester

Example: AB block copolymer of polyester (based caprolactam) and triethylenetetramine Typical functional groups for the A segment are carboxyl, amine, sulfate and phosphate for inogenous bonds or polyether and polyamide for hydrogen bonds. B represents the solvated side chain, molecular weights 1000 to 15000 g/mol, e.g. modified polyacrylates or polyhydroxystearates Hydrophilic moieties (e.g., polyethers) and pigment affinic groups (e.g. Groups) containing oligomers or polymers.

The following types are distinguished according to the number of monomer types used in the production:

Homopolymers: only one kind of monomer

Copolymers: two monomers

Terpolymers: three monomers

Classification according to distribution of the monomers in the polymer:

Statistical polymers: A and B segments are distributed arbitrarily

Block polymers: the monomers are grouped into blocks

Graft polymers: these consist of a linear homopolymer backbone on which side chains of other monomer blocks are grafted Some examples of dispersants for solvent-based systems are:

oligomeric titanates and silanes for inorganic pigments with OH or carboxy groups.

Oligomeric polymeric carboxylic acids for inorganic pigments (cationic).

Polyamines for inorganic pigments, e.g., cationic polymers.

Salts of long-chain polyamines and polycarboxylic acids for inorganic and organic pigments (electroneutral).

Amine/amide-functional polyesters/polyacrylates for the stabilization of organic pigments.

Polysilicones with and without functional groups including cyclic siloxanes, amine functional cyclic and linear siloxanes, carboxyl functional cyclic and linear siloxanes.

Some examples of dispersants for aqueous systems are:

Inorganic dispersants such as fine-grained $CaCO_3$, $Ca_3(PO_4)_2$, polyphosphates, polyphosphoric acids.

Nonionic surfactants such as ethoxylated fatty alcohol (e.g. Neodol 25-9), ethoxylated oils (e.g. ethxylated castor oil under the tradename Cremophore RH410)

Block and graft copolymers of the type having distinct hydrophilic and hydrophobic blocks (e.g. ethylene oxide-propylene oxide polymers under the tradename Poloxamer)

Anionic surfactants consisting of the unethoxylated or ethoxylated salts of acids (e.g. sodium ceteth-10-phosphate under the tradename Crodafos).

Examples and classes of nonionic surfactants that can function as dispersants include oligomers (e.g., example, oligomers have up to 20 monomeric units, polymers have at least 20 monomeric units), polymers, and/or a mixture of several thereof, bearing at least one functional group with strong affinity for the surface of the pigment microparticles. For example, they can physically or chemically attach to the surface of the pigment microparticles. These dispersants also contain at least one functional group that is compatible with or soluble in the continuous medium. For example, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name SOLSPERSE 21,000 by the company Avecia, polyglyceryl-2 dipolyhydroxystearate (CTFA name) sold under the reference DEHYMYLS PGPH by the company Henkel, or polyhydroxystearic acid such as the product sold under the reference ARLACEL P100 by the company Uniqema, and mixtures thereof. Similar dispersants will function to disperse the polar functional silicone polymers that are not readily dispersible and/or are not at least partially soluble in aqueous media.

The foregoing dispersant category involving cationic polymers includes polymers such as quaternary ammonium polymers. Examples of quaternary ammonium derivatives of polycondensed fatty acids include, such as for instance, SOLSPERSE 17,000 sold by the company Avecia, and polydimethylsiloxane/oxypropylene mixtures such as those sold by the company Dow Corning under the references DC2-5185 and DC2-5225 C.

The dispersant can be a polyolefin polymer. These dispersants include but are not limited to an olefinic polymer having a molecular weight of about 100 g/mol to about 5,000,000 g/mol, such as about 1,000 g/mol to about 1,000,000 g/mol. Examples of polymers, include, but are not limited to poly(ethylene), poly(propylene), poly(butylene), poly(isobutylene), poly(isoprene), poly(acetal), poly(ethylene glycol), poly(propylene glycol), poly(butylene glycol), poly(methylmethacrylate), poly(dimethylsiloxane), poly(vinylalcohol), poly(styrene), poly(maleic anhydride), poly(ethylmethacrylate), poly(isobutylmethacrylate), poly(methacrylate), poly(butylmethacrylate), poly(n-butylmethacrylate), poly(vinyl butyrate), poly(vinyl chloride), polysiloxane, and mixtures thereof. The polymers can be random, block, or alternating copolymers. In some embodiments, the polymer is a co-polymer that is made from two or more different monomers, such as the monomers that make the polymers described above. Examples of co-polymers include, but are not limited to polyethers, polyesters, polyamides, acrylics, and polystyrenes. The co-polymer can be alternating monomers, random, or block. Examples include a polyether of alternating or block PEO, PPO groups. Examples of acidic groups include, but are not limited to, carboxylic acids, sulfinic acids, sulfonic acids, phosphonic acids, phosphate esters, maleic anhydrides, and succinic anhydride. In some embodiments, the dispersive additive comprises a group selected from phosphonate, phosphate, phosphite, phosphine, and phosphate ester, such as a phosphate, phosphite, and phosphonic acid.

In some embodiments, the acidic group has been converted into a salt. Representative dispersants are also available from a variety of suppliers, and include various non-ionic (e.g., ethoxylated) and anionic (e.g., non-ethoxylated salt) forms including agents from Air Products and Chemicals, Inc. (e.g., SURFYNOL™ PSA336); Archer Daniels Midland Co. (e.g., ULTRALEC™ F deoiled lecithin); Ashland Inc. (e.g., NEKAL™ WS-25-I, which is a sodium bis(2,6-dimethyl 4heptyl)sulfosuccinate); BASF (e.g., DISPEX™ AA 4144, DISPEX ULTRA FA 4425 which is a fatty acid-modified emulsifier having a viscosity of 40,000 cps, DISPEX ULTRA FA 4420 which is a fatty acid-modified emulsifier and a dark brown liquid of unspecified viscosity, DISPEX ULTRA FA 4431 which is an aliphatic polyether with acidic groups having a viscosity of 350 cps, DISPEX ULTRA PA 4501 which is a fatty acid modified polymer having a viscosity of 10,000 cps, DISPEX ULTRA PA 4510, EFKA™ PU 4010, EFKA PU 4047 which is a modified polyurethane, EFKA PX 4300, EFKA ULTRA PA 4510 and EFKA ULTRA PA 4530 which are modified polyacrylates, EFKA FA 4620 which is an acidic polyether having a viscosity of 1,400 cps, EFKA FA 4642 which is an unsaturated polyamide and acid ester salt having a viscosity of 2,000 cps, HYDROPALAT™ WE 3135, HYDROPALAT WE 3136 and HYDROPALAT WE 3317 which are difunctional block copolymer surfactants terminating in primary hydroxyl groups and having respective viscosities of 375, 450 and 600 cps, and TETRONIC™ 901 and TERTRONIC 904 which are tetrafunctional block copolymers terminating in primary hydroxyl groups and having respective viscosities of 700 and 320 cps); Borchers (e.g., BORCHI™ Gen 0451 which is a polyurethane oligomer having a viscosity of about 30,000 cps, BORCHI Gen 0652 which is an amine neutralized acrylic acid copolymer having a viscosity of about 75-300 cps, and BORCHI Gen 1252 and BORCHI Gen 1253 which are acrylic ester copolymers having respective viscosities of about 1,500-3,500 and 50-300 cps); Byk-Chemie (e.g., BYK™ 156 which is a solution of an ammonium salt of an acrylate copolymer, DISPERBYK™ which is a solution of an alkyl ammonium salt of a low-molecular-weight polycarboxylic acid polymer, DISPERBYK-102 which is an acidic copolymer, DISPERBYK™-145 which is a phosphoric ester salt of a high molecular copolymer with pigment affinic groups and a liquid of unspecified viscosity, DISPERBYK-190 which is a solution of a high molecular weight block copolymer with pigment affinic groups, DISPERBYK-2013 which is a structured copolymer with pigment affinic groups having a viscosity of 8,600 cps, DISPERBYK-2055 which is a copolymer with pigment affinic groups and a liquid of unspecified viscosity, DISPERBYK-2060 which is a solution of a copolymer with pigment affinic groups having a viscosity of 3,600 cps, DISPERBYK-2061 which is a solution of a copolymer with pigment affinic groups having a viscosity of 491 cps, DISPERBYK-2091, DISPERBYK-2200 which is a high molecular weight copolymer with pigment affinic groups sold in solid form as pastilles and BYKJET™-9152 which is a copolymer with pigment affinic groups having a viscosity of 21,600 cps); Clariant (e.g., DISPERSOGEN™ 1728 which is an aqueous solution of a novolac derivative having a viscosity of 4,000 cps, DISPEROGEN 2774 which is a novolac alkoxylate having a viscosity of 4,000 cps, GENAPOL™ X 1003 and GENAPOL X 1005 which are fatty alcohol ethoxylates having respective viscosities of about 400 cps and 1,300 cps, HOSTAPAL BV concentrate which is a sulfate ester having a viscosity of about 2,700 cps); Cray Valley (e.g., SMA1440H which is an ammonia salt of a styrene maleic anhydride copolymer solution); Dow Chemical Co. (e.g., the TAMOL™ family of dispersants including TAMOL 165A and TAMOL 731A); Elementis (e.g., NUOSPERSE™ FA196 which has a viscosity of 1,200 cps); Lubrizol (e.g., SOLSPERSE™ 27000, SOLSPERSE 28000, SOLSPERSE 32000, SOLSPERSE 39000, SOLSPERSE 64000, SOLSPERSE 65000, SOLSPERSE 66000, SOLSPERSE 71000, SOLSPERSE M387, SOLPLUS™ R700 and SOLPLUS K500); Ethox Chemicals, LLC (e.g., the E-SPERSE™ family of dispersants and ETHOX™ 4658); Evonik (e.g., TEGO™ DISPERS 656, TEGO DISPERS 685, TEGO DISPERS 750W and TEGO DISPERS 757W); Rhodia Solvay Group (e.g., ABEX 2514 and ABEX 2525 which are nonionic surfactants, RHODACAL™ IPAM which is isopropyl amine dodecylbenzene sulfonate having a viscosity of 10,000 cps, RHODAFAC™ RS-710 which is a polyoxyethylene tridecyl phosphate ester, and the RHODOLINE™ family of dispersants including RHODOLINE 4170 and RHODOLINE 4188); Sasol Wax GmbH (e.g., ADSPERSE™ 100, ADSPERSE 500 and ADSPERSE 868) and Stepan Company (e.g., G-3300 which is an isopropyl amine salt of an alkyl aryl sulfonate having a viscosity of about 6000 cps, POLYSTEP™ A-15 which is a sodium dodecylbenzene sulfonate having a viscosity of about 85 cps, POLYSTEP B-11 and POLYSTEP B-23 which are ethoxylated ammonium lauryl ether sulfates respectively containing 4 or 12 moles of ethylene oxide and having respective viscosities of 66 and 42 cps, and POLYSTEP B-24 which is sodium lauryl sulfate having a viscosity of 100 cps).

Commercial dispersant compositions and systems of the synthetic kind described above are sold by several companies who manufacture polymer systems.

These include:
  BASF
    Water-based system—
      Dispex® Ultra FA, Dispex® AA, Dispex® CX, Dispex® Ultra PX, Dispex® Ultra PA solvent based system
      Efka® FA, Dispex® Ultra FA, Efka® FA, Efka® PU, Efka® PA, Efka® PX
  Clariant
    Dispersogen® 1728, Dispersogen® 2774, Dispersogen® 3169, Dispersogen® AN 100, Dispersogen® AN 200, Dispersogen® ECS, Dispersogen® ECO, Dispersogen® LFS 6, Dispersogen® PCE, Dispersogen® PL 30, Dispersogen® PL 40, Dispersogen® PTS, Dispersogen®, Emulsogen® LCN 217, Emulsogen® TS 200, Dispersogen®, Dispersogen® FN, Dispersogen® FSE, Dispersogen® MT 200, Dispersogen® LFH, Dispersogen® 145, Dispersogen® 4387, Hostapal® BV, Dispersogen® LEC, Dispersogen® PSM, Polyglykol 200 LVC, Polyglykol G500, Polyglykol 300, Polyglykol 400
  Lubrizol
    Solsperse™ 3000, Solsperse™, Solsperse™ 8000, Solsperse™, Solsperse™ 12000S, Solsperse™ 13300, Solsperse™ 13400, Solsperse™ 13500, Solsperse™ 13650, Solsperse™ 13940, Solsperse™ 16000, Solsperse™ 17000, Solsperse™ 17940, Solsperse™ 17000, Solsperse™ 18000, Solsperse™ 19000, Solsperse™ 20000, Solsperse™ 21000, Solsperse™

22000, Solsperse™ 24000SC, Solsperse™ 26000, Solsperse™ 27000, Solsperse™ 28000, Solsperse™ 32000, Solsperse™ 32500, Solsperse™ 32600, Solsperse™ 33000, Solsperse™ 35000, Solsperse™ 35100, Solsperse™ 35000, Solsperse™ 36000, Solsperse™ 36600, Solsperse™ 37500, Solsperse™ 38500, Solsperse™ 39000, solsperse W100.

Byk
  DISPERBYK-102, DISPERBYK-103, DISPERBYK-106, DISPERBYK-107, DISPERBYK-108, DISPERBYK-109, DISPERBYK-110, DISPERBYK-111, DISPERBYK-115, DISPERBYK-118, DISPERBYK-130, DISPERBYK-140, DISPERBYK-142, DISPERBYK-145, DISPERBYK-161, DISPERBYK-162, DISPERBYK-163, DISPERBYK-164, DISPERBYK-166, DISPERBYK-167, DISPERBYK-168, DISPERBYK-170, DISPERBYK-171, DISPERBYK-174, DISPERBYK-180, DISPERBYK-181, DISPERBYK-182, DISPERBYK-184, DISPERBYK-185, DISPERBYK-187, DISPERBYK-190, DISPERBYK-191, DISPERBYK-192, DISPERBYK-193, DISPERBYK-194 N, DISPERBYK-199, DISPERBYK-2000, DISPERBYK-2001, DISPERBYK-2008, DISPERBYK-2009, DISPERBYK-2010, DISPERBYK-2012, DISPERBYK-2013, DISPERBYK-2015, DISPERBYK-2022, DISPERBYK-2023, DISPERBYK-2025, DISPERBYK-2026, DISPERBYK-2050, DISPERBYK-2055, DISPERBYK-2060, DISPERBYK-2061, DISPERBYK-2062, DISPERBYK-2070, DISPERBYK-2080, DISPERBYK-2081, DISPERBYK-2096, DISPERBYK-2117, DISPERBYK-2118, DISPERBYK-2150, DISPERBYK-2151, DISPERBYK-2152, DISPERBYK-2155, DISPERBYK-2157, DISPERBYK-2158, DISPERBYK-2159, DISPERBYK-2163, DISPERBYK-2164, DISPERBYK-2200, DISPERBYK-2205

DOW
  TAMOL™ 1124; TAMOL™ 1254; TAMOL™ 165A; TAMOL™ 2002; TAMOL™ 2011; TAMOL™ 681; TAMOL™ 731A; TAMOL™ 851; TAMOL™ 901; TAMOL™ 945; TAMOL™ 960; TAMOL™ 963; TAMOL™

Following the foregoing principles and guidelines, the pigment microparticles can be dispersed in the composition with the addition of at least one of a dispersant and a wetting agent. While not wishing to be bound by any specific theory, it is believed that only when the pigments are de-aggregated into their primary particles do they deliver the optimum optical performance. For examples, pigments with a primary particle size of 0.02 micron which provide brilliant bright colors, when present as aggregates of around 0.3 micron provide duller colors.

The dispersant serves to protect the pigment microparticles against agglomeration or flocculation either in the dry state or in the solvent. Dispersants also serve as wetting agents. In this capacity, dispersants as wetting agents can be low or higher molecular weight monomeric surfactants (for example, anionic, cationic or amphoteric surfactants). Dispersants as wetting agents can be higher molecular weight surface-active or pigment particle affinic polymers (for example, polyelectrolyte dispersants such as maleic acid copolymers, and polyurethanes or polyacrylates containing carboxylic acid, amine or isocyanate pigment affinic anchor groups or polyethylene imines) or other type of polyelectrolytes.

Representative wetting agents include those available from a variety of suppliers including Air Products and Chemicals (e.g., CARBOWET™ GA-210 surfactant which has a viscosity of 80 cps, CARBOWET GA-221 surfactant which has a viscosity of 100 cps, DYNOL™ 607 superwetter which has a viscosity of 205 cps and DYNOL 800 superwetter which has a viscosity of 230 cps); Dow Chemical Co. (e.g., CAPSTONE™ fluorosurfactants FS 31, FS 34, FS 35, FS 61 and FS 64); and Stepan Company (e.g., STEPWET™ DOS-70 surfactant which contains 70% active ingredients and has a viscosity of 200 cps, and STEPWET DOS-70EA surfactant which contains 70% active ingredients and has a viscosity of 220 cps).

G. Incorporation of Pigment in Disperant

The pigments described herein can be chosen and/or modified to be similar enough such that a single dispersant can be used. In other instances, where the pigments are different, but compatible, two or more different dispersants can be used. Because of the extreme small size of the pigment microparticles and their affinity, combination of the pigment microparticles and dispersant to form a substantially homogeneous dispersion that can subsequently be modified and/or diluted as desired is to be accomplished before combination with any or all of the first, second and third components of the multicomponent composition.

The pigment microparticles can be dispersed and stabilized in the medium by one or more dispersants the properties and kinds of which are described above. Exemplary dispersants include non-ionic surfactants moderate weight hydrocarbons such as isododecane and silicone solvents/dispersants such as cyclopentasiloxane and similar cyclic siloxanes. The dispersant can either be added to the medium, or to a precursor medium or can form a coating on the microparticles to facilitate dispersion. It is also possible to provide the microparticles with a coating of a dispersant material and additionally provide a further dispersant to the medium, or to a precursor medium, which is used to form the final medium.

The dispersant, either added to the medium or provided as coating, facilitates wetting of the microparticles, dispersing of the microparticles in the medium, and stabilizing of the microparticles in the medium.

The wetting includes replacing of materials, such as air, adsorbed on the surface of the pigment microparticles and inside of agglomerates of the microparticles by the medium. Typically, a complete wetting of the individual microparticles is desired to singularize the particles and to break off agglomerates formed by microparticles adhering to each other.

After wetting, the microparticles can be subjected to de-aggregate and de-agglomerate step, generally referred to as dispersing step. The dispersing step typically includes the impact of mechanical forces such as shear to singularize the microparticles. In addition to shearing to singularize, the microparticles can be broken into even smaller microparticles using, for example, roller mills, high speed mixers, and bead mills. Usual practice involves substantially homogeneous dispersion of the pigments in dispersant through the use of high shear mixing; for example through use to the appropriate ball mill, ultra high pressure homogenizer or other system known by those skilled in the art of pigment dispersion.

During wetting and dispersing, the exposed total surface area of the microparticles increases which is wetted by the dispersant. The amount of the dispersant may be gradually increased during dispersing to account for the increased surface area.

The dispersant also functions as de-flocculation agent keeping the dispersed microparticles in a dispersed state and prevent that they flocculate to form loose aggregates. This stabilization is also needed for long term storage purposes. Different type of stabilization such as electrostatic stabilization and steric stabilization are possible, and the type of dispersant is selected in view of the medium and the material of the microparticles.

The dispersant may be added to a dry powder of the pigment particles when the particles are milled to a desired size. During milling, or any other suitable technique to singularize the pigment particles or to break them into smaller part, the dispersant comes in contact with and adheres to the surface of the microparticles. Freshly generated microparticle surface during milling will be coated by the dispersant so that, after milling, the microparticles with a coating formed by the dispersant are provided.

The coating with the dispersant can also be carried out in a liquid carrier medium to which the dispersant is added. The microparticles can also be milled in the liquid carrier.

H. Optional Components

Optional components of the composition include suspending agents, leveling agents and viscosity control agents. The suspending agents help maintain the pigment particles in dispersed condition and minimize or negate their agglomeration. Suspending agents include fatty acid esters of polyols such as polyethylene glycol and polypropylene glycol. These are similar to plasticizers and function in similar fashion to allow pigment particles to "slip" by each other without retarding or binding interaction. They act as grease in this fashion. Additionally, suspending agents in part participate in promoting the stable dispersion of the pigment particles and avoid settling. The silicone polymer also participates through its solubilization or interaction with the pigment particles and with the medium. The suspending agents provide another factor for maintaining the stable dispersion. They not only provide the "grease" to facilitate Brownian movement but also in part stabilize through interaction as emulsifiers of the pigment particles in the medium.

The multicomponent composition embodiments in accordance with the present invention can also optionally contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins, vitamins, propellants, oxyethylenated or non-oxyethylenated waxes, paraffins, $C_{10}$-$C_{30}$ fatty acids such as stearic acid or lauric acid, and $C_{10}$-$C_{30}$ fatty amides such as lauric diethanolamide.

The multicomponent composition embodiments in accordance with the present invention can further optionally contain one or more additives, including, but not limited to, antioxidants (e.g., phenolics, secondary amines, phosphites, thioesters, and combinations thereof), crosslinking agents, reactive diluents (e.g., low molecular weight mono- or di-functional, non-aromatic, (meth)acrylate monomers such as 1,6-hexanediol di(meth)acrylate, tripropylene glycol di(meth)acrylate, isobornyl(meth)acrylate, 2(2-ethoxyethoxy)ethyl(meth)acrylate, n-vinyl formamide, tetrahydrofurfuryl(meth)acrylate, polyethylene glycol di(meth)acrylate, tripropylene glycol di(meth)acrylate, neopentyl glycol dialkoxy di(meth)acrylate, polyethyleneglycol di(meth)acrylate, and mixtures thereof), non-reactive diluents (e.g., ethylene glycol, di(ethylene glycol), tetra(ethylene glycol), glycerol, 1,5-pentanediol, ethylene glycol monomethyl ether, ethylene glycol dimethyl ether, triethylene glycol monomethyl ether, 2-ethoxyethanol, solketal, benzonitrile, hexamethylphosphoramide, 2-N-methylpyrrolidinone and N,N-dimethylformamide); dyes, fillers (e.g., silica; carbon black; clay; titanium dioxide; silicates of aluminum, magnesium, calcium, sodium, potassium and mixtures thereof; carbonates of calcium, magnesium and mixtures thereof; oxides of silicon, calcium, zinc, iron, titanium, and aluminum; sulfates of calcium, barium, and lead; alumina trihydrate; magnesium hydroxide and mixtures thereof), plasticizers (e.g., petroleum oils such as ASTM D2226 aromatic oils; paraffinic and naphthenic oils; polyalkylbenzene oils; organic acid monoesters such as alkyl and alkoxyalkyl oleates and stearates; organic acid diesters such as dialkyl, dialkoxyalkyl, and alkyl aryl phthalates, terephthalates, sebacates, adipates, and glutarates; glycol diesters such as tri-, tetra-, and polyethylene glycol dialkanoates; trialkyl trimellitates; trialkyl, trialkoxyalkyl, alkyl diaryl, and triaryl phosphates; chlorinated paraffin oils; coumarone-indene resins; pine tars; vegetable oils such as castor, tall, rapeseed, and soybean oils and esters and epoxidized derivatives thereof; esters of dibasic acids (or their anhydrides) with monohydric alcohols such as o-phthalates, adipates and benzoates; and the like and combinations thereof), processing aids, ultraviolet stabilizers (e.g., a hindered amine, an o-hydroxy-phenylbenzotriazole, a 2-hydroxy-4-alkoxybenzophenone, a salicylate, a cyanoacrylate, a nickel chelate, a benzylidene malonate, oxalanilide, and combinations thereof), and combinations thereof.

An additional additive may be a tactile (hair feel) modification agent. These may include, but are not limited to, a softening and/or lubricating and/or anti-static and/or hair alignment and/or anti-frizz benefit and/or impact on the keratin fibres.

I. Content of First and Second Polymers in Compositon

Embodiments of the multicomponent composition include solids and liquids. The solids comprise any substance or material of the multicomponent composition that in a form uncombined with any other material, solvent, liquid or substance is has a solid physical form at ambient conditions. Included at least are the pigment microparticles and the base compound of the multicomponent composition. The medium and usually the silicone polymers, in contrast, are liquids. They all function as a solvent and/or dispersant and/or a liquid in which solid pigment microparticles are dispersed. The liquid or gel components such as the silicone polymers as well as the plasticizer, dispersing agent, surface treatment agent, and other materials added to the medium, if any, are included in the solids content as long as they remain with the pigment microparticles following application and setting of the multicomponent composition as a coating on strands of human hair. The solids/remaining liquids/liquids convertible to solids content of the multicomponent composition is quantified above in the section on concentration.

Testing the Flexibility of a Coating of the Multicomponent Composition

With the film prepared above, it can also be tested for optical density to check that the polymer film does not itself alter the hair appearance of the hair too significantly.

Further the polymer preferably can have a glass transition point (Tg) as described above so that it is possible to prevent the colored coating from being damaged or cracked and to secure washing and friction fastness.

The composition coating can have a surface energy between about 20 and about 50 mN m$^{-1}$. The composition coating preferably has high transmission, to ensure that it does not interfere with the optics of the hair color. The polymer preferably has a refractive index between 1.4 and 1.6.

Application of First, Second, Third and Optional Fourth Components to Substrate Material The first, second, third and fourth components of the multicomponent composition may be maintained in separate storage compartments or in separate kit form when the first, second and third functional groups of these components will react if together. Additionally, the substantive constituent of the fourth component is maintained separately if it will catalyze or otherwise cause reaction of such functional groups. A convenient storage means can be utilized such as plastic squeeze tubes, plastic bottles, glass containers, sachets, multi-compartment containers, tooles, spottles syringes and plunger operated dispensing devices. Unit amounts for combination can be formulated so that the entire contents of a unit of the first component can be combined with the entire contents of the second component for application to the substrate material. Alternatively, metered or calibrated dispensing containers for providing measured amounts of the components as directed by printed instructions can be provided. With some embodiments, multiple components can be pre-combined for storage and handling as long as a substantive constituent that would cause in situ linking is maintained in a separate compartment.

Use of the foregoing delivery means enables preparation of an embodiment for practice of the method of the present invention. This embodiment may comprise sequential, simultaneous or premixed application of the first and second components to substrate material. Pigment microparticles may be incorporated in either or both of the first and second components. This aspect of application provides a layer of combined first and second components on the substrate material that will undergo transformation to a coating in which the first and second functional groups of these components in situ interact to covalently bond as the completed coating. Preferably the pairs of first and second functional groups are chemically reactive so that covalent bonds are formed between the first and second silicone polymers and the base compound. With this aspect alone, the resulting coating on substrate material, such as but not limited to hair, provides good remanence against repeated shampooing, rinsing and contact with mild detergents, soap and similar wash substances.

Pretreatment with Third Component

Another embodiment of the method according to the present invention may comprise application of the third component to the substrate material as a pretreatment before application of the first and second components as described above. According to this embodiment of the method, the third component containing the base compound with or without pigment, and preferably without pigment, is applied on or to at least a portion of the substrate material such as hair, and preferably throughout the substrate material. While it is not a limitation of the invention, it is believed that the pretreatment addition of the third component enables enhancement of adhesion between the hair, pigments and first and second components. It is believed that the amine groups or mercapto groups, preferably amine groups of the third component interact with complementary chemical groups on the substrate material and interact with the first and second silicone polymers. Although it is not a limitation of the invention, it is further believed that the second functional groups also interact with complementary chemical groups of the substrate material. It is believed that these chemical interactions, which are covalent and also are supplemented by coordinate, electrostatic, ionic, dipolar and/or entanglement interactions function to meld together the substrate material, the pigment microparticles, the first and second silicone polymers and the base compound.

Pretreatment with the third component may be carried out prior to application of the first and second components. Pretreatment may be carried out immediately prior to application of the first and second components, or at least 1 hour prior to application of the first and second components, or at least 24 hours prior to application of the first and second components, or at least 10 days prior to application of the first and second components, or at least one month prior to application of the first and second components. Preferably, pretreatment may be carried out immediately prior to or within a few minutes up to an hour before application of the first and second components. Typically, the third component is at least partially dried with optional heating to at least substantially remove or otherwise eliminate the medium of the third component. For example excess medium may be removed by contacting with an absorbent fabric or surface or the hair may by heated with a hair drier. Preferably, removal of third component medium is accomplished before application of the first and second components.

Core and Shell Alternative

According to an embodiment in which pigment microparticles are incorporated into the third component, at least some of categories of the base compound can be employed to provide a "core-shell structure" (core-shell morphology) for the pigment microparticles. In the case that the base compound and pigment(s) have a "core-shell structure", the "core" corresponds to the "naked" pigment which features the same properties as defined hereinbefore with reference to the "pigment(s)". The "shell" corresponds to a coating layer of base compound surrounding the "core". The pigments having a core-shell structure may have a $D_{50}$(Vol)particle diameter of from 20 nm to 1 micron, typically 60 nm to 900 nm, more typically 100 nm to 600 nm. As such, embodiments of the present invention also relate to a substrate material treatment composition comprising a core-shell pigment microparticle arrangement, wherein the core comprises an inorganic and/or organic pigment microparticle material, and the shell comprises at least one base compound, the at least one core-shell construct having a $D_{50}$(Vol) particle diameter of 20 nm to 1 µm. The shell surrounding the core may comprise one or more polymeric shell layers. Typically, the shell may comprise a base compound wherein the base compound is a polymeric shell layer.

A further embodiment involving the core and shell alternative may be accomplished by pretreatment of a prepared dispersion of pigment microparticles with a portion of base compound in appropriate medium to provide a dispersion of pigment microparticles as the core and shell construct ready to be combined with any of the first, second and third components. The combination of the microparticle core and shell dispersion with any of the first, second and third components as desired can provide the core and shell microparticles dispersed in any of the first, second and third components, in any two or in all three components.

Application of First and Second Components Following Pretreatment

As described above, first and second components may be applied to the substrate material in combination with the foregoing pretreatment with the third component or may be applied without such pretreatment. In either arrangement, embodiments of the first and second components are maintained separately when the first and second functional groups constitute reactive pairs as described above. Application of the first and second components to pretreated or un-pretreated substrate material may be accomplished by sequential application of the first and second components or simultaneous application of these components to the hair. Typically for sequential application, either of the first and second components may be applied first, preferably the first component is applied first, especially for embodiments including pretreatment with the third component. Alternatively, the first and second components may be mixed together to form a premix immediately before application to the substrate material. Typically, the rate of reaction of the reactive pairs is pre-adjusted through concentration, steric interaction, temperature, and similar factors controlling reaction rate so that a premix preferably will not substantially interact before the premix is applied to the substrate material. The practice of this step with the pre-treatment embodiment initially introduces combined first and second components on top of the pretreatment layer of base compound on the substrate material. Because the first and second components are in a medium, penetration, combination, mixing and/or melding of the first and second components into the pretreatment layer is believed to be accomplished. The penetration is believed to enable the linking among the first and second silicone polymers, the base compound and the substrate material.

Application of the first and second components to pretreated substrate material is preferably carried out after pretreatment. This sequence may be carried out immediately after pretreatment, or at least 1 hour after pretreatment, or at least 24 hours after pretreatment, or at least 10 days after pretreatment, or at least one month after pretreatment.

The sequential, simultaneous or premix application of the first and second components may be applied to at least a portion of the substrate material or may be applied all over the substrate material. The portions of first and second components may be applied sequentially, simultaneously or as a premix in a single application over all the substrate material or may be applied step-by-step to the substrate material. The first and second components may be applied step-by-step, for example, in case the substrate material is damaged. Applying the first and second components in a step-by-step manner as described above, may help to ensure that the treated portions of the substrate material are saturated with the combined first and second components and may therefore provide a better coverage of the substrate material.

Manipulative Techniques for Application

After the pretreatment of the third component has been accomplished, and the pretreated substrate material optionally rinsed, the pretreated substrate material can be dried. The substrate material can be dried using an elevated temperature. The temperature of the substrate material can be increased to elevated temperatures above room temperature such as 40° C. or higher, for example using a hair drier. While the substrate material is being dried, some form of interdigitated implement can be used to help separate portions of the substrate material, and especially separate hair strands from one another. Examples of interdigitated devices include a comb or a brush. The substrate material can be dried with a hair drier while simultaneously being combed or brushed until it is dry to the touch. Alternatively, other means can be employed to dry and separate the substrate material such as hair simultaneously. For example, using a combination of air movement and vibrations will accomplish distribution of the multicomponent composition throughout the strands of hair.

Operational Method for Coating Hair

The performance of operational method aspects of the present invention can be applied to keratin fibers to form a coating of the multicomponent composition. This aspect of the invention concerns a method for coloring substrate material and comprises applying embodiments of one or more multicomponent compositions for a time sufficient to deposit an effective colored coating on the substrate material such as each keratin fiber or hair strand. A somewhat to substantially overall distribution of the coating on the length and circumference of each fiber is produced.

To accomplish this aspect, embodiments of the first, second and third components of multicomponent composition are applied to the substrate material according to the sequences described above by brushing, painting, spraying, atomizing, squeezing, printing, rubbing massaging or in some manner coating the substrate material such as hair strands with the embodiments. Following application of a compositional embodiment to the substrate material such as hair strands, the composition is set, cured, linked, coordinated and/or otherwise melded together preferably by warming with blown warm air from a hair dryer or similarly treated to remove the medium, initiate in situ linking of the first and second silicone polymers, the base compound, the substrate material and if present, remove the volatile base. The setting leaves a substantial to essentially complete overall linked coating of the first and second silicone polymers and base compound containing dispersed pigment microparticles and optional additional components.

The in situ linking of the substantive constituents of first, second and third components during application provides a linked coating that enables it to resist for a time destruction by washing with dilute mixtures of soap and water or shampoo and water. Color fastness (remanence) is developed so that washing with dilute aqueous soap solution or dilute aqueous shampoo will not substantially remove the coating, but the coating can be facilely removed by use of a transformation trigger. The properties of the coating include wash-fastness, flexibility, adhesion, abrasion resistance and remanence which are due at least in part to the linked character of the composition constituents including at least the first and second silicone polymers and the base compound and their intermolecular entwining, ionic and electrostatic intermolecular interaction, covalent and/or non-covalent linking, dipole interaction and lipophilic interaction of neutral moieties of these compositional constituents.

Selection of the substantive constituents of the multicomponent composition can be made on the basis of properties such as a solid lattice formation and interaction with the pigment microparticles. Such properties include the flexibility, the hardness, the adhesion, the remanence, the resistance to water or to other chemical compounds, and the abrasion resistance.

The multicomponent compositions in accordance with the present disclosure can have a viscosity that can be controlled to enable the product to be applied to the hair using either a brush and bowl or a bottle, but with sufficient rheology such that it does not drip and run from the hair onto the face or body. Alternatively, low viscosity formulations may be applied to the hair via a suitable application device such that it does not drip and run form the hair onto the face and body.

The multicomponent compositions can be utilized in concentrated form or in serial dilutions, to provide for a consistent color results substantially along the entire length of the keratin fibers.

The aspect of coloring mammalian or synthetic keratin fibers with a multicomponent composition as described above includes a method for this coloring.

The method comprises:
(i) applying the above-described multicomponent composition to keratin fibers an effective coloring amount of the first and second silicone polymers, base compound, pigment microparticles and optional additional components;
(ii) setting the multicomponent composition by removing or otherwise eliminating the medium (e.g., by drying the composition); and.
(iii) setting the interaction among the first, second and third functional groups of the multicomponent composition by initiating the in situ linking among these groups.

During the setting/drying step, color distribution can be facilitated by concurrently moving and/or stroking the hair with an interdigitating device. Interdigitating devices include a comb or brush. The interdigitating device needs to be pulled substantially along the hair strands from root to tip. It can be pulled through at a rate of 0.1 cm s$^{-1}$ to 50 cm s$^{-1}$ or at a rate between 0.5 cm s$^{-1}$ to 20 cm s$^{-1}$ The multicomponent composition is applied to the mammalian or synthetic keratin fibers in any suitable way including spraying the multicomponent composition, massaging the keratin fibers by hand, after applying the multicomponent composition to the hand or by combing, brushing or otherwise applying the multicomponent composition throughout the mammalian or synthetic keratin fibers.

Unlike current hair coloring approaches that use dyes, the color with the multicomponent compositions described herein occurs on the surface of the hair strands. Current dye based approaches do provide the head of hair with some color variation, as the strands are not identical, and some of these differences are preserved after coloring. There are also differences root to tip which also helps to provide some variation. Using a pigment based surface coloring system such as that of the present invention, the variation of the underlying hair can be substantially removed, leading to a more homogeneous color result. This color result can be a more homogenous application of color. To obtain a somewhat non-homogeneous application of color that tends toward a more natural look, the user can apply the inventive multicomponent composition by any of several techniques.

The methods by which the multicomponent compositions described herein are applied can be modified, such that the user applies the product in one region of the hair, and then can apply a diluted version in another region of the hair. The dilution formula is specially chosen to be compatible with the colorant formulation and reduces the coloring strength, while maintaining the longevity of the color result. This can effectively be a "blank" formulation, which contains broadly the same materials as the coloring formulation, but with lower or no pigments present. When diluted the ratio of the diluent to colorant can be between about 10:1 and about 1:10, about 8:1 and about 1:2 or about 5:1 and about 1:1.

Alternatively, the amount of multicomponent composition applied can be altered in different regions of the hair, for example half the product is applied in the lengths of the hair, leading to a less colorful result. The difference in amounts applied in one region of the hair versus another can be between about 4:1 and about 1:4 or about 2:1 and about 1:2.

Alternatively, a combination of this approaches may be used to deliver the target color variation.

When the foregoing techniques are not possible to be applied, rather than apply a single hair color, it may be possible to apply two or more hair colors to different regions of the hair. When this is done, the different in situ hair colors preferably provide complementary colors so as to develop an attractive result. The difference in colors that can be used, based on the end result on hair tresses such as—natural white hair non pre-bleached are as follows. As described within the CIELCh system:
Color 1 (LCh) versus Color 2 (LCh)
Color 1 L−15<Color 2 L<Color 1 L+15
0 or Color 1 C−10<Color 2 C<Color 1 C+10
Color 1 h−45<Color 2 h<Color 1 h+45

The method for use of the multicomponent composition in accordance with the present invention can occur during any suitable period. The period of application can be from about 0 to 30 minutes, but in any event a period that is sufficiently long to permit the coating of pigment microparticles to coat and adhere or bind to each separate keratin fiber, substantially along the entire length of each keratin fiber. The resultant is keratin fibers having a color and permanence that is at least equivalent to the color resulting from oxidative in situ hair color, except under much milder conditions.

The multicomponent compositions described herein can be prepared by the manufacturer as a full shade, e.g., one that is ready to apply to the hair, and then shipped as a discrete unit to the user. The user may need to re-blend the multicomponent composition prior to application to ensure that the multicomponent composition delivers the optimum performance. Such re-blending can require shaking the multicomponent composition for about 1 to about 120 seconds or from about 3 to about 60 seconds. Reblending may also be performed by stirring the multicomponent composition prior to use. This may occur for about 1 to about 120 seconds or from about 3 to about 60 seconds. Although the multicomponent compositions according to the present invention are designed to provide stable suspensions of the pigment particles, the re-blending to agitate the microparticles and resuspend them in a substantially uniform distribution is desirable.

Multiple compositions comprising different pigments can be blended together prior to application to the keratin fibers. Such blending can be done in a manner so as to apply a plurality of complementary surface colors to the keratin fibers.

The multicomponent compositions can include multiple layers, involving multiple applications of at least the first and second components following the first application of the three components. It may be beneficial also to periodically reapply the third component. The techniques for applying multiple layers follow the techniques described above for application of a single multicomponent composition.

The coating of pigment microparticles comprising at least one pigment in a coating of the substantive constituents of the multicomponent composition can be adhered to the substrate material such as hair utilizing a coating having a total thickness at any given point along the hair fiber of less than about 5 µm, preferably less than about 2 µm as measured using a scanning electron microscope (SEM). To make such measurements, a coated hair sample can be embedded in a suitable resin, and then sectioned root to tip using techniques known to those skilled in the art of scanning electron microscopy. The thickness of the layer on the surface can then be assessed along the line of cuticles over a length of at least 100 µm. The thickness of layer is determined by averaging 10 points evenly spaced over the section of interest.

As described above, application of the multicomponent composition to sections of substrate material such as sections of hair strands can be varied. In addition to varying the concentration of the pigment microparticles and optional coloring agent, different shades and/or colors of multicomponent composition can be applied to different sections of a strand of hair or a group of strands of hair. For example, the hair roots, mid sections and tips sometimes or often have different shades of color in their natural condition. This variation can be mimicked, altered or covered through use of differing shades or colors of the multicomponent composition. Roots, for example can be covered with a lighter shade and the tips can be covered with a darker shade to produce a two tone variation of the hair. Application to the hair of a first portion of multicomponent composition followed by stripping the composition from the hair mid sections and ends followed by setting the remaining composition on the hair roots will provide a first hair color coating on the roots. The mid-sections and tips can be dipped or brush applied with a second portion of multicomponent composition to complete the two color or two tone treatment. The use of multiple multicomponent compositions to produce multiple coatings on the hair can provide overlapping, sequential or coterminous coatings on the hair according to typical and routine techniques for applying multiple versions of hair color practiced by professional hair salons.

Post Treatment

An optional post treatment composition can be applied after treating the substrate material such as hair with the multicomponent compositions described herein. This can be applied either directly after completion of coloring with the multicomponent composition. The post treatment can be either single application or multiple application across time. The post treatment can be used to improve one or more of: feel, resistance to shampoo/conditioner/water washing treatments, and shine of the hair. Nonlimiting examples of materials used to improve the feel are those which impart lubricity to the substrate material such as hair strands and/or help the hair strands separate during the drying steps. These materials include, for example silicone conditioners, silicone polyethers, silicone polyglucose, polyisobutene, copolymers of ethylene and propylene oxide, and commonly used cosmetic oils and waxes. Nonlimiting examples of materials used to improve shampoo wash resistance are materials which act as a 'sacrificial layer' for example polymeric silicones and their copolymers, silicone resins, cosmetics oils and waxes. Nonlimiting examples of materials used to improve the shine of hair (meaning a decrease of the full width at half maximum parameter of the specular reflection curve as measured by a goniophotometer) are those materials which form a smooth film above the previously applied pigment polymer composite on the hair. In general, any cosmetically known film forming material can be used, but preferred are materials such as polymeric silicones and polycationic materials.

Removal of Color Coating

Hair colorants made from surface films consisting essentially of a multicomponent coating plus a pigment that are very resistant to everyday hair treatments (such as washing with shampoo, conditioner etc.) can be removed via use of specifically designed "removal formulations." These are specific chemical mixtures, described herein, and are designed to work via one or both of two broad mechanisms.

First, the mixture can be made to be a solvent for the pigment itself. In this case the mechanism of removal involves first dissolution of the pigment from the binding matrix, followed by removal from the hair via rinsing with water or some other carrier. In this case it is believed, whilst not being bound by theory, that the chemical nature of the pigment, even when in dissolved form, is such that there is minimal attraction/solubility in the hair matrix itself, thus allowing removal of the color.

Second, the 'removal formulation' can be made such that it dissolves, weakens or chemically breaks down the binder material holding the pigment on the hair. In this case it is believed, whilst not being bound by theory, that the pigments embedded in the binder matrix are released due to weakening or dissolution of the binder itself and, because the coloring material is a pigment, it has minimal attraction for the hair surface and is too big to penetrate the hair, and in consequence this facilitates removal of the color.

A combination of the above mechanisms will also aid in providing the desired result of removal of the color.

Changing the pH can have a dramatic impact on the properties of the coating which is adhered to the surface. A soluble base acting as a trigger agent to neutralize acid groups and enable the conjugate base to be readily soluble in a mixture of water and organic solvent will facilely remove the coating. Such bases include amino alcohols such as dimethylaminoethanol (dimethylethanolamine, DMEA), dimethylaminopropanol, and similar amino alkanol agents such as monoethanolamine, diethanolamine and triethanolamine and ammonia. Other bases such as NaOH and $Ca(OH)_2$ can also be used. The concentration of the trigger agent in aqueous solution optionally with an alcohol or ketone organic solvent such as methanol, ethanol, methyl ethyl ketone and the like may range from about 0.1% to about 15% by weight, preferably about 0.5% to about 10% by weight, more preferably about 1% to about 7.5% by weight relative to the total weight of the removal solution.

Remanence and Substrate Material Inspection

Damage caused to the hair by application of the multicomponent composition and removal of the resulting coating can be assessed by FT-IR (Fourier Transform Infrared) method, which has been established to be suitable for studying the effects on keratin surface damage. (Strassburger, J., J. Soc. Cosmet Chem., 36, 61-74 (1985); Joy, M. & Lewis, D. M., Int. J. Cosmet. Sci., 13, 249-261 (1991); Signori, V. and Lewis, D. M., Int. J. Cosmet. Sci., 19, 1-13 (1997)). In particular, these authors have shown that the method is suitable for quantifying the amount of cysteic acid that is produced from the oxidation of cystine. In general, the oxidation of cystine is thought to be a suitable marker by which to monitor the overall oxidation of the keratinous part of the fiber. Also, the measurement of cysteic acid units by FT-IR is commonly used to study the effects of oxidative treatments or environmental oxidation upon keratin protein containing fibers such as hair and wool.

Signori and Lewis (D. M., Int. J. Cosmet. Sci., 19, 1-13 (1997)) have shown that FT-IR using a diamond Attenuated Total Internal Reflection (ATR) cell is a sensitive and reproducible way of measuring the cysteic acid content of single fibers and bundles. Hence, the method that we have employed to measure the cysteic acid content of multiple fiber bundles and full hair switches, is based upon the FTIR diamond cell ATR method employed by Signori and Lewis (1997). The detailed description of the method used for testing the different damage inhibitors follows thereafter:

A Perkin Elmer Spectrum® 1 Fourier Transform Infrared (FTIR) system equipped with a diamond Attenuated Total Internal Reflection (ATR) cell was used to measure the cysteic acid concentration in mammalian or synthetic hair. In this method, hairswitches of various sizes and colors can be used. The switches were platted (~1 plait per cm) in order to minimize variations in surface area of contact between readings. The Oxidative hair Treatment Protocol described above was repeated for 5 cycles to mimic the behavior of hair after repeated bleaching cycles. Following this treatment, four readings per switch were taken (⅓ and ⅔s down the switch on both sides), and an average calculated. Backgrounds were collected every 4 readings, and an ATR cell pressure of 1 N/m was employed. The cell was cleaned with ethanol between each reading, and a contamination check performed using the monitor ratio mode of the instrument. As prescribed by Signori & Lewis in 1997, a normalized double derivative analysis routine was used. The original spectra were initially converted to absorbance, before being normalized to the 1450 $cm^{-1}$ band (the characteristic and invariant protein $CH_2$ stretch). This normalized absorbance was then twice derivatised using a 13 point averaging. The value of the 1450 $cm^{-1}$ normalized 2nd derivative of the absorbance at 1040 $cm^{-1}$ was taken as the relative concentration of cysteic acid. This figure was multiplied by $-1 \times 10^{-4}$ to recast it into suitable units. It was found that virgin mammalian or synthetic hair produced a value of around 20 cysteic acid units, and heavily oxidized hair produced values of around 170. The following instrumental conditions were employed:

Spectral Resolution—4 $cm^{-1}$

Data Interval—0.7 $cm^{-1}$

Mirror Scan Speed—0.2 cm $s^{-1}$

Number of Background Scans—20

Number of Sample Scans—20

Scan Range—4000 $cm^{-1}$ to 600 $cm^{-1}$

When the compositions of the current invention can be applied to the hair and then removed there can be a non-significant change to the level of oxidative damage to the hair, whereas with conventional oxidative colorants there can be a large increase in the measured damage.

The instant disclosure is not limited in scope by the specific compositions and methods described herein, since these embodiments are intended as illustration of several aspects of the disclosure. Any equivalents are intended to be within the scope of this disclosure. Indeed, various modifications in addition to those shown and described herein can be within the grasp of those with ordinary skill in the art. Such modifications are also intended to fall within the scope of the appended claims.

Color Selection

Also contemplated herein are multicomponent compositions having a given color area (gamut principle described above) defined by color coordinates (a*, b*) in the color space represented by the L*a*b* color system, which can be divided into a plurality of color areas. Each of the plurality of colors obtained from the area surrounding a given set of hair fibers is judged to belong to which color area of the colored area of a certain color. The number of colors judged for each color area is counted, and the color of the color area with the largest number of colors is selected as a representative color of the area surrounding a given set of hair fibers.

Also contemplated herein are multicomponent compositions that do not change the underlying hair color, but instead change some other feature of the hair including shine (e.g., making it shinier or matte), the thickness of the hair and/or the feel of the hair.

When the color is removed from the substrate material such as hair, the waste water/composition can be treated to remove the pigments from the waste water effluent system. This can be achieved by filtration, or through cyclone technology, where the density differences are used to force the pigments to the settle, and the water

EXAMPLES

General

The coloring compositions described herein within the examples are generally applied to a hair tress, 1 gram of composition per gram of hair, on a flat plate and brushed into the hair to ensure that all of the strands look visibly coated with the composition. The hair tress is then dried by heating with a hair dryer while combing until it is dry to the touch and the strands are individualized and optionally heated with a hair straightening flat iron to further set the color coating on the hair.

Preparation and Application of a First and Second Silicone Component to Hair Pre-Treated with a Third Component Containing a Base Compound:

General Description of Steps:

Preparation procedure for third component which can be used as a pre-treatment

Preparation procedure for the first component containing a first silicone polymer with first functional groups with optional pigment Preparation procedure for the second component containing a second silicone polymer with second functional groups Preparation procedure for the multicomponent coloring composition Application of multicomponent color composition to hair tresses Standard Wash Procedure Color Removal Composition Application of color removal composition Preparation procedure for the third component which can be used as a pre-treatment. The separate third component or pre-treatment composition containing a base compound is prepared by combining the base compound, in this example a polymer and water and mixing until uniform. The resulting mixture is the third component or pre-treatment composition.

TABLE A

Example of a third component comprising base compound and medium.

| Material | Name | Supplier | Amount (g) |
|---|---|---|---|
| Base compound | Polyethyleneimine Epomin P-1050 | Nippon Shokubai | 1.0 |
| Water | DI water | Lab source | Qs to 100 |

Preparation Procedure for the First Component Containing a First Silicone Polymer with First Functional Groups with Optional Pigment.

The pigment is combined with isododecane. The first silicone component is then also added and then mixed until uniform using standard lab methods. The description of components is described in the following table.

TABLE B

Example of a first component comprising pigment, first silicone polymer and medium.

| Material | Name | Supplier | Amount (g) |
|---|---|---|---|
| Pigment Red 112 | Permanent Red FGR 70 | Clariant | 2.0 |
| Isododecane | 2,2,4,6,6-Pentamethylheptane | Brenntag | Qs to 100.0 |
| First silicone | Silmer OHT C50 | Siltech | 4.0 |

Preparation Procedure for the Second Component Containing a Silicone Polymer with Second Functional Groups.

The second silicone is added to the medium and mixed until uniform using standard lab mixing methods.

TABLE C

Example of a second component comprising second silicone polymer and medium.

| Material | Name | Supplier | Amount (g) |
|---|---|---|---|
| Isododecane | 2,2,4,6,6-Pentamethylheptane | Brenntag | Qs to 100.0 |
| Second silicone | Silmer NCO Di 50 | Siltech | 6.0 |

Preparation Procedure for the Multicomponent Coloring Composition.

Equal amounts of the first and second compositions prepared according the procedure above and combined and mixed until uniform. This mixture is the multicomponent color composition and is to be prepared just before application to the hair tresses.

Application of Multicomponent Coloring Composition to Hair Tresses.

Hair preparation: Two types of hair were used: un-damaged and damaged.

Un-damaged hair: Natural white undamaged human hair was purchased from Kerling International Haarfabrik GmbH, Backnang, Germany company in the form of 10 cm long and 1 cm wide strands. This hair was used as received. Natural dark brown, Level 4 hair was purchased from Kerling International Haarfabrik GmbH, Backnang, Germany company in the form of 10 cm long, 1 cm wide strands. This hair was used as received.

Damaged hair which was produced following this procedure: Natural white undamaged human hair was purchased from Kerling International Haarfabrik GmbH, Backnang, Germany company in the form of 10 cm long and 1 cm wide strands and was bleached. The strand was treated with a mixture of Blondor Multi-Blonde bleach powder available from Wella Professionals mixed 1 part with 1.5 parts of 12% Welloxon Perfect available from Wella Professionals. About 4 g of this mixture was applied to each gram of hair. The tresses were then incubated in an oven at 45 C for 30 minutes after which they are rinsed in water, 37+−2 C with a flow rate of 4 L/min for 2 minutes and the hair is then dried with a standard Hair dryer from Wella.

Organic pigments were tested on the natural white hair as received and treated according to the protocol described above to assess the initial color and color remanence. TiO2 and Metal flakes were tested on the dark brown hair described above to initial color and color remanence.

Hair pre-treatment: Hair prepared as described above was treated with the pre-treatment composition described above, one gram of composition per one gram of hair.

The composition was left on the hair between 1 and 5 min. The hair was then dried using a blow dryer to result in dry hair. Alternatively, the hair could be left wet, the excess of the composition was removed with an absorbent material, for example a towel.

General Coloring Procedure: To the pre-treated hair tress described above is added a freshly prepared multicomponent coloring composition as described above, 1 gram per 1 gram of hair. Application is accomplished by a slow distribution and spreading on the hair tress, for example, with fingers, brush, comb or other manipulation instrument. The slow distribution can be accomplished by application with a syringe or a pipette serially to portions of the hair tress. Excess is removed with absorbent tissue material and the resulting colored hair tress is blow dried with combing using a hair dryer to achieve better hair individualization. The hair was then pulled 3 times through a flat iron at 150° C., 2 seconds for each pull of the tress through the flat iron. Treated hair tresses may be kept at rest for a time period as much as a day at room temperature or at least above 17° C.

Standard wash procedure: The standard wash procedure is used to determine the remanence of the colored hair tresses.

1. Rinse the hair tress for approximately 10 seconds with water (4 L min$^{-1}$) at approximately 37+/−2 C.
2. Apply 0.1 g "Wella Professional Brilliance Shampoo for fine and normal hair" without dilution to the individual colored hair tress weighing about 1 g described above.
3. Shampoo is worked into the colored hair tress in the absence of water dilution for 30 sec with fingers by using a stroking motion into the hair.
4. The shampooed colored hair tress is rinsed with water for approximately 30 seconds.
5. The rinsed colored hair tress is then dried using a hot blow dryer while mechanically separating the fibers in the substrate material until uniformly dry.
6. Steps 1-5 described above represent one cycle of the standard wash procedure.
7. Repeat of standard wash cycle for multiple cycles and comparison of the multiply washed hair tress to an unwashed colored hair tress which indicates the degree of color remanence using the Color Remanence Scoring Values described below.

Remanence was assessed visually by comparing the washed samples versus a retained tress which had been colored but not washed. They were graded on a 5 point scale according to the following criteria. 1 no color left, 2 faint color, 3 washed-out color, 4 intense color with some color loss, 5 color unchanged versus reference.

Film performance. This procedure was used to study the bulk film properties of the material formed when combining the first and second components. A film of the mixture of the two silicones allowed to cure for 1 day prior to measurement for Shore OO hardness.

Procedure Details:

1. In a cylindrical aluminum weighing tray (radius ~ 3.5 cm) 10 gram of the silicone mixture was dispensed and then mixed. The ratio of the silicones in wt. % was adjusted to replicate the ratio of wt. % mixtures studied with the coloring compositions when mixed together. No other materials were added to the mixed silicone system.
2. The weigh boats were then placed in a 105 C oven for 60 minutes and then left overnight in a fume hood to cure for a further 24 hours before being measured.
3. The film was assessed with a plastic pipette to see if the material had cured to form a film. If the mixture was still liquid, it was not measured for Shore Hardness to prevent damaging the measurement device. Instead a value of 0 was recorded, to represent a very soft material. Films that were measured were assessed for Shore 00 using HT-6510 00 Shore hardness tester (Guangzhou Landtek Instruments Co. Ltd).

At least five repeat measurements were performed on each sample and the average reported.

Example 1: Multicomponent Coloring Composition with a First Component Containing a Silicone with Polyol and a Second Component Containing a Silicone Isocyanate

TABLE 1

First Components containing first silicone with first functional groups, pigment(s) and medium

| Material | Name | Supplier | 1A | 1B | 1C | 1D | 1E | 1F |
|---|---|---|---|---|---|---|---|---|
| Pigment(s) | | | | | | | | |
| Pigment Red 112 | Permanent Red FGR 70 | Clariant | 2.0% | 0.42% | | 1.0% | | 1.0% |
| Pigment Yellow 83 | Novoperm Yellow HR 70 M250 | Clariant | | 1.36% | | | | |
| Pigment Black 6 | Midnight Black carbon black | Geotech | | 0.22% | | | | |
| TiO2 | Hombitan AFDC | Venator | | | | | 10.0% | |
| Aluminum Flake | Velvet SL | Toyal | | | 10.0% | | | |
| First Silicone | | | | | | | | |
| OH silicone | Silmer OHT C50 | Siltech | 5.0% | 5.0% | 15.0% | 5.0% | 10.0% | |
| Aminosilicone | Silmer NH E47 | Siltech | | | | | | 5.0% |
| Medium | | | | | | | | |
| Isododecane | 2,2,4,6,6-Pentamethylheptane | Brenntag | Qs 100% | Qs 100% | Qs 100% | Qs 100% | Qs 100% | Qs 100% |

TABLE 2

Second Components containing second silicone with second functional groups, optionally pigment(s) and medium

| Material | Name | Supplier | 2A | 2B | 2C | 2D | 2E |
|---|---|---|---|---|---|---|---|
| Pigment(s) | | | | | | | |
| Pigment Red 112 | Permanent Red FGR 70 | Clariant | | | | 1.0% | |
| Second Silicone | | | | | | | |
| Isocyanate silicone | Silmer NCO Di-50 | Siltech | 5.0% | 5.0% | 15.0% | 5.0% | 10.0% |
| Medium | | | | | | | |
| Isododecane | 2,2,4,6,6-Pentamethylheptane | Brenntag | Qs 100% | Qs 100% | Qs 100% | Qs 100% | Qs 100% |

TABLE 3

Third Components containing base compound and medium

| Material | Name | Supplier | 3A | 3B | 3C |
|---|---|---|---|---|---|
| Base Compound | | | | | |
| Aminosilane | (3-Aminopropyl)triethoxysilane | Aldrich | 1.0% | | |
| Polyethyleneimine | Epomin P-1050 | Nippon Shukobai | | 1.0% | |
| Mercapto silane | KBE 803 | Shin Etsu | | | 1.0% |
| Medium | | | | | |
| Water | DI Water | Lab source | Qs 100% | Qs 100% | Qs 100% |
| Co-medium | Ethanol | Sigma Aldrich | | | 10% |
| Acid | Acetic Acid | Sigma Aldrich | | | 1% |

The following table (Table 4) captures the results of Example 1 encompassing various combinations of silicone polyols with silicone isocyanates applied to tresses pre-treated and not pre-treated (prior to application of the multicomponent coloring composition) with a variety of third component compositions described in Table 3 above.

TABLE 4

Color remanence results combination of silicone polyols with Silicone Isocyanates on hair pre-treated or not with a third component.

| Example | Third Component Table 3 | First Component Table 1 | Second Component Table 2 | Ratio[a] | Undamaged 5 × wash | Undamaged 15 × wash | Damaged 5 × wash | Damaged 15 × wash | Shore OO hardness |
|---|---|---|---|---|---|---|---|---|---|
| 1.1 | None | 1 part 1A | 1 part 2A | 1:1.33 | 3 | 2 | 3 | 2 | 70.0 |
| 1.2 | 3A | 1 part 1A | 1 part 2A | 1:1.33 | 5 | 5 | 5 | 5 | 70.0 |
| 1.3 | 3B | 1 part 1A | 1 part 2A | 1:1.33 | 5 | 5 | 5 | 5 | 70.0 |
| 1.4 | 3A | 1 part 1D | None | 1:0 | 4 | 3 | 4 | 3 | 0[b] |
| 1.5 | 3B | 1 part 1D | None | 1:0 | 5 | 3 | 5 | 3 | 0[b] |
| 1.6 | 3A | None | 1 part 2D | 0:1 | 5 | 4 | 5 | 4 | 6.8 |
| 1.7 | 3B | None | 1 part 2D | 0:1 | 5 | 4 | 5 | 4 | 6.8 |
| 1.8 | 3A | 1 part 1D | 4 part 2D | 1:5.3 | 5 | 5 | 5 | 5 | 64.1 |
| 1.9 | 3B | 1 part 1D | 4 part 2D | 1:5.3 | 5 | 5 | 5 | 5 | 64.1 |
| 1.10 | 3A | 2 part 1D | 3 part 2D | 1:2 | 5 | 5 | 5 | 5 | 80.0 |
| 1.11 | 3B | 2 part 1D | 3 part 2D | 1:2 | 5 | 5 | 5 | 5 | 80.0 |
| 1.12 | 3A | 3 part 1D | 2 part 2D | 1.125:1 | 5 | 4 | 5 | 5 | 31.4 |
| 1.13 | 3B | 3 part 1D | 2 part 2D | 1.125:1 | 5 | 4 | 5 | 5 | 31.4 |
| 1.14 | 3A | 4 part 1D | 1 part 2D | 3:1 | 4 | 3 | 4 | 3 | 0[b] |
| 1.15 | 3B | 4 part 1D | 1 part 2D | 3:1 | 5 | 3 | 5 | 3 | 0[b] |
| 1.16 | None | 1 part 1C | 1 part 2C | 1:1.33 | 3 | 1 | n/a[c] | n/a[c] | 70.0 |
| 1.17 | 3A | 1 part 1C | 1 part 2C | 1:1.33 | 5 | 4 | n/a[c] | n/a[c] | 70.0 |
| 1.18 | 3B | 1 part 1C | 1 part 2C | 1:1.33 | 5 | 3 | n/a[c] | n/a[c] | 70.0 |
| 1.19 | None | 1 part 1E | 1 part 2E | 1:1.33 | 3 | 1 | n/a[c] | n/a[c] | 70.0 |
| 1.20 | 3A | 1 part 1E | 1 part 2E | 1:1.33 | 4 | 4 | n/a[c] | n/a[c] | 70.0 |
| 1.21 | 3B | 1 part 1E | 1 part 2E | 1:1.33 | 3 | 3 | n/a[c] | n/a[c] | 70.0 |
| 1.22 | None | 1 part 1B | 1 part 2B | 1:1.33 | 3 | 2 | 3 | 2 | 70.0 |
| 1.23 | 3A | 1 part 1B | 1 part 2B | 1:1.33 | 5 | 5 | 5 | 5 | 70.0 |
| 1.24 | 3B | 1 part 1B | 1 part 2B | 1:1.33 | 5 | 5 | 5 | 5 | 70.0 |

[a]Ratio - First polymer MPC × weight percent:second polymer MPC × weight percent
[b]0 value assigned when film remains fluid and cannot be measured for shore Hardness 00.
[c]n/a lightening pigment - only assessed on pigmented dark hair - with no bleaching step.

When either the first or second component is described as "none" the multicomponent coloring composition only comprises a single component.

Table 4 demonstrates the importance of having a pre-treatment (third component) and the impact of changing the ratio of the silicone with first functional groups and silicone with second functional groups. For all of the examples 1.1 through to 1.24, the tresses after application of the multicomponent coloring composition and then subsequently drying the tresses were visually assessed to transform the hair from natural white to a bright red color.

Example 1.1 illustrates that when multicomponent coloring composition comprising the first and second components are applied to hair without a third component or pre-treatment or second component, there is a moderate level of color remanence as assessed by the color remanence grading scale as described above, after both 5 and 15 washes on damaged and undamaged hair.

Example 1.2 used the same multicomponent coloring composition of Example 1.1, but the hair had a pre-treatment using a third component 3A which contained an aminosilane as the base compound. Compared to the example without pre-treatment 1.1 there is an improvement in the level of color remanence as assessed by the color remanence grading scale as described above, after both 5 and 15 washes on damaged and undamaged hair.

Example 1.3 is similar to example 1.2 with a pre-treatment using a different third component, 3B, containing a polymeric base compound. Compared to the example without pre-treatment, there is an improvement in the level of color remanence as assessed by the color remanence grading scale as described above, after both 5 and 15 washes on damaged and undamaged hair.

Figure 7:
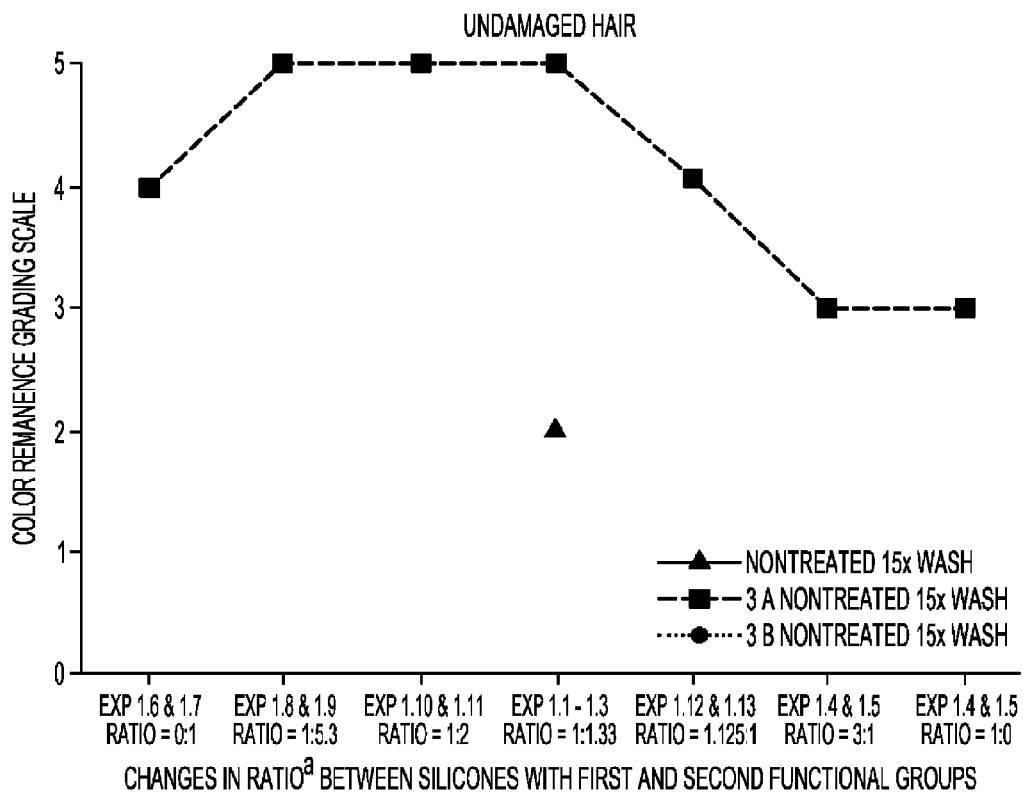
FIG. 7 shows a graph of experimental results for color remanence of a coating on undamaged hair.
Figure 8:
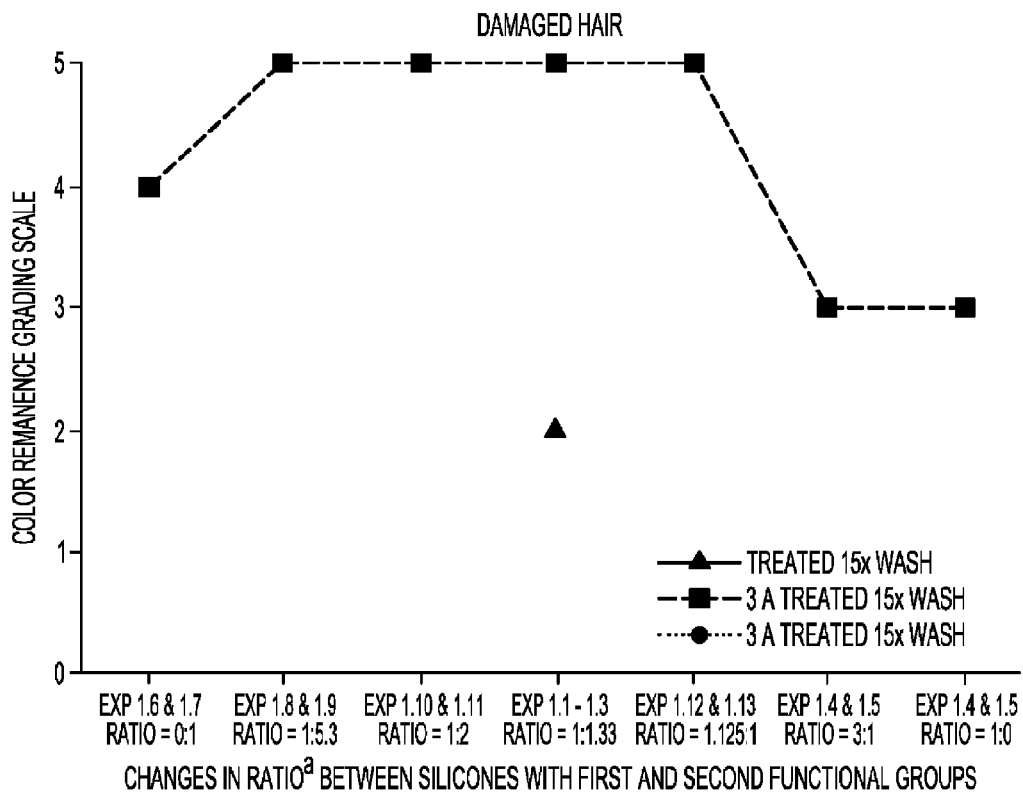
FIG. 8 shows a graph of experimental results for color remanence of a coating on damaged hair.

The results from the studies performed using different ratios of silicones with first functional groups and silicones with second functional groups are now described. FIG. 7 shows the color remanence as assessed by the color remanence grading scale after 15 washes on undamaged hair tresses for different ratios of the multicomponent coloring composition, in some case with no pre-treatment, in others where 3A was used as a pretreatment wherein the third component contained an aminosilane as the base compound, and a final series where 3B was used as a pretreatment wherein the third component contained a polymer as a base compound. FIG. 8 shows the same multicomponent coloring compositions with the same combinations of pretreatment assessed by the color remanence grading scale after 15 washes however on damaged hair. For clarity, the data points and lines for the series with 3A and 3B as a pretreatment overlap and cannot be seen as distinct data points.

Within FIGS. 7 and 8, the examples 1.1-1.3 with a ratio calculated with the approach described above of 1:1.33 visually show the advantage of the use of a pre-treatment (1.2 and 1.3) versus no pre-treatment (1.1) as was described above.

Figure 9:
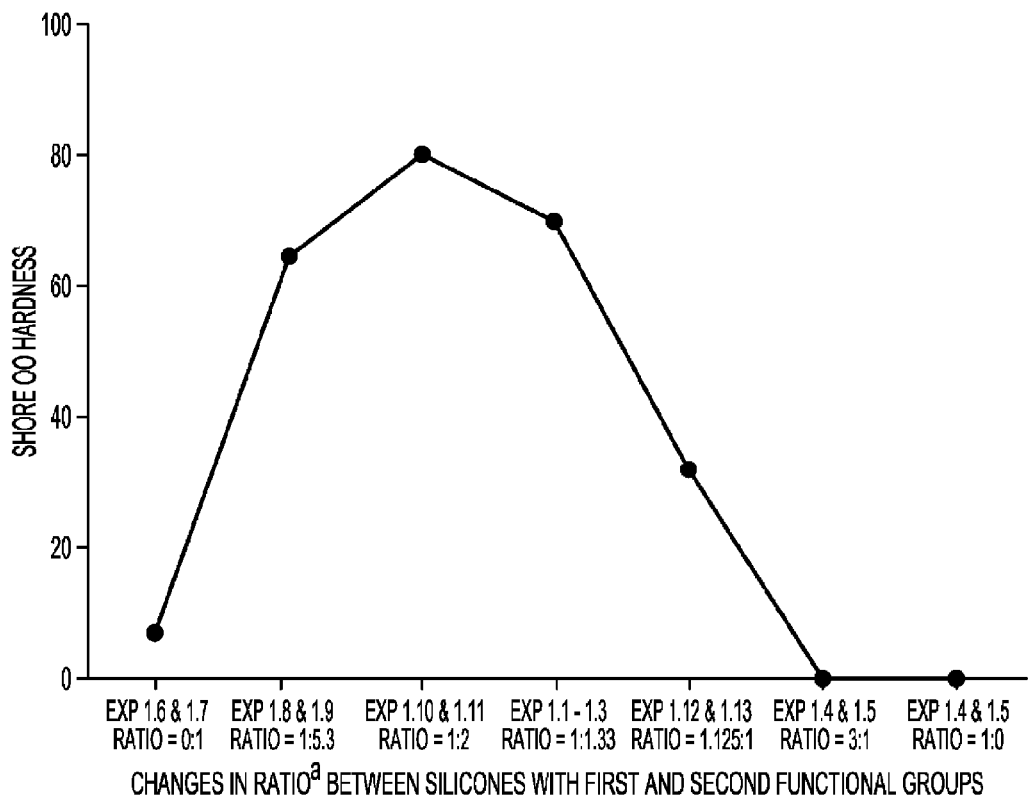
FIG. 9 shows a graph of experimental results for shore hardness of a coating on hair.

Comparing the impact of changing the ratio of the silicone with first functional groups and silicone with second functional groups within FIGS. 7 and 8 shows that the performance of the multicomponent coloring composition comprising both a first and a second component (1.2 and 1.3) is superior to the use of either the first composition alone (1.4 and 1.5) or the second composition alone (1.6 and 1.7). Plotted separately within FIG. 9 are the measured Shore 00 hardness measured according to the procedure described above. This shows that the Shore 00 hardness also has a maximum region for certain ratio of the first and second components. Whilst not wishing to be bound to theory, it believed that the higher Shore 00 hardness may be indicative of a stronger film, which may help to facilitate higher remanence to washing on hair.

Experiments 1.16 through to 1.18 show the results obtained when metal flakes were used instead of the red pigment. Note that a higher level of flakes and silicones were used in these experiments. The initially dark hair tresses looked metallic after the color application. These again show that the combination of the two components provided some color remanence 1.16, but with the addition of third components either 3A (1.17) or 3B (1.18) the remanence was increased.

Experiments 1.19 through to 1.21 show the results obtained when titanium dioxide was used. The initially dark hair tresses looked whiter after the color application. These again show that the combination of the two components provide some color remanence (1.19), but with the addition of third components either 3A (1.20) or 3B (1.21) the color remanence was increased.

Finally with this system, experiments 1.22 to 1.24 show the results obtained when a mixture of pigments which combine to provide a natural brown color on white hair after initial application were tested. A multicomponent composition comprising a combination of the two components provide some color remanence 1.22, but with the addition of third components either 3A (1.23) or 3B (1.24) the remanence was increased.

Example 2: Multicomponent Coloring Composition with a First Component Containing Amino Silicone and a Second Component Containing a Silicone Isocyanate The following table (Table 5) captures the results of Example 2 encompassing various combinations of aminosilicone with silicone isocyanates applied to tresses pre-treated and not pre-treated (prior to application of the multicomponent coloring composition) with a variety of third components described in Table 3 above

TABLE 5

Color remanence results combination of amino silicone with silicone isocyanates on hair pre-treated or not with a third component.

| Experiment | Third Component Table 3 | First Component Table 1 | Second Component Table 2 | Ratio$^a$ | Undamaged 5 × wash | Undamaged 15 × wash | Damaged 5 × wash | Damaged 15 × wash |
|---|---|---|---|---|---|---|---|---|
| 2.1 | None | None | 1 Part 2D | 0:1 | 3 | 2 | 3 | 2 |
| 2.2 | 3A | None | 1 Part 2D | 0:1 | 5 | 4 | 5 | 4 |
| 2.3 | 3B | None | 1 Part 2D | 0:1 | 5 | 4 | 5 | 4 |
| 2.4 | None | 1 Part 1F | None | 1:0 | 4 | 4 | 4 | 3 |
| 2.5 | 3A | 1 Part 1F | None | 1:0 | 3 | 2 | 4 | 2 |
| 2.6 | 3B | 1 Part 1F | None | 1:0 | 5 | 3 | 5 | 3 |
| 2.7 | None | 1 Part 1F | 4 Part 2D | 1:5.3 | 2 | 1 | 3 | 2 |
| 2.8 | 3A | 1 Part 1F | 4 Part 2D | 1:5.3 | 5 | 3.5 | 5 | 4 |
| 2.9 | 3B | 1 Part 1F | 4 Part 2D | 1:5.3 | 5 | 4 | 5 | 4 |
| 2.10 | None | 2 Part 1F | 3 Part 2D | 1:2 | 3 | 2 | 4 | 3 |
| 2.11 | 3A | 2 Part 1F | 3 Part 2D | 1:2 | 5 | 4 | 5 | 4 |
| 2.12 | 3B | 2 Part 1F | 3 Part 2D | 1:2 | 5 | 5 | 5 | 5 |
| 2.13 | None | 1 Part 1F | 1 Part 2D | 1:1.33 | 2 | 1 | 3 | 2 |
| 2.14 | 3A | 1 Part 1F | 1 Part 2D | 1:1.33 | 5 | 5 | 5 | 5 |
| 2.15 | 3B | 1 Part 1F | 1 Part 2D | 1:1.33 | 5 | 5 | 5 | 5 |
| 2.16 | None | 3 Part 1F | 2 Part 2D | 1.125:1 | 2 | 1 | 3 | 2 |
| 2.17 | 3A | 3 Part 1F | 2 Part 2D | 1.125:1 | 5 | 5 | 5 | 3 |
| 2.18 | 3B | 3 Part 1F | 2 Part 2D | 1.125:1 | 5 | 5 | 5 | 5 |
| 2.19 | None | 4 Part 1F | 1 Part 2D | 3:1 | 5 | 3 | 5 | 3.5 |
| 2.20 | 3A | 4 Part 1F | 1 Part 2D | 3:1 | 5 | 3 | 5 | 3 |
| 2.21 | 3B | 4 Part 1F | 1 Part 2D | 3:1 | 5 | 3 | 5 | 3 |

$^a$Ratio - First polymer MPC × weight percent:second polymer MPC × weight percent.

Figure 10:
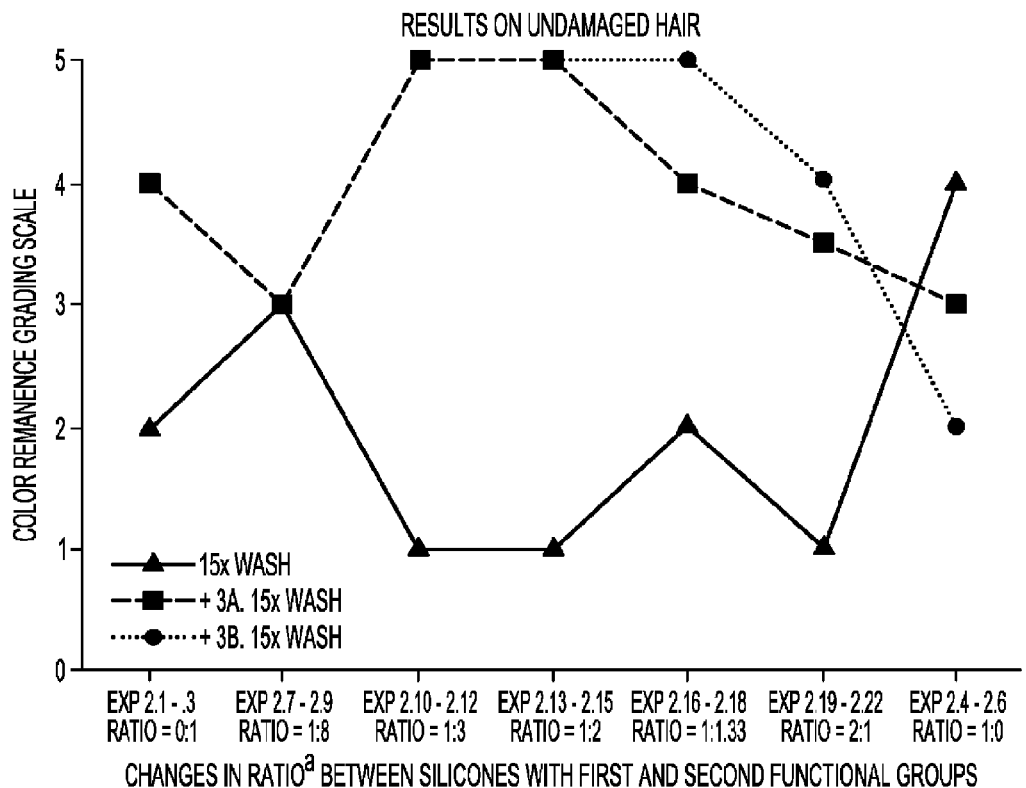
FIG. 10 shows a graph of experimental results for color remanence of a coating on undamaged hair.
Figure 11:
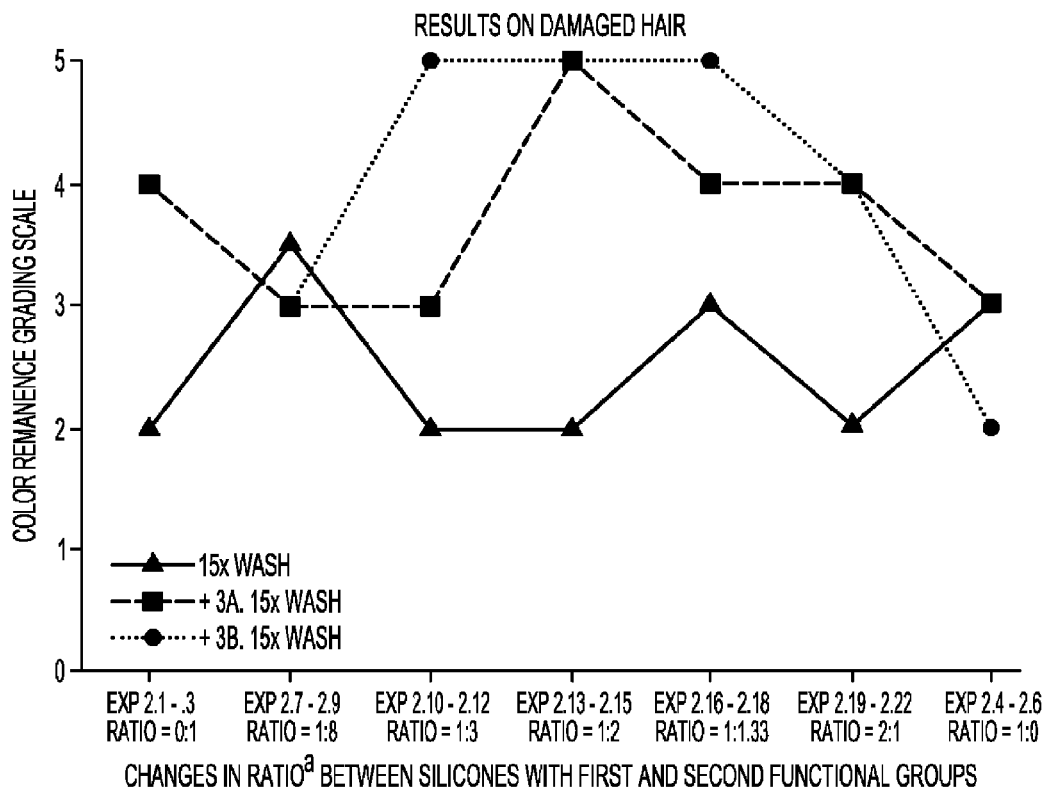
FIG. 11 shows a graph of experimental results for color remanence of a coating on damaged hair.

The results from the studies performed using different ratios of silicones with first functional groups and silicones with second functional groups are now described. FIG. 10 shows the color remanence as assessed by the color remanence grading scale after 15 washes on un-damaged hair tresses for different ratios of the multicomponent coloring composition, with no pre-treatment, in others where 3A was used as a pretreatment wherein the third component contained an aminosilane as the base compound, and a final series were 3B was used as a pretreatment wherein the third component contained a polymer as a base compound. FIG. 11 shows the same multicomponent coloring compositions with the same combinations of pretreatment assessed by the color remanence grading scale after 15 washes however on damaged hair.

The results from these experiments show that generally the performance is stronger on the hair that has been pretreated with either 3A or 3B, and that for systems utilizing reactive first and second components with a pretreatment step there is stronger performance for a multicomponent composition comprising a mixture of a first and second component versus either a sole first or sole second component.

Example 3: Multicomponent Coloring Compositions with a First Component Containing an Amino Silicone and a Second Component Containing an Epoxy Silicone The first components containing the silicone with the first functional groups are described within Table 6.

TABLE 6

| First components containing amino silicone | | | | | | |
|---|---|---|---|---|---|---|
| Material | Name | Supplier | 1G | 1H | 1I | 1K |
| Pigment(s) | | | | | | |
| Pigment Red 112 | Permanent Red FGR 70 | Clariant | 1% | | | |
| Pigment Yellow 83 | Novoperm Yellow HR 70 M250 | Clariant | | 2% | | |
| Pigment Black 6 | Midnight Black carbon black | Geotech | | | 2% | |
| TiO2 | Hombitan AFDC Velvet SL | Venator | | | | |
| Aluminum Flake | | Toyal | | | | 10% |
| First Silicone(s) | | | | | | |
| Aminosilicone Medium | Silmer NH E47 | Siltech | 5% | 5% | 5% | 15% |
| Isododecane | 2,2,4,6,6-Pentamethyl-heptane | Brenntag | Qs 100% | Qs 100% | Qs 100% | Qs 100% |

The second components containing the silicone with the second functional groups are described within Table 7.

TABLE 7

| Second Components containing epoxy silicones | | | | | |
|---|---|---|---|---|---|
| Material | Name | Supplier | 2F | 2G | 2I |
| Pigment(s) | | | | | |
| Pigment Red 112 | Permanent Red FGR 70 | Clariant | 1% | | |
| Second Silicone | | | | | |
| Epoxy Silicone Medium | Silmer EP C50 | Siltech | 5% | 5% | 15% |
| Isododecane | 2,2,4,6,6-Pentamethylheptane | Brenntag | Qs 100% | Qs 100% | Qs 100% |

The fourth components containing a cure catalyst are described in Table 8.

TABLE 8

| Fourth Component containing a cure catalyst | | | |
|---|---|---|---|
| Material | Name | Supplier | 4A |
| Cure Catalyst(s) | | | |
| Lewis acid catalyst | K-Pure CXC-1613 | King Industries | 100% |

The following (table 9) captures the results of Example 3 encompassing various combinations of aminosilicone with an expoxy silicone applied to tresses pre-treated and not pre-treated (prior to application of the multicomponent coloring composition) with a variety of third components described in Table 3 above.

TABLE 9

Color remanence results of the combination of amino silicone with epoxy Silicone on hair pre-treated or not with a third component.

| Experiment | Third Component Table 3 | First Composition Table 6 | Second Composition Table 7 | Forth Component[d] Table 8 | Ratio[a] | Undamaged 5 × wash | Undamaged 15 × wash | Damaged 5 × wash | Damaged 15 × wash | Shore OO hardness |
|---|---|---|---|---|---|---|---|---|---|---|
| 3.1 | None | 1 part 1G | None | 1:100 | 1:0 | 4 | 3 | 4 | 3 | 0 |
| 3.2 | 3A | 1 part 1G | None | 1:100 | 1:0 | 4 | 3 | 4 | 4 | 0 |
| 3.3 | 3B | 1 part 1G | None | 1:100 | 1:0 | 4 | 3 | 4 | 3.5 | 0 |
| 3.4 | None | None | 1 part 2F | 1:100 | 0:1 | 3 | 1 | 4 | 3 | 0 |

TABLE 9-continued

Color remanence results of the combination of amino silicone with epoxy Silicone on hair pre-treated or not with a third component.

| Experiment | Third Component Table 3 | First Composition Table 6 | Second Composition Table 7 | Forth Component[d] Table 8 | Ratio[a] | Undamaged 5 × wash | Undamaged 15 × wash | Damaged 5 × wash | Damaged 15 × wash | Shore OO hardness |
|---|---|---|---|---|---|---|---|---|---|---|
| 3.5 | 3A | None | 1 part 2F | 1:100 | 0:1 | 3.5 | 2.5 | 3.5 | 3 | 0 |
| 3.6 | 3B | None | 1 part 2F | 1:100 | 0:1 | 3 | 2 | 3 | 2 | 0 |
| 3.7 | None | 4 part 1G | 1 part 2F | 1:100 | 4:1 | 3.5 | 1.5 | 3 | 1.5 | 26 |
| 3.8 | 3A | 4 part 1G | 1 part 2F | 1:100 | 4:1 | 3 | 2 | 4 | 4.5 | 26 |
| 3.9 | 3B | 4 part 1G | 1 part 2F | 1:100 | 4:1 | 3 | 2 | 3 | 3 | 26 |
| 3.10 | None | 3 part 1G | 2 part 2F | 1:100 | 1.5:1 | 3 | 1.5 | 3 | 1.5 | 30 |
| 3.11 | 3A | 3 part 1G | 2 part 2F | 1:100 | 1.5:1 | 3 | 2 | 3.5 | 3.5 | 30 |
| 3.12 | 3B | 3 part 1G | 2 part 2F | 1:100 | 1.5:1 | 3 | 2 | 3 | 3 | 30 |
| 3.13 | None | 1 part 1G | 1 part 2F | 1:100 | 1:1 | 3 | 1.5 | 3 | 1.5 | 40 |
| 3.14 | 3A | 1 part 1G | 1 part 2F | 1:100 | 1:1 | 4 | 3 | 4 | 3.5 | 40 |
| 3.15 | 3B | 1 part 1G | 1 part 2F | 1:100 | 1:1 | 4 | 2 | 4 | 3 | 40 |
| 3.16 | None | 2 part 1G | 3 part 2F | 1:100 | 1:1.5 | 3.5 | 1.5 | 3.5 | 1.5 | 51 |
| 3.17 | 3A | 2 part 1G | 3 part 2F | 1:100 | 1:1.5 | 4 | 3 | 4 | 3.5 | 51 |
| 3.18 | 3B | 2 part 1G | 3 part 2F | 1:100 | 1:1.5 | 4 | 2 | 4 | 3 | 51 |
| 3.19 | None | 1 part 1G | 4 part 2F | 1:100 | 1:4 | 3 | 1.5 | 3 | 2 | 0 |
| 3.20 | 3A | 1 part 1G | 4 part 2F | 1:100 | 1:4 | 4 | 3 | 4 | 3.5 | 0 |
| 3.21 | 3B | 1 part 1G | 4 part 2F | 1:100 | 1:4 | 4 | 2 | 4 | 2.5 | 0 |
| 3.22 | None | 1 part 1H | 1 part 2G | 1:100 | 1:1 | 3 | 2 | 3 | 2 | 40 |
| 3.23 | 3A | 1 part 1H | 1 part 2G | 1:100 | 1:1 | 3 | 1.5 | 3 | 1.5 | 40 |
| 3.24 | 3B | 1 part 1H | 1 part 2G | 1:100 | 1:1 | 3 | 2 | 3 | 2 | 40 |
| 3.25 | None | 1 part 1I | 1 part 2G | 1:100 | 1:1 | 1.5 | 1 | 2 | 1 | 40 |
| 3.26 | 3A | 1 part 1I | 1 part 2G | 1:100 | 1:1 | 3.5 | 1.5 | 3.5 | 2 | 40 |
| 3.27 | 3B | 1 part 1I | 1 part 2G | 1:100 | 1:1 | 2 | 1 | 3 | 1 | 40 |
| 3.28 | None | 1 part 1K | 1 part 2I | 1:100 | 1:1 | 2 | 1 | 4 | 2.5 | 40 |
| 3.29 | 3A | 1 part 1K | 1 part 2I | 1:100 | 1:1 | 1.5 | 1 | 3 | 1.5 | 40 |
| 3.30 | 3B | 1 part 1K | 1 part 2I | 1:100 | 1:1 | 1.5 | 1 | 3 | 2 | 40 |

[a]Ratio - First polymer MPC × weight percent:second polymer MPC × weight percent
[d]The multicomponent coloring composition was prepared by mixing together part 1 and part 2 in the ratios described. To this mixture, the fourth component was then added at the ratio described, i.e. such that the fourth component is 1% of the final multicomponent coloring composition.

Figure 12:
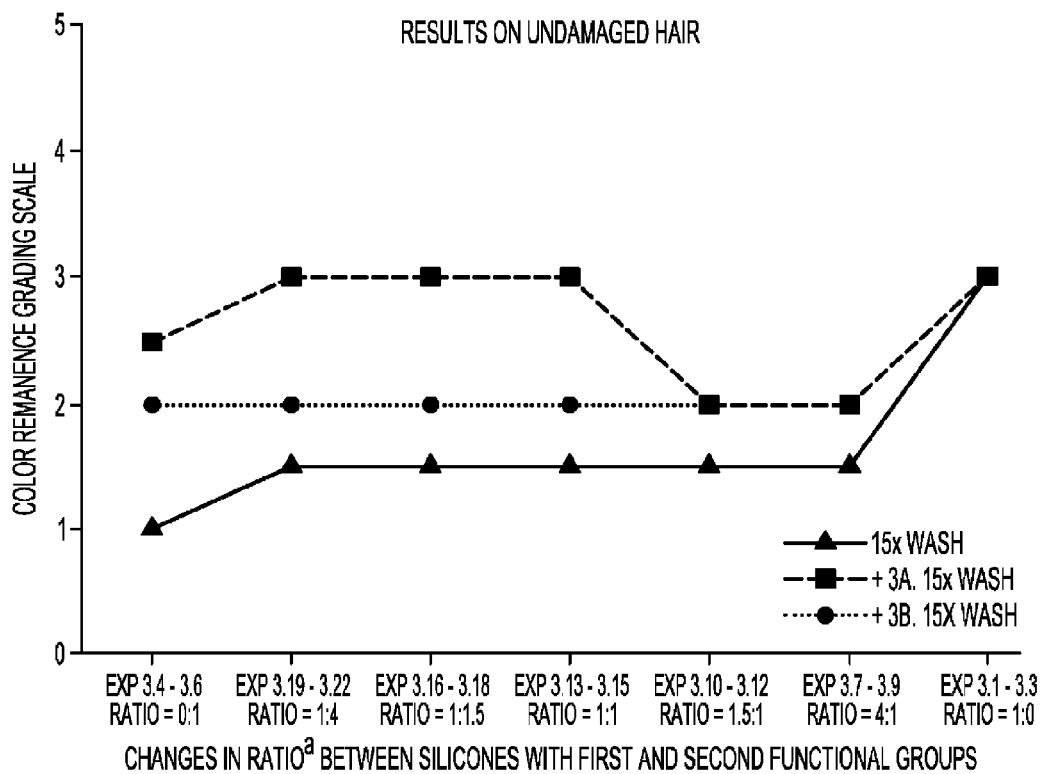
FIG. 12 shows a graph of experimental results for color remanence of a coating on undamaged hair.
Figure 13:
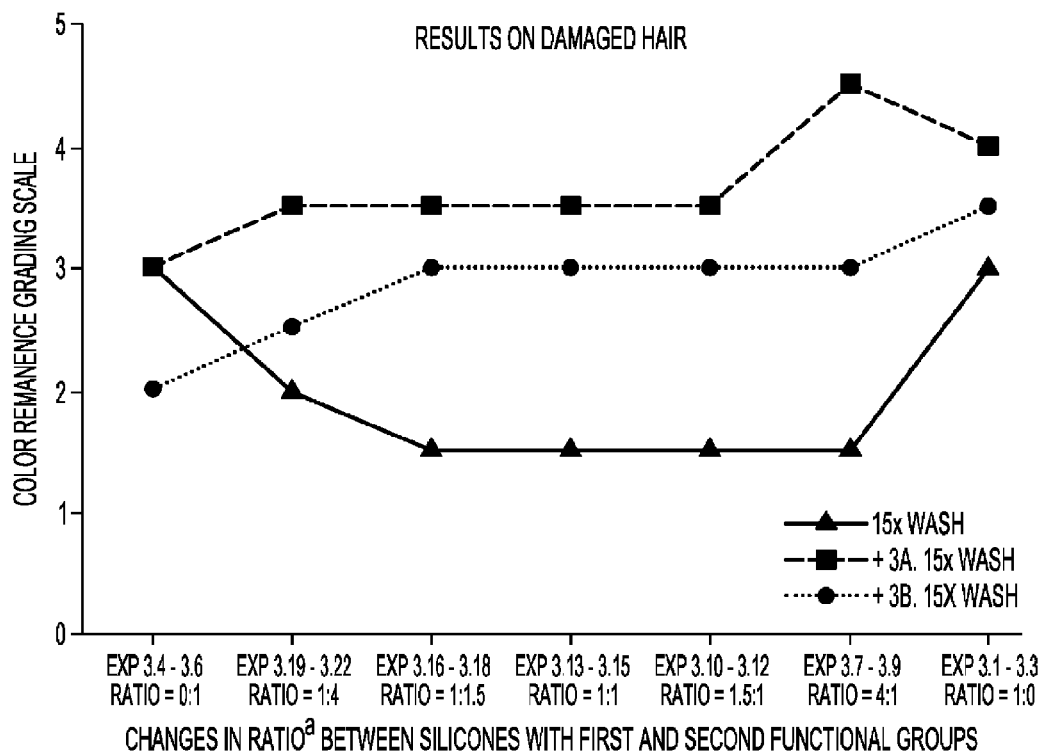
FIG. 13 shows a graph of experimental results for color remanence of a coating on damaged hair.
Figure 14:
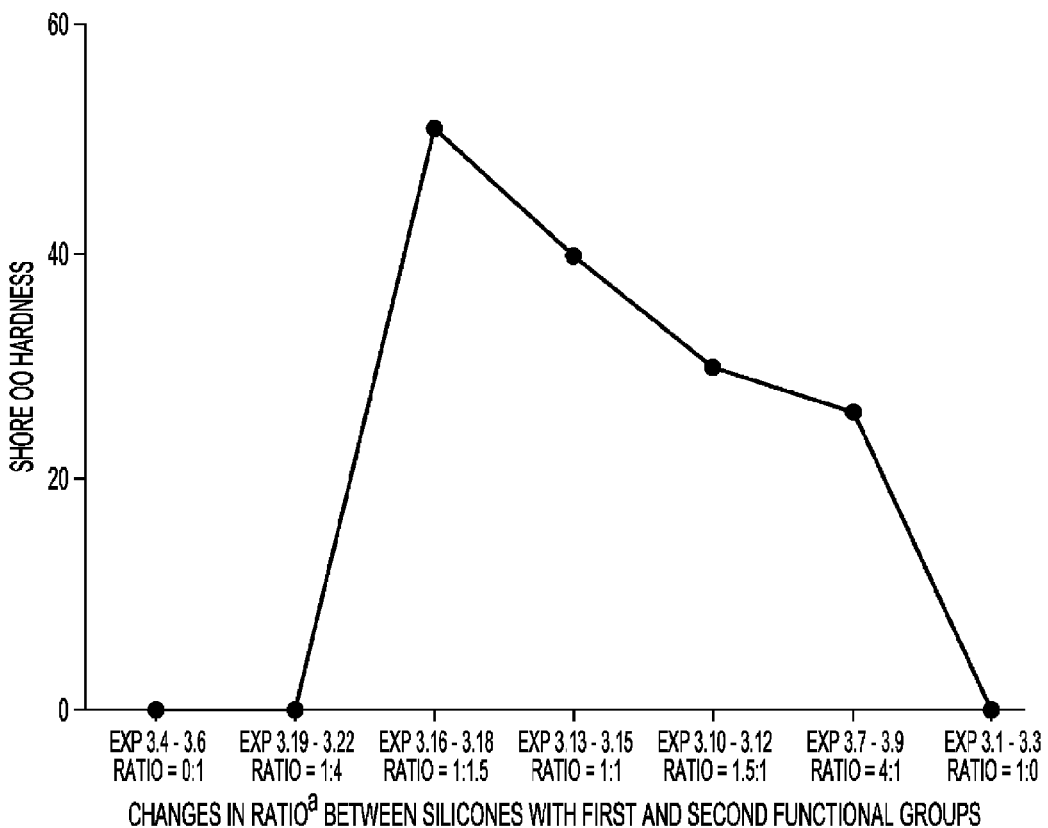
FIG. 14 shows a graph of experimental results for shore hardness of a coating on hair.

The results from the studies performed using different ratios of silicones with first functional groups and silicones with second functional groups are now described. FIG. 12 shows the color remanence as assessed by the color remanence grading scale after 15 washes on undamaged hair tresses for different ratios of the multicomponent coloring composition, with no pre-treatment, in others where 3A was used as a pretreatment wherein the third component contained an aminosilane as the base compound, and a final series were 3B was used as a pretreatment wherein the third component contained a polymer as a base compound. FIG. 13 shows the same multicomponent coloring compositions with the same combinations of pretreatment assessed by the color remanence grading scale after 15 washes however on damaged hair.

The experiments and graphs show that the inclusion of a pre-treatment enhances the performance of the multicomponent system containing both a first and second component when a third component either 3A or 3B is used. When the third component is 3B the performance is generally even better than when the third component is 3A.

Plotted separately within FIG. 13 are the measured Shore 00 hardness measured according to the procedure described above. This shows that the Shore 00 hardness also has a maximum region for certain ratio of the first and second components. Whilst not wishing to be bound to theory, it believed that the higher Shore 00 hardness may be indicative of a stronger film, which may help to facilitate higher remanence to washing on hair.

Experiments 3.22 through to 3.24 show the results obtain when a yellow pigment was used instead of the red pigment. Initially the tresses were visually assessed as being yellow after application and drying of the multicomponent coloring composition. There was a measurable level of color remanence as assessed by the color remanence grading scale after both 5 and 15 washes on undamaged and damaged hair tresses for the mixture of first and second components within the multicomponent coloring composition.

Experiments 3.25 through to 3.27 show the results obtain when a black pigment was used. Initially the tresses were visually assessed as being black after application and drying of the multicomponent coloring composition. There was a measurable level of color remanence as assessed by the color remanence grading scale after both 5 and 15 washes on undamaged and damaged hair tresses for the mixture of first and second components within the multicomponent coloring composition. The color remanence was higher after five cycles when a pretreatment, either 3A or 3B had been used as a pre-treatment.

Experiments 3.28 through to 3.30 show the results obtain when a metal flake pigment was used. Initially the tresses were visually assessed as being metallic looking after application and drying of the multicomponent coloring composition. There was a measurable level of color remanence as assessed by the color remanence grading scale after both 5 and 15 washes on undamaged and damaged hair tresses for the mixture of first and second components within the multicomponent coloring composition.

Example 4: Multicomponent Coloring Compositions with a First Component Containing as Amino Silicone and a Second Component Containing an Olefinoyloxy Silicone The first components containing the silicone with the first functional groups are described within Table 10.

TABLE 10

First components containing amino silicone

| Material | Name | Supplier | 1L | 1M | 1N | 1O | 1P |
|---|---|---|---|---|---|---|---|
| Pigment(s) | | | | | | | |
| Pigment Red 112 | Permanent Red FGR 70 | Clariant | 1% | | | | |
| Pigment Yellow 83 | Novoperm Yellow HR 70 M250 | Clariant | | 5% | | | |
| Pigment Black 6 | Midnight Black carbon black | Geotech | | | 5% | | |
| TiO2 | Hombitan AFDC | Venator | | | | 5% | |
| Aluminum Flake | Velvet SL | Toyal | | | | | 5% |
| First silicone | | | | | | | |
| Amino-silicone Medium | Silmer NH E47 | Siltech | 5% | 5% | 5% | 10% | 15% |
| Isododecane | 2,2,4,6,6-Penta-methyl-heptane | Brenntag | Qs 100% | Qs 100% | Qs 100% | Qs 100% | Qs 100% |

The second components containing the silicone with the second functional groups are described within Table 11.

TABLE 11

Second Components containing olefinoyloxy silicone

| Material | Name | Supplier | 2J | 2K | 2L | 2M |
|---|---|---|---|---|---|---|
| Pigment(s) | | | | | | |
| Pigment Red 112 | Permanent Red FGR 70 | Clariant | 1% | | | |
| TiO2 | Hombitan AFDC | Venator | | | 5% | |
| Aluminum Flake | Velvet SL | Toyal | | | | 5% |
| Second silicone | | | | | | |
| Acrolyl Silicone Medium | Silmer OH ACR Di-400 | Siltech | 5% | 5% | 10% | 15% |
| Isododecane | 2,2,4,6,6-Pentamethyl-heptane | Brenntag | Qs 100% | Qs 100% | Qs 100% | Qs 100% |

The following (table 12) captures the results of Example 4 encompassing various combinations of aminosilicone with an olefinoyloxy silicone applied to tresses pre-treated or not (prior to application of the multicomponent coloring composition) with a variety of third components described in Table 3 above.

TABLE 12

Color remanence results of the combination of amino silicone with olefinoyloxy Silicone on hair pre-treated or not with a third component.

| Experiment | Third Component Table 3 | First Composition Table 10 | Second Composition Table 11 | Ratio[a] | Undamaged 5 × wash | Undamaged 15 × wash | Damaged 5 × wash | Damaged 15 × wash | Shore OO hardness[b] |
|---|---|---|---|---|---|---|---|---|---|
| 4.1 | 3A | None | 1 Part 2J | 0:1 | 4 | 2.5 | 4 | 3 | 0* |
| 4.2 | 3B | None | 1 Part 2J | 0:1 | 3.5 | 2 | 3.5 | 2 | 0* |
| 4.3 | 3A | 1 Part 1 L | 4 Part 2J | 1:1 | 5 | 4.5 | 4 | 4.5 | 0* |
| 4.4 | 3B | 1 Part 1 L | 4 Part 2J | 1:1 | 5 | 3.5 | 5 | 3.5 | 0* |
| 4.5 | 3A | 2 Part 1 L | 3 Part 2J | 2.67:1 | 5 | 4 | 5 | 4.5 | 33.6 |
| 4.6 | 3B | 2 Part 1 L | 3 Part 2J | 2.67:1 | 5 | 4 | 5 | 4 | 33.6 |
| 4.7 | 3A | 1 Part 1 L | 1 Part 2J | 4:1 | 5 | 3.5 | 5 | 3.5 | 25.0 |
| 4.8 | 3B | 1 Part 1 L | 1 Part 2J | 4:1 | 5 | 4 | 5 | 4 | 25.0 |
| 4.9 | 3A | 3 Part 1 L | 2 Part 2J | 6:1 | 5 | 3.5 | 5 | 4 | 14.0 |
| 4.10 | 3B | 3 Part 1 L | 2 Part 2J | 6:1 | 5 | 3 | 5 | 3.5 | 14.0 |
| 4.11 | None | 4 Part 1 L | 1 Part 2J | 16:1 | 5 | 3 | 5 | 2 | 0* |
| 4.12 | 3A | 4 Part 1 L | 1 Part 2J | 16:1 | 5 | 3.5 | 5 | 3.5 | 0* |
| 4.13 | 3B | 4 Part 1 L | 1 Part 2J | 16:1 | 5 | 4 | 5 | 4 | 0* |
| 4.14 | 3A | 1 Part 1 L | None | 1:0 | 4 | 3 | 4 | 3 | 0* |
| 4.15 | 3B | 1 Part 1 L | None | 1:0 | 4 | 3 | 4 | 3 | 0* |
| 4.16 | None | 1 Part 1 M | 4 Part 2 K | 1:1 | 3 | 2 | 3 | 2 | 0* |
| 4.17 | 3A | 1 Part 1 M | 4 Part 2 K | 1:1 | 4 | 3 | 4 | 3 | 0* |
| 4.18 | 3B | 1 Part 1 M | 4 Part 2 K | 1:1 | 3.5 | 2.5 | 3.5 | 2.5 | 0* |
| 4.19 | None | 1 Part 1 N | 4 Part 2 K | 1:1 | 3 | 1 | 3 | 1 | 0* |
| 4.20 | 3A | 1 Part 1 N | 4 Part 2 K | 1:1 | 4 | 2 | 4 | 2 | 0* |
| 4.21 | 3B | 1 Part 1 N | 4 Part 2 K | 1:1 | 3.5 | 1 | 3.5 | 1 | 0* |
| 4.22 | None | 1 Part 1 O | 4 Part 2 L | 1:1 | 1.5 | 1 | 2 | 1 | 0* |
| 4.23 | 3A | 1 Part 1 O | 4 Part 2 L | 1:1 | 2 | 1 | 3 | 2 | 0* |
| 4.24 | 3B | 1 Part 1 O | 4 Part 2 L | 1:1 | 2 | 1 | 3 | 1.5 | 0* |
| 4.25 | None | 1 Part 1 P | 4 Part 2 M | 1:1 | 1.5 | 1 | 2 | 1 | 0* |

TABLE 12-continued

Color remanence results of the combination of amino silicone with olefinoyloxy Silicone on hair pre-treated or not with a third component.

| Experiment | Third Component Table 3 | First Composition Table 10 | Second Composition Table 11 | Ratio$^a$ | Undamaged 5 × wash | Undamaged 15 × wash | Damaged 5 × wash | Damaged 15 × wash | Shore OO hardness$^b$ |
|---|---|---|---|---|---|---|---|---|---|
| 4.26 | 3A | 1 Part 1 P | 4 Part 2 M | 1:1 | 3 | 1 | 4 | 2 | 0* |
| 4.27 | 3B | 1 Part 1 P | 4 Part 2 M | 1:1 | 2 | 1 | 3 | 1.5 | 0* |

$^a$Ratio - First polymer MPC × weight percent:second polymer MPC × weight percent
$^b$0* value assigned when film remains fluid and cannot be measured for shore Hardness 00.

Comparing the results across the experiments, shown graphically within the figures, it is possible to see the benefit of the third component, and that there is a better performance for the mixture of a first and second component versus either used individually.

Figure 15:
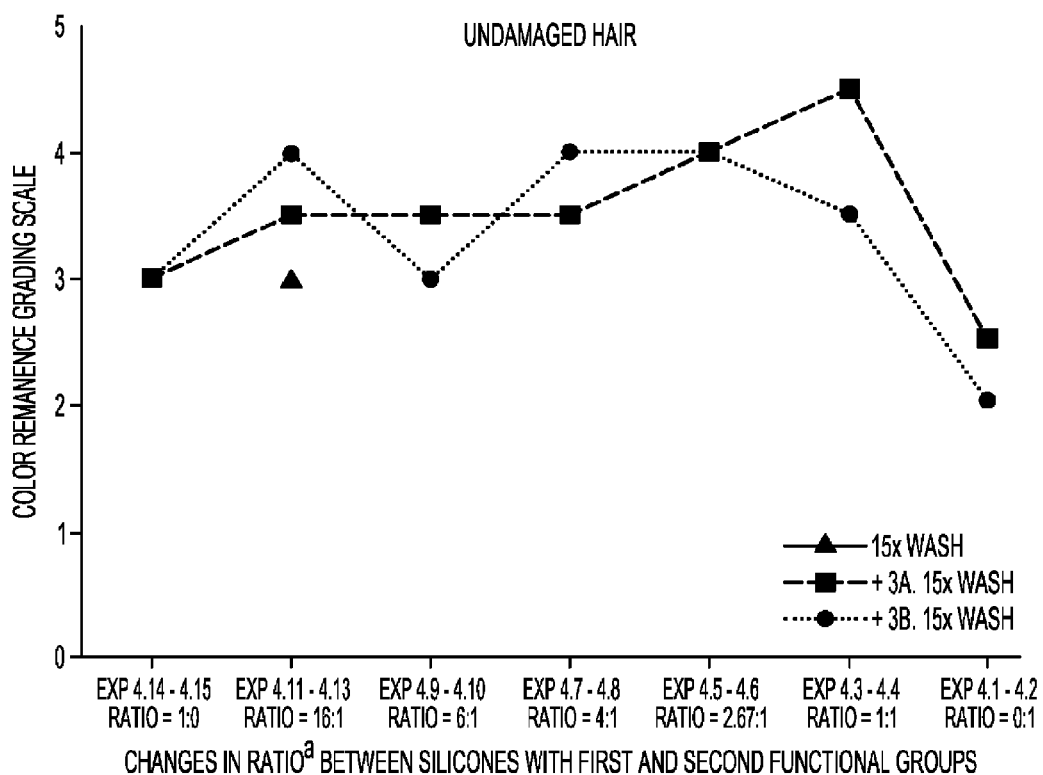
FIG. 15 shows a graph of experimental results for color remanence of a coating on undamaged hair.
Figure 16:
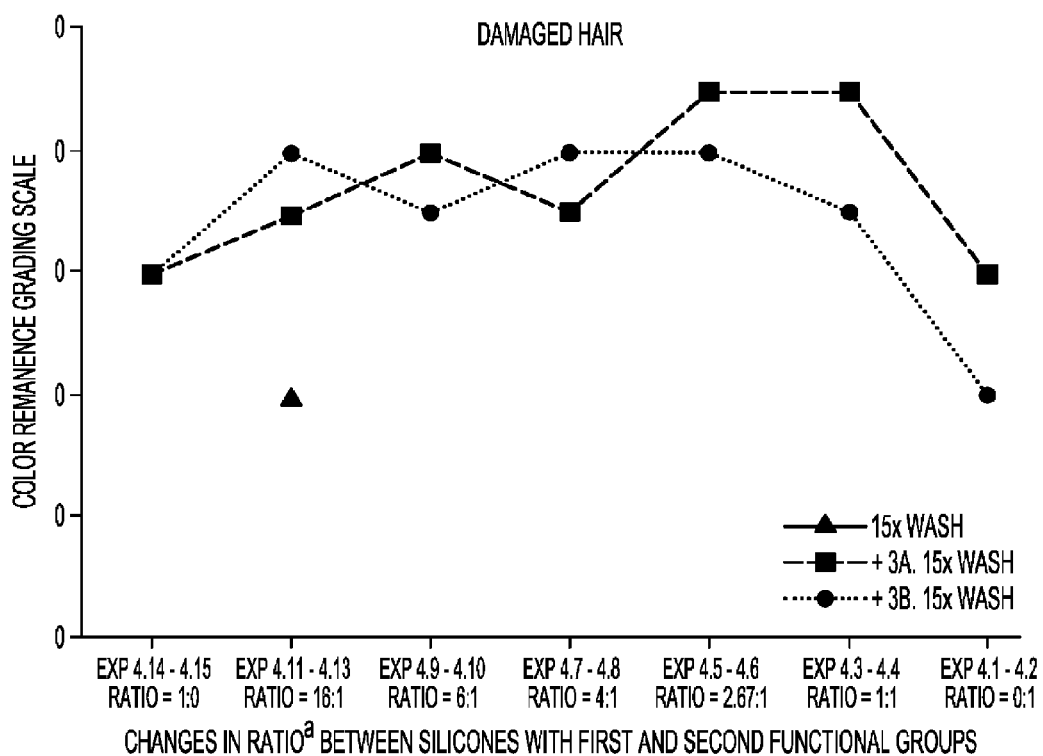
FIG. 16 shows a graph of experimental results for color remanence of a coating on damaged hair.

The results from the studies performed using different ratios of silicones with first functional groups and silicones with second functional groups are now described. FIG. 15 shows the color remanence as assessed by the color remanence grading scale after 15 washes on undamaged hair tresses for different ratios of the multicomponent coloring composition, in some case with no pre-treatment, in others where 3A was used as a pretreatment wherein the third component contained an aminosilane as the base compound, and a final series were 3B was used as a pretreatment wherein the third component contained a polymer as a base compound. FIG. 16 shows the same multicomponent coloring compositions with the same combinations of pretreatment assessed by the color remanence grading scale after 15 washes however on damaged hair.

Within FIGS. 15 and 16 the examples 4.11-4.13 with a ratio calculated with the approach described above of 16:1 visually show the advantage of the use of a pre-treatment (4.12 and 4.13) versus no pre-treatment (4.12). So either pretreatment 3A or 3B increases the color remanence within this example.

Looking at the performance as the mixing ratio of the first and second components is altered it can be seen that the mixed systems provide stronger performance versus either the first or second component when used alone.

Figure 17:
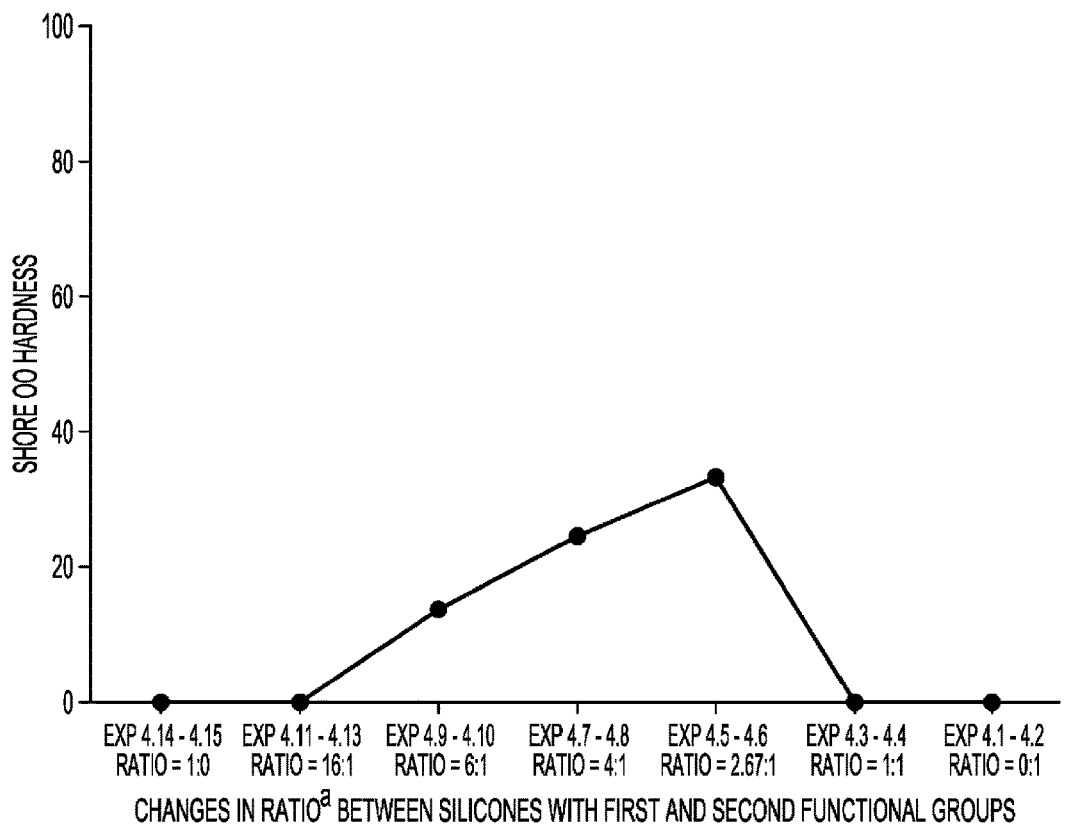
FIG. 17 shows a graph of experimental results for shore hardness of a coating on hair.

Plotted separately within FIG. 17 are the measured Shore 00 hardness measured according the procedure described above. This shows that the Shore 00 hardness also has a maximum region for certain mixtures of the first and second components. Whilst not wishing to be bound to theory, it is believed that the higher Shore 00 hardness may be indicative of a strong film, which may help to facilitate higher remanence to washing on hair.

Example 5: Multicomponent Coloring Compositions with a First and Second Components Containing Either Condensation or Hydrosilylation Based Silicone Systems The first components containing the silicone with the first functional groups are described within Table 13

TABLE 13

| First components for condensation or hydrosilylation silicones. | | | | | | | |
|---|---|---|---|---|---|---|---|
| Material | Name | Supplier | 1Q | 1R | 1T* | 1U | 1V |
| Pigment(s) | | | | | | | |
| Pigment Red 112 | Permanent Red FGR 70 | Clariant | 1% | 1% | | | |
| Pigment Red 122 | Hostaperm Pink E | Clariant | | | | 1% | 1% |
| Pigment Black 6 | Midnight Black carbon black | Geotech | | | | | |
| TiO2 | Hombitan AFDC | Venator | | | | | |
| Aluminum Flake | Velvet SL | Toyal | | | | | |
| First Silicone | | | | | | | |
| Alkoxy silicone | Silmer TMS C50 | Siltech | 7.68% | 7.49 | | | |
| Alkoxy silicone | Silmer TMS Di10 | Siltech | 0.32% | 0.31 | | | |
| Alkoxy silicone | Silmer TMS Di50 | Siltech | 2% | 1.95 | | | |
| Alkoxy silicone* | X-40-2327 | Shin Etsu | | | 10% | | |
| Hydrosilylation | KNS-30021 | Shin Etsu | | | | | 10% |
| Medium | | | | | | | |
| Isododecane | 2,2,4,6,6-Pentamethylheptane | Brenntag | Qs 100% | Qs 100% | | | |
| D5 | Cyclopentasiloxane | Dow | | | | Qs 100% | Qs 100% |
| Other | | | | | | | |
| Catalyst | Cat-PL-56 | Shin Etsu | | | 1.0% | | |

*when X-40-2327 was used a cure catalyst was also added into the first component. Whilst not wishing to be bound to theory, it's believed that such a cure catalyst may accelerate the condensation curing of the silicone mixture within X-40-2327.

The second components containing the silicone with the second functional groups are described within Table 14

TABLE 14

| | Second Components | | | | |
|---|---|---|---|---|---|
| Material | Name | Supplier | 2O | 2P | 2R |
| Pigment(s) | | | | | |
| Pigment Red 112 | Hostaperm Pink EO-EDW VP4034 | Clariant | 1% | 1% | |
| Pigment Red 122 | Hostaperm Pink E | Clariant | | | 1% |
| Aluminum Flake | Velvet SL | Toyal | | | |
| Second Silicone | | | | | |
| | Silamine 2972 | Siltech | | 2.0% | |
| | Silmer NH E47 | Siltech | | | |
| Medium | | | | | |
| Isododecane D5 | 2,2,4,6,6-Pentamethylheptane Cyclopentasiloxane | Brenntag Dow | Qs 100% | Qs 100% | Qs 100% |

The following table 15 captures the results of Example 5 encompassing various combinations condensation and hydrosilylation curing silicones to tresses pre-treated or not (prior to application of the multicomponent coloring composition) with a variety of third components described in Table 3 above.

With the inclusion of an amino silicone into the multi-component coloring composition, 5.4 there is in an improvement in the performance of systems that did not have a pre-treatment with a third composition compared to 5.1. This shows that the inclusion of a high molecular weight aminosilicone can improve the color remanence in the absence of a pre-treatment with a third composition.

TABLE 15

Color remanence results of the the combination of a first and second components containing either condensation hydrosilylation based silicone systems.

| Experiment | Third Component Table 3 | First Composition Table 13 | Second Composition Table 14 | Undamaged 5 × wash | Undamaged 15 × wash | Damaged 5 × wash | Damaged 15 × wash |
|---|---|---|---|---|---|---|---|
| 5.1 | None | 1 Part 1 Q | 1 Part 2 O | 2 | 1 | 3 | 2 |
| 5.2 | 3A | 1 Part 1 Q | 1 Part 2 O | 3 | 2 | 4.5 | 3 |
| 5.3 | 3B | 1 Part 1 Q | 1 Part 2 O | 4 | 1 | 4 | 4 |
| 5.4 | None | 1 Part 1 R | 1 Part 2 P | 3 | 2 | 4 | 3 |
| 5.5 | None | 1 Part 1 T | 1 Part 2 R | 1 | 1 | 1 | 1 |
| 5.6 | 3B | 1 Part 1 T | 1 Part 2 R | 2 | 1.5 | 3 | 2 |
| 5.7 | 3C | 1 Part 1 T | 1 Part 2 R | 2 | 1.5 | 3 | 3 |
| 5.8 | None | 1 Part 1 U | 1 Part 2 R | 1 | 1 | 2 | 2 |
| 5.9 | 3A | 1 Part 1 U | 1 Part 2 R | 3 | 1 | 3 | 2.5 |
| 5.10 | 3B | 1 Part 1 U | 1 Part 2 R | 3 | 1 | 3 | 1 |

For experiments 5.1 through to 5.5, after the multicomponent system was applied and the hair dried, the hair was then dipped into the 1% solution of Titanum(IV)-2-ethylhexyloxide (Sigma Aldrich), and then dried again.

Figure 18:
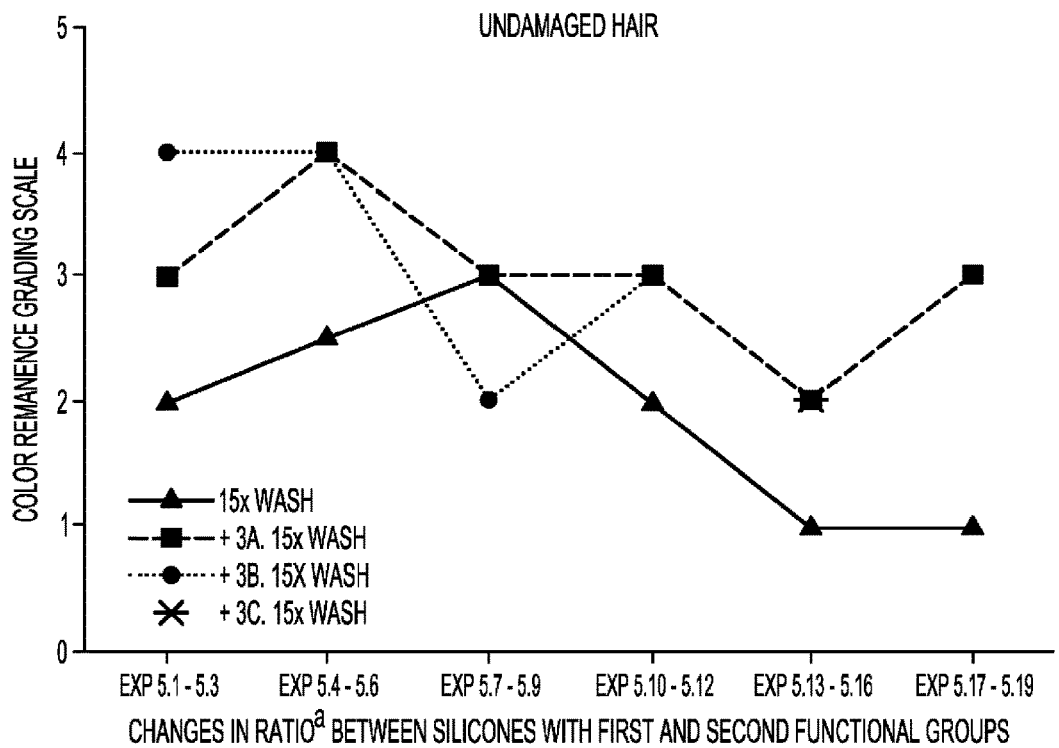
FIG. 18 shows a graph of experimental results for color remanence of a coating on undamaged hair.
Figure 19:
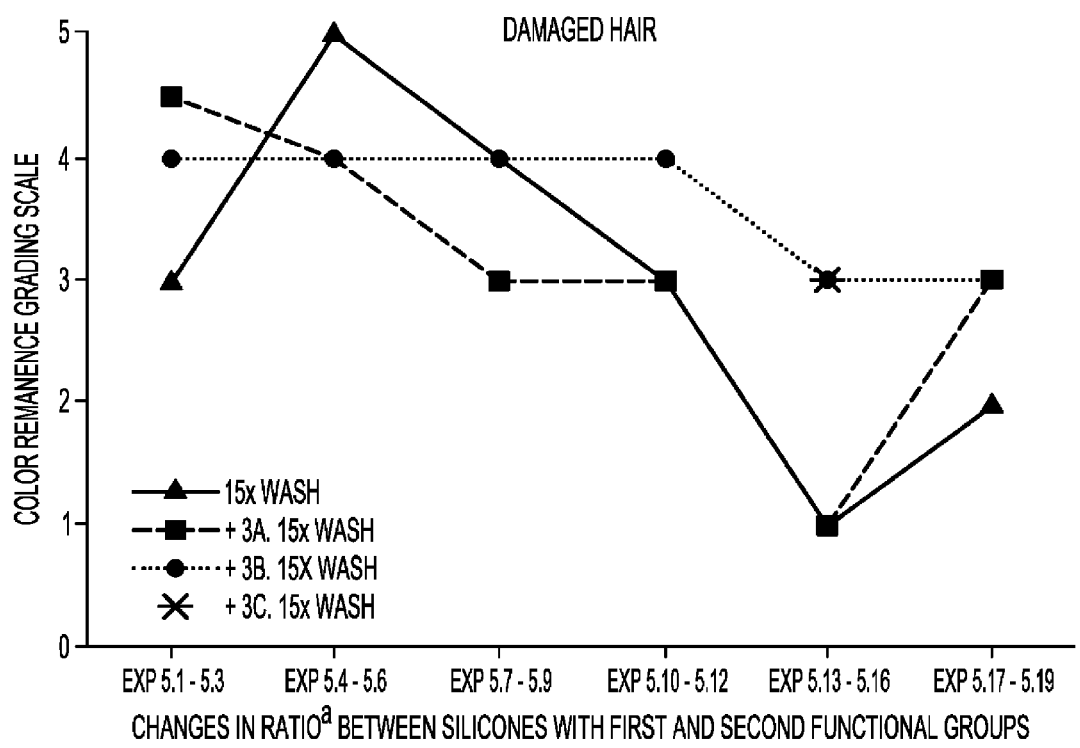
FIG. 19 shows a graph of experimental results for color remanence of a coating on damaged hair.

The results from the studies performed using different first compositions and second compositions are now described. FIG. 18 shows the color remanence as assessed by the color remanence grading scale after 5 washes on undamaged hair tresses for different ratios of the multicomponent coloring composition, in some case with no pre-treatment, in others where 3A or 3B or 3C were used as third component or pretreatments. FIG. 19 shows the same multicomponent coloring compositions with the same combinations of pre-treatment assessed by the color remanence grading scale after 5 washes however on damaged hair.

These show that:

The condensation cure system within 5.1 can deliver some color remanence as assessed by the color remanence grading scale after 5 washes on undamaged and damaged hair. The inclusion of a third component as a pre-treatment, either 3A or 3B, increases the color remanence, 5.2 and 5.3.

With the use of different condensation curable system, 5.5-5.7, again the benefit of pretreatment is clear with increased color remanence as assessed by the color remanence grading scale after 5 washes on undamaged and damaged hair across both 3B and 3C when used as a pre-treatment.

Finally, with the hydrosilylation system 5.8-5.10, the benefit of pretreatment is again clear with increased color remanence as assessed by the color remanence grading scale after 5 washes on undamaged and damaged hair across both 3A and 3B when used as a pre-treatment.

Example 6: Color Removal

Color Removal Composition

General Procedure: Combine active agent with a medium, the medium may contain solvent, thickener, polyelectrolyte, detergent builders and combine and mix until uniform.

Color Removal Application
1. Apply 1 gram of color removal composition to 1 gram of colored hair tress.
2. The color removal composition is worked into the colored hair tress in the absence of water dilution for approximately between 30 sec to 1 minute with fingers or a comb of manipulation instrument by using stroking motion into the hair.
3. Leave the color removal composition onto the colored hair tress for approximately 1 min or longer undisturbed.
5. Remove excess color removal composition with an absorbent tissue material.
6. Apply 0.1 g of "Wella Professional Brilliance Shampoo for fine and normal hair" without water dilution and work into the colored hair tress for 30 sec with fingers by using stroking motion into the hair.
7. The shampooed colored hair tress is rinsed with water for approximately 30 seconds.
8. The rinsed colored hair tress is then dried using a hot blow dryer until uniformly dry.

Table 16 presents the different color removal compositions.

TABLE 16

Compositions for color removal

| Material | Name | Supplier | 5A | 5B | 5C | 5D |
|---|---|---|---|---|---|---|
| Medium | | | | | | |
| Solvent | N-octyl-pyrrolidone | Sigma Aldrich | 100% | Qs 100% | | |
| Solvent | Isododecane | Brenntag | | | 100% | Qs 100% |
| Agent | | | | | | |
| Fluoride source | Tetrabutylammonium fluoride (75 wt % in H2O) | Sigma Aldrich | | 1.3% | | |
| Acid | Dodecyl benzene sulfonic acid (70% in 2-Propanol) | Sigma Aldrich | | | | 5.7% |

The compositions were prepared my mixing together the different materials using standard laboratory means.

Multicomponent Compositions for Removal Testing.

TABLE 17

First Components containing first silicone with first functional groups, pigment(s) and medium.

| Material | Name | Supplier | 1W | 1X | 1Y | 1Z |
|---|---|---|---|---|---|---|
| Pigment(s) | | | | | | |
| Pigment Red 112 | Permanent Red FGR 70 | Clariant | 2.0% | 0.42% | 2.0% | 0.42% |
| Pigment Yellow 83 | Novoperm Yellow HR 70 M250 | Clariant | | 1.36% | | 1.36% |
| Pigment Black 6 | Midnight Black carbon black | Geotech | | 0.22% | | 0.22% |
| First Silicone | | | | | | |
| Amino silicone | Silmer NH E47 | Siltech | 2.0% | 2.0% | | |
| OH silicone | Silmer OHT C50 | Siltech | | | 4.0% | 4.0% |
| Medium | | | | | | |
| Isododecane | 2,2,4,6,6-Pentamethylheptane | Brenntag | Qs 100% | Qs 100% | Qs 100% | Qs 100% |

TABLE 18

Second Components containing second silicone with second functional groups, optionally pigment(s) and medium

| Material | Name | Supplier | 2T | 2U | 2V |
|---|---|---|---|---|---|
| Pigment(s) | | | | | |
| Pigment Red 112 | Permanent Red FGR 70 | Clariant | | | |
| Second Silicone | | | | | |
| Acrolyl Silicone | Silmer OH ACR Di-400 | Siltech | 8.0% | 8.0% | |
| Isocyante Silicone | Silmer NCO Di-50 | Siltech | | | 6.0% |
| Medium | | | | | |
| Isododecane | 2,2,4,6,6-Pentamethylheptane | Brenntag | Qs 100% | Qs 100% | Qs 100% |

The following table 19 captures the results of Example where a series of different removal compositions were tested on two different shades:

TABLE 19

| Experiment | Third Component Table 3 | First component Table 17 | Second component Table 18 | Color removal composition Table 16 | Color remanence after color removal |
|---|---|---|---|---|---|
| 6.1 | 3B | 1 Part 1W | 1 Part 2T | 5A | 3 |
| 6.2 | 3B | 1 Part 1W | 1 Part 2T | 5B | 1 |
| 6.3 | 3B | 1 Part 1W | 1 Part 2T | 5C | 4 |
| 6.4 | 3B | 1 Part 1W | 1 Part 2T | 5D | 1 |
| 6.5 | 3B | 1 Part 1X | 1 Part 2U | 5A | 3 |
| 6.6 | 3B | 1 Part 1X | 1 Part 2U | 5B | 1 |
| 6.7 | 3B | 1 Part 1X | 1 Part 2U | 5C | 4 |
| 6.8 | 3B | 1 Part 1X | 1 Part 2U | 5D | 1 |
| 6.9 | 3B | 1 Part 1Y | 1 Part 2V | 5A | 3 |
| 6.10 | 3B | 1 Part 1Y | 1 Part 2V | 5B | 1 |
| 6.11 | 3B | 1 Part 1Y | 1 Part 2V | 5C | 4 |
| 6.12 | 3B | 1 Part 1Y | 1 Part 2V | 5D | 1 |
| 6.13 | 3B | 1 Part 1Z | 1 Part 2V | 5A | 3 |
| 6.14 | 3B | 1 Part 1Z | 1 Part 2V | 5B | 1 |
| 6.15 | 3B | 1 Part 1Z | 1 Part 2V | 5C | 4 |
| 6.16 | 3B | 1 Part 1Z | 1 Part 2V | 5D | 1 |

Within these studies the ability for the color to be removed was tested, both through the use of a straight solvent application, and the combination of the solvent with an active agent. The color remanence was assessed by the color remanence grading scale used above, but in this case we want to see a low value, to indicate that the color is no longer there and the removal has been successful.

For the "red" colored hair systems 6.1 through to 6.4, while there is some color removed with a solvent only application (6.1 and 6.3) this is greatly increased with the addition of the removal actives (6.2 and 6.4) where the color is effectively completely removed.

For the "brown" colored hair systems which use a combination of three pigments, 6.5 through to 6.8, while there is some color removed with a solvent only application (6.5 and 6.7) this is greatly increased with the addition of the actives (6.6 and 6.8) where the color is effectively completely removed.

This was also shown using a different combination of first and second silicone polymer in experiments 6.9 through to 6.16. Again for both systems while some color was removed using the solvents alone, 6.9, 6.11, 6.13 and 6.15, it was completely removed with the addition of actives, 6.10, 6.12, 6.14 and 6.16.

Example 7

Preparation and Application of a First and Second Silicone Component to Cotton Cloth Pre-Treated with a Third Component Containing a Base Compound General Description of Steps:
Preparation procedure for the third component also called pre-treatment
Preparation procedure for the first component containing a first silicone polymer with first functional groups with optional pigment
Preparation procedure for the second component containing a second silicone polymer with second functional groups
Preparation procedure for the multicomponent coloring composition
Application of color multicomponent composition to cotton cloth
Standard Wash Procedure
Color removal composition
Application of color removal composition
Preparation Procedure for a the Third Component Also Called Pre-Treatment
This was prepared as described above.
Preparation Procedure for the First Component Containing a First Silicone Polymer with First Functional Groups with Optional Pigment
This was prepared as described above.
Preparation Procedure for the Second Component Containing a Second Silicone Polymer with Second Functional Groups
This was prepared as described above.
Preparation Procedure for the Multicomponent Coloring Composition
This was prepared as described above.
Application of Color Multicomponent Composition to Cotton Cloth
Cotton Cloth Preparation:
The cotton cloth are 2 cm wide and 8 cm long with zig-zag edges.
Cotton Cloth Pre-Treatment
Cotton cloth as described above is treated with the pre-treatment composition described above, one gram of composition per one gram of cotton cloth. The application is accomplished by a slow distribution and spreading on the cotton cloth, for example, with fingers. The cotton cloth was left to soak in for 5 min. The cotton cloth was then placed in an oven at 25° C. for 1h. Alternatively, the cotton cloth could be left wet, the excess of the composition removed with an absorbant material, for example a towel.
General Coloring Procedure:
To the pre-treated cotton cloth described above is added a freshly prepared color multicomponent composition as described above, 1 gram per 1 gram of cotton cloth. The application is accomplished by a slow distribution and spreading on the cotton cloth, for example, with fingers. The slow distribution can be accomplished by application with a syringe or a pipette serially to portions of the cotton cloth. The excess is removed with absorbent tissue material and the resulting colored cotton cloth is then placed in an oven at 25° C. overnight to fully dry.
Standard Wash Procedure
The standard wash procedure is used to determine the remanence of the colored cotton cloth.
1. Rinse the cotton cloth for approximately 10 seconds with water (4 L/min) at approximately 37+/−2 C.
2. Apply 0.1 g "Wella Professional Brilliance Shampoo for fine and normal hair" without dilution to the cotton cloth described above.
3. Shampoo is worked into the colored cloth in the absence of water dilution for 30 sec with fingers by using stroking motion into the cloth.
4. The shampooed colored cotton cloth is rinsed with water for approximately 30 seconds.
5. The rinsed colored cotton cloth is then dried using a hot blow dryer until uniformly dry.
6. Steps 1-5 described above represent one cycle of the standard wash procedure.
7. Repeat of standard wash cycle for multiple cycles and comparison of the multiply washed cotton cloth to an unwashed colored cotton cloth which indicates the degree of color remanence.

Following the application procedure and technique described above, table 20 summarises the combinations of first, and second and third components used.

TABLE 20

Combination of first, and second and third components applied to cotton cloth

| Experiment: | Third component Pre-treatment from Table 3 | First Component Table 1 | Second Component Table 2 | Color remanence at 5 washes | Color remanence at 15 washes |
|---|---|---|---|---|---|
| EXP 7.1 | None | 1 D | None | 3 | 2 |
| EXP 7.2 | P3 | 1 D | None | 4 | 3 |
| EXP 7.3 | None | 2 part 1D | 3 part 2D | 5 | 4 |
| EXP 7.4 | P3 | 2 part 1D | 3 part 2D | 5 | 5 |

EXP 7.1 illustrates, that when only the first silicone component alone is used there is only moderate color remanence as assessed by the color remanence grading scale as described above for both 5 and 15 washes.

EXP 7.2 illustrates, that the addition of a third component, 3B, as a pre-treatment to the first component alone improves the color remanence as assessed by the color remanence grading scale as described above for both 5 and 15 washes compared to Exp 7.1. This shows the advantage of the use of the third component.

EXP 7.3 illustrates, that the addition of a second silicone component to the first silicone component without pre-treatment improves the color remanence as assessed by the color remanence grading scale as described above for both 5 and 15 washes compared to Exp 7.1. this shows the advantage of the addition of the second component.

EXP 7.4 illustrates, that the combination of the first silicone component with a third component as a pre-treatment and a second silicone component shows the strongest color remanence as assessed by the color remanence grading scale as described above for both 5 and 15 washes. This shows that the most preferred combination with a first, second and third component delivers the strongest performance.

Color Removal Composition
General Procedure:
This was already described above.
Color Removal Application
1. Apply 1 gram of color removal composition to 1 gram of colored cotton cloth.
2. The color removal composition is worked into the colored cotton cloth in the absence of water dilution for approximately between 30 sec to 1 minute with fingers by using stroking motion into the cloth.
3. Leave the color removal composition onto the colored cotton cloth for approximately 1 min or longer undisturbed.
5. Remove excess color removal composition with an absorbent tissue material.
6. Apply 0.1 g of "Wella Professional Brilliance Shampoo for fine and normal hair" without water dilution and work into the cotton cloth for 30 sec with fingers by using stroking motion into the cotton cloth.
7. The shampooed cotton cloth is rinsed with water for approximately 30 seconds.
8. The rinsed cloth is then dried using a hot blow dryer until uniformly dry.

Table 21 presents the results of one color removal composition tested on the combinations presented in Table 20.

TABLE 21

Color remanence results after color removal composition was applied to the combination of table 20

| Experiment | Third component Pre-treatment from Table 5 | First Component Table 1 | Second Component Table 2 | Color removal composition | Color remanence after color removal |
|---|---|---|---|---|---|
| EXP 7.5 | None | 1 D | None | 5B | 1 |
| EXP 7.6 | P3 | 1 D | None | 5B | 1 |
| EXP 7.7 | None | 2 part 1D | 3 part 2D | 5B | 1 |
| EXP 7.8 | P3 | 2 part 1D | 3 part 2D | 5B | 1 |

EXP 7.5 to 7.8 illustrate that the color removal on the cotton cloth was successful.

Embodiment Statements

1. A multicomponent in situ linkable composition for coloring substrate material, comprising a first component comprising a first silicone polymer having first functional groups; a second component comprising a second silicone polymer having second functional groups; a third component comprising a base compound having third functional groups; pigment microparticles in one or more of the first and/or second and/or third components; one or more of the first, second and third components comprising a medium.
2. A multicomponent composition of statement 1 further comprising a fourth component comprising a catalyst or curing accelerator or curing inhibitor capable of promoting the covalent, ionic, electrostatic, entanglement or coordination in situ linkage among any two or more of the first, second and third functional groups.
3. A multicomponent composition of a linear and/or branched silicone polymer comprising non-reactive organosiloxane monomer units and reactive organosiloxane monomer units, the reactive organosiloxane monomer units having functional groups which are arranged to be complementary reactive pairs or a self-reactive functional group, the functional groups comprising isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, pentadienyl, azido, Si—OH, Si—OR, Si—O—N=CHR. Si—OAc, Si—CH=$CH_2$ or Si—H where R is C1-C6 alkyl.

4. A multicomponent composition of statement 3 comprising first and second components wherein each component comprises a silicone polymer having reactive organosiloxane monomers with functional groups that comprise one half of the complementary reactive pairs of functional groups or the first and second components comprise a silicone polymer having reactive organosiloxane monomers with a self-reactive functional group.

5. A multicomponent composition of statement 4 further comprising a third component comprising a base compound having amine, mercapto, sulfonate, carboxylate or carbamate groups.

6. a multicomponent composition of statement 5 wherein the base compound has amine groups.

7. A multicomponent composition of statement 4 wherein the first component comprises a first silicone polymer and the second component comprise a second silicone polymer;

Wherein:
the first silicone polymer and second silicone polymer respectively comprise reactive organosiloxane monomeric units of Formulas I and II, wherein X1 and Y1 are complementary reactive pairs of functional groups, X2 and Y2 are self-reactive functional groups, CU is a divalent organic connecting unit and $R^4$ is oxygen, a C1-C6 alkyl or phenyl:

Formula I: reactive organosiloxane monomeric unit is —$(O)_{(4-a-c)/2}SiR^4_c[CU-X1 \text{ or } CU-X2]_d$ Formula II: reactive organosiloxane monomeric unit is —$(O)_{(4-a-c)/2}SiR^4_c[CU-Y1 \text{ or } CU-Y2]_d$ d is 1 to 3, c is 0 to 2 and d+c is between 1 and 3,
X1 comprises isocyanato, thioisocyanato, carboxyl, linear, branched or cyclic epoxyalkyl, olefinoyloxy, malonic anhydrido, formyl, mercapto, vinyl, alkynyl;
Y1 comprises hydroxyl, amino, mercapto, furanyl, cyclopentadienyl or azido;
X2 and Y2 each comprise mercapto or isocyanate; or $Si(OR)_3$ or
X2 and Y2 each comprise OH, oxime, acetoxy, hydrogen or $OR^5$ with $R^{15}$ being a C1-C6 alkyl group wherein X2 and Y2 are covalently bonded to CU or bonded directly to silicon and CU is absent.

8. A multicomponent composition of statement 7 wherein the first and second silicone polymers comprise a majority of non-reactive siloxane units $(R)_nSi(O)_{(4-n)/2}$ forming backbone and branch chains with R is a C1-C6 alkyl or phenyl and n is zero or an integer of 1 to 3 and the first silicone polymer comprises at least two reactive organosiloxane units of Formula I and the second silicone polymer comprises at least two reactive organosiloxane units of Formula II.

9. A multicomponent composition of any of statements 7 and 8 wherein the divalent organic connecting unit CU comprises a linear and/or branched and/or cyclic saturated C1-C48 aliphatic chain, a linear and/or branched and/or cyclic C1-C48 heteroaliphatic chain or an aromatic and/or heteroaromatic group of one, two or three separate or fused rings, each ring being a 5 or 6 member single ring or a bicyclic 10 member ring; wherein the aliphatic chain comprises a linear and/or branched and/or cyclic C1-C48 polymethylenyl chain and the heteroaliphatic chain comprises a linear and/or branched and/or cyclic C1-C48 polymethylenyl chain wherein portions of the chain are linked together by heteroatom linking groups selected from ether, sulfur, amino, carboxyl, amido, urethano, ureido, carbonyl, carbonato and/or imino.

10. A multicomponent composition of any of the preceding statements, wherein the first, second and third functional groups form reactive pairs of functional groups wherein the reactive pairs are isocyanate and hydroxyl, amine or mercapto or any combination of hydroxyl, amine and mercapto; carboxyl and hydroxyl, amine or mercapto or any combination of hydroxyl, amine and mercapto; alkylepoxy and hydroxyl, amine or mercapto or any combination of hydroxyl, amine and mercapto; olefinoyloxy and hydroxyl, amine, mercapto, furanyl or pentadienyl or any combination of hydroxyl, amine, mercapto, furanyl or pentadienyl; malonic anhydrido and hydroxyl, amine or mercapto or any combination of hydroxyl, amine and mercapto; formyl and amine or mercapto or any combination of amine and mercapto; vinyl and amine or mercapto or a combination of amine and mercapto; vinyl and furanyl or cyclopentadienyl or a combination of furanyl and cyclopentadieny or azido and alkynyl.

11. A multicomponent composition of any of the preceding statements wherein the functional groups are a self-reactive functional group and comprise any combination of Si—OH, Si—OR, Si—O—N=CHR. Si—OAc or comprise mercapto and mercapto, or comprise isocyanate and isocyanate.

12. A multicomponent composition of any of the preceding statements wherein the first and second functional groups are a reactive pair of vinyl and H and the reactive organosiloxane units have silicon as Si-vinyl and Si—H.

13. A multicomponent composition of any of the preceding statements wherein the reactive pairs are isocyanate and hydroxyl, amine or mercapto or any combination of hydroxyl, amine and mercapto; epoxy and hydroxyl, amine, or mercapto or any combination any two or more of hydroxyl, amine and mercapto; olefinoyloxy and hydroxyl, amine or mercapto or any combination of any two or more of hydroxyl and amine and mercapto; carboxyl and hydroxyl, amine or mercapto or any combination of any two or more of hydroxyl, amine and mercapto.

14. A multicomponent composition of any of the preceding statements wherein the reactive pairs are isocyanate and hydroxyl, amine or mercapto or any combination of hydroxyl, amine and mercapto; epoxy and hydroxyl, amine or mercapto or any combination of hydroxyl, amine and mercapto; carboxyl and hydroxyl or amine or a combination of hydroxyl and amine.

15. A multicomponent composition of any of the preceding statements wherein the reactive pair is isocyanate and hydroxyl, amine or mercapto or any combination of hydroxyl, amine and mercapto.

16. A multicomponent composition of any of the preceding statements wherein the reactive pair is any combination of silanol, acetoxy, oxime and alkoxy.

17. A multicomponent composition of any of the preceding statements wherein the reactive pair is epoxy and hydroxyl, amine or mercapto or any combination of hydroxyl, amine and mercapto.
18. A multicomponent composition of any of the preceding statements wherein the reactive pair is carboxyl and hydroxyl or amine or a combination of hydroxyl and amine and the fourth component is a carbodiimide.
19. A multicomponent composition of any of the preceding statements wherein the reactive pair is olefinoyloxy and hydroxyl, amine or mercapto or any combination of hydroxyl, amine and mercapto.
20. A multicomponent composition of preceding statements wherein the olefinoyloxy group is (meth)acryloyloxy or crotonyloxy.
21. A multicomponent composition of any of the preceding statements wherein the reactive pair is isocyanate and isocyanate.
22. A multicomponent composition of any of the preceding statements wherein the reactive pair is mercapto and mercapto.
23. A multicomponent combination of any of the preceding statements wherein the third component further comprises pigment microparticles that are the same as or different from the pigment microparticles of the first component and/or second component.
24. A multicomponent composition of any of the preceding statements wherein the concentration of each the first and second silicone polymers and base compound in the multicomponent composition ranges from about 0.25 wt % to about 20 wt %, preferably about 0.5 wt % to about 15 w5%, more preferably about 0.75 wt % to about 10 wt % relative to the total weight of the multicomponent composition and the combined concentration of first and second silicone polymers and the base compound is in a range of about 0.5 wt % to about 35 wt %.
25. A multicomponent composition of any of the preceding statements wherein the first functional groups of the first silicone polymer are isocyanate groups and the second functional groups of the second silicone polymer are hydroxyl groups and the base compound is polyethyleneimine.
26. A multicomponent composition of any of the preceding statements wherein the first, second and third functional groups are capable of producing at least one or more of urethane linkages, urea linkages and/or thiourethane linkages.
27. A multicomponent composition of any of the preceding statements wherein a third component is present and one of the first and second silicone polymer has an average molecular weight in a range of 1.5 KDa to 150 KDa and the other silicone polymer has an average molecular weight in a range of 150 Da to 150 KDa.
28. A multicomponent composition of any of the preceding statements wherein a third component is absent and the first and second silicone polymers independently have an average molecular weight in a range of 1.5 KDa to 150 KDa, and a polydispersity wherein the molecular weight fraction below 1KDa of the first and second silicone polymers is less than 5 wt %, preferably less than 1 wt %, more preferably less than 0.1 wt % or virtually indetectable relative to the average molecular weights of the first and second silicone polymers.
29. The multicomponent composition of any of the preceding statements, wherein at least one portion of the pigment microparticles is an organic pigment.
30. The multicomponent composition of any of the preceding statements, wherein the composition has a pigment solids content of about 0.1 wt % to about 30 wt % preferably about 0.2 wt % to about 10 wt % relative to the total weight of the composition.
31. The multicomponent composition of any of the preceding statements, wherein the pigments selected has a hair color gamut of greater than about 250.
32. A multicomponent composition of any of the preceding statements any combination thereof further comprising one or more of a plasticizer, a dispersant, wetting agent, anti-agglomeration agent, preservative, fragrance, an organic dye compound, a feel-modification agent, or a thickening agent; the dispersant, anti-agglomeration agent capable of providing dispersion of the pigment particles, the plasticizer and thickener capable of providing viscosity parameters to enable flow and hold of the composition on the keratin fibers.
33. A multicomponent composition of any of the preceding statements and any combination thereof, wherein the composition has a viscosity of from about 0.001 to about 2000 Pa s−1.
34. A multicomponent composition of any of the preceding statements wherein the composition has the physical character of a foam.
35. A multicomponent composition of any of the preceding composition statements further comprising a medium wherein the medium comprises at least one liquid selected from the group consisting of water, protic organic medium, protic organic non-aqueous medium, an aprotic, non-aqueous organic medium, a silicone medium and any compatible combination thereof.
36. A multicomponent composition of any of the preceding statements wherein the medium is water or a non-aqueous organic medium.
37. A multicomponent composition of any of the preceding statements wherein the medium is an aprotic non-aqueous organic or silicone medium that has a boiling point at standard pressure at a temperature of from ambient to about 250° C.
38. A multicomponent composition of any of the preceding statements wherein the medium is a nonpolar, aprotic organic medium selected from decane, isodecane, isododecane, a liquid silicone, cyclomethicone, glyme or decamethyl cyclopentasiloxane.
39. A multicomponent composition of any of the preceding statements wherein the combined concentration of the first and second silicone polymers compared with the concentration of the pigment particles such that the minimum baseline concentration ratio of combined polymers to pigment microparticles is 0.3:1 relative to the total weight of the composition.
40. A multicomponent composition according to any of the preceding statements, further comprising an excipient selected from a dispersing agent, a preservative, a fragrance, a surfactant, a tactile-modification agent, and a thickening agent or a combination thereof.
41. A multicomponent composition of any of the preceding statements wherein the excipient includes at least a dispersing agent and the concentration of the dispersing agent is in an amount able to generate a positive or negative zeta potential in the composition.
42. A multicomponent composition of any of the preceding statements wherein the dispersing agent is a surfactant selected from silicone based surfactants, ethoxylated aliphatic alcohol, polyoxyethylene glycol, esters of fatty acids and glycerol, polyethylene glycol esters of fatty acids, anhydrosorbitol esters, polyethoxylated sorbitol esters, polysorbates, poloxamer, nonoxynol, fatty alcohol, tritan, tween, alkoxylated, hydrogenated castor oil.

43. A method for preparing the multicomponent composition of any of the preceding statements, comprising:
dispersing dry pigment microparticles in a portion of medium to form a slurry, adding additional medium to the slurry and applying a high energy dispersing procedure to prepare a premix of the pigment particles in the medium.

44. A method of preceding statements further comprising combining the first or second component or the first and second components with portions of the premix to form a substantially uniform dispersion of the pigment particles in the first or second component or in both of the first and second components.

45. A method of statement 44 wherein the pigment particles are dispersed in one of the first and second components.

46. A method of statement 44 wherein the pigment particles are dispersed in the first and second components.

47. A method of statement 46 wherein the pigment particles with the first component differ from the pigment particles with the second component.

48. A method of any of previous method statements wherein the high energy dispersing technique includes ultra-high speed, high energy mixing.

49. A composition according to the preceding composition statements including the third component wherein the first component is maintained in a first compartment, the second component is maintained in a second compartment and the third component is maintained in a third compartment.

50. A kit comprising the first, second and third compartments with first, second and third components according to claim 49.

51. A composition according to the preceding composition statements not including the third component wherein the first component is maintained in a first compartment, the second component is maintained in a second compartment.

52. A composition according to statement 49 comprising a preapplication formulation prepared by mixing together the first and second components.

53. A method for coloring substrate material comprising applying first to the substrate material the third component of statement 49 to form pretreated substrate material.

54. A method of statement 53 further comprising optionally or at least partially drying the third component on the substrate material.

55. A method of statement 53 or 54 further comprising combining the first and second components of statement 49 to form to form an in situ coloring mixture, applying the in situ coloring mixture to the pretreated substrate material and causing the in situ coloring mixture to form a colored coating on the substrate material.

56. A method of statement 55 further comprising drying the colored coating on the substrate material while mechanically separating the fibers in the substrate material.

57. A method for coloring substrate material comprising combining the first and second components of preceding composition statements to form a color formulation and applying the color formulation to the substrate material to form a coated substrate material and causing the coated substrate material to form a colored coating on the substrate material.

58. A colored coating for hair strands produced according to the method of statements 53-57.

59. A colored coating for hair strands according to statement 58 wherein the composition forms a solid, flexible elastic film on each individualized hair fibre in which are embedded the pigment particles.

60. A colored coating for hair strands according to statement 59 wherein the film has the microscopic appearance of a semicontinuous or continuous coating.

61. A colored coating for hair strands according to statements 59 which are resistant to color fading by repeated washings according to a standard wash procedure.

62. A colored coating for hair strands according to statement 61 wherein the repeated washings number 5 to 15.

63. A colored coating for hair strands according to statement 62 wherein the repeated washing number 15 or more.

64. A color removal composition for applying to color coated hair strands of statement 58 comprising applying one or more of surfactant, solvent, acid, base, polymer, polyelectrolyte, salt sources of fluorine, ionic liquids to remove the color coating.

65. A color removal composition of statement 55 comprising a source of fluorine.

66. A color removal composition comprising a medium with a Hansen solubility parameter according to the ranges $12<\delta d<22$ and $0<\delta p<7$ and $0<\delta h<9$.

67. A method of removing the colored coating of statement 58 comprising combining the colored hair strands with an aqueous-organic mixture of a fluorine source, agitating the mixture on the hair and washing with a basic aqueous solution of detergent with optional brushing.

68. A method of removing the colored coating of the preceding statements by combining the removal composition with either heat, electromagnetism, mechanical energy, or cooling.

69. A method of selecting the removal composition to chemically break down covalent bonds in the in situ linked multicomponent composition.

70. A multicomponent composition of a linear and/or branched silicone polymer and a linear and/or branched organic polymer comprising a silicone polymer of non-reactive organosiloxane monomer units and reactive organosiloxane monomer units and an organic polymer having reactive organic monomeric units, the reactive organosiloxane monomer units and the reactive organic monomeric units having functional groups which are arranged to be complementary reactive pairs or a self-reactive functional group, the functional groups comprising isocyanato, thioisocyanato, carboxyl, linear, branched or cyclic epoxyalkyl, olefinoyloxy, malonic anhydrido, formyl, mercapto, vinyl, alkynyl, hydroxyl, amino, mercapto, furanyl, pentadienyl, azido, Si—OH, Si—OR, Si—O—N═CHR. Si—OAc, Si—CH═CH$_2$ or Si—H where R is CT-C6 alkyl; the complementary reactive pairs being arranged so that a functional group of one half of the complementary reactive pair is present with the reactive organosiloxane monomeric unit and a functional group of the other half of the complementary reactive pair is present with the reactive organic monomeric unit; or the reactive organic monomeric unit and the reactive organic monomeric unit both have the same self-reactive functional group.

SUMMARY STATEMENTS

The inventions, examples and results described and claimed herein may have attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A method for coloring substrate material comprising applying to the substrate material a third component to form pretreated substrate material, and applying to the pretreated substrate material sequentially, simultaneously or as a premix, a first silicone component and a second silicone component; wherein:
   the first silicone component comprises a first linear and/or branched silicone polymer comprising non-reactive organosiloxane monomer units and reactive organosiloxane monomer units, the reactive organosiloxane monomer units having functional groups which are arranged as complementary reactive pairs or as a self-reactive functional group, the functional groups comprising Si—OH, Si—OR, Si—O—N=CR$_2$, Si-OAc, where R is C1-C6 alkyl;
   the second silicone component comprises a second linear and/or branched silicone polymer comprising non-reactive organsiloxane monomer units and reactive organosiloxane monomer units, the reactive organosiloxane monomer units having functional groups which are arranged as complementary reactive pairs or as a self-reactive functional group, the functional groups comprising Si—OH, Si—OR, Si—O—N=CR$_2$, Si—OAc where R is C1-C6 alkyl;
   each of the first and the second silicone components with non-reactive organosiloxane monomer units and reactive organosiloxane monomer units comprises an MDTQ linear and/or branched silicone polymer, with no crosslinking, with the reactive organosiloxane monomer units being at least two of the M and/or D and/or T units and with the weight average molecular weight of each being from about 1KDa to about 1 MDa,
   the third component comprises a base compound having third functional groups which are amine groups;
   the first and/or second and/or third component comprise pigment particles.

2. The method of claim 1 wherein the first silicone polymer and second silicone polymer respectively comprise reactive organosiloxane monomeric units of Formulas I and II, X2 and Y2 are self-reactive functional groups, CU is a divalent organic connecting unit and R$^4$ is a C1-C6 alkyl or phenyl:

$$\text{reactive organosiloxane monomeric unit is} \\ \text{—(O)}_{(4-d-c)/2}\text{SiR}^4{}_c\text{[CU-X2]}_d \quad \text{Formula I:}$$

$$\text{reactive organosiloxane monomeric unit is} \\ \text{—(O)}_{(4-d-c)/2}\text{SiR}^4{}_c\text{[CU-Y2]}_d \quad \text{Formula II:}$$

d is 1 to 3, c is 0 to 2 and d+c is between 1 and 3;
X2 and Y2 each comprise Si(OR)$_3$ wherein R is C1-C6 alkyl; or
X2 and Y2 each comprise OH, oxime, acetoxy, hydrogen or OR$^{15}$ with R$^{15}$ being a C1-C6 alkyl group wherein X2 and Y2 are covalently bonded to CU or are bonded directly to silicon and CU is absent.

3. The method of claim 2 wherein the first and second silicone polymers comprise a majority of non-reactive siloxane units (R)$_n$Si(O)$_{(4-n)/2}$ forming backbone and branch chains with R is a C1-C6 alkyl or phenyl and n as zero or an integer of 0 to 3 and the first silicone polymer comprises at least two reactive organosiloxane units of Formula I and the second silicone polymer comprises at least two reactive organosiloxane units of Formula II.

4. The method of claim 2 wherein the divalent organic connecting unit CU comprises a linear and/or branched and/or cyclic saturated C1-C48 aliphatic chain, a linear and/or branched and/or cyclic saturated C1-C48 heteroaliphatic chain or an aromatic and/or heteroaromatic group of one, two or three separate or fused rings, each ring being a 5 or 6 single ring or a bicyclic 10 member ring; wherein the aliphatic chain comprises a linear and/or branched and/or cyclic C1-C48 polymethylenyl chain and the heteroaliphatic chain comprises a linear and/or branched and/or cyclic C1-C48 polymethylenyl chain wherein portions of the chain are linked together by heteroatom linking groups selected from ether, sulfur, amino, carboxyl, amido, urethano, ureido, carbonyl, carbonato and/or imino.

5. The method of claim 1 wherein
the molar ratio of non-reactive organosiloxane monomeric units to reactive organosiloxane monomeric units of the first and second silicone polymer is in a range of about 2000:1 to about 3:1; preferably about 1250:1 to about 3:1, more preferably about 800:1 to about 3:1, most preferably about 500:1 to 3:1, especially most preferably about 250:1 to 3:1.

6. The method of claim 1 wherein the MW of the first and second silicone polymers is in the range of 1.5 KDa to about 150 KDa.

7. The method of claim 6 wherein the first and second silicone polymers have a polydispersity wherein the molecular weight below 1 KDa is less than 5% of the weight of the first and second silicone polymers.

8. The method of claim 1 wherein the base compound of the third component has a weight average molecular weight of about 150 Da to about 1 MDa and the base compound is selected from aminosilane, aminosiloxane, aminosilicone or a linear or branched polymer comprising linear polyethyleneimine, branched polyethylene imine, a copolymer of aminoethyl (meth)acrylate and ethyl (meth)acrylate, polyallylamine hydrochloride, polydiallyldimethyl ammonium chloride, polyvinylamine, (vinylamine-styrene) copolymer, poly(omega-aminoalkyl(meth)acrylate), polyvinylpyrrolidone poly (2-vinyloxazoline), aminopolysaccharide, tri or tetra mercapto tri or tetra alkyl methane and random or block copolymers thereof and mixtures thereof.

9. The method of claim 8 wherein the base compound is polyethyleneimine.

10. The method of claim 1 wherein the base compound content of the third component is from about 0.1 wt % to about 5 wt % relative to the total weight of the composition containing the third component.

11. The method of claim 1 wherein any combination thereof further comprises one or more of a plasticizer, a dispersant, wetting agent, anti-agglomeration agent, preservative, fragrance, an organic dye compound, a feel-modification agent, or a thickening agent; the dispersant, anti-agglomeration agent capable of providing dispersion of the pigment particles, the plasticizer and thickener capable of providing viscosity parameters to enable flow and hold of the composition on the keratin fibers.

12. The method of claim 1 wherein the composition has the physical character of a foam.

13. The method of claim 1 further comprising a medium wherein the medium comprises at least one liquid selected from the group consisting of water, protic organic medium, protic organic non-aqueous medium, an aprotic, non-aqueous organic medium, a silicone and any compatible combination thereof.

14. The method of claim 1 comprising an excipient and the excipient includes at least a dispersing agent and the concentration of the dispersing agent is in an amount able to generate a positive or negative zeta potential in the composition.

15. The method of claim 14 wherein the dispersing agent is a surfactant selected from silicone based surfactants, ethoxylated aliphatic alcohol, polyoxyethylene glycol, esters of fatty acids and glycerol, polyethylene glycol esters of fatty acids, anhydrosorbitol esters, polyethoxylated sorbitol esters, polysorbates, poloxamer, nonoxynol, fatty alcohol, tritan, tween, alkoxylated hydrogenated castor oil.

16. A kit comprising a container with at least three compartments, each compartment containing one of the first, second and third components of claim 1.

17. A method of claim 1 further comprising optionally or at least partially drying the third component on the substrate material before applying the first and second components.

18. A method of claim 1 further comprising combining the first and second components to form to form a coloring mixture, applying the coloring mixture to the pretreated substrate material and causing the coloring mixture to form a colored coating on the substrate material.

19. A colored coating on a substrate material produced according to the method of claim 1 wherein the substrate material comprises hair strands.

* * * * *